United States Patent
Weiss et al.

(10) Patent No.: US 10,668,067 B2
(45) Date of Patent: Jun. 2, 2020

(54) PYRIDINE SULFONAMIDES

(71) Applicant: AMGEN INC., Thousand Oaks, CA (US)

(72) Inventors: Matthew Weiss, Boston, MA (US); John R. Butler, Somerville, MA (US); Benjamin Charles Milgram, Cambridge, MA (US); Gwenaella Rescourio, Cambridge, MA (US); Alessandro Boezio, Somerville, MA (US); Brian Andrew Sparling, Melrose, MA (US); Daniel La, Chestnut Hill, MA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 16/319,783

(22) PCT Filed: Jul. 20, 2017

(86) PCT No.: PCT/US2017/043173
§ 371 (c)(1),
(2) Date: Jan. 22, 2019

(87) PCT Pub. No.: WO2018/017896
PCT Pub. Date: Jan. 25, 2018

(65) Prior Publication Data
US 2019/0167682 A1    Jun. 6, 2019

Related U.S. Application Data

(60) Provisional application No. 62/364,437, filed on Jul. 20, 2016.

(51) Int. Cl.
| | |
|---|---|
| *A61K 31/506* | (2006.01) |
| *A61K 31/4439* | (2006.01) |
| *A61P 25/00* | (2006.01) |
| *C07D 213/75* | (2006.01) |
| *C07D 401/12* | (2006.01) |
| *C07D 413/12* | (2006.01) |
| *C07D 417/12* | (2006.01) |

(52) U.S. Cl.
CPC ........ *A61K 31/506* (2013.01); *A61K 31/4439* (2013.01); *A61P 25/00* (2018.01)

(58) Field of Classification Search
None
See application file for complete search history.

(56) References Cited

FOREIGN PATENT DOCUMENTS

| WO | WO 2007/120647 A2 | * | 10/2007 |
| WO | WO 2009/012242 A2 | * | 1/2009 |
| WO | WO 2011/02640 A1 | * | 3/2011 |
| WO | WO 2012/007861 A1 | * | 1/2012 |

OTHER PUBLICATIONS

Database PubChem Compound, Database Accession No. CID 57349262, Jul. 12, 2012).*
Database PubChem Compound, Database Accession No. CID 57372894, Jul. 13, 2012).*
Database PubChem Compound, Database Accession No. CID 57372835 Jul. 13, 2012).*
Database PubChem Compound, Database Accession No. CID 57374397, Jul. 13, 2012).*
Database PubChem Compound, Database Accession No. CID 57374398, Jul. 13, 2012).*
Database PubChem Compound, Database Accession No. CID 573749263, Jul. 12, 2012).*
Wang et al, British Journal of Pharmacology, vol. 172 , No. 20, pp. 4905-4918, Oct. 1, 2015).*
International Search Report for PCT/US2017/043173, completed Sep. 13, 2017).*

* cited by examiner

*Primary Examiner* — Zinna Northington Davis
(74) *Attorney, Agent, or Firm* — Elsa D. Lemoine

(57) ABSTRACT

The present invention provides compounds of Formula (I), as defined in the specification, or pharmaceutically acceptable salts thereof, that are inhibitors of voltage-gated sodium channels, in particular Nav 1.7. The compounds are useful for the treatment of diseases treatable by inhibition of sodium channels such as pain disorders, cough, or itch. Also provided are pharmaceutical compositions containing compounds of the present invention.

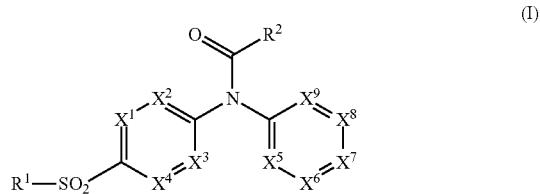

18 Claims, No Drawings

PYRIDINE SULFONAMIDES

CROSS-REFERENCE TO RELATED APPLICATIONS

This application is a national stage application under 35 U.S.C. § 371 of International Application No. PCT/US2017/43173, having an international filing date of Jan. 20, 2017, which claims the benefit of U.S. Provisional Patent Application No. 62/364,437, filed on Jul. 20, 2016, which is hereby incorporated by reference in its entirety.

FIELD OF THE INVENTION

The examples presented below illustrate specific embodiments of the present invention. These examples are meant to be representative and are not intended to limit the scope of the claims in any manner. The present invention provides compounds that are inhibitors of voltage-gated sodium channels (Navy), in particular Nav 1.7, and are useful for the treatment of diseases treatable by inhibition of sodium channels such as pain disorders. Also provided are pharmaceutical compositions containing compounds of the present invention.

BACKGROUND OF THE INVENTION

Chronic pain by definition involves abnormal electrical spiking of neurons in the pain pathways: peripheral sensory neurons, spinal cord neurons, neurons in the pain matrix of the brain (e.g., somatosensory cortex, insular cortex, anterior cingulate cortex), and/or neurons in brainstem. Although firing of these neurons is modulated and governed by many different receptors, enzymes, and growth factors, in most neurons the fast upstroke of the electrical spike is produced by entry of sodium ions through voltage-gated sodium channels (Hille B, Ion Channels of Excitable Membranes. Sinauer Associates, Inc.: Sunderland Mass., $3^{rd}$ Ed. 2001). There are nine different isoforms of voltage-gated sodium channel (Nav 1.1-Nav 1.9), and they have distinct expression patterns in tissues including neurons and cardiac and skeletal muscle (Goldin, A. L, "Resurgence of sodium channel research," *Ann Rev Physiol* 63:871-894, 2001; Wood, J. N. and, Boorman, J. "Voltage-gated sodium channel blockers; target validation and therapeutic potential," *Curr. Top Med. Chem.* 5:529-537, 2005). The various isoforms of voltage-gated sodium channels are:

Nav 1.1—found in the peripheral nervous system (PNS) and central nervous system (CNS), and believed associated with epilepsy, pain, seizures and neurodegeneration;

Nav 1.2—found in the CNS and believed associated with epilepsy and neurodegeneration;

Nav 1.3—found in the CNS and believed associated with pain;

Nav 1.4—found in the skeletal muscle and believed associated with myotonia;

Nav 1.5—found almost exclusively in cardiac tissue and believed to play a key role in cardiac action potential and propagation of electrical impulses, resulting in and associated with arrhythmia (Liu H, et al., *Am. J. Pharmacogenomics*, 3:173-179 (2003));

Nav 1.6—found in the CNS and PNS and believed associated with pain;

Nav 1.7—found in the PNS and believed associated with pain;

Nav 1.8—found in the PNS and believed associated with pain; and

Nav 1.9—found in the PNS and believed associated with pain.

Voltage-gated sodium channel isoforms have been divided into two subfamilies, based on those isoforms which are sensitive to blocking by tetrodotoxin (TTX-sensitive) and those which are resistant to blocking by tetrodotoxin (TTX-resistant). Nonselective sodium channel inhibitors such as lidocaine, mexiletine, and carbamazepine show clinical efficacy in chronic pain, including neuropathic pain, but they are limited in dose and in use, likely due to effects on sodium channels outside the pain pathway.

Recent evidence from several independent genetic studies has shown that the tetrodotoxin-sensitive voltage-gated sodium ion channel Nav 1.7 (SCN9A) is required to sense pain. Rare genetic forms of severe chronic pain, Primary Erythromelalgia and Paroxysmal Extreme Pain Disorder, result from mutations that increase the activity of Nav 1.7 (Fertleman C. R., Baker M. D., Parker K. A., Moffatt S., et al., "SCN9A mutations in paroxysmal extreme pain disorder: allelic variants underlie distinct channel defects and phenotypes," *Neuron* 52:767-774, 2006; Yang Y., Wang Y., Li S, et al., "Mutations in SCN9A, encoding a sodium channel alpha subunit, in patients with primary erythermalgia," *J. Med. Genet.* 41:171-174, 2004; Drenth J. P. H., te Morsche R. H. M., Guillet G., Taieb A., et al., "SCN9A mutations define primary erythermalgia as a neuropathic disorder of voltage gated sodium channels," *J Invest Dermatol* 124:1333-1338). Conversely, two separate clinical studies have determined that the root cause of the genetic disorder Congenital Indifference to Pain (CIP) is a loss of function of Nav 1.7 via mutations that truncate the protein and destroy function (Cox J. J., Reimann F, Nicholas A. K., et al. "An SCN9A channelopathy causes congenital inability to experience pain," *Nature* 444:894-898, 2006; Goldberg Y. P., MacFarlane J., MacDonald M. L., Thompson J., et al. "Loss-of-function mutations in the Nav1.7 gene underlie congenital indifference to pain in multiple human populations," *Clin Genet* 71:311-319, 2007). The disorder is inherited in Mendelian recessive manner with 100% penetrance. The phenotype associated with CIP is extreme: affected individuals are reported to have experienced painless burns, childbirth, appendicitis, and bone fractures, as well as to have insensitivity to clinical measures of pain such as pinprick or tendon pressure. Yet sensory, motor, autonomic, and other measured functions are normal, with the only reported abnormality being anosmia (inability to smell). These studies indicate that among the many possible targets in the pain pathway, Nav 1.7 governs one or more control points critical for pain perception.

Nav 1.7 intervention may also be implicated in respiratory and respiratory tract diseases. In general, a cough results from various kinds of respiratory conditions and diseases. The cough reflex primarily protects the airway from possible harm via the clearance of foreign particulate and uninvited debris. Within the respiratory epithelium, nerve endings, sensing incoming irritants, transmit information regarding the presence of tussive stimuli to the brain, thereby inducing a cough reflex or cough response. When the cough progresses to a chronic cough, believed to be dry and unproductive, it is frequently associated with the development of lung damage, which is typically irreversible and commonly referred to as chronic pulmonary obstructive disease (CPOD). Such conditions (COPD) become a nuisance and progressively deteriorate one's quality of life. It has been shown that Nav 1.7 inhibitors have the potential to treat such respiratory and respiratory tract conditions, including post viral cough, viral cough and acute viral cough (PCT Publication WO2013006596). Accordingly, a therapeutic agent that inhibits Nav 1.7 should effectively treat pain and/or cough in humans.

SUMMARY OF THE INVENTION

The present invention provides compounds, or pharmaceutically acceptable salts thereof, of Formula (I):

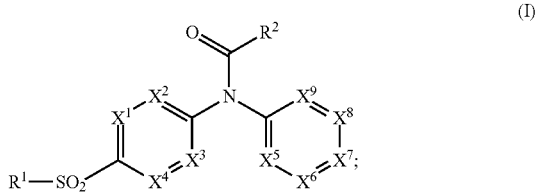

$X^1$ is N or $CR^3$;
$X^2$ is N or $CR^4$;
$X^3$ is N or $CR^5$;
$X^4$ is N or $CR^6$;
$X^5$ is N or $CR^7$;
$X^6$ is N or $CR^8$;
$X^7$ is $CR^9$ or $CL^1$;
$X^8$ is $CR^{10}$ or $CL^1$;
$X^9$ is N or $CR^{11}$;
wherein 0, 1, 2, 3, or 4 of $X^1$, $X^2$, $X^3$, $X^4$, $X^5$, $X^6$ and $X^9$ are N;
$R^1$ is —NH-$L^2$;
$R^2$ is $NH_2$, $NHC_{1-8}$alk, $NHC_{1-4}$haloalk, NH—$OR^a$, NH—$OR^c$, —$OR^a$, or —$OR^c$;
$R^3$ is H, halo, CN, $C_{1-8}$alk, or $C_{1-4}$haloalk;
$R^4$ is H, halo, CN, $C_{1-8}$alk, or $C_{1-4}$haloalk;
$R^5$ is H, halo, CN, $C_{1-8}$alk, or $C_{1-4}$haloalk;
$R^6$ is H, halo, CN, $C_{1-8}$alk, or $C_{1-4}$haloalk;
$R^7$ is CN, halo, $C_{1-8}$alk, or $C_{1-4}$haloalk, —$OR^a$, or —$OR^c$;
$R^8$ is H, halo, $C_{1-8}$alk, or $C_{1-4}$haloalk;
$R^9$ is H, halo, $C_{1-8}$alk, or $C_{1-4}$haloalk; or $R^9$ is H, halo, $C_{1-20}$alk, or $C_{1-20}$haloalk;
$R^{10}$ is H, halo, $C_{1-8}$alk, or $C_{1-4}$haloalk;
$R^{11}$ is H, halo, $C_{1-8}$alk, or $C_{1-4}$haloalk;
$L^1$ is $C_{0-6}$alk-linked saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atoms selected from O and S, which is substituted by 0, 1, 2 or 3 $R^d$ groups selected from F, Cl, Br, $C_{1-6}$alk —$OR^a$, —$OR^c$, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{1-6}$alk$NR^aR^a$, —$OC_{1-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{1-6}$alk$NR^aR^a$, —$NR^aC_{1-6}$alk$OR^a$, and oxo; wherein each of said $C_{1-6}$alk is substituted by 0, 1, 2 or 3 substituents selected from halo, $C_{1-3}$haloalk, —$OR^a$, —$NR^aR^a$, —N($R^a$)C(=O)$R^b$, —OC(=O)$R^b$, C(=O)$NR^aR^a$, or C(=O)$OR^a$;
$L^2$ is $C_{0-6}$alk-linked saturated, partially-saturated or unsaturated 5- or 6-membered monocyclic ring containing 0, 1, 2 or 3 N atoms and 0 or 1 atoms selected from O and S, which is substituted by 0, 1, 2 or 3 $R^e$ groups selected from F, Cl, Br, $C_{1-6}$alk, or $C_{1-4}$haloalk;
$R^a$ is independently, at each instance, H or $R^b$;
$R^b$ is independently, at each instance, phenyl, benzyl or $C_{1-6}$alk, wherein the phenyl, benzyl and $C_{1-6}$alk is substituted by 0, 1, 2 or 3 substituents selected from halo, $C_{1-4}$alk, $C_{1-3}$haloalk, —$OC_{1-4}$alk, —$NH_2$, —$NHC_{1-4}$alk, and —N($C_{1-4}$alk)$C_{1-4}$alk; and
$R^c$ is a $C_{0-1}$alk-linked saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atoms selected from O and S, which is substituted by 0, 1, 2 or 3 $R^{13}$ groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$ and oxo.

In embodiment 2, the present invention provides compounds, or pharmaceutically acceptable salts thereof, in accordance with embodiment 1 wherein $X^3$ is N.

In embodiment 3, the present invention provides compounds, or pharmaceutically acceptable salts thereof, in accordance with any one of embodiments 1 or 2 wherein $X^7$ is $CR^9$ and $X^8$ is $CL^1$.

In embodiment 4, the present invention provides compounds, or pharmaceutically acceptable salts thereof, in accordance with any one of embodiments 1 or 2 wherein $X^7$ is $CL^1$ and $X^8$ is $CR^{10}$.

In embodiment 5, the present invention provides compounds, or pharmaceutically acceptable salts thereof, in accordance with any one of embodiments 1 to 4 wherein each of $X^1$, $X^2$ and $X^4$ are CH and $X^3$ is N.

In embodiment 6, the present invention provides compounds, or pharmaceutically acceptable salts thereof, in accordance with any one of embodiments 1 to 5 wherein $X^5$ is $CR^7$; $X^6$ is $CR^8$; and $X^9$ are $CR^{11}$.

In embodiment 7, the present invention provides compounds, or pharmaceutically acceptable salts thereof, in accordance with any one of embodiments 1 to 6 wherein $R^2$ is $NH_2$, $NH(CH_3)$, $NH(OCH_3)$, or —$OCH_3$.

In embodiment 8, the present invention provides compounds, or pharmaceutically acceptable salts thereof, in accordance with any one of embodiments 1 to 7 wherein $R^7$ is —$OR^a$.

In embodiment 9, the present invention provides compounds, or pharmaceutically acceptable salts thereof, in accordance with any one of embodiments 1 to 8, wherein $R^7$ is —$OCH_3$.

In embodiment 10, the present invention provides compounds, or pharmaceutically acceptable salts thereof, in accordance with any one of embodiments 1 to 9, wherein $R^{10}$ is halo.

In embodiment 11, the present invention provides compounds, or pharmaceutically acceptable salts thereof, in accordance with any one of embodiments 1 to 10, wherein each of $R^3$, $R^4$, $R^6$, $R^8$, and $R^{11}$ are H; $R^7$ is —$OCH_3$; and $R^9$ is H, F, Cl, methyl, or ethyl; or $R^9$ is H, F, Cl, methyl, ethyl, propyl, isopropyl, butyl, isobutyl, sec-butyl, tert-butyl, pentyl, neopentyl, hexyl, heptyl, octyl, vinyl, allyl, or longer linear or branched $C_{9-20}$alk group, including but not limited to nonyl, decyl, undecyl, dodecyl, tridecyl, tetradecyl, pentadecyl, hexadecyl, heptadecyl, octadecyl, nonadecyl, or hexadecyl.

In embodiment 12, the present invention provides compounds, or pharmaceutically acceptable salts thereof, in accordance with any one of embodiments 1 to 11, wherein $R^1$ is-N-$L^2$, wherein $L^2$ is unsaturated 5- or 6-membered monocyclic ring containing 0, 1, 2 or 3 N atoms.

In embodiment 13, the present invention provides compounds, or pharmaceutically acceptable salts thereof, in accordance with any one of embodiments 1 to 12, wherein $L^2$ is oxazolyl, imidazolyl, thiadiazolyl, pyrazinyl, pyridinyl, pyrimidinyl, or pyridazinyl, each of which is substituted by 0, 1, 2 or 3 $R^e$ groups selected from F, Cl, Br, $C_{1-6}$alk, $C_{1-4}$haloalk, or —$OR^a$.

In embodiment 14, the present invention provides compounds, or pharmaceutically acceptable salts thereof, in accordance with any one of embodiments 1 to 13 wherein $L^2$ is selected from:

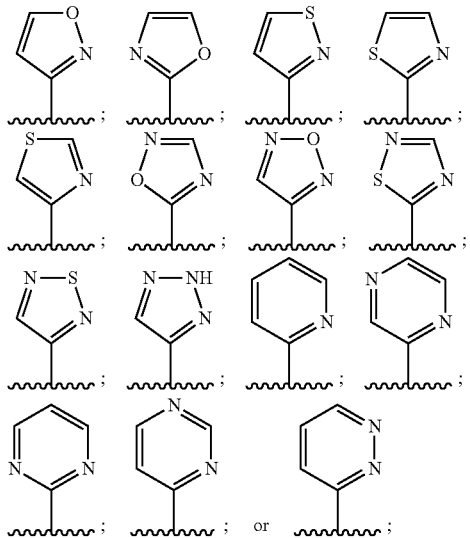

each of which is substituted by 0, 1, 2 or 3 $R^e$ groups selected from F, Cl, Br, $C_{1-6}$alk, $C_{1-14}$haloalk, or —O—$C_{1-6}$alk.

In embodiment 15, the present invention provides compounds, or pharmaceutically acceptable salts thereof, in accordance with any one of embodiments 1 to 14, wherein $L^1$ is saturated 3-, 4-, 5-, or 6-membered monocyclic ring containing 0, 1, 2 or 3 N atoms, or unsaturated 5- or 6-membered monocyclic ring containing 0, 1, 2 or 3 N atoms.

In embodiment 16, the present invention provides compounds, or pharmaceutically acceptable salts thereof, in accordance with any one of embodiments 1 to 15, wherein $L^1$ is cyclopropyl, —C≡C-cyclopentyl, phenyl, or pyridinyl ring.

In embodiment 17, the present invention provides compounds, or pharmaceutically acceptable salts thereof, in accordance with any one of embodiments 1 to 16, wherein $R^9$ is H, halo, $C_{1-8}$alk, or $C_{1-4}$haloalk. In a sub embodiment, $R^9$ is H, F, Cl, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, hexadecyl, isopropyl, isobutyl, sec-butyl, tert-butyl, neopentyl, vinyl, or allyl.

In embodiment 18, the present invention provides compounds, or pharmaceutically acceptable salts thereof, in accordance with any one of embodiments 1 to 16, wherein $L^1$ is phenyl ring having the formula:

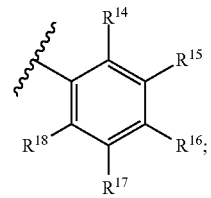

wherein:
$R^{14}$ is H, halo, $C_{1-8}$alk, $C_{1-4}$haloalk, —$OR^a$ or —$OR^c$;
$R^{15}$ is H, halo, $C_{1-8}$alk, $C_{1-4}$haloalk, —$OR^a$ or —$OR^c$;
$R^{16}$ is H, halo, $C_{1-8}$alk, $C_{1-4}$haloalk, —$OR^a$ or —$OR^c$;
$R^{17}$ is H, halo, $C_{1-8}$alk, $C_{1-4}$haloalk, —$OR^a$ or —$OR^c$; and
$R^{18}$ is H, halo, $C_{1-8}$alk, $C_{1-4}$haloalk, —$OR^a$ or —$OR^c$.

In embodiment 19, the present invention provides compounds, or pharmaceutically acceptable salts thereof, in accordance with any one of embodiments 1-5, and 7-17, wherein each of $X^1$, $X^2$, $X^4$, $X^6$, and $X^9$ are CH;
$X^3$ is N;
$X^5$ is —C(OCH$_3$);
$X^7$ is CH, CF, CCl, or C-methyl;
$X^8$ is C$L^1$, wherein $L^1$ is phenyl or pyridinyl ring, each of which is substituted by 0, 1, 2 or 3 $R^d$ groups selected from F, Cl, Br, $C_{1-6}$alk, $C_{1-4}$haloalk, or —$OR^a$;
$R^1$ is —N-$L^2$, wherein $L^2$ is unsaturated 5- or 6-membered monocyclic ring containing 0, 1, 2 or 3 N atoms, each of which is substituted by 0, 1, 2 or 3 $R^e$ groups selected from F, Cl, Br, $C_{1-6}$alk, $C_{1-4}$haloalk, or —$OR^a$; and
$R^2$ is NH$_2$, NH(CH$_3$), NH(OCH$_3$), or —OCH$_3$.

In embodiment 20, the present invention provides compounds, or pharmaceutically acceptable salts thereof, in accordance with any one of embodiments 1-4, and 6-17, wherein each of $X^1$, $X^2$, $X^4$, $X^6$, and $X^9$ are CH;
$X^3$ is N;
$X^5$ is —C(OCH$_3$);
$X^7$ is C$L^1$, wherein $L^1$ is cyclopropyl, —C≡C-cyclopentyl, phenyl or pyridinyl ring, each of which is substituted by 0, 1, 2 or 3 $R^d$ groups selected from F, Cl, Br, $C_{1-6}$alk, $C_{1-4}$haloalk, or —$OR^a$;
$X^8$ is CH, CF, CCl, or C-methyl;
$R^1$ is —N-$L^2$, wherein $L^2$ is unsaturated 5- or 6-membered monocyclic ring containing 0, 1, 2 or 3 N atoms, each of which is substituted by 0, 1, 2 or 3 $R^e$ groups selected from F, Cl, Br, $C_{1-6}$alk, $C_{1-4}$haloalk, or —$OR^a$; and $R^2$ is NH$_2$, NH(CH$_3$), NH(OCH$_3$), or —OCH$_3$.

In embodiment 21, the present invention provides compounds of Formula I, or pharmaceutically acceptable salts thereof, in accordance with any one of embodiments 1 to 19, selected from (Ex. stands for Example no.):

| Ex. | Name |
|---|---|
| 1-1 | 6-((4'-chloro-2-fluoro-5-methoxy-3'-methyl-4-biphenylyl)(methylcarbamoyl)amino)-N-3-isoxazolyl-3-pyridinesulfonamide |
| 1-2 | 6-((4'-chloro-2-fluoro-5-methoxy-3'-methyl-4-biphenylyl)(methylcarbamoyl)amino)-N-3-pyridazinyl-3-pyridinesulfonamide |

| Ex. | Name |
|---|---|
| 1-3 | 6-((2-fluoro-5-methoxy-3'-(trifluoromethyl)-4-biphenylyl)(methylcarbamoyl)amino)-N-3-pyridazinyl-3-pyridinesulfonamide |
| 1-4 | 6-((2-fluoro-5-methoxy-3'-(trifluoromethyl)-4-biphenylyl)(methylcarbamoyl)amino)-N-3-isoxazolyl-3-pyridinesulfonamide |
| 1-5 | 6-((3'-chloro-2,5'-difluoro-5-methoxy-4-biphenylyl)(methylcarbamoyl)amino)-N-3-isoxazolyl-3-pyridinesulfonamide |
| 1-6 | 6-((3'-chloro-2-fluoro-5,5'-dimethoxy-4-biphenylyl)(methylcarbamoyl)amino)-N-3-isoxazolyl-3-pyridinesulfonamide |
| 1-7 | 6-((2-fluoro-3',5-dimethoxy-5'-(trifluoromethoxy)-4-biphenylyl)(methylcarbamoyl)amino)-N-3-isoxazolyl-3-pyridinesulfonamide |
| 1-8 | 6-((2-fluoro-3',5-dimethoxy-4-biphenylyl)(methylcarbamoyl)amino)-N-3-isoxazolyl-3-pyridinesulfonamide |
| 1-9 | 6-((2-fluoro-3',5-dimethoxy-5'-(trifluoromethyl)-4-biphenylyl)(methylcarbamoyl)amino)-N-3-isoxazolyl-3-pyridinesulfonamide |
| 1-10 | 6-((3',4'-dichloro-2-fluoro-5-methoxy-4-biphenylyl)(methylcarbamoyl)amino)-N-3-isoxazolyl-3-pyridinesulfonamide |
| 1-11 | 6-((4'-chloro-2-fluoro-5-methoxy-3'-(trifluoromethyl)-4-biphenylyl)(methylcarbamoyl)amino)-N-3-isoxazolyl-3-pyridinesulfonamide |
| 1-12 | 6-((2-fluoro-5-methoxy-3'-(2,2,2-trifluoroethoxy)-4-biphenylyl)(methylcarbamoyl)amino)-N-3-isoxazolyl-3-pyridinesulfonamide |
| 1-13 | 6-((3'-cyclopropyl-2-fluoro-5-methoxy-4-biphenylyl)(methylcarbamoyl)amino)-N-3-isoxazolyl-3-pyridinesulfonamide |
| 1-14 | 6-((2-fluoro-5-methoxy-3'-(trifluoromethoxy)-4-biphenylyl)(methylcarbamoyl)amino)-N-3-isoxazolyl-3-pyridinesulfonamide |
| 1-15 | 6-((2,3'-difluoro-5-methoxy-4'-methyl-4-biphenylyl)(methylcarbamoyl)amino)-N-3-isoxazolyl-3-pyridinesulfonamide |
| 1-16 | 6-((2,4'-difluoro-5-methoxy-3'-methyl-4-biphenylyl)(methylcarbamoyl)amino)-N-3-isoxazolyl-3-pyridinesulfonamide |
| 1-17 | 6-((3'-chloro-2-fluoro-5-methoxy-4'-methyl-4-biphenylyl)(methylcarbamoyl)amino)-N-3-isoxazolyl-3-pyridinesulfonamide |
| 1-18 | 6-((2,3'-difluoro-5-methoxy-5'-methyl-4-biphenylyl)(methylcarbamoyl)amino)-N-3-isoxazolyl-3-pyridinesulfonamide |
| 1-19 | 6-((3'-chloro-2-fluoro-5-methoxy-5'-methyl-4-biphenylyl)(methylcarbamoyl)amino)-N-3-isoxazolyl-3-pyridinesulfonamide |
| 1-20 | 6-((4'-chloro-2,3'-difluoro-5-methoxy-4-biphenylyl)(methylcarbamoyl)amino)-N-3-isoxazolyl-3-pyridinesulfonamide |
| 1-21 | 6-((3'-chloro-2,4'-difluoro-5-methoxy-4-biphenylyl)(methylcarbamoyl)amino)-N-3-isoxazolyl-3-pyridinesulfonamide |
| 1-22 | N-3-isoxazolyl-6-((methylcarbamoyl)(2,3',4'-trifluoro-5-methoxy-4-biphenylyl)amino)-3-pyridinesulfonamide |
| 1-23 | 6-((2,4'-difluoro-3',5,5'-trimethoxy-4-biphenylyl)(methylcarbamoyl)amino)-N-3-isoxazolyl-3-pyridinesulfonamide |
| 1-24 | N-3-isoxazolyl-6-((methylcarbamoyl)(2,3',4',5'-tetrafluoro-5-methoxy-4-biphenylyl)amino)-3-pyridinesulfonamide |
| 1-25 | 6-((3'-chloro-2,4'-difluoro-5,5'-dimethoxy-4-biphenylyl)(methylcarbamoyl)amino)-N-3-isoxazolyl-3-pyridinesulfonamide |
| 1-26 | 6-((2,4'-difluoro-5-methoxy-3'-(trifluoromethyl)-4-biphenylyl)(methylcarbamoyl)amino)-N-3-isoxazolyl-3-pyridinesulfonamide |
| 1-27 | 6-((2,4'-difluoro-5-methoxy-3'-(trifluoromethoxy)-4-biphenylyl)(methylcarbamoyl)amino)-N-3-isoxazolyl-3-pyridinesulfonamide |
| 1-28 | 6-((2-chloro-4'-fluoro-5-methoxy-3'-methyl-4-biphenylyl)(methylcarbamoyl)amino)-N-3-isoxazolyl-3-pyridinesulfonamide |
| 1-29 | 6-((2,4'-dichloro-5-methoxy-3'-methyl-4-biphenylyl)(methylcarbamoyl)amino)-N-3-isoxazolyl-3-pyridinesulfonamide |
| 1-30 | 6-((2,3'-dichloro-5'-fluoro-5-methoxy-4-biphenylyl)(methylcarbamoyl)amino)-N-3-isoxazolyl-3-pyridinesulfonamide |
| 1-31 | 6-((2-chloro-5-methoxy-3'-(trifluoromethyl)-4-biphenylyl)(methylcarbamoyl)amino)-N-3-isoxazolyl-3-pyridinesulfonamide |
| 1-32 | 6-((2,3'-dichloro-5,5'-dimethoxy-4-biphenylyl)(methylcarbamoyl)amino)-N-3-isoxazolyl-3-pyridinesulfonamide |
| 1-33 | 6-((2,4'-dichloro-3',5-dimethoxy-4-biphenylyl)(methylcarbamoyl)amino)-N-3-isoxazolyl-3-pyridinesulfonamide |
| 1-34 | 6-((2,5'-dichloro-5-methoxy-2'-methyl-4-biphenylyl)(methylcarbamoyl)amino)-N-3-isoxazolyl-3-pyridinesulfonamide |
| 1-35 | 6-((4'-chloro-2-fluoro-3',5-dimethoxy-4-biphenylyl)(methylcarbamoyl)amino)-N-3-isoxazolyl-3-pyridinesulfonamide |
| 1-36 | 6-((2-chloro-3',5-dimethoxy-5'-(trifluoromethyl)-4-biphenylyl)(methylcarbamoyl)amino)-N-3-isoxazolyl-3-pyridinesulfonamide |
| 1-37 | 6-((2-chloro-5-methoxy-3'-(2,2,2-trifluoroethoxy)-4-biphenylyl)(methylcarbamoyl)amino)-N-3-isoxazolyl-3-pyridinesulfonamide |
| 1-38 | 6-((2-chloro-3'-cyclopropyl-5-methoxy-4-biphenylyl)(methylcarbamoyl)amino)-N-3-isoxazolyl-3-pyridinesulfonamide |
| 1-39 | 6-((2-chloro-5-methoxy-3'-(trifluoromethoxy)-4-biphenylyl)(methylcarbamoyl)amino)-N-3-isoxazolyl-3-pyridinesulfonamide |
| 1-40 | 6-((5-chloro-2-methoxy-4-(2-methoxy-5-(trifluoromethyl)-3-pyridinyl)phenyl)(methylcarbamoyl)amino)-N-3-isoxazolyl-3-pyridinesulfonamide |
| 1-41 | 6-((5-chloro-4-(5-chloro-2-methoxy-3-pyridinyl)-2-methoxyphenyl)(methylcarbamoyl)amino)-N-3-isoxazolyl-3-pyridinesulfonamide |
| 1-42 | 6-((5-chloro-2-methoxy-4-(2-methoxy-6-((trifluoromethyl)-4-pyridinyl)phenyl)(methylcarbamoyl)amino)-N-3-isoxazolyl-3-pyridinesulfonamide |
| 1-43 | 6-((5-chloro-2-methoxy-4-(2-(trifluoromethyl)-4-pyridinyl)phenyl)(methylcarbamoyl)amino)-N-3-isoxazolyl-3-pyridinesulfonamide |
| 1-44 | 6-((2-chloro-4'-fluoro-5-methoxy-4-biphenylyl)(methylcarbamoyl)amino)-N-3-isoxazolyl-3-pyridinesulfonamide |
| 1-45 | 6-((2-chloro-5-methoxy-4'-(trifluoromethyl)-4-biphenylyl)(methylcarbamoyl)amino)-N-3-isoxazolyl-3-pyridinesulfonamide |
| 1-46 | 6-((2-chloro-3',5-dimethoxy-4'-(trifluoromethyl)-4-biphenylyl)(methylcarbamoyl)amino)-N-3-isoxazolyl-3-pyridinesulfonamide |
| 1-47 | 6-((2-chloro-3'-(difluoromethoxy)-5-methoxy-4-biphenylyl)(methylcarbamoyl)amino)-N-3-isoxazolyl-3-pyridinesulfonamide |
| 1-48 | 6-((2-chloro-5-methoxy-3'-(1-methylethoxy)-4-biphenylyl)(methylcarbamoyl)amino)-N-3-isoxazolyl-3-pyridinesulfonamide |
| 1-49 | 6-((2-chloro-3'-fluoro-5-methoxy-5'-(trifluoromethyl)-4-biphenylyl)(methylcarbamoyl)amino)-N-3-isoxazolyl-3-pyridinesulfonamide |
| 1-50 | 6-((2-chloro-4'-fluoro-3',5-dimethoxy-5'-methyl-4-biphenylyl)(methylcarbamoyl)amino)-N-3-isoxazolyl-3-pyridinesulfonamide |
| 1-51 | 6-((2-chloro-3',5-dimethoxy-5'-(trifluoromethoxy)-4-biphenylyl)(methylcarbamoyl)amino)-N-3-isoxazolyl-3-pyridinesulfonamide |
| 1-52 | 6-((2-chloro-3',4',5'-trifluoro-5-methoxy-4-biphenylyl)(methylcarbamoyl)amino)-N-3-isoxazolyl-3-pyridinesulfonamide |
| 1-53 | 6-((2,3'-dichloro-5'-cyano-5-methoxy-4-biphenylyl)(methylcarbamoyl)amino)-N-3-isoxazolyl-3-pyridinesulfonamide |

| Ex. | Name |
|---|---|
| 1-54 | 6-((2,4'-dichloro-3'-cyano-5-methoxy-4-biphenylyl)(methylcarbamoyl)amino)-N-3-isoxazolyl-3-pyridinesulfonamide |
| 1-55 | 6-((2-chloro-2'-fluoro-5-methoxy-5'-(trifluoromethyl)-4-biphenylyl)(methylcarbamoyl)amino)-N-3-isoxazolyl-3-pyridinesulfonamide |
| 1-56 | 6-((2-chloro-2',5-dimethoxy-5'-(trifluoromethyl)-4-biphenylyl)(methylcarbamoyl)amino)-N-3-isoxazolyl-3-pyridinesulfonamide |
| 1-57 | 6-((2-chloro-4'-fluoro-5-methoxy-3'-(2,2,2-trifluoroethoxy)-4-biphenylyl)(methylcarbamoyl)amino)-N-3-isoxazolyl-3-pyridinesulfonamide |
| 1-58 | 6-((2-chloro-4'-fluoro-5-methoxy-3'-(trifluoromethyl)-4-biphenylyl)(methylcarbamoyl)amino)-N-3-isoxazolyl-3-pyridinesulfonamide |
| 1-59 | 6-((5-chloro-4-cyclopropyl-2-methoxyphenyl)(methylcarbamoyl)amino)-N-3-isoxazolyl-3-pyridinesulfonamide |
| 1-60 | 6-((2,3'-dichloro-4'-fluoro-5-methoxy-4-biphenylyl)(methylcarbamoyl)amino)-N-3-isoxazolyl-3-pyridinesulfonamide |
| 1-61 | 6-((2,3'-dichloro-5-methoxy-4'-methyl-4-biphenylyl)(methylcarbamoyl)amino)-N-3-isoxazolyl-3-pyridinesulfonamide |
| 1-62 | 6-((2-chloro-3'-fluoro-5-methoxy-4'-methyl-4-biphenylyl)(methylcarbamoyl)amino)-N-3-isoxazolyl-3-pyridinesulfonamide |
| 1-63 | 6-((2,4'-dichloro-3'-fluoro-5-methoxy-4-biphenylyl)(methylcarbamoyl)amino)-N-3-isoxazolyl-3-pyridinesulfonamide |
| 1-64 | 6-((2-chloro-3',5,5'-trimethoxy-4-biphenylyl)(methylcarbamoyl)amino)-N-3-isoxazolyl-3-pyridinesulfonamide |
| 1-65 | 6-((2-chloro-3',4'-difluoro-5-methoxy-4-biphenylyl)(methylcarbamoyl)amino)-N-3-isoxazolyl-3-pyridinesulfonamide |
| 1-66 | 6-((2-chloro-4'-fluoro-3',5,5'-trimethoxy-4-biphenylyl)(methylcarbamoyl)amino)-N-3-isoxazolyl-3-pyridinesulfonamide |
| 1-67 | 6-((2-chloro-3'-ethoxy-4'-fluoro-5-methoxy-4-biphenylyl)(methylcarbamoyl)amino)-N-3-isoxazolyl-3-pyridinesulfonamide |
| 1-68 | 6-((2-chloro-3',4'-difluoro-5,5'-dimethoxy-4-biphenylyl)(methylcarbamoyl)amino)-N-3-isoxazolyl-3-pyridinesulfonamide |
| 1-69 | 6-((2-chloro-4'-fluoro-5-methoxy-3'-(trifluoromethoxy)-4-biphenylyl)(methylcarbamoyl)amino)-N-3-isoxazolyl-3-pyridinesulfonamide |
| 1-70 | 6-((2,4'-dichloro-5-methoxy-4-biphenylyl)(methylcarbamoyl)amino)-N-3-isoxazolyl-3-pyridinesulfonamide |
| 1-71 | 6-((4'-fluoro-3-methoxy-3'-methyl-4-biphenylyl)(methylcarbamoyl)amino)-N-3-isoxazolyl-3-pyridinesulfonamide |
| 1-72 | 6-((3'-chloro-3,5'-dimethoxy-4-biphenylyl)(methylcarbamoyl)amino)-N-3-isoxazolyl-3-pyridinesulfonamide |
| 1-73 | 6-((4'-chloro-3-methoxy-3'-methyl-4-biphenylyl)(methylcarbamoyl)amino)-N-3-isoxazolyl-3-pyridinesulfonamide |
| 1-74 | 6-((3'-chloro-5'-fluoro-3-methoxy-4-biphenylyl)(methylcarbamoyl)amino)-N-3-isoxazolyl-3-pyridinesulfonamide |
| 1-75 | 6-((2,4'-dichloro-3'-cyano-5-methoxy-4-biphenylyl)(methylcarbamoyl)amino)-N-2-pyrimidinyl-3-pyridinesulfonamide |
| 1-76 | 6-((2-chloro-3',4'-difluoro-5-methoxy-4-biphenylyl)(methylcarbamoyl)amino)-N-2-pyrimidinyl-3-pyridinesulfonamide |
| 1-77 | 6-((2,4'-dichloro-3',5-dimethoxy-4-biphenylyl)(methylcarbamoyl)amino)-N-2-pyrimidinyl-3-pyridinesulfonamide |
| 1-78 | 6-((2,3'-dichloro-5'-cyano-5-methoxy-4-biphenylyl)(methylcarbamoyl)amino)-N-2-pyrimidinyl-3-pyridinesulfonamide |
| 1-79 | 6-((2-chloro-3',5,5'-trimethoxy-4-biphenylyl)(methylcarbamoyl)amino)-N-2-pyrimidinyl-3-pyridinesulfonamide |
| 1-80 | 6-((4'-chloro-2-fluoro-5-methoxy-3'-methyl-4-biphenylyl)(methylcarbamoyl)amino)-N-2-pyrimidinyl-3-pyridinesulfonamide |
| 1-81 | 6-((2-fluoro-5-methoxy-3'-(trifluoromethyl)-4-biphenylyl)(methylcarbamoyl)amino)-N-2-pyrimidinyl-3-pyridinesulfonamide |
| 1-82 | 6-((2-fluoro-3',5-dimethoxy-5'-(trifluoromethyl)-4-biphenylyl)(methylcarbamoyl)amino)-N-2-pyrimidinyl-3-pyridinesulfonamide |
| 1-83 | 6-((3',4'-dichloro-2-fluoro-5-methoxy-4-biphenylyl)(methylcarbamoyl)amino)-N-2-pyrimidinyl-3-pyridinesulfonamide |
| 1-84 | 6-((2-fluoro-5-methoxy-3'-(trifluoromethoxy)-4-biphenylyl)(methylcarbamoyl)amino)-N-2-pyrimidinyl-3-pyridinesulfonamide |
| 1-85 | 6-((2,4'-difluoro-5-methoxy-3'-(trifluoromethyl)-4-biphenylyl)(methylcarbamoyl)amino)-N-2-pyrimidinyl-3-pyridinesulfonamide |
| 1-86 | 6-((methylcarbamoyl)(2,3',4',5'-tetrafluoro-5-methoxy-4-biphenylyl)amino)-N-2-pyrimidinyl-3-pyridinesulfonamide |
| 1-87 | 6-((2,4'-difluoro-5-methoxy-3'-(trifluoromethoxy)-4-biphenylyl)(methylcarbamoyl)amino)-N-2-pyrimidinyl-3-pyridinesulfonamide |
| 1-88 | 6-((2,4'-difluoro-5-methoxy-3'-(2,2,2-trifluoroethoxy)-4-biphenylyl)(methylcarbamoyl)amino)-N-2-pyrimidinyl-3-pyridinesulfonamide |
| 1-89 | 6-((4'-chloro-2-fluoro-5-methoxy-3'-(trifluoromethyl)-4-biphenylyl)(methylcarbamoyl)amino)-N-2-pyrimidinyl-3-pyridinesulfonamide |
| 1-90 | 6-((2-fluoro-5-methoxy-3'-(trifluoromethyl)-4-biphenylyl)(methoxycarbamoyl)amino)-N-3-isoxazolyl-3-pyridinesulfonamide |
| 2-1 | 6-((3'-(difluoromethyl)-2,4'-difluoro-5-methoxy-4-biphenylyl)(methylcarbamoyl)amino)-N-2-pyrimidinyl-3-pyridinesulfonamide |
| 2-2 | 6-((3'-chloro-2,4'-difluoro-5-methoxy-4-biphenylyl)(methylcarbamoyl)amino)-N-2-pyrimidinyl-3-pyridinesulfonamide |
| 2-3 | 6-((3'-(difluoromethyl)-2,4',5'-trifluoro-5-methoxy-4-biphenylyl)(methylcarbamoyl)amino)-N-2-pyrimidinyl-3-pyridinesulfonamide |
| 2-4 | 6-((2-chloro-4'-fluoro-5-methoxy-3'-(2,2,2-trifluoroethoxy)-4-biphenylyl)(methylcarbamoyl)amino)-N-3-pyridazinyl-3-pyridinesulfonamide |
| 2-5 | 6-((2-chloro-3',4',5'-trifluoro-5-methoxy-4-biphenylyl)(methylcarbamoyl)amino)-N-3-pyridazinyl-3-pyridinesulfonamide |
| 2-6 | 6-((5-chloro-2-methoxy-4-(2-methoxy-6-((trifluoromethyl)-4-pyridinyl)phenyl)(methylcarbamoyl)amino)-N-3-pyridazinyl-3-pyridinesulfonamide |
| 2-7 | 6-((4'-fluoro-3-methoxy-3'-(trifluoromethoxy)-4-biphenylyl)(methylcarbamoyl)amino)-N-2-pyrimidinyl-3-pyridinesulfonamide |
| 2-8 | 6-((4'-fluoro-3-methoxy-3'-(trifluoromethyl)-4-biphenylyl)(methylcarbamoyl)amino)-N-2-pyrimidinyl-3-pyridinesulfonamide |
| 2-9 | 6-((3'-(difluoromethyl)-4'-fluoro-3-methoxy-4-biphenylyl)(methylcarbamoyl)amino)-N-2-pyrimidinyl-3-pyridinesulfonamide |
| 2-10 | 6-((2-chloro-4'-fluoro-5-methoxy-3'-(trifluoromethoxy)-4-biphenylyl)(methylcarbamoyl)amino)-N-2-pyrimidinyl-3-pyridinesulfonamide |
| 2-11 | 6-((1-(5-Fluoro-2-methoxy-4-tetradecylphenyl)-3-methylureido)-N-(pyrimidin-2-yl)pyridine-3-sulfonamide |
| 2-12 | 6-((1-(2,4'-difluoro-5-methoxy-3'-(trifluoromethoxy)-[1,1'-biphenyl]-4-yl)-3-methylureido)-N-(4-methylisoxazol-3-yl)pyridine-3-sulfonamide |
| 2-13 | 6-((1-(2,4'-difluoro-5-methoxy-3'-(trifluoromethyl)-[1,1'-biphenyl]-4-yl)-3-methylureido)-N-(4-methylisoxazol-3-yl)pyridine-3-sulfonamide |
| 2-14 | 6-((1-(2,4'-difluoro-5-methoxy-3'-(2,2,2-trifluoroethoxy)-[1,1'-biphenyl]-4-yl)-3-methylureido)-N-(4-methylisoxazol-3-yl)pyridine-3-sulfonamide |
| 3-1 | 6-((2-chloro-4'-fluoro-5-methoxy-3'-(2,2,2-trifluoroethoxy)-4-biphenylyl)(methylcarbamoyl)amino)-N-2-pyrimidinyl-3-pyridinesulfonamide |

| Ex. | Name |
|---|---|
| 3-2 | 6-((2-chloro-4'-fluoro-5-methoxy-3'-(2,2,2-trifluoroethoxy)-4-biphenylyl)(methylcarbamoyl)amino)-N-1,2,5-thiadiazol-3-yl-3-pyridinesulfonamide |
| 3-3 | 6-((2-chloro-4'-fluoro-5-methoxy-3'-(2,2,2-trifluoroethoxy)-4-biphenylyl)(methylcarbamoyl)amino)-N-(6-fluoro-2-pyridinyl)-3-pyridinesulfonamide |
| 3-4 | 6-((2-chloro-4'-fluoro-5-methoxy-3'-(2,2,2-trifluoroethoxy)-4-biphenylyl)(methylcarbamoyl)amino)-N-1,3-oxazol-2-yl-3-pyridinesulfonamide |
| 3-5 | 6-((2-chloro-4'-fluoro-5-methoxy-3'-(2,2,2-trifluoroethoxy)-4-biphenylyl)(methylcarbamoyl)amino)-N-(2-methyl-4-pyrimidinyl)-3-pyridinesulfonamide |
| 3-6 | 6-((2-chloro-4'-fluoro-5-methoxy-3'-(2,2,2-trifluoroethoxy)-4-biphenylyl)(methylcarbamoyl)amino)-N-4-pyrimidinyl-3-pyridinesulfonamide |
| 3-7 | 6-((2-chloro-4'-fluoro-5-methoxy-3'-(trifluoromethyl)-4-biphenylyl)(methylcarbamoyl)amino)-N-2-pyrimidinyl-3-pyridinesulfonamide |
| 3-8 | 6-((2-chloro-4'-fluoro-5-methoxy-3'-(trifluoromethyl)-4-biphenylyl)(methylcarbamoyl)amino)-N-1,2,5-thiadiazol-3-yl-3-pyridinesulfonamide |
| 3-9 | 6-((2-chloro-4'-fluoro-5-methoxy-3'-(trifluoromethyl)-4-biphenylyl)(methylcarbamoyl)amino)-N-(6-fluoro-2-pyridinyl)-3-pyridinesulfonamide |
| 3-10 | 6-((2-chloro-4'-fluoro-5-methoxy-3'-(trifluoromethyl)-4-biphenylyl)(methylcarbamoyl)amino)-N-1,3-oxazol-2-yl-3-pyridinesulfonamide |
| 3-11 | 6-((2-chloro-4'-fluoro-5-methoxy-3'-(trifluoromethyl)-4-biphenylyl)(methylcarbamoyl)amino)-N-(2-methyl-4-pyrimidinyl)-3-pyridinesulfonamide |
| 3-12 | 6-((2-chloro-4'-fluoro-5-methoxy-3'-(trifluoromethyl)-4-biphenylyl)(methylcarbamoyl)amino)-N-4-pyrimidinyl-3-pyridinesulfonamide |
| 3-13 | 6-((2,4'-difluoro-5-methoxy-3'-(trifluoromethoxy)-4-biphenylyl)(methylcarbamoyl)amino)-N-3-pyridazinyl-3-pyridinesulfonamide |
| 3-14 | 6-((2,4'-difluoro-5-methoxy-3'-(trifluoromethoxy)-4-biphenylyl)(methylcarbamoyl)amino)-N-1,3-oxazol-2-yl-3-pyridinesulfonamide |
| 3-15 | 6-((2,4'-difluoro-5-methoxy-3'-(trifluoromethoxy)-4-biphenylyl)(methylcarbamoyl)amino)-N-4-pyrimidinyl-3-pyridinesulfonamide |
| 3-16 | 6-((2,4'-difluoro-5-methoxy-3'-(trifluoromethoxy)-4-biphenylyl)(methylcarbamoyl)amino)-N-(2-methyl-4-pyrimidinyl)-3-pyridinesulfonamide |
| 4.1 | 6-((3'-chloro-4,5'-dimethoxy-3-biphenylyl)(methylcarbamoyl)amino)-N-3-isoxazolyl-3-pyridinesulfonamide |
| 4.2 | N-3-isoxazolyl-6-((4-methoxy-3'-(trifluoromethyl)-3-biphenylyl)(methylcarbamoyl)amino)-3-pyridinesulfonamide |
| 4.3 | 6-((3'-fluoro-4-methoxy-3-biphenylyl)(methylcarbamoyl)amino)-N-3-isoxazolyl-3-pyridinesulfonamide |
| 4.4 | 6-((3'-chloro-5'-fluoro-4-methoxy-3-biphenylyl)(methylcarbamoyl)amino)-N-3-isoxazolyl-3-pyridinesulfonamide |
| 4.5 | 6-((3'-chloro-4-methoxy-4'-methyl-3-biphenylyl)(methylcarbamoyl)amino)-N-3-isoxazolyl-3-pyridinesulfonamide |
| 4.6 | 6-((6-chloro-4-methoxy-3'-(trifluoromethyl)-3-biphenylyl)(methylcarbamoyl)amino)-N-3-isoxazolyl-3-pyridinesulfonamide |
| 4.7 | 6-((6-chloro-3'-fluoro-4-methoxy-3-biphenylyl)(methylcarbamoyl)amino)-N-3-isoxazolyl-3-pyridinesulfonamide |
| 4.8 | 6-((3',6-dichloro-4,5'-dimethoxy-3-biphenylyl)(methylcarbamoyl)amino)-N-3-isoxazolyl-3-pyridinesulfonamide |
| 4.9 | 6-((3',6-dichloro-4-methoxy-4'-methyl-3-biphenylyl)(methylcarbamoyl)amino)-N-3-isoxazolyl-3-pyridinesulfonamide |
| 5.1 | 6-((1-(2-chloro-5-methoxy-3'-(trifluoromethyl)-[1,1'-biphenyl]-4-yl)ureido)-N-(isoxazol-3-yl)pyridine-3-sulfonamide |
| 5.2 | 6-((carbamoyl(2,4'-dichloro-3'-fluoro-5-methoxy-4-biphenylyl)amino)-N-3-isoxazolyl-3-pyridinesulfonamide |
| 5.3 | 6-((carbamoyl(2,3'-dichloro-5'-cyano-5-methoxy-4-biphenylyl)amino)-N-3-isoxazolyl-3-pyridinesulfonamide |
| 5.4 | 6-((carbamoyl(2-chloro-3',5-dimethoxy-5'-(trifluoromethyl)-4-biphenylyl)amino)-N-3-isoxazolyl-3-pyridinesulfonamide |
| 5.5 | 6-((carbamoyl(2-chloro-5-methoxy-3'-(2,2,2-trifluoroethoxy)-4-biphenylyl)amino)-N-3-isoxazolyl-3-pyridinesulfonamide |
| 6 | Methyl (2-chloro-5-methoxy-3'-(trifluoromethyl)-[1,1'-biphenyl]-4-yl)(5-(N-(isoxazol-3-yl)sulfamoyl)pyridine-2-yl)carbamate |
| 7 | 6-((5-chloro-4-(cyclopentylethynyl)-2-methoxyphenyl)(methylcarbamoyl)amino)-N-3-isoxazolyl-3-pyridinesulfonamide |
| 8 | 6-((5-fluoro-2-methoxy-4-(3,3,3-trifluoropropyl)phenyl)(methylcarbamoyl)amino)-N-3-isoxazolyl-3-pyridinesulfonamide |
| 9 | 4-(1-(4'-chloro-3-methoxy-3'-methyl-[1,1'-biphenyl]-4-yl)-3methylureido)-N-(isoxazol-3-yl)benzenesulfonamide |
| 10 | 4-(1-(2,4'-difluoro-5-methoxy-3'-(trifluoromethoxy)-[1,1'-biphenyl]-4-yl)-3-methylureido)-N-(isoxazol-3-yl)benzenesulfonamide |

In embodiment 22, the present invention provides compounds of Formula (I), or pharmaceutically acceptable salts thereof, selected from:

((2,4'-difluoro-5-methoxy-3'-(trifluoromethoxy)-4-biphenylyl)(methylcarbamoyl)amino)-N-2-pyrimidinyl-3-pyridinesulfonamide;

6-((4'-fluoro-3-methoxy-3'-(trifluoromethoxy)-4-biphenylyl)(methylcarbamoyl)amino)-N-2-pyrimidinyl-3-pyridinesulfonamide;

6-((2,4'-difluoro-5-methoxy-3'-(trifluoromethyl)-4-biphenylyl)(methylcarbamoyl)amino)-N-2-pyrimidinyl-3-pyridinesulfonamide;

6-((2-chloro-4'-fluoro-5-methoxy-3'-(trifluoromethyl)-4-biphenylyl)(methylcarbamoyl)amino)-N-2-pyrimidinyl-3-pyridinesulfonamide;

6-((2-chloro-4'-fluoro-5-methoxy-3'-(2,2,2-trifluoroethoxy)-4-biphenylyl)(methylcarbamoyl)amino)-N-2-pyrimidinyl-3-pyridinesulfonamide;

6-(1-(5-Fluoro-2-methoxy-4-tetradecylphenyl)-3-methylureido)-N-(pyrimidin-2-yl)pyridine-3-sulfonamide; or 6-(1-(5-Fluoro-2-methoxy-4-tetradecylphenyl)-3-methylureido)-N-(pyrimidin-2-yl)pyridine-3-sulfonamide.

In embodiment 23, the invention provides each individual compound, or a pharmaceutically acceptable salt thereof, or a sub-set of compounds, as described in the examples herein.

In embodiment 24, the present invention provides pharmaceutical compositions comprising a compound, or a pharmaceutically acceptable salt thereof, in accordance with any one of embodiments 1 to 23, or a pharmaceutically acceptable salt thereof, and a pharmaceutically acceptable excipient.

In embodiment 25, the present invention provides methods of treating pain, the methods comprising administering to a patient in need thereof a therapeutically effective amount of a compound, or a pharmaceutically acceptable salt thereof, in accordance with any one of embodiments 1 to 24, or a pharmaceutically acceptable salt thereof.

In embodiment 26, the present invention provides methods of embodiment 25 wherein the treatment is for chronic pain, acute pain, neuropathic pain, pain associated with rheumatoid arthritis, pain associated with osteoarthritis, pain associated with cancer or a cough selected from the group consisting of post viral cough, viral cough, and acute viral cough.

In embodiment 27, the present invention provides methods of treating cough, the methods comprising administering to a patient in need thereof a therapeutically effective amount of a compound, or a pharmaceutically acceptable salt thereof, in accordance with any one of embodiments 1 to 23, or a pharmaceutically acceptable salt thereof.

In embodiment 28, the present invention provides methods of embodiment 27 wherein the treatment is for post viral cough, viral cough, or acute viral cough.

In embodiment 29, the present invention provides methods of treating itch, the methods comprising administering to a patient in need thereof a therapeutically effective amount of a compound, or a pharmaceutically acceptable salt thereof, in accordance with any one of embodiments 1 to 23, or a pharmaceutically acceptable salt thereof.

In embodiment 30, the present invention provides methods of embodiment 29 wherein the treatment is for a) psoriatic pruritis, itch due to hemodyalisis, aguagenic pruritis, and itching caused by skin disorders, systemic disorders, neuropathy, psychogenic factors or a mixture thereof, b) itch caused by allergic reactions, insect bites, hypersensitivity, inflammatory conditions or injury, c) itch associated with vulvar vestibulitis, d) skin irritation or inflammatory effect from administration of another therapeutic selected from antibiotics, antivirals, or antihistamines, or e) itch due to activation of PAR-2 G-protein coupled receptors.

The term "$C_{\alpha-\beta}$alk" means an alkyl group comprising a minimum of $\alpha$ and a maximum of $\beta$ carbon atoms in a branched, cyclical or linear relationship or any combination of the three, wherein $\alpha$ and $\beta$ represent integers. The alkyl groups described in this section may also contain one or two double or triple bonds. A designation of $C_0$alk indicates a direct bond. Examples of $C_{1-6}$alkyl include, but are not limited to the following:

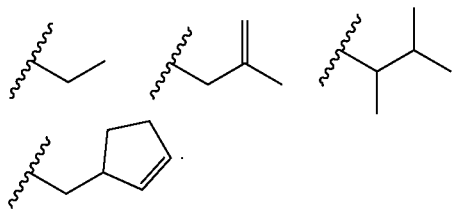

The term "Benzo group", alone or in combination, means the divalent radical $C_4H_4$=, one representation of which is —CH=CH—CH=CH—, that when vicinally attached to another ring forms a benzene-like ring, for example tetrahydronaphthylene, indole and the like.

The terms "oxo" and "thioxo" represent the groups =O (as in carbonyl) and =S (as in thiocarbonyl), respectively.

"Halo" or "halogen" means a halogen atoms selected from F, Cl, Br and I.

"$C_{\alpha-\beta}$haloalk" means an alk group, as described above, wherein any number—at least one—of the hydrogen atoms attached to the alk chain are replaced by F, Cl, Br or I.

The group N($R^a$)$R^a$ and the like include substituents where the two $R^a$ groups together form a ring, optionally including a N, O or S atom, and include groups such as:

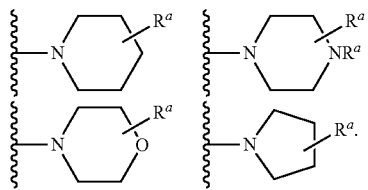

The group N($C_{\alpha-\beta}$alk) $C_{\alpha-\beta}$alk, wherein $\alpha$ and $\beta$ are as defined above, include substituents where the two $C_{\alpha-\beta}$alk groups together form a ring, optionally including a N, O or S atom, and include groups such as:

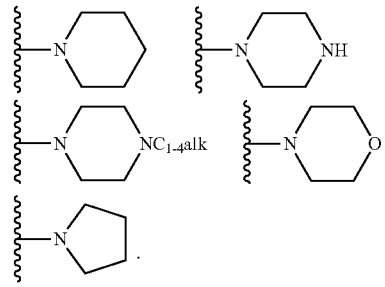

"Carbocycle" means a ring comprising by itself or in combination with other terms, represents, unless otherwise stated, cyclic version of "$C_{\alpha-\beta}$alk". Thus, the term "carbocycle" is meant to be included in the terms "$C_{\alpha-\beta}$alk". Examples of carbocycle include cyclopentyl, cyclohexyl, 1-cyclohexenyl, 3-cyclohexenyl, cycloheptyl, cyclobutylene, cyclohexylene and the like.

"Heterocycle" means a ring comprising at least one carbon atom and at least one other atom selected from N, O and S. Examples of heterocycles that may be found in the claims include, but are not limited to, the following:

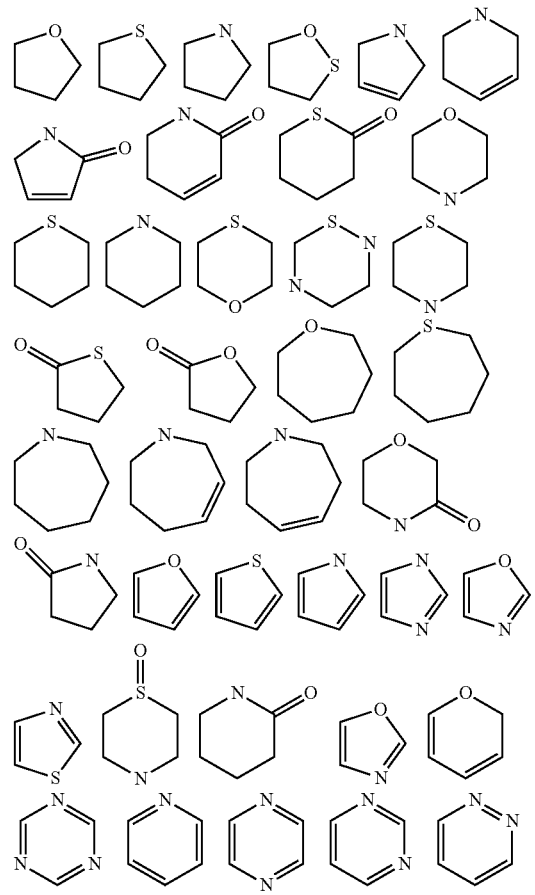

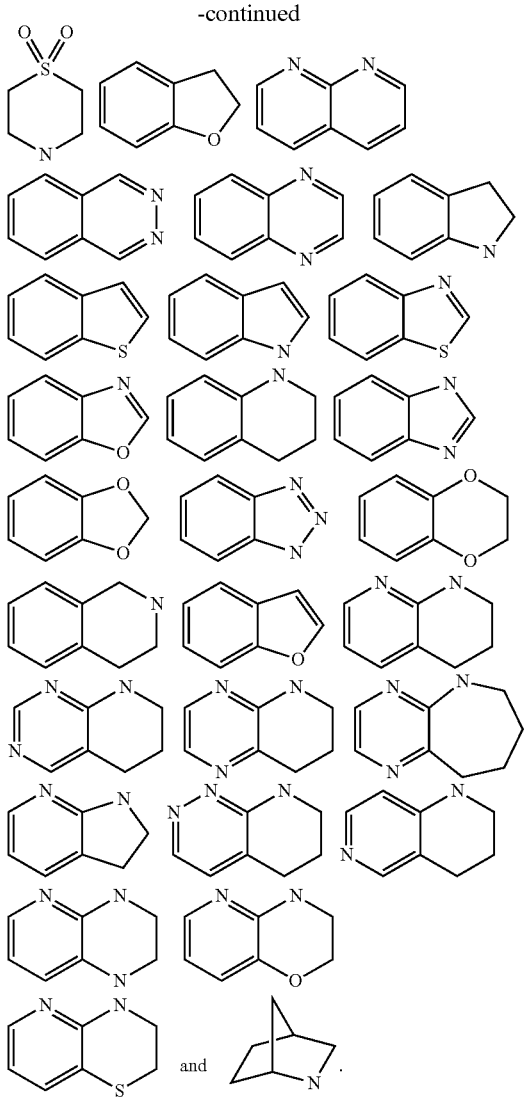

Representative examples of five to six membered unsaturated rings, optionally having one or two heteroatoms, are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl, and pyrazinyl.

Representative examples of partially saturated, fully saturated or fully unsaturated five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyndazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-(3 oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, optionally having one to four heteroatoms, are indolizinyl, indolyl, isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)pyridinyl, pyrido(3,2-b)pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "substituted" means that a hydrogen atom on a molecule or group is replaced with a group or atom. Typical substitutents include: halogen, $C_{1-8}$alkyl, hydroxyl, $C_{1-8}$alkoxy, —$NR^xR^x$, nitro, cyano, halo or perhalo$C_{1-8}$alkyl, $C_{2-8}$alkenyl, $C_{2-8}$alkynyl, —$SR^x$, —$S(=O)_2R^x$, —$C(=O)OR^x$, —$C(=O)R^x$, wherein each $R^x$ is independently hydrogen or $C_1$-$C_8$ alkyl. It is noted that when the substituent is —$NR^xR^x$, the $R^x$ groups may be joined together with the nitrogen atom to form a ring.

A group or atom that replaces a hydrogen atom is also called a substituent.

Any particular molecule or group can have one or more substituent depending on the number of hydrogen atoms that can be replaced.

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated, partially-saturated or unsaturated" includes substituents saturated with hydrogens, substituents completely unsaturated with hydrogens and substituents partially saturated with hydrogens.

The term "heteroatom" as used herein means an oxygen, nitrogen or sulfur atom.

The symbol "-" represents a covalent bond and can also be used in a radical group to indicate the point of attachment to another group. In chemical structures, the symbol is commonly used to represent a methyl group in a molecule The term "therapeutically effective amount" means an amount of a compound that ameliorates, attenuates or eliminates one or more symptom of a particular disease or condition, or prevents or delays the onset of one of more symptom of a particular disease or condition.

The term "patient" means animals, such as dogs, cats, cows, horses, sheep and humans. Particular patients are mammals. The term patient includes males and females.

The term "pharmaceutically acceptable" means that the referenced substance, such as a compound of the present invention or a formulation containing a compound of the present invention, or a particular excipient, are suitable for administration to a patient.

The terms "treating", "treat" or "treatment" and the like include preventative (e.g., prophylactic) and palliative treatment.

The term "patient in need thereof" means a patient who has or is at risk of having a disease and/or condition that can be treated by inhibition of Nav 1.7, such as chronic pain.

The term "excipient" means any pharmaceutically acceptable additive, carrier, diluent, adjuvant, or other ingredient, other than the active pharmaceutical ingredient (API), which is typically included for formulation and/or administration to a patient.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered by a tablet, while another is administered by injection or orally as a syrup. All combinations, delivery methods and administration sequences are contemplated.

The compounds of the present invention may be used in the manufacture of a medicament for the treatment of a disease and/or condition mediated by Nav 1.7, such as pain.

Pain is typically divided into primary types: chronic and acute pain based on the duration of the pain. Typically, chronic pain lasts for longer than 3 months. Examples of chronic pain include pain associated with rheumatoid arthritis, osteoarthritis, lumbosacral radiculopathy or cancer. Chronic pain also includes idiopathic pain, which is pain that has no identified cause. An example of idiopathic pain is fibromyalgia.

Another type of pain is nociceptive pain. Nociceptive pain is caused by stimulation of peripheral nerve fibers that respond to highly noxious events such as thermal, mechanical or chemical stimuli.

Still another type of pain is neuropathic pain. Neuropathic pain is pain that is caused by damage or disease affecting a part of the nervous system. Phantom limb pain is a type of neuropathic pain. In phantom limb pain, the body detects pain from a part of a body that no longer exists. For example, a person who has had a leg amputated may feel leg pain even though the leg no longer exists.

In one embodiment of the methods of treatment provided by the present invention using the compounds of Formula I, or pharmaceutically acceptable salts thereof, the disease is chronic pain. In another aspect, the chronic pain is associated with, but are not limited to, post-herpetic neuralgia (shingles), rheumatoid arthritis, osteoarthritis, diabetic neuropathy, complex regional pain syndrome (CRPS), cancer or chemotherapy-induced pain, chronic back pain, phantom limb pain, trigeminal neuralgia, HIV-induced neuropathy, cluster headache disorders, and migraine, primary erythromelalgia, and paroxysmal extreme pain disorder. Other indications for Nav 1.7 inhibitors include, but are not limited to, depression (Morinville et al., *J Comp Neurol.*, 504:680-689 (2007)), bipolar and other CNS disorders (Ettinger and Argoff, *Neurotherapeutics*, 4:75-83 (2007)), epilepsy: ibid., and Gonzalez, Termin, Wilson, *Methods and Principles in Medicinal Chemistry*, 29:168-192 (2006)), multiple sclerosis (Waxman, *Nature Neurosci.* 7:932-941 (2006)), Parkinson's (Do and Bean, *Neuron* 39:109-120 (2003); Puopolo et al., *J. Neurosci.* 27:645-656 (2007)), restless legs syndrome, ataxia, tremor, muscle weakness, dystonia, tetanus (Hamann M., et. al., *Exp. Neurol.* 184(2):830-838, 2003), anxiety, depression: McKinney B. C, et. al., *Genes Brain Behav.* 7(6):629-638, 2008), learning and memory, cognition (Woodruff-Pak D. S., et. al., *Behav. Neurosci.* 120(2):229-240, 2006), cardiac arrhythmia and fibrillation, contractility, congestive heart failure, sick sinus syndrome (Haufe V., et. al., *J Mol. Cell Cardiol.* 42(3):469-477, 2007), schizophrenia, neuroprotection after stroke, drug and alcohol abuse (Johannessen L. C., *CNS Drugs* 22(1)27-47, 2008), Alzheimer's (Kim D. Y., et. al., *Nat. Cell. Biol.* 9(7):755-764, 2007), and cancer (Gillet L., et. al., *J Biol Chem* 2009, January 28 (epub)).

Another aspect of the invention relates to a method of treating acute and/or chronic inflammatory and neuropathic pain, dental pain, general headache, migraine, cluster headache, mixed-vascular and non-vascular syndromes, tension headache, general inflammation, arthritis, rheumatic diseases, rheumatoid arthritis, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound according to the present invention. A preferred type of pain to be treated is chronic neuropathic pain.

Another preferred type of pain to be treated is chronic inflammatory pain. Yet another preferred type of pain to be treated is migraine.

In another aspect of the invention, the compounds of the present invention can be used in combination with other compounds that are used to treat pain. Examples of such other compounds include, but are not limited to aspirin, celecoxib, hydrocodone, oxycodone, codeine, fentanyl, ibuprofen, ketoprofen, naproxen, acetaminophen, gabapentin and pregabalin. Examples of classes of medicines that contain compounds that can be used in combination with the compounds of the present invention include non-steroidal anti-inflammatory compounds (NSAIDS), steroidal compounds, cycloxogenase inhibitors and opioid analgesics.

The compounds of the present invention may also be used to treat obesity and facilitate weight loss.

The compounds of the present invention may be used in combination with other pharmaceutically active compounds. It is noted that the term "pharmaceutically active compounds" can include biologics, such as proteins, antibodies and peptibodies.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed by said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or fit compounds are admixed under sterile condition with a physiologically acceptable carrier, and any preservatives, buffers, or propellants that may be required. Opthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

The compounds of the present invention can be administered as pharmaceutically acceptable salts, cocrystyals, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$-$C_{12}$) alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

In addition, if a compound of the present invention comprises a sulfonamide moiety, a prodrug can be formed by replacement of the sulfonamide N(H) with a group such as —CH$_2$P(O)(O($C_1$-$C_6$)alkyl)$_2$ or —CH$_2$OC(O)($C_1$-$C_6$)alkyl.

The compounds of the present invention also include tautomeric forms of prodrugs.

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as S and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diastereomeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls).

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. For example, all of the tautomeric forms of the tetrazole moiety are included in this invention. Also, for example, all keto-enol or imine-enamine forms of the compounds are included in this invention. Another example of tautomerism is as follows:

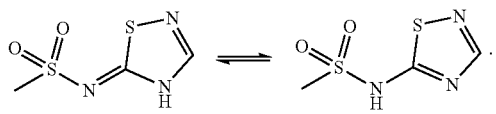

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{16}$O, $^{17}$O, $^{31}$P, $^{32}$P, $^{35}$S, $^8$F, and $^{36}$Cl. In another aspect, the compounds of the present invention contain one or more deuterium atoms (2H) in place of one or more hydrogen atoms.

Compounds of the present invention that contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

In synthesizing compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., SCH$_3$), N-hydroxysuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

All patents and other publications recited herein are hereby incorporated by reference in their entirety.

EXAMPLES

The examples presented below illustrate specific embodiments of the present invention. These examples are meant to be representative and are not intended to limit the scope of the claims in any manner.

It is noted that when a percent (%) is used with regard to a liquid, it is a percent by volume with respect to the solution. When used with a solid, it is the percent with regard to the solid composition. Materials obtained from commercial suppliers were typically used without further purification. Reactions involving air or moisture sensitive reagents were typically performed under a nitrogen or argon atmosphere. Purity was measured using high performance liquid chromatography (HPLC) system with UV detection at 254 nm and 215 nm (System A: Agilent Zorbax Eclipse XDB-C8 4.6×150 mm, 5 μm, 5 to 100% $CH_3CN$ in $H_2O$ with 0.1% TFA for 15 min at 1.5 mL/min; System B: Zorbax SB-C8, 4.6×75 mm, 10 to 90% $CH_3CN$ in $H_2O$ with 0.1% formic acid for 12 min at 1.0 mL/min) (Agilent Technologies, Santa Clara, Calif.). Silica gel chromatography was generally performed with prepacked silica gel cartridges (Biotage, Uppsala, Sweden or Teledyne-Isco, Lincoln, Nebr.). $^1H$ NMR spectra were recorded on a Bruker AV-400 (400 MHz) spectrometer (Bruker Corporation, Madison, Wis.) or a Varian (Agilent Technologies, Santa Clara, Calif.) 400 MHz spectrometer at ambient temperature. All observed protons are reported as parts per million (ppm) downfield from tetramethylsilane (TMS) or other internal reference in the appropriate solvent indicated. Data are reported as follows: chemical shift, multiplicity (s=singlet, d=doublet, t=triplet, q=quartet, br=broad, m=multiplet), coupling constants, and number of protons. Low-resolution mass spectral (MS) data were determined on an Agilent 1100 Series (Agilent Technologies, Santa Clara, Calif.) LC/MS with UV detection at 254 nm and 215 nm and a low resonance electrospray mode (ESI).

The following abbreviations may be used herein:

| | |
|---|---|
| AmPhos | 4-(di-tert-butylphosphino)-N,N-dimethylaniline |
| AcCl | acetyl chloride |
| ACN | Acetonitrile |
| AcOH | acetic acid |
| aq or aq. | Aqueous |
| BOC or Boc | tert-butyloxycarbonyl |
| CPhos | 2-Dicyclohexylphosphino-2',6'-bis(dimethylamino)-1,1'-biphenyl |
| DAST | diethylaminosulfur trifluoride |
| DCM | Dichloromethane |
| DMAP | 4-dimethylaminopyridine |
| DMB | Dimethoxybenzyl |
| DME | Dimethoxyethane |
| DMF | N,N-dimethylformamide |
| DMSO | dimethyl sulfoxide |
| Dppf, DPPF or dppf | 1,1'-bis(diphenylphosphino)ferrocene |
| ESI or ES | electrospray ionization |
| Et | Ethyl |
| $Et_2O$ | diethyl ether |
| TEA or $Et_3N$ | Trimethylamine |
| EtOAc | ethyl acetate |
| eq or eq. or equiv. | Equivalent |
| G | Grams |
| h or hr | Hour |
| HPLC | high pressure liquid chromatography |
| iPr | Isopropyl |
| $iPr_2Net$ or DIPEA | N-ethyl diisopropylamine (Hunig's base) |
| KOAc | potassium acetate |
| KHMDS | potasium hexamethyldisilazide |
| LC MS, LCMS, LC-MS or LC/MS | liquid chromatography mass spectroscopy |
| LHMDS or | lithium hexamethyldisilazide |
| m/z | mass divided by charge |
| Me | Methyl |
| MeOH | Methanol |
| MeCN or ACN | Acetonitrile |
| mg | Milligrams |
| min | Minutes |
| mL | Milliliters |
| MPLC | medium pressure liquid chromatography |
| MS | mass spectra |
| NaHMDS | sodium hexamethyldisilazide |
| NBS | N-bromosuccinimide |
| NCS | N-chlorosuccinimide |
| n-BuLi | n-butyllithium |

-continued

| | |
|---|---|
| NMI | 1-methylimidazole or N-methylimidazole |
| NMR | nuclear magnetic resonance |
| $Pd_2(dba)_3$ | tris(dibenzylideneacetone)dipalladium(0) |
| PFP | Pentafluorophenol |
| Ph | Phenyl |
| PMB | p-methoxybenzyl |
| PR or PG | protecting group |
| RBF | round-bottom flask |
| RP-HPLC | reverse phase high pressure liquid chromatography |
| RT or rt | room temperature |
| SCX | strong cation exchange |
| SEM | 2-(trimethylsilypethoxymethyl |
| SFC | supercritical fluid chromatography |
| TBAF | tetra-n-butylammonium fluoride |
| t-BuOH | tert-butanol |
| TIPS-Cl | triisopropylsilyl chloride |
| TFA | trifluoroacetic acid |
| THF | Tetrahydrofuran |
| UV | Ultraviolet |
| Xantphos | 4,5-bis(diphenylphosphino)-9,9-dimethylxanthene |
| X-Phos | 2-dicyclohexylphosphino-2',4',6'-triisopropyl-1,1'-biphenyl |

Unless otherwise stated, starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds of Formula (I) can generally be prepared as illustrated and described in Scheme A.

Scheme A

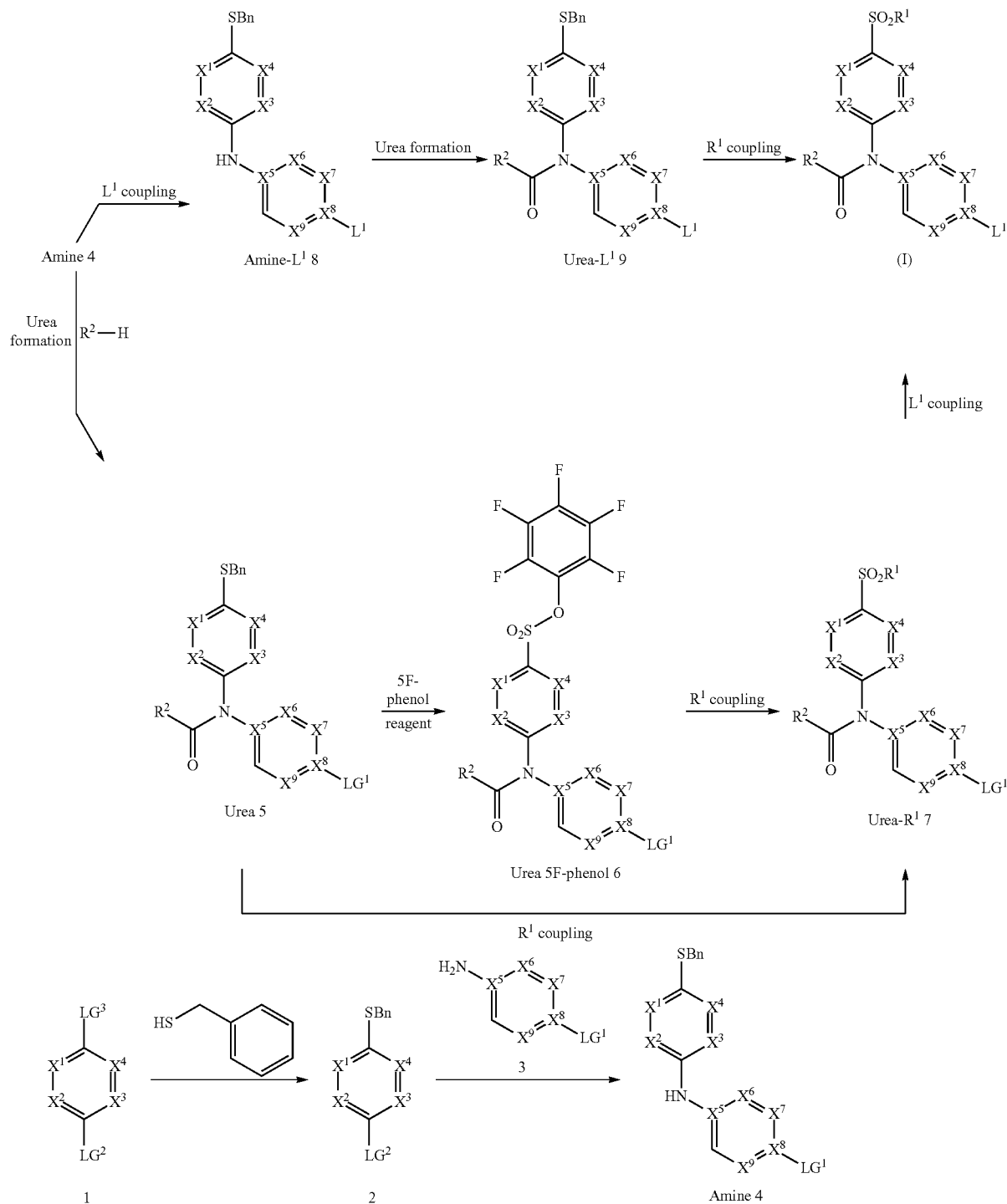

According to Scheme A, in one embodiment, Compound of Formula (I) can be prepared by Step (1) Urea Formation Step from Amine 4 to Urea 5, Step (2) Urea-5F-phenol Formation Step from Urea 5 to Urea-5F-phenol 6, Step (3) $R^1$ coupling Step from Urea-5F-phenol 6 to Urea-$R^1$ 7, followed by Step (4) $L^1$ coupling Step from Urea-$R^1$ 7 to form a Compound of Formula (I).—SBn is defined as —S-benzyl group.

Step 1: Urea Formation Step: Amine 4 to Urea 5.

In the Urea Formation Step, an amine starting material of formula 4, wherein $X^1$, $X^2$, $X^3$, $X^4$, $X^5$, $X^6$, $X^7$, $X^8$, and $X^9$ are as defined in the summary of the inventions, and $LG^1$ is a leaving group, such as halo, for example bromo or chloro, can be reacted with bis(trichloromethyl) carbonate, in an organic solvent, such as DCM and then treated with a compound of formula $R^2$—H in the presence of a base, such as triethyl amine. The solution can be cooled initially in an ice-water bath to maintain an internal temperature under 10° C., to form Urea 5.

Step 2: Urea-5F-Phenol Formation Step from Urea 5 to Urea-5F-Phenol 6.

In the Urea-5F-phenol Formation Step, Urea 5 can be reacted with 1,3-dichloro-5,5-dimethylimidazolidine-2,4-dione to form a sulfonyl chloride intermediate, followed by a 5F-phenol reagent, such as 2,3,4,5,6-pentafluorophenol, in the presence of a base, such as triethyl amine, in various solvents, such as acetonitrile, or DCM, in an ice-water bath to maintain an internal temperature under 10° C., to form Urea-5F-phenol compound 6.

Step 3: $R^1$ Coupling Step from Urea-5F-Phenol 6 to Urea-$R^1$ 7.

In the $R^1$ coupling Step, Urea-5F-phenol 6 can be reacted with an $R^1$ coupling agent, for example an $R^1$ containing amine compound, such as 2-aminopyrimidine or 3-aminoisoxazole, under a nitrogen atmosphere, in a solvent such as THF or THF/DMSO mixture, in an ice-water bath to maintain an internal temperature under 10° C., in the presence of a base, such as sodium tert-pentoxide, to form Urea-$R^1$ 7.

Alternatively, in another embodiment, Urea-$R^1$ 7 can be prepared directly from Urea 5 by reacting Urea 5 with 1,3-dichloro-5,5-dimethylimidazolidine-2,4-dione to form a sulfonyl chloride intermediate and then treated with an $R^1$ containing amine compound, such as 2-aminopyrimidine or 3-aminoisoxazole, under a nitrogen atmosphere, in a solvent such as DCM, or acetonitrile, in an ice-water bath to maintain initially an internal temperature under 10° C., in the presence of a base, such as pyridine, to form Urea-$R^1$ 7.

Step 4: $L^1$ Coupling Step from Urea-$R^1$ 7 to Form Compounds of Formula (I).

In the $L^1$ coupling Step, Urea-$R^1$ 7 can be reacted with an $L^1$ coupling agent, for example an $L^1$ containing boron compound, such as boronic acid or ester reagent of formula $(OH)_2$—B-$L^1$, or 2-(3-(difluoromethyl)-4-fluorophenyl)-4,4,5,5-tetramethyl-1,3,2-dioxaborolane, in a solvent such as a water/dioxane mixture or DMF, at an elevated temperature, such as 80° C.° C., in the presence of a base, such as sodium tert-pentoxide, and a catalyst, such as 1,1'-bis(diphenylphosphino)ferrocene palladium(II)dichloride dichloromethane adduct, to form a Compound of Formula (I).

According to Scheme A, in another embodiment, Compound of Formula (I) can be prepared by Step (1) $L^1$ coupling Step from Amine 4 to Amine-$L^1$ 8, Step (2) Urea Formation Step from Amine-$L^1$ 8 to Urea-$L^1$ 9, followed by Step (3) $R^1$ coupling Step from to Urea-$L^1$ 9 to form a Compound of Formula (I).

Step 1: $L^1$ Coupling Step from Amine 4 to Amine-$L^1$ 8.

In the $L^1$ coupling Step, an amine starting material of formula 4, wherein $X^1$, $X^2$, $X^3$, $X^4$, $X^5$, $X^6$, $X^7$, $X^8$, and $X^9$ are as defined in the summary of the inventions, and $LG^1$ is a leaving group, such as halo, for example bromo or chloro, can be reacted with an $L^1$ coupling agent, for example an $L^1$ containing boron compound, $L^1$ containing boron compound, such as boronic acid or ester reagent of formula $(OH)_2$—B-$L^1$, such as (3-(trifluoromethyl)phenyl)boronic acid, in a solvent such as a water/dioxane mixture, or DMF, at an elevated temperature, such as 80° C., in the presence of a base, such as potassium carbonate, and a catalyst, such as 1,1'-bis(diphenylphosphino)ferrocene palladium(II)dichloride dichloromethane adduct, to form Amine-$L^1$ 8.

Step 2: Urea Formation Step: Amine-$L^1$ 8 to Urea-$L^1$ 9.

In the Urea Formation Step, Amine-$L^1$ 8 can be reacted with bis(trichloromethyl) carbonate, in an organic solvent, such as a polar ethereal solvent, such as THF and then treated with a compound of formula $R^2$—H in the presence of a base, such as Hunig's base. The solution can be cooled in an ice-water bath to maintain an internal under 10° C. initially, to form Urea-$L^1$ 9.

Alternatively, in another embodiment, Amine-$L^1$ 8 can be reacted with trichloroacetyl isocyanate, in an organic solvent, such as acetonitrile, in the presence of a base, such as N-methylimidazole to form a trichloroacetyl urea intermediate and then treated with an alcoholic solvent such as methanol and a base such as triethyl amine. The solution can be cooled in an ice-water bath to maintain an internal temperature under 10° C. initially, to form Urea-$L^1$ 9

Step (3) $R^1$ Coupling Step from to Urea-$L^1$ 9 to Form a Compound of Formula (I).

In the $R^1$ coupling Step, Urea-$L^1$ 9 can be reacted with 1,3-dichloro-5,5-dimethylimidazolidine-2,4-dione to form a sulfonyl chloride intermediate and then treated with an $R^1$ coupling agent, for example an $R^1$ containing amine compound, such as 3-aminoisoxazole, under a nitrogen atmosphere, in a solvent such as DCM, in an ice-water bath to maintain an internal temperature under 10° C. initially, in the presence of a base, such as pyridine, to form a Compound of Formula (I).

Preparation of Amine 4:

According to Scheme A, in another embodiment, amine starting material of formula 4 can be prepared by Step (1) reacting compound 1, wherein each of $LG^2$ and $LG^3$ is a leaving group, such as halo, for example bromo or chloro, with benzylmercaptan, in the presence of a catalyst, such as tris(dibenzylideneacetone)dipalladium (0), a bidentate ligand, such as Xantphos, and a base, such as Hunig's base, in a organic solvent, such as 1,4-dioxane, or DMF, at an elevated temperature, such as 80° C., to form compound 2; followed by Step (2) reacting compound 2 with an amine compound 3, wherein $LG^1$ is a leaving group, such as halo, for example bromo or chloro, in the presence of a catalyst, such as tris(dibenzylideneacetone)dipalladium (0), a bidentate ligand, such as Xantphos, and a base, such as $Cs_2CO_3$, in an organic solvent, such as 1,4-dioxane, or DMF, at an elevated temperature, such as 80° C., to form amine 4.

Compounds of Formula (I) can alternatively be prepared as illustrated and described in Scheme B.

Scheme B:

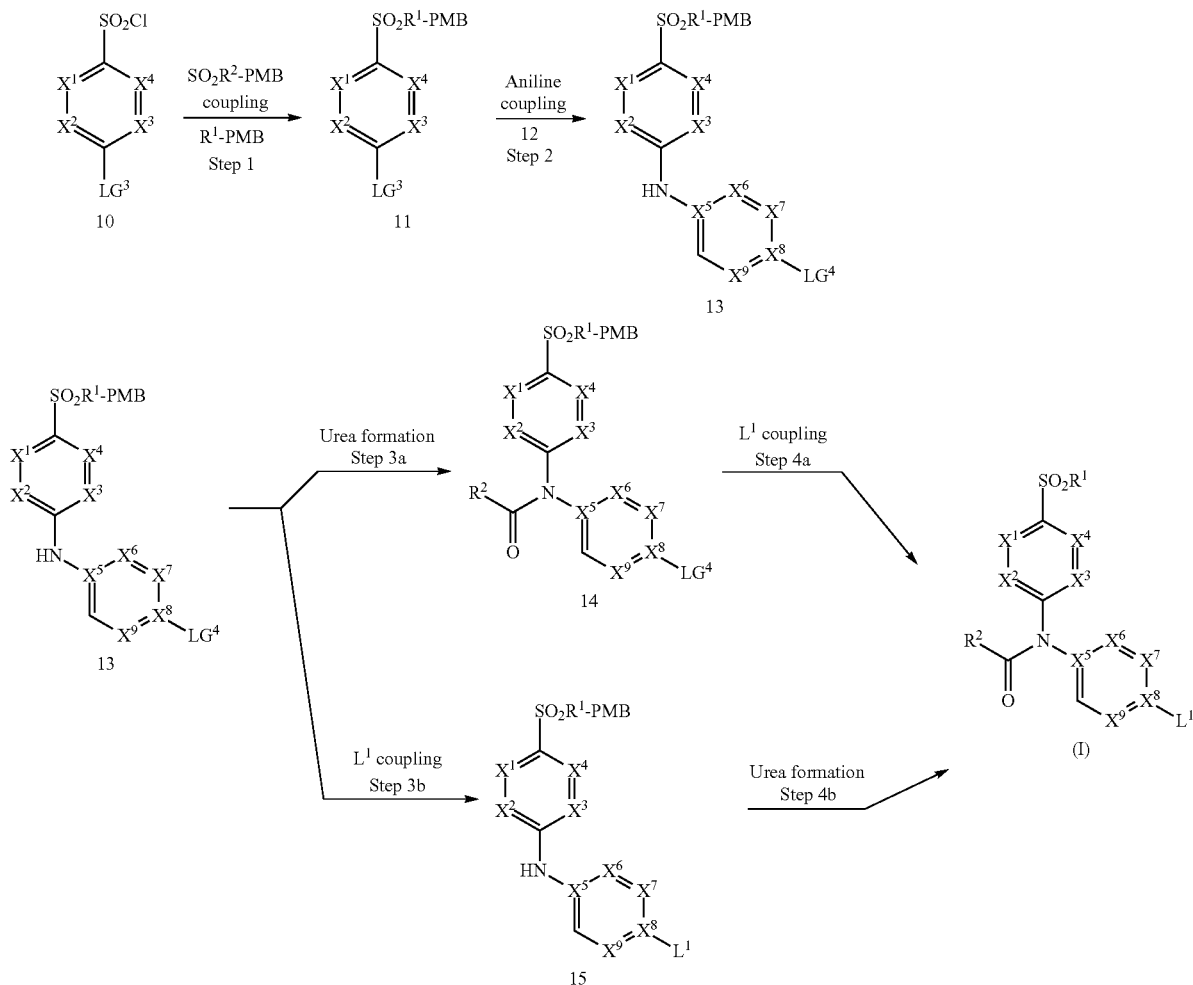

According to Scheme B, in one embodiment, Compound of Formula (I) can be prepared by Step (1) $SO_2R^1$-PMB Coupling Step from Compound 10 to Compound 11, Step (2) Aniline Coupling Step by reacting Compound 11 with compound 12 to form Compound 13, Step (3a) Urea Formation Step from Compound 13 to Urea 14, followed by Step (4a) $L^1$ coupling Step from Urea 14 to form a Compound of Formula (I).—PMB is defined as—para-methoxybenzyl group.

Step 1: $SO_2R^1$-PMB Coupling Step: Compound 10 to 11.

In the $SO_2R^1$-PMB Coupling Step, a starting material compound of formula 10, wherein $X^1$, $X^2$, $X^3$, and $X^4$ are as defined in the summary of the inventions, and $LG^3$ is a leaving group, such as halo, for example bromo or chloro, can be reacted with $R^1$-PMB, in an organic solvent, such as pyridine, to form Compound 11.

Step 2: Aniline Coupling Step from 11 to 13.

In the Aniline Coupling Step, Compound 11 can be reacted with a suitable aniline compound 12 in the presence of a catalyst, such as palladium catalyst and potassium phosphate, in various solvents, such as dioxane, under nitrogen atmosphere and at an elevated temperate, such as 100° C., to form Compound 13.

Step 3A: Urea Formation Step from Compound 13 to Urea 14.

In the Urea Formation Step 3a, Compound 13 can be reacted with a urea forming agent, for example (methylimino)(oxo)methane, in a solvent, such as acetonitrile, at an elevated temperature, such as 80° C. to 120° C., to form Compound 14.

Step 4A: $L^1$ Coupling Step from Compound 14 to Form Compounds of Formula (I).

In the $L^1$ coupling Step, Compound 14 can be reacted with an $L^1$ coupling agent, for example an $L^1$ containing boron compound, at an elevated temperature, such as 80° C.°, under nitrogen atmosphere, to form a Compound of Formula (I).

According to Scheme B, in another embodiment, Compound 13 can be reacted in Step (3b) $L^1$ coupling Step to form Compound 15, which is reacted in Step (4b) Urea Formation Step to form as compound of Formula (I).

Step 3b: $L^1$ Coupling Step from Compound 13 to Form Compound 15.

In the $L^1$ coupling Step, Compound 13 can be reacted with an $L^1$ coupling agent, for example an $L^1$ containing boron compound, at an elevated temperature, such as 80° C., under nitrogen atmosphere, to form Compound 15.

Step 4b: Urea Formation Step: Compound 15 to Form a Compound of Formula (I).

In the Urea Formation Step, Compound 15 can be reacted with a urea forming agent, for example (methylimino)(oxo)methane, in a solvent, such as acetonitrile, at an elevated temperature, such as 80° C. to 120° C., to form a compound of Formula (I).

EXAMPLES

Example 1-1

6-(1-(4'-chloro-2-fluoro-5-methoxy-3'-methyl-[1,1'-biphenyl]-4-yl)-3-methylureido)-N-(isoxazol-3-yl)pyridine-3-sulfonamide

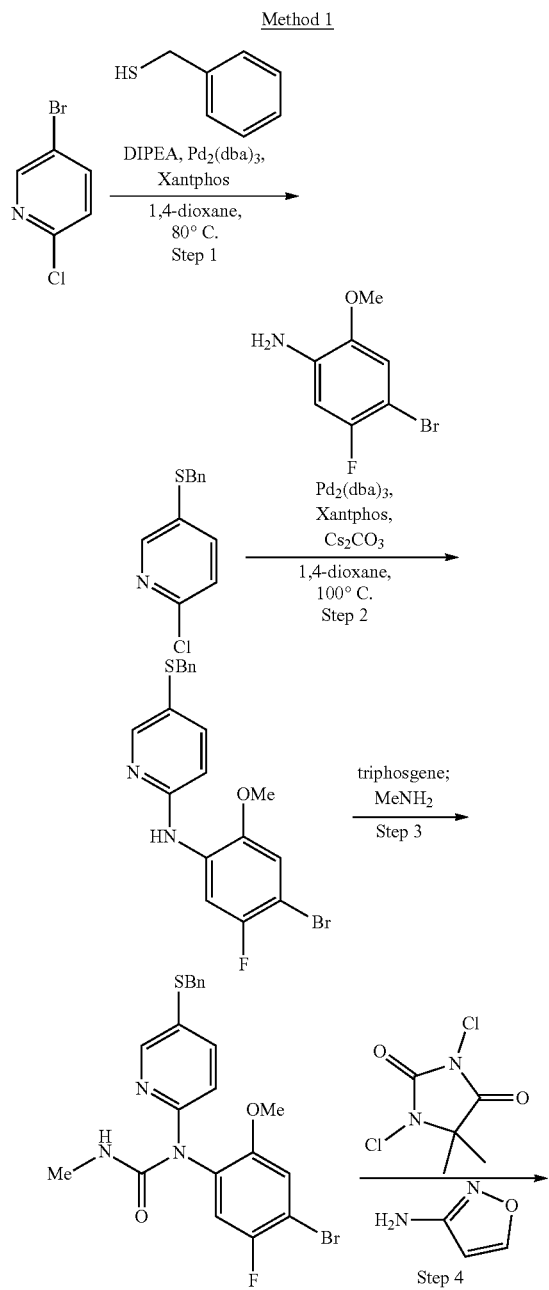

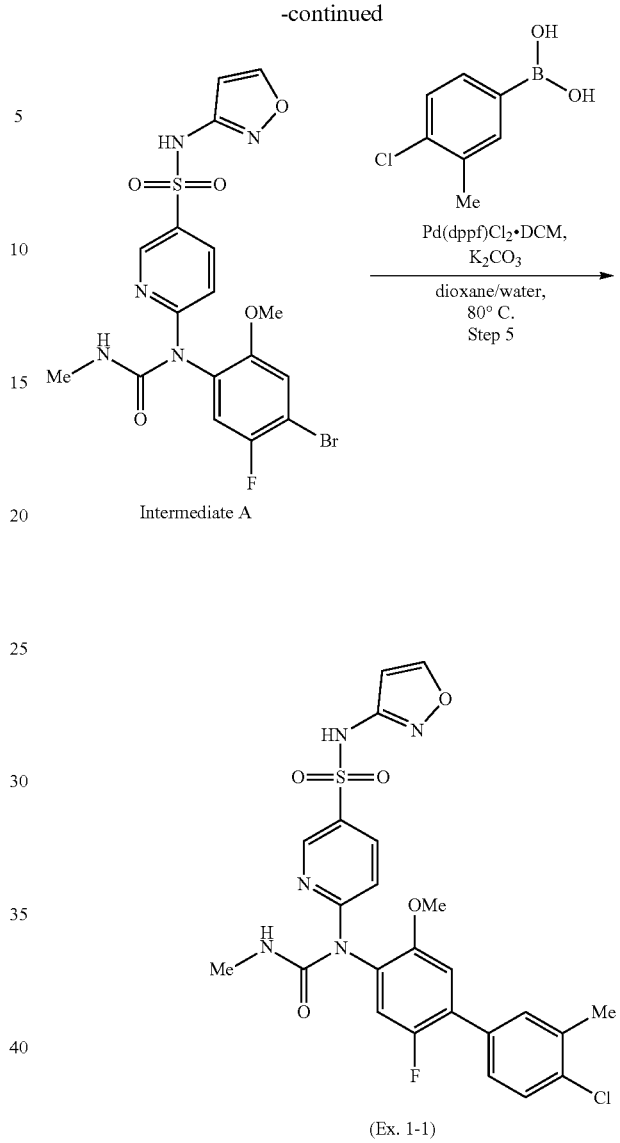

(Ex. 1-1)

Step 1: 5-(benzylthio)-2-chloropyridine

A 500 mL round bottomed flask was charged with 5-bromo-2-chloropyridine (10 g, 52.0 mmol), Xantphos (3.01 g, 5.20 mmol), Pd$_2$(dba)$_3$ (2.379 g, 2.60 mmol), 1,4-dioxane (208 ml), Hunig's base (18.15 ml, 104 mmol). The flask was evacuated and backfilled three times with N$_2$ and then heated at 80° C. for 1.5 h. LCMS showed full conversion. 200 ml of Me-THF was added as the reaction cooled and after stirring overnight the reaction was filtered over CELITE® to provide an orange oil that was purified by MPLC (340 g SnapUltra, 0-30% EtOAc/heptane) to provide 5-(benzylthio)-2-chloropyridine (8.95 g, 38.0 mmol, 73.1% yield) as a yellow oil. $^1$H NMR (400 MHz, CHLOROFORM-d) δ ppm 4.09 (s, 2H) 7.19 (dd, J=8.29, 0.73 Hz, 1H) 7.24-7.34 (m, 5H) 7.49 (dd, J=8.29, 2.49 Hz, 1H) 8.28 (dd, J=2.59, 0.62 Hz, 1H).

Step 2: 5-(benzylthio)-N-(4-bromo-5-fluoro-2-methoxyphenyl)pyridin-2-amine 4-bromo-5-fluoro-2-methoxyaniline (5 g, 22.72 mmol) (commercially available or available in 2 steps from 1-bromo-2,5-difluoro-4-nitrobenzene), tris(dibenzylideneacetone)dipalladium (0) (1.04 g, 1.14 mmol), Cs$_2$CO$_3$ (8.14 g, 25.00 mmol), and (9,9-dimethyl-9H-xanthene-4,5-diyl)bis(diphenylphosphine) (1.32 g, 2.27 mmol) were added to a 200 mL flask. 1,4-dioxane (60 mL) was added followed by 5-(benzylthio)-2-chloropyridine (5.36 g, 22.7 mmol) while the reaction was sparged with N$_2$. After 10 min the reaction was heated to 80° C. for 6 h when full conversion was observed by LC/MS. The reaction was cooled and diluted with 100 ml of Me-THF and filtered over CELITE® washing with Me-THF. After concentrating the residue was purified by MPLC (280 g Grace column, 0-50% ethyl acetate:heptane) to provide impure material which was subjected to additional MPLC (340 g Snap ultra, 0-45% ethyl acetate:heptane) to provide 5-(benzylthio)-N-(4-bromo-5-fluoro-2-methoxyphenyl)pyridin-2-amine (3.9 g, 9.30 mmol, 41% yield) as a yellow solid. m/z (ESI) M+H: 419.0, 420.0 $^1$H NMR (400 MHz, DMSO-d6) ppm 3.32 (s, 1H) 3.88 (s, 3H) 4.08 (s, 2H) 6.98 (br s, 1H) 7.12-7.32 (m, 8H) 7.57 (dd, J=8.71, 2.49 Hz, 1H) 8.09 (d, J=2.18 Hz, 1H) 8.49 (d, J=11.97 Hz, 1H) 8.60 (s, 1H).

Step 3: 1-(5-(benzylthio)pyridin-2-yl)-1-(4-bromo-5-fluoro-2-methoxyphenyl)-3-methylurea DCM (5.0 ml) was added to bis(trichloromethyl) carbonate (0.10 g, 0.36 mmol) and 5-(benzylthio)-N-(4-bromo-5-fluoro-2-methoxyphenyl)pyridin-2-amine (0.43 g, 1.03 mmol) in a 20 ml vial. Hunig's base (0.45 ml, 2.6 mmol) was added slowly while the reaction was stirred at room temperature. After 1.5 h, no starting material remained by LC/MS and a solution of methylamine in THF (2.0 ml, 4 mmol) was added. After 1.5 h full conversion was observed by LC/MS. The reaction was diluted with ethyl acetate and saturated NH$_4$Cl. The aqueous layer was separated, extracted twice and the combined organics were washed with brine, dried over Na$_2$SO$_4$, concentrated, and used crude in the next step. m/z (ESI) M+H 476.0, 478.0.

Step 4: 6-(1-(4-bromo-5-fluoro-2-methoxyphenyl)-3-methylureido)-N-(isoxazol-3-yl)pyridine-3-sulfonamide (Intermediate A)

1-(5-(benzylthio)pyridin-2-yl)-1-(4-bromo-5-fluoro-2-methoxyphenyl)-3-methylurea (0.49 g, 1.03 mmol) was dissolved in acetonitrile (9.7 ml), acetic acid (0.37 ml) and water (0.24 ml) in a 20 mL vial and cooled to 0° C. in an ice bath. 1,3-dichloro-5,5-dimethylimidazolidine-2,4-dione (0.28 g, 1.44 mmol) was added slowly. The reaction turned dark initially and lightened over time. After 1.5 h the sulfonyl chloride is observed by LC/MS. NaHSO$_3$ was added at 0° C. and the reaction was diluted with EtOAc. Na$_2$SO$_4$ was added and after filtering the reaction was concentrated, brought up in toluene with a small amount of EtOAc and filtered over a 2 inch pad of silica gel, washing with 50 ml of 50% ethyl acetate: heptane. The filtrate was concentrated, azeotroped with toluene and brought up in DCM (10 ml). 3-aminoisoxazole (0.104 ml, 1.343 mmol) and pyridine (0.842 ml, 10.33 mmol) were added. Full conversion was observed after stirring overnight at room temperature. After concentrating, MPLC purification (50 g Snap Ultra, 5-75% ethyl acetate: heptane) provided 0.44 g of the title compound as a pale orange solid (85% yield). LC/MS M+500.0, 502.0.

TABLE 1

Intermediates B-F were prepared following the procedure described in Method 1, Steps 1-4, above as follows (In stands for Intermediate):

| In | Chemical Structure | Name | Preparation | Analytical |
|---|---|---|---|---|
| B | 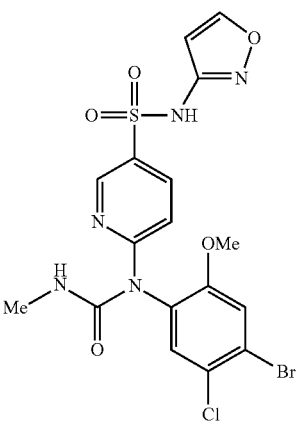 [SMILES: CNC(=O)N(c1ccc(S(=O)(=O)Nc2ccon2)cn1)c1cc(Cl)c(Br)cc1OC] | 6-(1-(4-bromo-5-chloro-2-methoxyphenyl)-3-methylureido)-N-(isoxazol-3-yl)pyridine-3-sulfonamide | 4-bromo-5-chloro-2-methoxyaniline was used in place of 4-bromo-5-fluoro-2-methoxyaniline in Step 2 | m/z (ESI) M+ 516.0, 518.0 |

TABLE 1-continued

Intermediates B-F were prepared following the procedure described in Method 1, Steps 1-4, above as follows (In stands for Intermediate):

| In | Chemical Structure | Name | Preparation | Analytical |
|---|---|---|---|---|
| C | 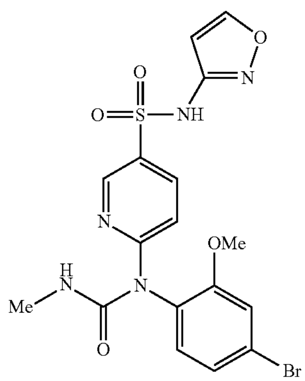 [SMILES: CNC(=O)N(c1ccc(S(=O)(=O)Nc2ccon2)cn1)c1ccc(Br)cc1OC] | 6-(1-(4-bromo-2-methoxyphenyl)-3-methylureido)-N-(isoxazol-3-yl)pyridine-3-sulfonamide | 4-bromo-2-methoxyaniline was used in place of 4-bromo-5-fluoro-2-methoxyaniline in Step 2 | m/z (ESI) M − H: 480.1, 482.1 |
| D | 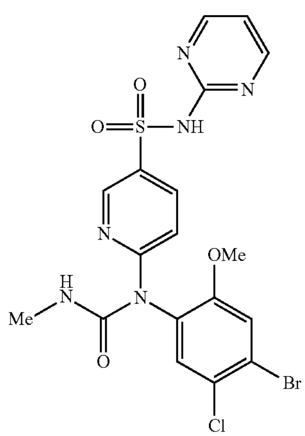 [SMILES: CNC(=O)N(c1ccc(S(=O)(=O)Nc2ncccn2)cn1)c1cc(Cl)c(Br)cc1OC] | 6-(1-(4-bromo-5-chloro-2-methoxyphenyl)-3-methylureido)-N-(pyrimidin-2-yl)pyridine-3-sulfonamide | 2-aminopyrimidine was used in place of 3-aminoisoxazole in Step 4 | m/z (ESI) M+ 527.0, 529.0 |
| E | 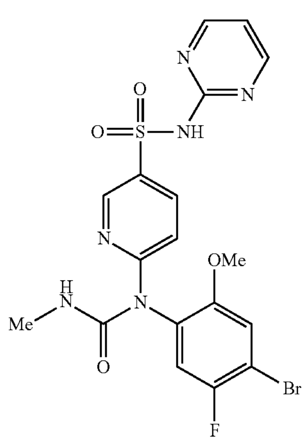 [SMILES: CNC(=O)N(c1ccc(S(=O)(=O)Nc2ncccn2)cn1)c1cc(F)c(Br)cc1OC] | 6-(1-(4-bromo-5-fluoro-2-methoxyphenyl)-3-methylureido)-N-(pyrimidin-2-yl)pyridine-3-sulfonamide | 2-aminopyrimidine was used in place of 3-aminoisoxazole in Step 4 | m/z (ESI) M+ 511.0, 512.8 |

TABLE 1-continued

Intermediates B-F were prepared following the procedure
described in Method 1, Steps 1-4, above as follows (In stands for Intermediate):

| In | Chemical Structure | Name | Preparation | Analytical |
|---|---|---|---|---|
| F | 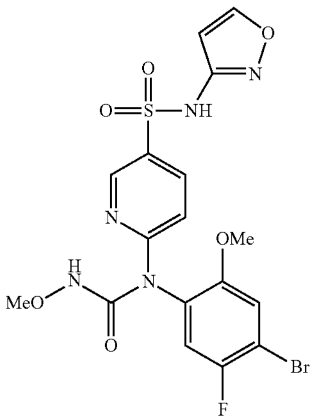 [SMILES: CONC(=O)N(c1ccc(S(=O)(=O)Nc2ccon2)cn1)c1cc(F)c(Br)cc1OC] | 6-(1-(4-bromo-5-fluoro-2-methoxyphenyl)-3-methoxyureido)-N-(isoxazol-3-yl)pyridine-3-sulfonamide | N-methoxyamine hydrochloride was used in place of methylamine in Step 3 | m/z (ESI) 516.0 (M + H)$^+$ |
| G | 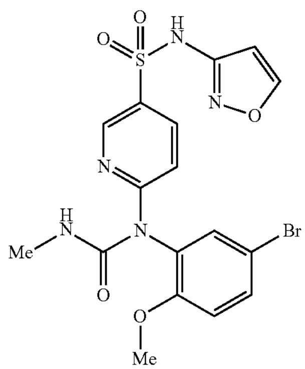 [SMILES: CNC(=O)N(c1ccc(S(=O)(=O)Nc2ccon2)cn1)c1cc(Br)ccc1OC] | 6-(1-(5-bromo-2-methoxyphenyl)-3-methylureido)-N-(isoxazol-3-yl)pyridine-3-sulfonamide | 5-bromo-2-methoxyaniline was used in place of 4-bromo-5-fluoro-2-methoxyaniline in Step 2 | m/z (ESI) 482.0, 483.0 (M + H)$^+$ |
| H | 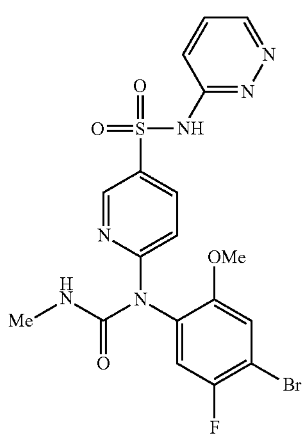 [SMILES: CNC(=O)N(c1ccc(S(=O)(=O)Nc2cccnn2)cn1)c1cc(F)c(Br)cc1OC] | 6-(1-(4-bromo-5-fluoro-2-methoxyphenyl)-3-methylureido)-N-(pyridazin-3-yl)pyridine-3-sulfonamide | 2-aminopyridizine was used in place of 3-aminoisoxazole in Step 4 | m/z (ESI) 511.0, 512.8 (M + H)$^+$ |

Step 5: 6-(1-(4'-chloro-2-fluoro-5-methoxy-3'-methyl-[1,1'-biphenyl]-4-yl)-3-methylureido)-N-(isoxazol-3-yl)pyridine-3-sulfonamide To a 20 ml vial PdCl$_2$(dppf)-CH$_2$Cl$_2$ adduct (0.012 g, 0.015 mmol), K$_2$CO$_3$ (0.104 g, 0.750 mmol), (4-chloro-3-methylphenyl)boronic acid (0.051 g, 0.300 mmol), and 6-(1-(4-bromo-5-fluoro-2-methoxyphenyl)-3-methylureido)-N-(isoxazol-3-yl)pyridine-3-sulfonamide (0.075 g, 0.150 mmol) were added followed by 1,4-dioxane (0.562 ml) and water (0.187 ml). The vial was evacuated and backfilled three times with N$_2$ with stirring then sealed with a fresh cap and heated to 80° C. for 4 h. The reaction was cooled to ambient temperature and extracted three times with EtOAc. The combined organic layers were concentrated, dissolved in MeCN, filtered through a 0.45 m syringe filter and purified by RP-HPLC (Gilson, 35-95% MeCN/H$_2$O w/0.1% TFA) Fractions containing products were combined and lyophilized to provide 0.016 g of the title compound as the TFA salt (16% yield). Alternatively, the final compound was obtained via MPLC purification (25 g Snap Ultra, 10-100% [3:1 ethyl acetate: ethanol]: heptane) to provide the title compound. (See Table 7 for analytical data)

Example 2-1

6-((3'-chloro-2,4'-difluoro-5-methoxy-4-biphenylyl)(methylcarbamoyl)amino)-N-2-pyrimidinyl-3-pyridinesulfonamide

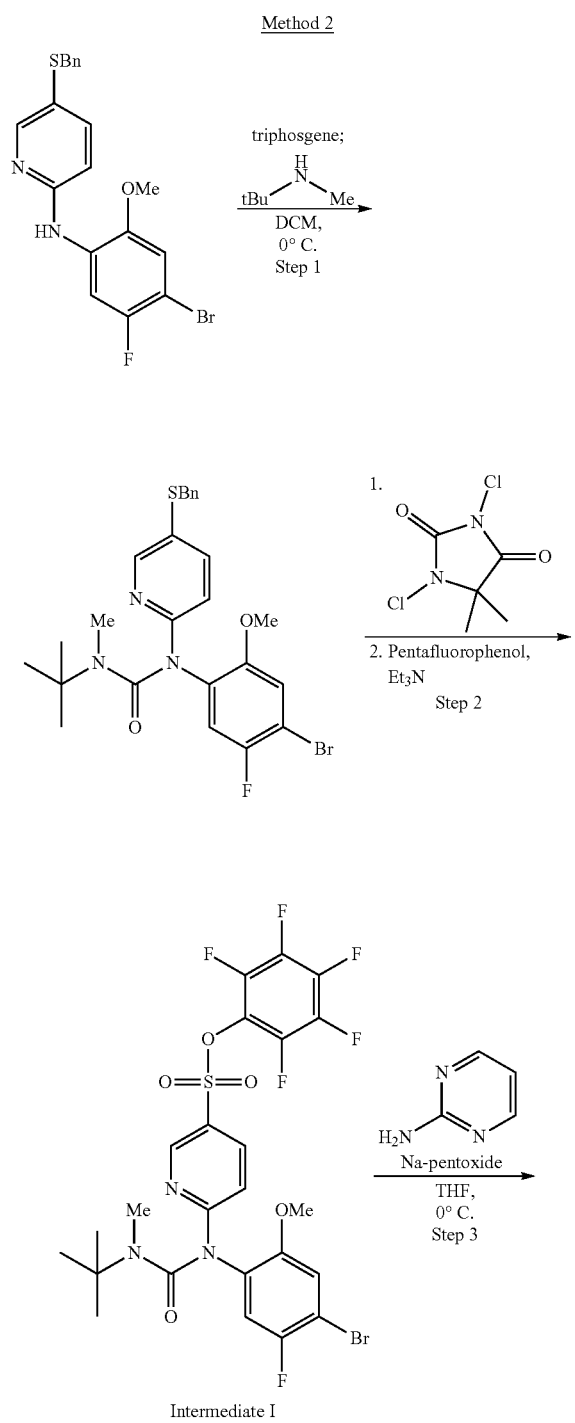

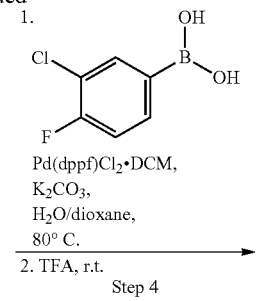

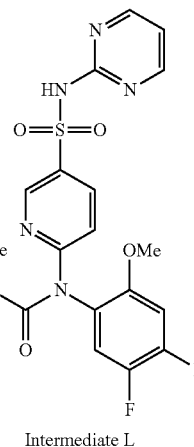

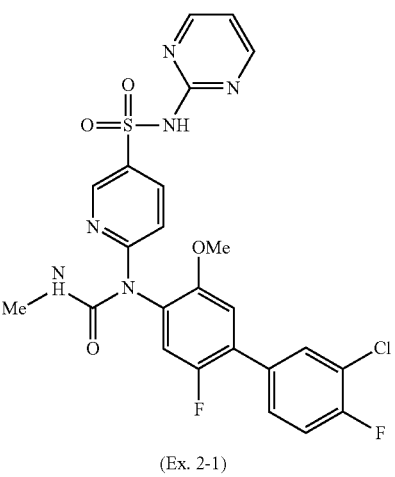 [SMILES: CNC(=O)N(c1ccc(S(=O)(=O)Nc2ncccn2)cn1)c1cc(F)c(-c2ccc(F)c(Cl)c2)cc1OC]

Step 1: 1-(5-(benzylthio)pyridin-2-yl)-1-(4-bromo-5-fluoro-2-methoxyphenyl)-3-(tert-butyl)-3-methylurea A 100 ml three-neck round bottomed flask with overhead stirrer and $N_2$ inlet was charged with 5-(benzylthio)-N-(4-bromo-5-fluoro-2-methoxyphenyl)pyridine-2-amine (2.86 g, 6.82 mmol) and bis(trichloromethyl) carbonate (0.813 g, 2.74 mmol). The flask was evacuated and backfilled three times with nitrogen before dichloromethane (22 ml) was added. The solution was cooled in an ice-water bath while triethylamine (2.377 ml, 17.05 mmol) was added dropwise to maintain an internal temperature under 10° C. After completion of the addition the bath was removed and stirring was continued. After 1 hour conversion to the chloroformamide was complete by LC/MS. The reaction was cooled in an ice bath to <5° C. while N-tert-butylmethylamine (0.9 ml, 7.55 mmol) was added and the reaction was stirred at room temperature overnight. 0.5 M HCl (20 mL) was added and the layers were separated. The organic layer was concentrated to a dark red oil (4.7 g) that was used in the following step without purification.

Step 2: perfluorophenyl 6-(1-(4-bromo-5-fluoro-2-methoxyphenyl)-3-(tert-butyl)-3-methylureido)pyridine-3-sulfonate (Intermediate I)

Crude 1-(5-(benzylthio)pyridine-2-yl)-1-(4-bromo-5-fluoro-2-methoxyphenyl)-3-(tert-butyl)-3-methylurea (4.7 g) was dissolved in acetonitrile (36 ml) and treated with acetic acid (2.4 ml, 41.6 mmol), water (1.5 ml, 83 mmol), and cooled in an ice-water bath. 1,3-dichloro-5,5-dimethylimidazolidine-2,4-dione (2.047 g, 10.39 mmol) was added portion-wise to give a dark brown mixture that was stirred for 1 h when full conversion to the sulfonyl chloride was observed by LC/MS. 2,3,4,5,6-pentafluorophenol (1.0 ml, 9.9 mmol) and triethylamine (4.75 ml, 34.1 mmol) were added and the cooling bath was removed. After 1 h the reaction was partitioned with EtOAc/water. The layers were separated and the aqueous was extracted with EtOAc. The combined organic layers were concentrated and purified by column chromatography (5 to 15% EtOAc/heptanes, 50 g SiO$_2$) to give a tan foam (3 g, 86% yield). LC/MS M+H 656.0, 658.0.

TABLE 2

Intermediates J and K were prepared following the procedure described in Method 2, Steps 1-2, above as follows (In stands for Intermediate):

| In | Chemical Structure | Name | Preparation | Analytical |
|---|---|---|---|---|
| J | 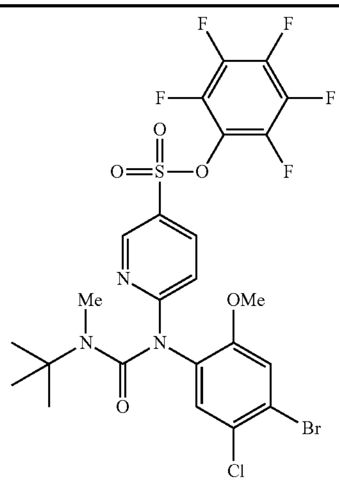 | perfluorophenyl 6-(1-(4-bromo-5-chloro-2-methoxyphenyl)-3-(tert-butyl)-3-methylureido)pyridine-3-sulfonate | Compound J-1 was prepared according to Method 1: Steps 1-2, wherein compound J-2 was used in place of 4-bromo-5-fluoro-2-methoxyaniline in Step 1. Compound J-1 was used in place of 5-(benzylthio)-N-(4-bromo-5-fluoro-2-methoxyphenyl)pyridine-2-amine in Method 2, Step 1, to prepare Intermediate J | m/z (ESI) M+ 516.0, 518.0 |
| K | 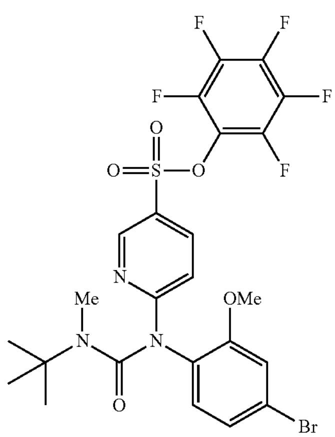 [SMILES: COc1cc(Br)ccc1N(C(=O)N(C)C(C)(C)C)c1ccc(S(=O)(=O)Oc2c(F)c(F)c(F)c(F)c2F)cn1] | perfluorophenyl 6-(1-(4-bromo-2-methoxyphenyl)-3-(tert-butyl)-3-methylureido)pyridine-3-sulfonate | Compound K-1 was prepared according to Method 1: Steps 1-2, wherein compound K-2 was used in place of 4-bromo-5-fluoro-2-methoxyaniline in Step 1. Compound K-1 was used in place of 5-(benzylthio)-N-(4-bromo-5-fluoro-2-methoxyphenyl)pyridine-2-amine in Method 2, Step 1, to prepare Intermediate K | m/z (ESI) M + H 638.0, 640.0 |

Step 3: 6-(1-(4-bromo-5-fluoro-2-methoxyphenyl)-3-(tert-butyl)-3-methylureido)-N-(pyrimidin-2-yl)pyridine-3-sulfonamide (Intermediate L)

To a 250 mL 3-neck round-bottom flask fitted with a Claisen adapter, N$_2$ inlet, overhead stirrer and addition funnel was added 6-(1-(4-bromo-5-fluoro-2-methoxyphenyl)-3-(tert-butyl)-3-methylureido)-N-(pyrimidin-2-yl)pyridine-3-sulfonamide (3.6 g, 6.34 mmol) and 2-aminopyrimidine (0.88 g, 9.20 mmol). The flask was evacuated and backfilled three times with N$_2$ before tetrahydrofuran (38.2 ml) was added. The mixture was cooled in an ice-water bath and sodium tert-pentoxide, 1.4 M in tetrahydrofuran (13.0 ml, 18.2 mmol) was added to an addition funnel, and was added to the reaction at a rate to maintain an internal temperature <3° C. After completion was observed by LC/MS (1-2 h) the reaction was quenched into a 250 mL flask with EtOAc (50 mL) and 1N HCl (50 mL) that was cooled in an ice-water bath to ~5° C. The layers were separated and the aqueous was re-extracted with EtOAc (2×10 mL). The combined organics were washed with brine and concentrated to an orange oil. THF (50 mL) and IPA (50 mL) were added and the solution was concentrated to a slurry. The solids were isolated by filtration and washed with IPA to provide 6-(1-(4-bromo-5-fluoro-2-methoxyphenyl)-3-(tert-butyl)-3-methylureido)-N-(pyrimidin-2-yl)pyridine-3-sulfonamide (3.6 g, 83% yield). LC/MS M+H 567.0, 569.0.

Example 2-11

6-(1-(5-Fluoro-2-methoxy-4-tetradecylphenyl)-3-methylureido)-N-(pyrimidin-2-yl)pyridine-3-sulfonamide

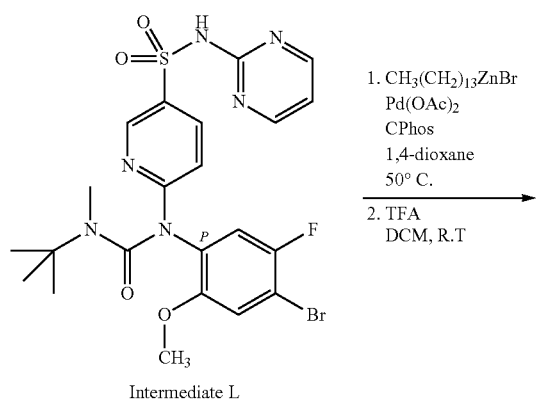

1. CH$_3$(CH$_2$)$_{13}$ZnBr
   Pd(OAc)$_2$
   CPhos
   1,4-dioxane
   50° C.
2. TFA
   DCM, R.T Intermediate L

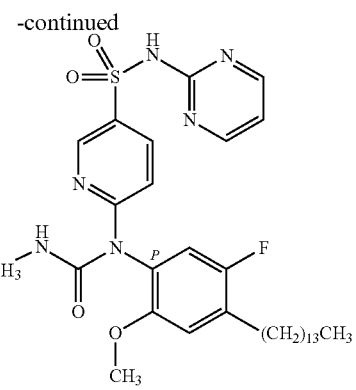

Example 2-11

To a solution of 6-(1-(4-bromo-5-fluoro-2-methoxyphenyl)-3-(tert-butyl)-3-methylureido)-N-(pyrimidin-2-yl)pyridine-3-sulfonamide (Intermediate L) 0.2 g, 0.35 mmol) and 2'-(dicyclohexylphosphino)-N2,N2,N6,N6-tetramethyl-[1,1'-biphenyl]-2,6-diamine (0.062 g, 0.14 mmol) in 1,4-dioxane (1.76 mL) was added diacetoxypalladium (0.016 g, 0.070 mmol). The reaction mixture was sparged with argon, and then tetradecylzinc bromide (2.1 mL, 1.05 mmol) was added. The reaction was stirred at 50° C. for 5 hours.

The reaction mixture was partitioned between ethyl acetate and aqueous 1N HCl solution; and the organic layer was concentrated. The product was purified via MPLC, eluting with 10-50% (3:1 EtOAc/ethanol) in heptane/10% dichloromethane. The intermediate was dissolved in dichloromethane (1.6 mL) and trifluoroacetic acid (500 μL, 6.4 mmol) was added. The reaction mixture was stirred at ambient temperature for 2 hours. The reaction was then diluted with DCM and neutralized with saturated aqueous sodium bicarbonate. The organic phase was concentrated in vacuo to provide the title compound (68 mg, 0.108 mmol, 30.9% yield) as white solid. $^1$H NMR (400 MHz, DMSO-d$_6$) δ ppm 8.74 (1H, d, J=2.38 Hz), 8.53 (2H, d, J=4.87 Hz), 8.42 (1H, br s), 8.13 (1H, dd, J=8.97, 2.54 Hz), 7.06 (3H, m), 6.97 (1H, d, J=8.91 Hz), 3.61 (3H, s), 2.71 (3H, d, J=4.56 Hz), 1.61 (2H, m), 1.24 (24H, bs), 0.85 (3H, m).

TABLE 3

Intermediates M, N, and O were prepared following the procedure described in Method 2, Steps 1-3, above as follows (The term "In" stands for Intermediate):

| In | Chemical Structure | Name | Preparation | Analytical |
|---|---|---|---|---|
| M | 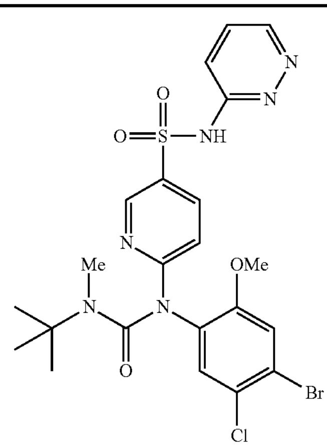 | 6-(1-(4-bromo-5-chloro-2-methoxyphenyl)-3-(tert-butyl)-3-methylureido)-N-(pyridazin-3-yl)pyridine-3-sulfonamide | Intermediate J was used in place of Intermediate H and 2-aminopyridazine was used in place of 2-aminopyrimidine in Step 3. | m/z (ESI) M + H 585.0, 587.0 |

TABLE 3-continued

Intermediates M, N, and O were prepared following the procedure described in Method 2, Steps 1-3, above as follows (The term "In" stands for Intermediate):

| In | Chemical Structure | Name | Preparation | Analytical |
|----|--------------------|------|-------------|------------|
| N | 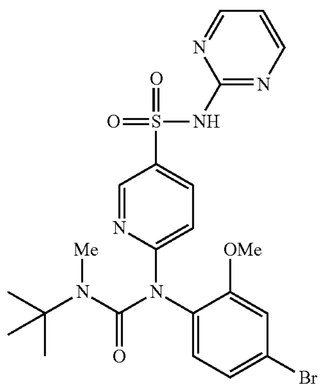 [SMILES: COc1cc(Br)ccc1N(C(=O)N(C)C(C)(C)C)c1ccc(S(=O)(=O)Nc2ncccn2)cn1] | 6-(1-(4-bromo-2-methoxy-phenyl)-3-(tert-butyl)-3-methylureido)-N-(pyrimidin-2-yl)pyridine-3-sulfonamide | Intermediate K was used in place of Intermediate H in Step 3. | m/z (ESI) M + H 551.0, 549.0 |
| O | 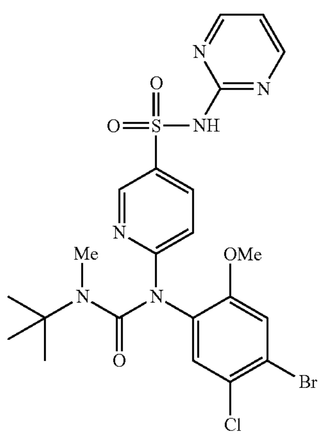 [SMILES: COc1cc(Br)c(Cl)cc1N(C(=O)N(C)C(C)(C)C)c1ccc(S(=O)(=O)Nc2ncccn2)cn1] | 6-(1-(4-bromo-5-chloro-2-methoxy-phenyl)-3-(tert-butyl)-3-methylureido)-N-(pyrimidin-2-yl)pyridine-3-sulfonamide | Intermediate J was used in place of Intermediate H in Step 3. | m/z (ESI) M + H 583.0, 585.0 |

Step 4: 6-((3'-chloro-2,4'-difluoro-5-methoxy-4-biphenylyl)(methylcarbamoyl)amino)-N-2-pyrimidinyl-3-pyridinesulfonamide 6-((3'-chloro-2,4'-difluoro-5-methoxy-4-biphenylyl)(methylcarbamoyl)amino)-N-2-pyrimidinyl-3-pyridinesulfonamide (0.09 g, 0.16 mmol), 1,1'-bis(diphenylphosphino)ferrocene palladium(II)dichloride dichloromethane adduct (0.013 g, 0.016 mmol), (3-chloro-4-fluorophenyl)boronic acid (0.055 g, 0.32 mmol), $K_2CO_3$ (0.08 g, 0.63 mmol), 1,4-dioxane (0.6 ml) and water (0.2 ml) were added to a 4 ml vial. The vial was evacuated and backfilled with $N_2$ 3× before being sealed with a cap with a new septa and heated at 80° C. for 3 h when complete conversion was observed. The organic layer was separated and the aq. layer extracted 2× with EtOAc. The combined organics were concentrated and treated with 1 ml of TFA. After 30 min the reaction was concentrated, azeotroped with heptane, diluted in MeOH/MeCN, filtered through a 0.45 μm filter and purified by reverse phase HPLC (Gilson, 30-80% MeCN/$H_2O$ w0.1% TFA). Clean fractions were combined and lyophilized to provide the TFA salt of the product as a white solid (5 mg, 10% yield). Alternatively, the final compound was obtained via MPLC purification (25 g Snap Ultra, 10-100% [3:1 ethyl acetate: ethanol]: heptane) to provide the title compound. (See Table 7 for analytical data).

Example 2-12

6-(1-(2,4'-difluoro-5-methoxy-3'-(trifluoromethoxy)-[1,1'-biphenyl]-4-yl)-3-methylureido)-N-(4-methylisoxazol-3-yl)pyridine-3-sulfonamide Method 2A

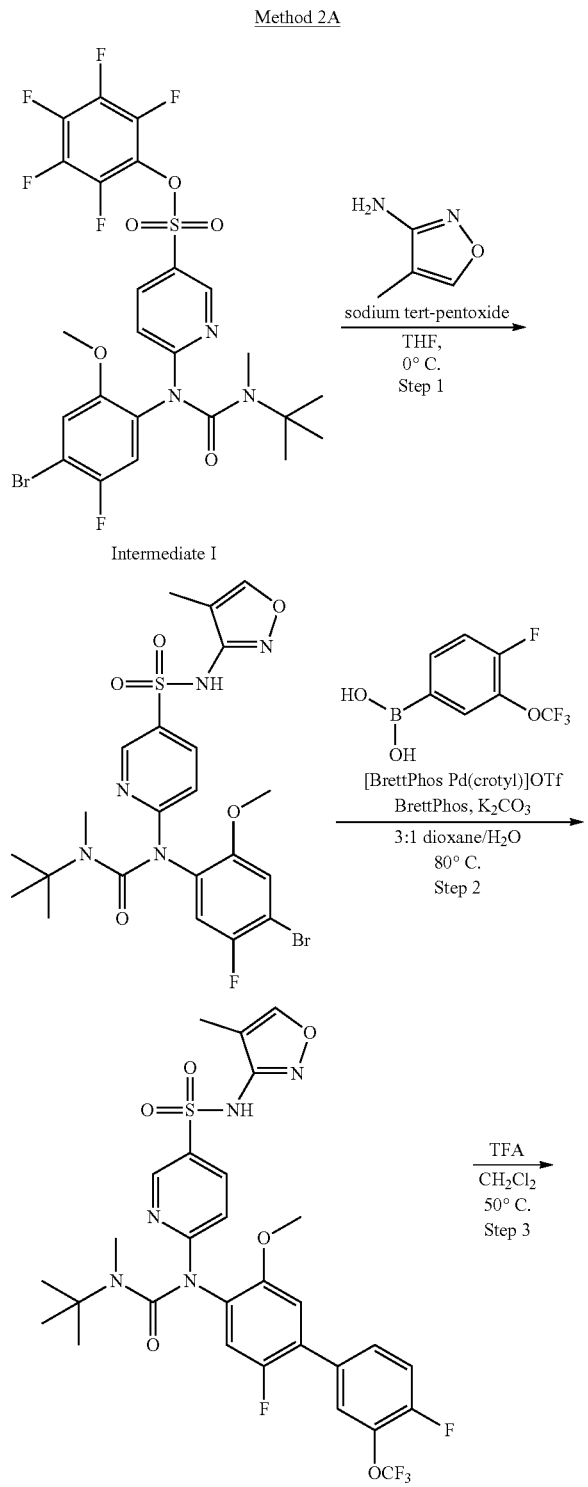

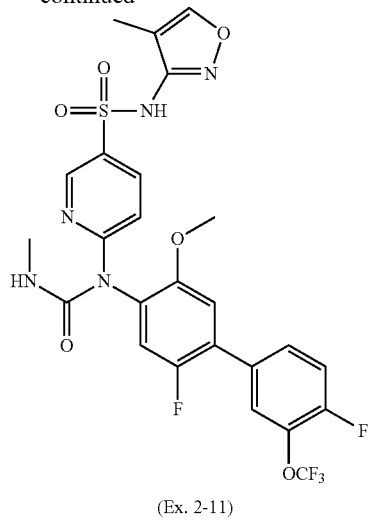

(Ex. 2-11)

Step 1: 6-(1-(4-bromo-5-fluoro-2-methoxyphenyl)-3-(tert-butyl)-3-methylureido)-N-(4-methylisoxazol-3-yl)pyridine-3-sulfonamide A THF (7 mL) solution of perfluorophenyl 6-(1-(4-bromo-5-fluoro-2-methoxyphenyl)-3-(tert-butyl)-3-methylureido)pyridine-3-sulfonate (Intermediate I from Example 2-1, 0.998 g, 1.52 mmol) and 3-amino-4-methylisoxazole (0.164 g, 1.672 mmol) in a 40-mL vial was cooled to 0° C. Sodium tert-pentoxide solution (1.4 M in THF, 2.4 ml, 3.34 mmol) was added slowly to the reaction over 2 min. The resulting yellow-orange solution was stirred at 0° C. for 30 min. The reaction was then quenched at 0° C. with 1 N HCl and extracted thrice with EtOAc. The organic extracted were combined, washed with brine, dried over $Na_2SO_4$, filtered, and concentrated in vacuo to afford a yellow oil. Column chromatography (50 g $SiO_2$ column, 0-100% EtOAc/hept) afforded 6-(1-(4-bromo-5-fluoro-2-methoxyphenyl)-3-(tert-butyl)-3-methylureido)-N-(4-methylisoxazol-3-yl)pyridine-3-sulfonamide (0.8114 g, 1.422 mmol, 94% yield) as a white amorphous solid. $^1$H NMR (500 MHz, DMSO-$d_6$) δ ppm 10.94 (s, 1H), 8.54 (dd, J=7.79, 1.56 Hz, 2H), 8.08 (dd, J=8.95, 2.47 Hz, 1H), 7.46 (d, J=6.49 Hz, 1H), 7.22 (d, J=9.08 Hz, 1H), 7.09 (d, J=8.82 Hz, 1H), 3.68 (s, 3H), 2.61 (s, 3H), 1.87 (d, J=1.04 Hz, 3H), 1.35 (s, 9H). m/z (ESI) 570.0 (M+H)$^+$.

Step 2: 6-(3-(tert-butyl)-1-(2,4'-difluoro-5-methoxy-3'-(trifluoromethoxy)-[1,1'-biphenyl]-4-yl)-3-methylureido)-N-(4-methylisoxazol-3-yl)pyridine-3-sulfonamide A 2-dram vial was charged with 6-(1-(4-bromo-5-fluoro-2-methoxyphenyl)-3-(tert-butyl)-3-methylureido)-N-(4-methylisoxazol-3-yl)pyridine-3-sulfonamide (125 mg, 0.219 mmol), (4-fluoro-3-(trifluoromethoxy)phenyl)boronic acid (59 mg, 0.26 mmol), potassium carbonate (121 mg, 0.877 mmol), BrettPhos (4.7 mg, 8.77 μmol), and [BrettPhos Pd(crotyl)]OTf (8.2 mg, 9.64 μmol) followed by dioxane (1.6 mL) and water (0.55 mL). After purging through three cycles of vacuum/N2, the vial was sealed and stirred at 80° C. for 2 h. The vial was then cooled to rt, quenched with 1 N HCl (2 mL), and diluted with $CH_2Cl_2$ (2 mL). The reaction was then filtered through a phase separator, rinsing twice with CH$_2$Cl$_2$. The filtrate was concentrated in vacuo to afford 6-(3-(tert-butyl)-1-(2,4'-difluoro-5-methoxy-3'-(trifluoromethoxy)-[1,1'-biphenyl]-4-yl)-3-methylureido)-N-(4-methylisoxazol-3-yl)pyridine-3-sulfonamide that was used without further purification. m/z (ESI) 670.2 (M+H)$^+$.

Step 3: 6-(1-(2,4'-difluoro-5-methoxy-3'-(trifluoromethoxy)-[1,1'-biphenyl]-4-yl)-3-methylureido)-N-(4-methylisoxazol-3-yl)pyridine-3-sulfonamide 6-(3-(Tert-butyl)-1-(2,4'-difluoro-5-methoxy-3'-(trifluoromethoxy)-[1,1'-biphenyl]-4-yl)-3-methylureido)-N-(4-methylisoxazol-3-yl)pyridine-3-sulfonamide from the previous step was dissolved in DCM (1.5 mL) and TFA (1.5 mL) in a 40-mL vial. The orange solution was stirred at 50° C. for 30 min and then concentrated under a stream of N$_2$. The residue was purified via reverse-phase HPLC (19×100 mm, 10 m Xbridge column, MeCN/water (with 0.1% formic acid) gradient) to afford 6-(1-(2,4'-difluoro-5-methoxy-3'-(trifluoromethoxy)-[1,1'-biphenyl]-4-yl)-3-methylureido)-N-(4-methylisoxazol-3-yl)pyridine-3-sulfonamide. $^1$H NMR (600 MHz, DMSO-d$_6$) δ ppm 11.01 (br s, 1H), 8.63 (s, 1H), 8.53 (d, J=1.09 Hz, 1H), 8.23 (br d, J=6.98 Hz, 1H), 8.07 (dd, J=9.11, 2.57 Hz, 1H), 7.86 (br d, J=7.01 Hz, 1H), 7.75-7.81 (m, 1H), 7.69 (dd, J=10.16, 8.76 Hz, 1H), 7.37 (d, J=10.67 Hz, 1H), 7.32 (d, J=7.16 Hz, 1H), 7.24 (d, J=8.95 Hz, 1H), 3.74 (s, 3H), 2.73 (d, J=4.52 Hz, 3H), 1.88 (d, J=1.09 Hz, 3H). m/z (ESI) 614.2 (M+H)$^+$.

TABLE 3A

Intermediates O-1 and O-2 were prepared following the procedure described in Method 2A, Step 2, above, as follows (The term "In" stands for Intermediate):

| In | Chemical Structure | Name | Preparation | Analytical |
|---|---|---|---|---|
| O-1 | 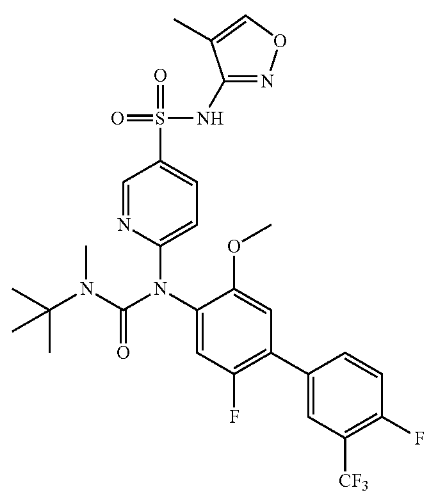 [SMILES: COc1cc(-c2ccc(F)c(C(F)(F)F)c2)c(F)cc1N(C(=O)N(C)C(C)(C)C)c1ccc(S(=O)(=O)Nc2nocc2C)cn1] | 6-(3-(tert-butyl)-1-(2,4'-difluoro-5-methoxy-3'-(trifluoromethyl)-[1,1'-biphenyl]-4-yl)-3-methylureido)-N-(4-methylisoxazol-3-yl)pyridine-3-sulfonamide | 4-fluoro-3-trifluoromethyl phenylboronic acid (Combi-Blocks) was used in place of (4-fluoro-3-(trifluoromethoxy) phenyl)boronic acid in Step 2 | m/z (ESI) 654.2 (M + H)$^+$ |
| O-2 | 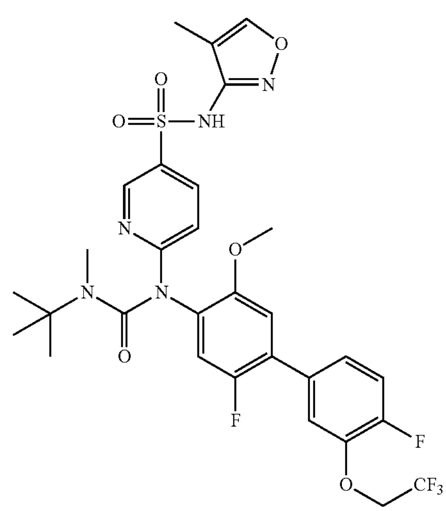 [SMILES: COc1cc(-c2ccc(F)c(OCC(F)(F)F)c2)c(F)cc1N(C(=O)N(C)C(C)(C)C)c1ccc(S(=O)(=O)Nc2nocc2C)cn1] | 6-(3-(tert-butyl)-1-(2,4'-difluoro-5-methoxy-3'-(2,2,2-trifluoroethoxy)-[1,1'-biphenyl]-4-yl)-3-methylureido)-N-(4-methylisoxazol-3-yl)pyridine-3-sulfonamide | 4-fluoro-3-(2,2,2-trifluoroethoxy) phenylboronic acid (Combi-Blocks) was used in place of (4-fluoro-3-(trifluoromethoxy) phenyl)boronic acid in Step 2 | m/z (ESI) 684.1 (M + H)$^+$. |

Example 3-1

6-(1-(2-chloro-4'-fluoro-5-methoxy-3'-(2,2,2-trifluoroethoxy)-[1,1'-biphenyl]-4-yl)-3-methylureido)-N-(pyrimidin-2-yl)pyridine-3-sulfonamide

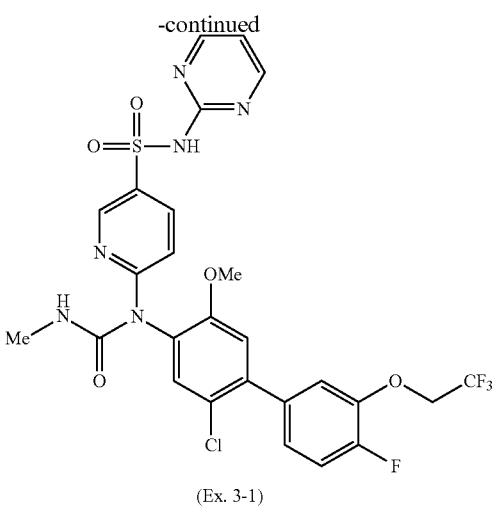

(Ex. 3-1)

Method 3

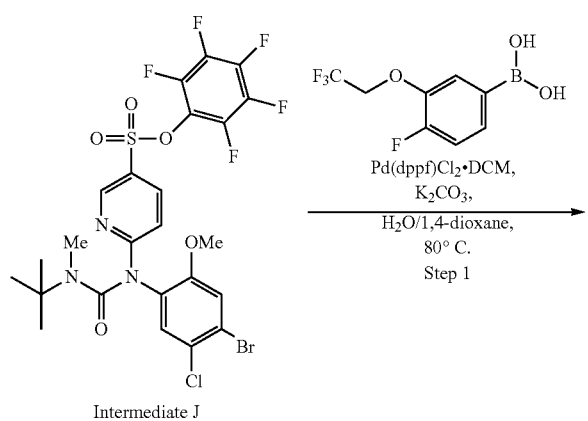

Step 1: perfluorophenyl 6-(3-(tert-butyl)-1-(2-chloro-4'-fluoro-5-methoxy-3'-(2,2,2-trifluoroethoxy)-[1,1'-biphenyl]-4-yl)-3-methylureido)pyridine-3-sulfonate (Intermediate P)

Perfluorophenyl 6-(1-(4-bromo-5-chloro-2-methoxyphenyl)-3-(tert-butyl)-3-methylureido)pyridine-3-sulfonate (1.025 g, 1.523 mmol), 1,1'-bis(diphenylphosphino)ferrocene palladium(ii)dichloride dichloromethane adduct (0.124 g, 0.152 mmol), (4-fluoro-3-(2,2,2-trifluoroethoxy)phenyl)boronic acid (0.725 g, 3.05 mmol), $K_2CO_3$ (0.842 g, 6.09 mmol), 1,4-dioxane (5.71 ml) and water (1.904 ml) were added to a 40 ml vial. The vial was evacuated and backfilled with $N_2$ 3× then sealed and heated at 80° C. for 2 hr to give a mixture of product and cross-coupled sulfonic acid. The reaction was cooled and the organic layer separated. The aq. layer was extracted 3× with EtOAc. The combined organics were washed with brine, dried over $Na_2SO_4$, filtered and concentrated. MPLC purification (100 g snap ultra, 0-30% EtOAc/heptane) gave perfluorophenyl 6-(3-(tert-butyl)-1-(2-chloro-4'-fluoro-5-methoxy-3'-(2,2,2-trifluoroethoxy)-[1,1'-biphenyl]-4-yl)-3-methylureido)pyridine-3-sulfonate (0.68 g, 0.865 mmol, 56.8% yield) as a pale yellow foam. LC/MS M+H 756.0, 758.0.

Table 4: Intermediates Q-R were prepared following the procedure described in Method 3, Step 1, above as follows (In stands for Intermediate):

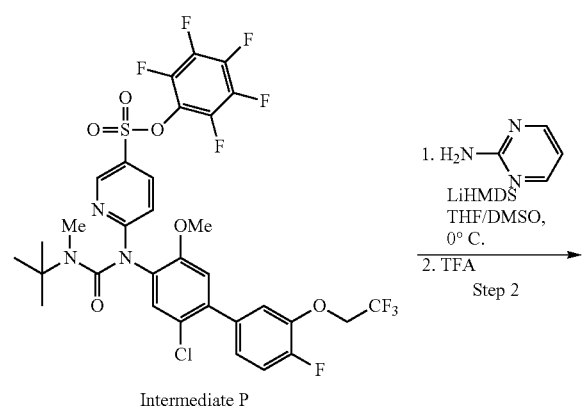

Intermediate P

| In | Chemical Structure | Name | Preparation | Analytical |
|---|---|---|---|---|
| Q | 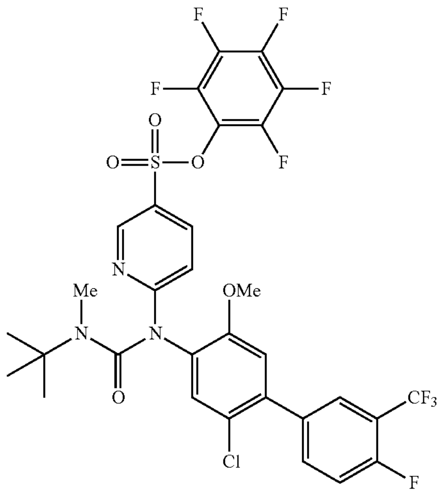 [SMILES: COc1cc(-c2ccc(F)c(C(F)(F)F)c2)c(Cl)cc1N(C(=O)N(C)C(C)(C)C)c1ccc(S(=O)(=O)Oc2c(F)c(F)c(F)c(F)c2F)cn1] | perfluorophenyl 6-(3-(tert-butyl)-1-(2-chloro-4'-fluoro-5-methoxy-3'-(trifluoromethyl)-[1,1'-biphenyl]-4-yl)-3-methylureido)pyridine-3-sulfonate | (4-fluoro-3-(trifluoromethyl)phenyl)boronic acid (Matrix Sci.) was used in place of (4-fluoro-3-(2,2,2-trifluoroethoxy)phenyl)boronic acid in Step 1 | m/z (ESI) M + H 756.0, 758.0 |
| R | 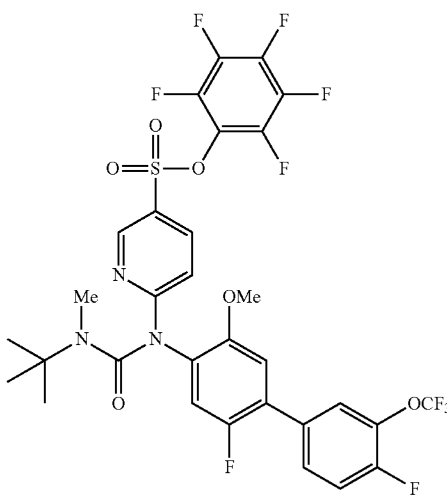 | perfluorophenyl 6-(3-(tert-butyl)-1-(2,4'-difluoro-5-methoxy-3'-(trifluoromethoxy)-[1,1'-biphenyl]-4-yl)-3-methylureido)pyridine-3-sulfonate | (4-fluoro-3-(trifluoromethoxy)phenyl)boronic acid (Afferchem) was used in place of (4-fluoro-3-(2,2,2-trifluoroethoxy)phenyl)boronic acid in Step 1 | m/z (ESI) M + H 756.2 |

Step 2: 6-(1-(2-chloro-4'-fluoro-5-methoxy-3'-(2,2,2-trifluoroethoxy)-[1,1'-biphenyl]-4-yl)-3-methylureido)-N-(pyrimidin-2-yl)pyridine-3-sulfonamide A 2 dram vial was charged with perfluorophenyl 6-(3-(tert-butyl)-1-(2-chloro-4'-fluoro-5-methoxy-3'-(2,2,2-trifluoroethoxy)-[1,1'-biphenyl]-4-yl)-3-methylureido)pyridine-3-sulfonate (0.1 g, 0.127 mmol) and 2-aminopyrimidine (0.018 g, 0.191 mmol) (or other amino heterocycle). DMSO (0.159 ml) was added to give a solution which was then diluted with THF (0.477 ml). The vial was cooled in an ice-water bath, then lithium bis(trimethylsilyl)amide (1M in THF) (0.318 ml, 0.318 mmol) was added dropwise. After 15 min LC/MS showed complete conversion and the mixture was diluted with saturated NH$_4$Cl and EtOAc. The layers were separated and the combined organic layer was dried over sodium sulfate, filtered, and concentrated. 2 mL of TFA was added to the residue and the solution was stirred for 10 min and then concentrated. The residue was dissolved in 3 ml of MeCN w/0.1% TFA, filtered through a 0.45 μm filter and purified by RP-HPLC (Gilson, 30-80% MeCN/H$_2$O w/0.1% TFA). Fractions containing the products were lyophilized to provide the TFA salt of 6-(1-(2-chloro-4'-fluoro-5-methoxy-3'-(2,2,2-trifluoroethoxy)-[1,1'-biphenyl]-4-yl)-3-methylureido)-N-(pyrimidin-2-yl)pyridine-3-sulfonamide as a white solid. Alternatively, the final compound was obtained via MPLC purification (25 g Snap Ultra, 10-100% [3:1 ethyl acetate:ethanol]:heptane) to provide the title compound. (See table 7 for analytical data).

Example 4-1

6-(1-(3'-chloro-4,5'-dimethoxy-[1,1'-biphenyl]-3-yl)-3-methylureido)-N-(isoxazol-3-yl)pyridine-3-sulfonamide Method 4

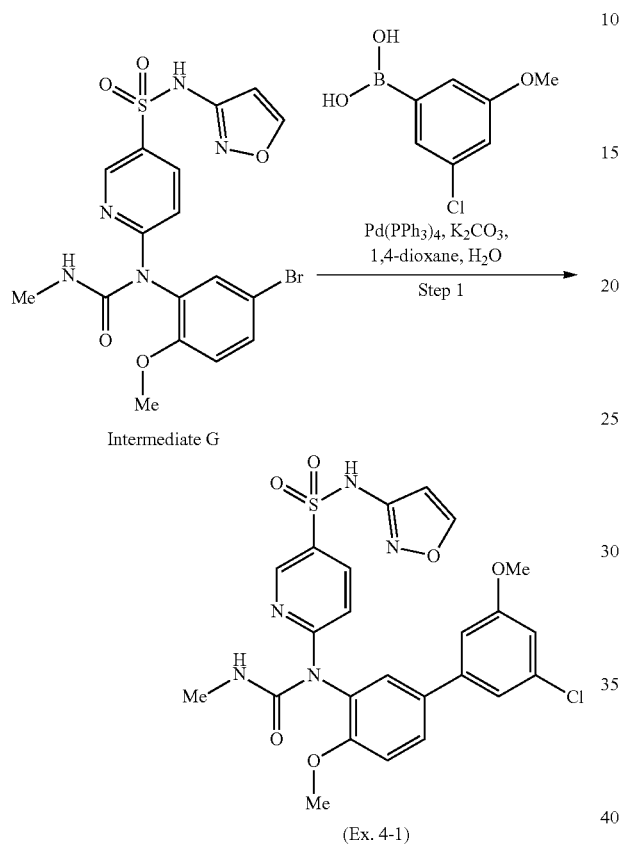

Intermediate G (Ex. 4-1)

Step1: 6-(1-(3'-chloro-4,5'-dimethoxy-[1,1'-biphenyl]-3-yl)-3-methylureido)-N-(isoxazol-3-yl)pyridine-3-sulfonamide To a vial containing 6-(1-(5-bromo-2-methoxyphenyl)-3-methylureido)-N-(isoxazol-3-yl)pyridine-3-sulfonamide (100 mg, 0.207 mmol), (3-chloro-5-methoxyphenyl)boronic acid (58 mg, 0.311 mmol), potassium carbonate (86 mg, 0.622 mmol), and tetrakis(triphenylphosphine) palladium (24 mg, 0.021 mmol) were added 1,4-dioxane (0.78 mL) and water (0.26 mL). The reaction mixture was purged under nitrogen and was then heated to 80° C. for 90 mins, until reaction complete as shown by LCMS. The reaction was cooled to RT and partitioned between saturated aqueous NH$_4$Cl and DCM. The organic phase was separated and the aqueous phase was further extracted with DCM (2×). The combined organic layers were then dried with MgSO$_4$, filtered and concentrated in vacuo. The resulting crude material was absorbed onto a plug of silica gel and purified by chromatography through a RediSep® Rf Gold R prepacked silica gel column (12 g), eluting with a gradient of 50% to 90% ethyl acetate in heptane, to provide 6-(1-(3'-chloro-4,5'-dimethoxy-[1,1'-biphenyl]-3-yl)-3-methylureido)-N-(isoxazol-3-yl)pyridine-3-sulfonamide (63.4 mg, 0.117 mmol, 56.2% yield) as white solid, (see Table 7 for analytical data).

Preparation of 2-(3-(difluoromethyl)-4-fluorophenyl)-4,4,5,5-tetramethyl-1,3,2-dioxaborolane

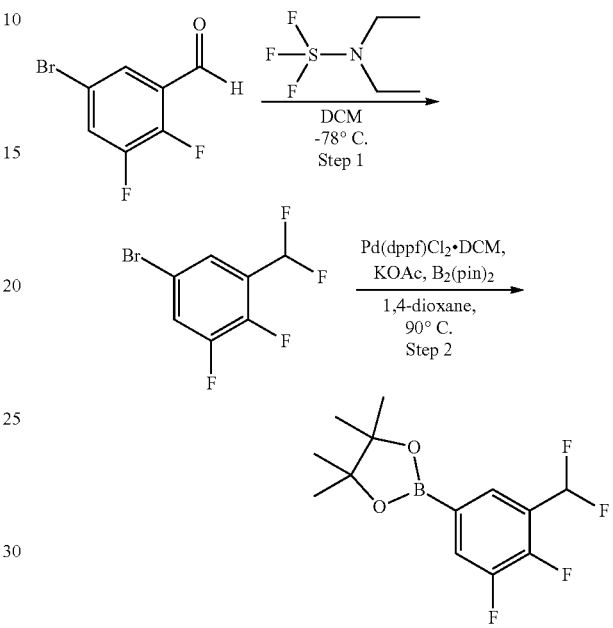

Step 1: 5-bromo-1-(difluoromethyl)-2,3-difluorobenzene

To a stirred solution of 5-bromo-2,3-difluorobenzaldehyde (10 g, 45.2 mmol) in dichloromethane (100 mL, 10.00 mL/g) cooled to −78° C. was added diethylaminosulfur trifluoride (23.91 ml, 181 mmol). The reaction mixture was allowed to warm to room temperature and stirred for 2 h. The reaction mixture was quenched with saturated NaHCO$_3$ solution and the aqueous layer was extracted with dichloromehane (2×100 ml). The organic layer was washed with brine (50 ml) and dried over Na$_2$SO4. The organic layer was filtered and concentrated under reduced pressure to afford 5-bromo-1-(difluoromethyl)-2,3-difluorobenzene (10.1 g, 41.6 mmol) as an orange oil. The material was taken crude into the next step.

Step 2: 2-(3-(difluoromethyl)-4-fluorophenyl)-4,4,5,5-tetramethyl-1,3,2-dioxaborolane To a 500-mL round-bottomed flask was added 5-bromo-1-(difluoromethyl)-2,3-difluorobenzene (10.1 g, 41.6 mmol) and Bis(pinacolato)diboron (12.67 g, 49.9 mmol) in 1,4-dioxane (150 mL, 14.85 mL/g) under N$_2$ atmosphere. Potassium acetate (12.24 g, 125 mmol) was added to the reaction mixture and the reaction mixture was sparged with N$_2$ for 15 min. 1,1'-bis(diphenylphosphino)ferrocene palladium(II)dichloride dichloromethane adduct (3.39 g, 4.16 mmol) was added to the reaction mixture and the reaction mass was heated at 90° C. for 2 h. The reaction mass was filtered through celite and washed with ethyl acetate (500 ml). The filtrate was concentrated under reduced pressure to afford a black oil. The crude material was absorbed onto a plug of silica gel and purified by chromatography through a RediSep® Rf Gold® pre-packed silica gel column (120 g), eluting with a gradient of 0% to 10% EtOAc in hexane, to provide 2-(4-(difluoromethyl)-3-fluorophenyl)-4,4,5,5-tetramethyl-1,3,2-dioxaborolane (5.8 g, 48.1% yield) as a yellow oil. m/z (ESI, neg, formic acid modifier)=253.0 (M+formate, −pinacol)

TABLE 5

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 1-1 | 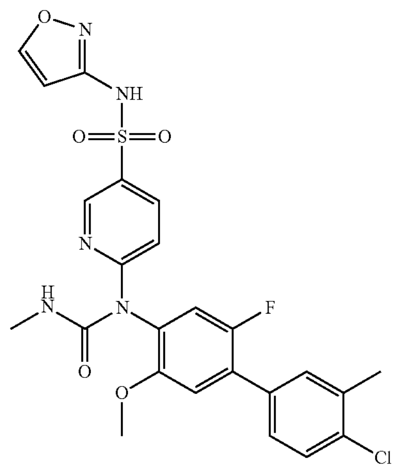 [SMILES: CNC(=O)N(c1ccc(S(=O)(=O)Nc2ccon2)cn1)c1cc(F)c(-c2ccc(Cl)c(C)c2)cc1OC] | 6-((4'-chloro-2-fluoro-5-methoxy-3'-methyl-4-biphenylyl)(methylcarbamoyl)amino)-N-3-isoxazolyl-3-pyridinesulfonamide | 1 | A | (4-chloro-3-methylphenyl)boronic acid |
| 1-2 | 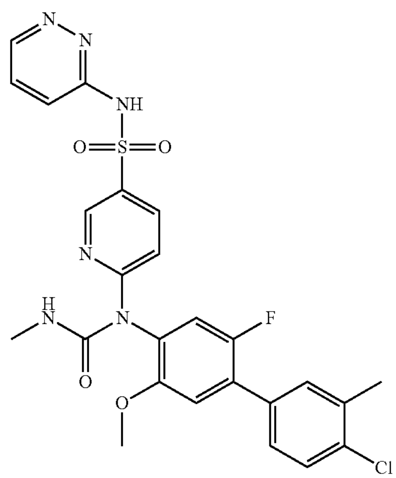 [SMILES: CNC(=O)N(c1ccc(S(=O)(=O)Nc2cccnn2)cn1)c1cc(F)c(-c2ccc(Cl)c(C)c2)cc1OC] | 6-((4'-chloro-2-fluoro-5-methoxy-3'-methyl-4-biphenylyl)(methylcarbamoyl)amino)-N-3-pyridazinyl-3-pyridinesulfonamide | 1 | H | (4-chloro-3-methylphenyl)boronic acid |
| 1-3 | 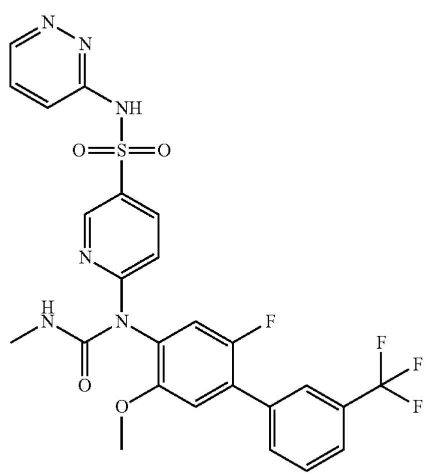 [SMILES: CNC(=O)N(c1ccc(S(=O)(=O)Nc2cccnn2)cn1)c1cc(F)c(-c2cccc(C(F)(F)F)c2)cc1OC] | 6-((2-fluoro-5-methoxy-3'-(trifluoromethyl)-4-biphenylyl)(methylcarbamoyl)amino)-N-3-pyridazinyl-3-pyridinesulfonamide | 1 | H | (3-(trifluoromethyl)phenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M stands for starting material, for example, S.M. A is Intermediate A.

| Ex. # | Chemical Structure | Name | Mtd | S.M | Reagent |
|---|---|---|---|---|---|
| 1-4 | 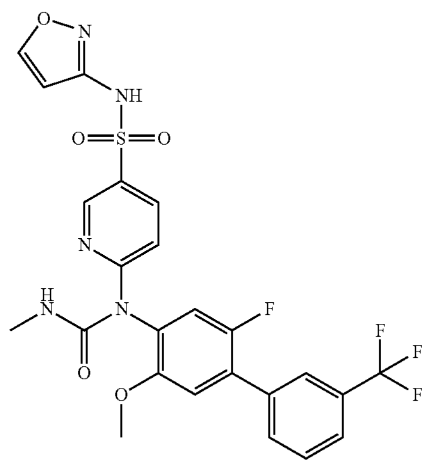 [SMILES: CNC(=O)N(c1ccc(S(=O)(=O)Nc2ccon2)cn1)c1cc(F)c(-c2cccc(C(F)(F)F)c2)cc1OC] | 6-((2-fluoro-5-methoxy-3'-(trifluoromethyl)-4-biphenylyl)(methyl-carbamoyl)amino)-N-3-isoxazolyl-3-pyridinesulfonamide | 1 | A | (3-(trifluoromethyl)phenyl)boronic acid |
| 1-5 | 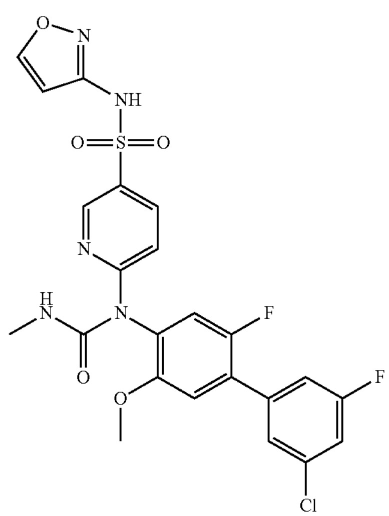 [SMILES: CNC(=O)N(c1ccc(S(=O)(=O)Nc2ccon2)cn1)c1cc(F)c(-c2cc(F)cc(Cl)c2)cc1OC] | 6-((3'-chloro-2,5'-difluoro-5-methoxy-4-biphenylyl)(methylcarbamoyl)amino)-N-3-isoxazolyl-3-pyridinesulfonamide | 1 | A | (3-chloro-5-fluorophenyl)boronic acid |
| 1-6 | 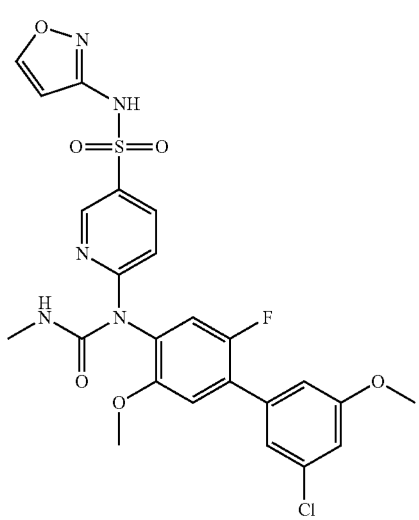 | 6-((3'-chloro-2-fluoro-5,5'-dimethoxy-4-biphenylyl)(methyl-carbamoyl)amino)-N-3-isoxazolyl-3-pyridinesulfonamide | 1 | A | (3-chloro-5-methoxyphenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 1-7 | 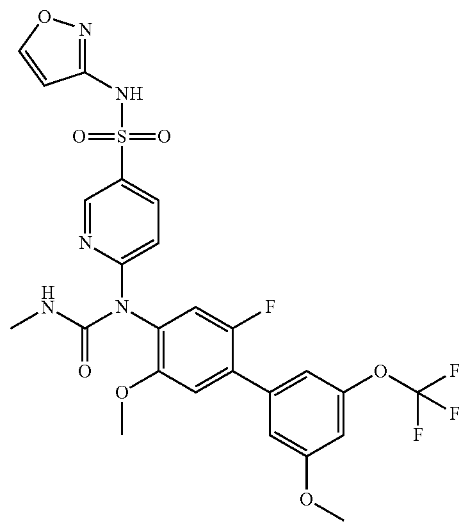 [SMILES: CNC(=O)N(c1ccc(S(=O)(=O)Nc2ccon2)cn1)c1cc(F)c(-c2cc(OC)cc(OC(F)(F)F)c2)cc1OC] | 6-((2-fluoro-3',5-dimethoxy-5'-(trifluoromethoxy)-4-biphenylyl)(methyl-carbamoyl)amino)-N-3-isoxazolyl-3-pyridinesulfonamide | 1 | A | (3-methoxy-5-(trifluoromethoxy)phenyl)boronic acid |
| 1-8 | 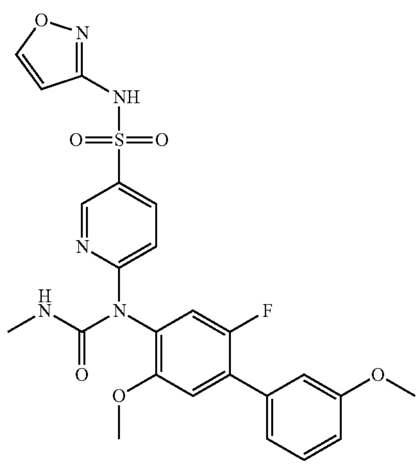 | 6-((2-fluoro-3',5-dimethoxy-4-biphenylyl)(methyl-carbamoyl)amino)-N-3-isoxazolyl-3-pyridinesulfonamide | 1 | A | 3-methoxyphenyl-boronic acid |
| 1-9 | 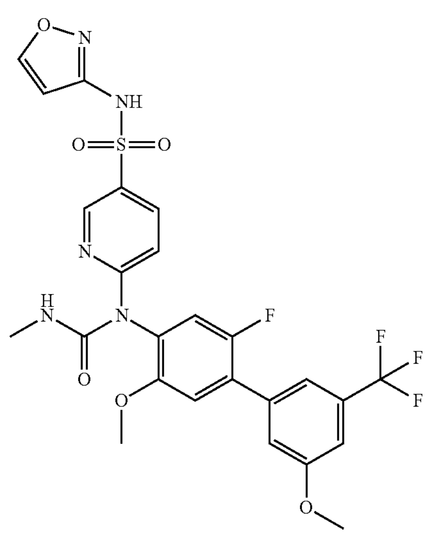 [SMILES: CNC(=O)N(c1ccc(S(=O)(=O)Nc2ccon2)cn1)c1cc(F)c(-c2cc(OC)cc(C(F)(F)F)c2)cc1OC] | 6-((2-fluoro-3',5-dimethoxy-5'-(trifluoromethyl)-4-biphenylyl)(methyl-carbamoyl)amino)-N-3-isoxazolyl-3-pyridinesulfonamide | 1 | A | 3-methoxy-5-(trifluoromethyl)phenylboronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 1-10 | 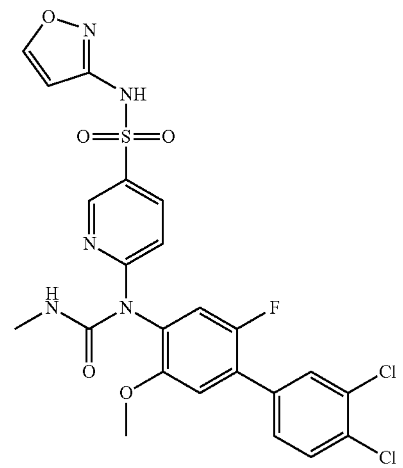 [SMILES: CNC(=O)N(c1ccc(S(=O)(=O)Nc2ccon2)cn1)c1cc(F)c(-c2ccc(Cl)c(Cl)c2)cc1OC] | 6-((3',4'-dichloro-2-fluoro-5-methoxy-4-biphenylyl)(methyl-carbamoyl)amino)-N-3-isoxazolyl-3-pyridinesulfonamide | 1 | A | 3,4-dichlorophenyl-boronic acid |
| 1-11 | 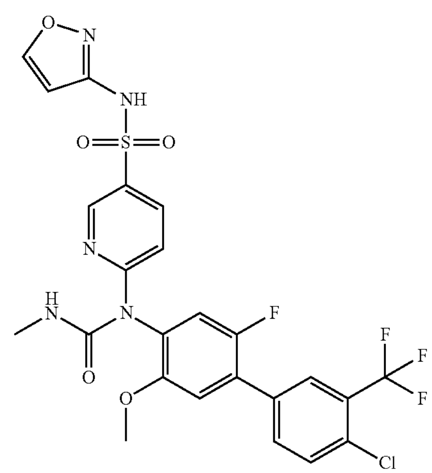 [SMILES: CNC(=O)N(c1ccc(S(=O)(=O)Nc2ccon2)cn1)c1cc(F)c(-c2ccc(Cl)c(C(F)(F)F)c2)cc1OC] | 6-((4'-chloro-2-fluoro-5-methoxy-3'-(trifluoromethyl)-4-biphenylyl)(methyl-carbamoyl)amino)-N-3-isoxazolyl-3-pyridinesulfonamide | 1 | A | 4-chloro-3-trifluoromethyl-phenylboronic acid |
| 1-12 | 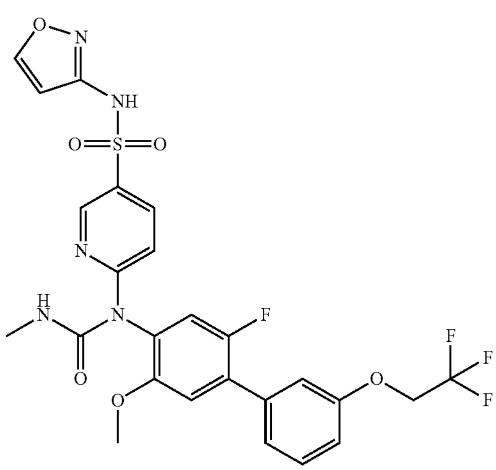 [SMILES: CNC(=O)N(c1ccc(S(=O)(=O)Nc2ccon2)cn1)c1cc(F)c(-c2cccc(OCC(F)(F)F)c2)cc1OC] | 6-((2-fluoro-5-methoxy-3'-(2,2,2-trifluoroethoxy)-4-biphenylyl)(methyl-carbamoyl)amino)-N-3-isoxazolyl-3-pyridinesulfonamide | 1 | A | 3-(trifluoromethoxy)phenylboronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 1-13 | 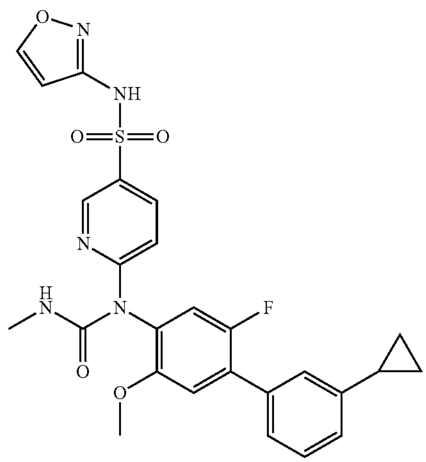 [SMILES: CNC(=O)N(c1ccc(S(=O)(=O)Nc2ccon2)cn1)c1cc(F)c(-c2cccc(C3CC3)c2)cc1OC] | 6-((3'-cyclopropyl-2-fluoro-5-methoxy-4-biphenylyl)(methyl-carbamoyl)amino)-N-3-isoxazolyl-3-pyridinesulfonamide | 1 | A | 2-(3-cyclopropyl-phenyl)-4,4,5,5-tetramethyl-[1,3,2]dioxaborolane |
| 1-14 | 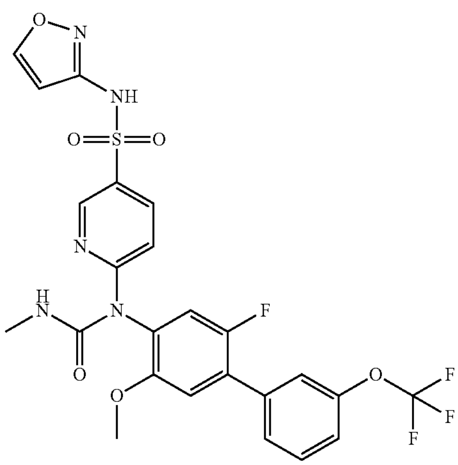 [SMILES: CNC(=O)N(c1ccc(S(=O)(=O)Nc2ccon2)cn1)c1cc(F)c(-c2cccc(OC(F)(F)F)c2)cc1OC] | 6-((2-fluoro-5-methoxy-3'-(trifluoromethoxy)-4-biphenylyl)(methyl-carbamoyl)amino)-N-3-isoxazolyl-3-pyridinesulfonamide | 1 | A | 3-(trifluoromethoxy)phenylboronic acid |
| 1-15 | 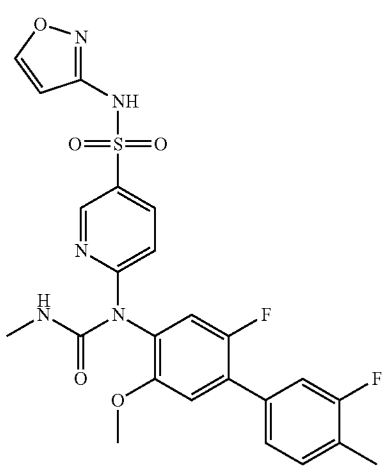 [SMILES: CNC(=O)N(c1ccc(S(=O)(=O)Nc2ccon2)cn1)c1cc(F)c(-c2ccc(C)c(F)c2)cc1OC] | 6-((2,3'-difluoro-5-methoxy-4'-methyl-4-biphenylyl)(methylcarbamoyl)amino)-N-3-isoxazolyl-3-pyridinesulfonamide | 1 | A | (3-fluoro-4-methylphenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 1-16 | 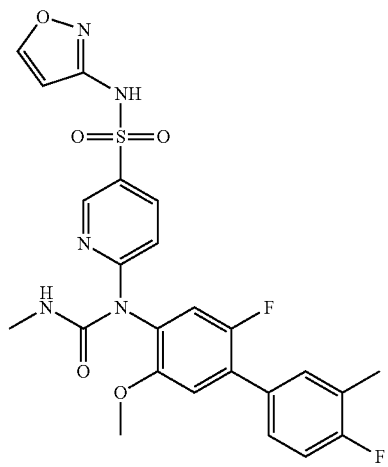 [SMILES: CNC(=O)N(c1ccc(S(=O)(=O)Nc2ccon2)cn1)c1cc(F)c(-c2ccc(F)c(C)c2)cc1OC] | 6-((2,4'-difluoro-5-methoxy-3'-methyl-4-biphenylyl)(methylcarbamoyl)amino)-N-3-isoxazolyl-3-pyridinesulfonamide | 1 | A | (4-fluoro-3-methylphenyl)boronic acid |
| 1-17 | 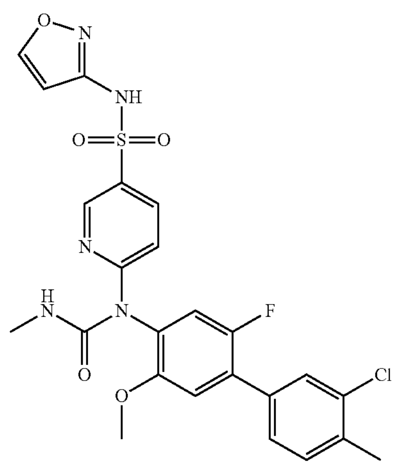 [SMILES: CNC(=O)N(c1ccc(S(=O)(=O)Nc2ccon2)cn1)c1cc(F)c(-c2ccc(C)c(Cl)c2)cc1OC] | 6-((3'-chloro-2-fluoro-5-methoxy-4'-methyl-4-biphenylyl)(methylcarbamoyl)amino)-N-3-isoxazolyl-3-pyridinesulfonamide | 1 | A | (3-chloro-4-methylphenyl)boronic acid |
| 1-18 | 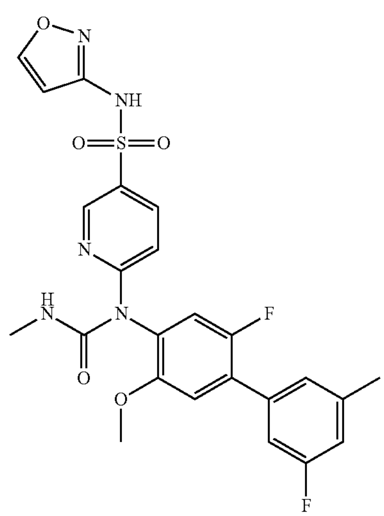 | 6-((2,3'-difluoro-5-methoxy-5'-methyl-4-biphenylyl)(methylcarbamoyl)amino)-N-3-isoxazolyl-3-pyridinesulfonamide | 1 | A | (3-fluoro-5-methylphenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 1-19 | 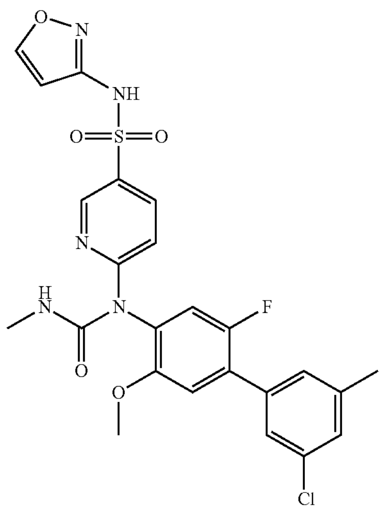 | 6-((3'-chloro-2-fluoro-5-methoxy-5'-methyl-4-biphenylyl)(methyl-carbamoyl)amino)-N-3-isoxazolyl-3-pyridinesulfonamide | 1 | A | (3-chloro-5-methylphenyl) boronic acid |
| 1-20 | 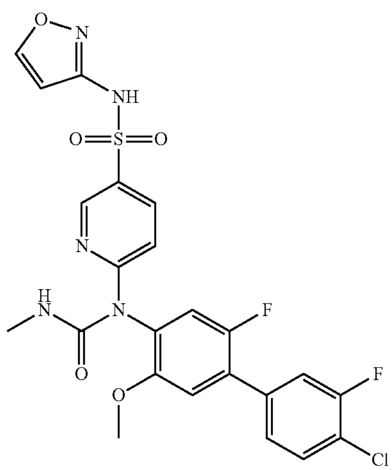 [SMILES: CNC(=O)N(c1ccc(S(=O)(=O)Nc2ccon2)cn1)c1cc(F)c(-c2ccc(Cl)c(F)c2)cc1OC] | 6-((4'-chloro-2,3'-difluoro-5-methoxy-4-biphenylyl)(methylcarbamoyl)amino)-N-3-isoxazolyl-3-pyridinesulfonamide | 1 | A | (4-chloro-3-fluorophenyl) boronic acid |
| 1-21 | 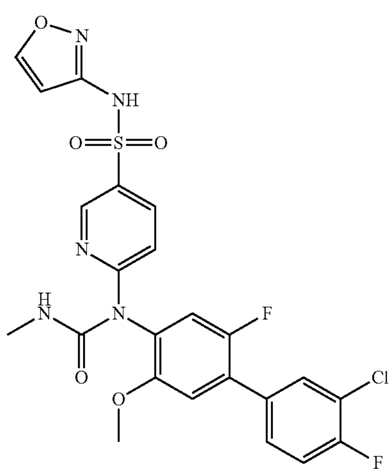 [SMILES: CNC(=O)N(c1ccc(S(=O)(=O)Nc2ccon2)cn1)c1cc(F)c(-c2ccc(F)c(Cl)c2)cc1OC] | 6-((3'-chloro-2,4'-difluoro-5-methoxy-4-biphenylyl)(methylcarbamoyl)amino)-N-3-isoxazolyl-3-pyridinesulfonamide | 1 | A | (3-chloro-4-fluorophenyl) boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 1-22 | 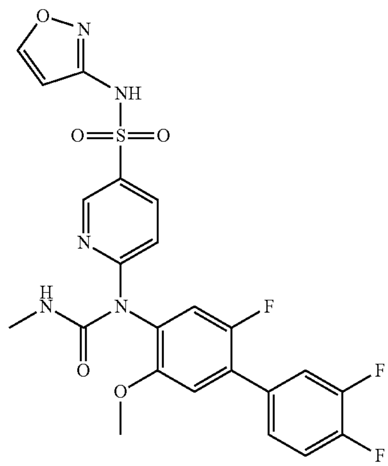 [SMILES: CNC(=O)N(c1ccc(S(=O)(=O)Nc2ccon2)cn1)c1cc(F)c(-c2ccc(F)c(F)c2)cc1OC] | N-3-isoxazolyl-6-((methylcarbamoyl)(2,3',4'-trifluoro-5-methoxy-4-biphenylyl)amino)-3-pyridinesulfonamide | 1 | A | (3,4-difluorophenyl)boronic acid |
| 1-23 | 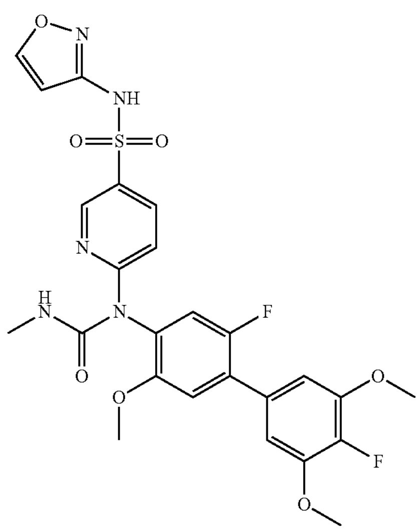 | 6-((2,4'-difluoro-3',5,5'-trimethoxy-4-biphenylyl)(methyl-carbamoyl)amino)-N-3-isoxazolyl-3-pyridinesulfonamide | 1 | A | (4-fluoro-3,5-dimethoxyphenyl)boronic acid |
| 1-24 | 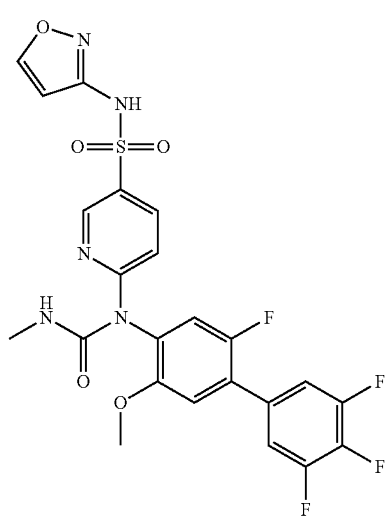 [SMILES: CNC(=O)N(c1ccc(S(=O)(=O)Nc2ccon2)cn1)c1cc(F)c(-c2cc(F)c(F)c(F)c2)cc1OC] | N-3-isoxazolyl-6-((methylcarbamoyl)(2,3',4',5'-tetrafluoro-5-methoxy-4-biphenylyl)amino)-3-pyridinesulfonamide | 1 | A | (3,4,5-trifluorophenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 1-25 | 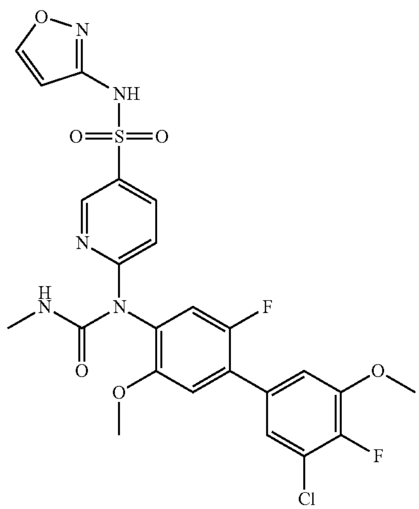 | 6-((3'-chloro-2,4'-difluoro-5,5'-dimethoxy-4-biphenylyl)(methyl-carbamoyl)amino)-N-3-isoxazolyl-3-pyridinesulfonamide | 1 | A | (3-chloro-4-fluoro-5-methoxyphenyl)boronic acid |
| 1-26 | 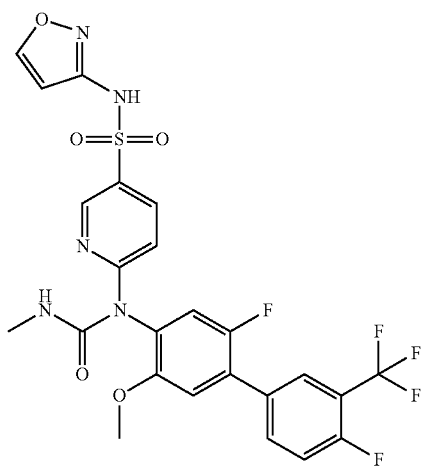 [SMILES: CNC(=O)N(c1ccc(S(=O)(=O)Nc2ccon2)cn1)c1cc(F)c(-c2ccc(F)c(C(F)(F)F)c2)cc1OC] | 6-((2,4'-difluoro-5-methoxy-3'-(trifluoromethyl)-4-biphenylyl)(methyl-carbamoyl)amino)-N-3-isoxazolyl-3-pyridinesulfonamide | 1 | A | (4-fluoro-3-(trifluoromethyl)phenyl)boronic acid |
| 1-27 | 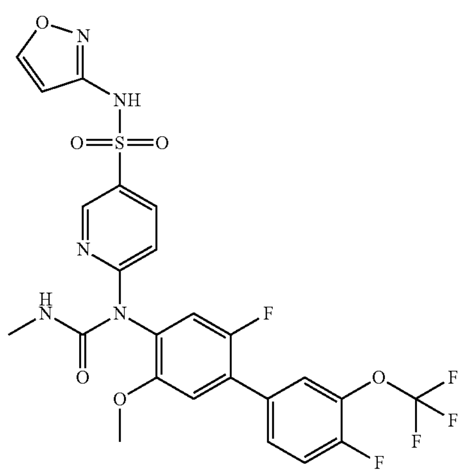 [SMILES: CNC(=O)N(c1ccc(S(=O)(=O)Nc2ccon2)cn1)c1cc(F)c(-c2ccc(F)c(OC(F)(F)F)c2)cc1OC] | 6-((2,4'-difluoro-5-methoxy-3'-(trifluoromethoxy)-4-biphenylyl)(methyl-carbamoyl)amino)-N-3-isoxazolyl-3-pyridinesulfonamide | 1 | A | (4-fluoro-3-(trifluoromethoxy)phenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 1-28 | 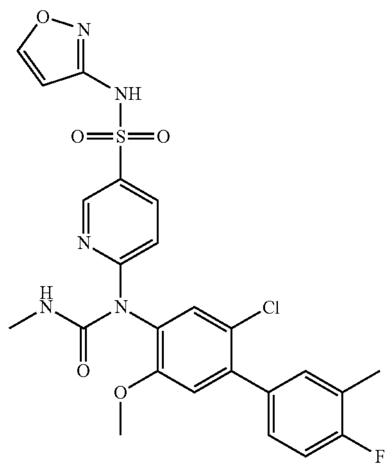 [SMILES: CNC(=O)N(c1ccc(S(=O)(=O)Nc2ccon2)cn1)c1cc(Cl)c(-c2ccc(F)c(C)c2)cc1OC] | 6-((2-chloro-4'-fluoro-5-methoxy-3'-methyl-4-biphenylyl)(methyl-carbamoyl)amino)-N-3-isoxazolyl-3-pyridinesulfonamide | 1 | B | (4-fluoro-3-methylphenyl)boronic acid |
| 1-29 | 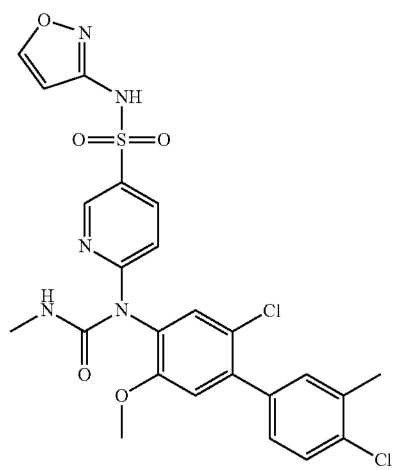 [SMILES: CNC(=O)N(c1ccc(S(=O)(=O)Nc2ccon2)cn1)c1cc(Cl)c(-c2ccc(Cl)c(C)c2)cc1OC] | 6-((2,4'-dichloro-5-methoxy-3'-methyl-4-biphenylyl)(methylcarbamoyl)amino)-N-3-isoxazolyl-3-pyridinesulfonamide | 1 | B | (4-chloro-3-methylphenyl)boronic acid |
| 1-30 | 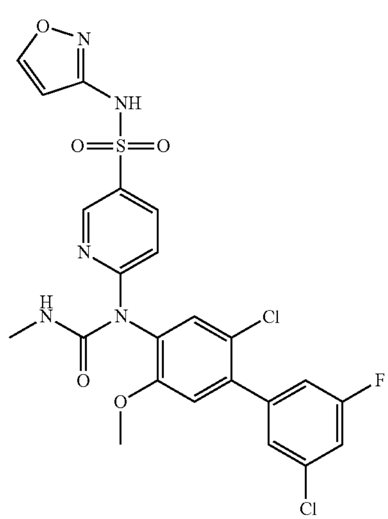 [SMILES: CNC(=O)N(c1ccc(S(=O)(=O)Nc2ccon2)cn1)c1cc(Cl)c(-c2cc(F)cc(Cl)c2)cc1OC] | 6-((2,3'-dichloro-5'-fluoro-5-methoxy-4-biphenylyl)(methyl-carbamoyl)amino)-N-3-isoxazolyl-3-pyridinesulfonamide | 1 | B | (3-chloro-5-fluorophenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 1-31 | 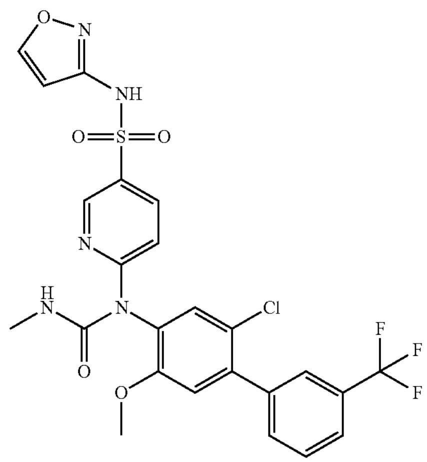 [SMILES: CNC(=O)N(c1ccc(S(=O)(=O)Nc2ccon2)cn1)c1cc(Cl)c(-c2cccc(C(F)(F)F)c2)cc1OC] | 6-((2-chloro-5-methoxy-3'-(trifluoromethyl)-4-biphenylyl)(methyl-carbamoyl)amino)-N-3-isoxazolyl-3-pyridinesulfonamide | 1 | B | (3-(trifluoromethyl)phenyl)boronic acid |
| 1-32 | 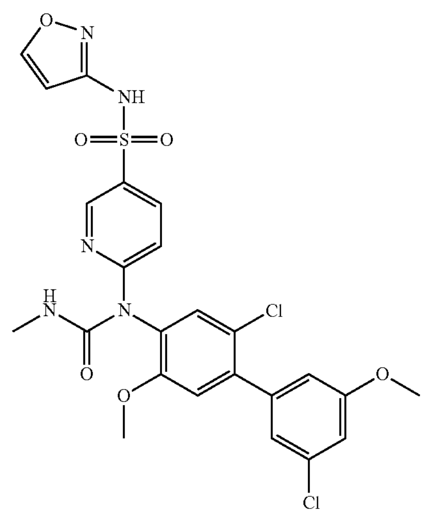 | 6-((2,3'-dichloro-5,5'-dimethoxy-4-biphenylyl)(methyl-carbamoyl)amino)-N-3-isoxazolyl-3-pyridinesulfonamide | 1 | B | (3-chloro-5-methoxyphenyl)boronic acid |
| 1-33 | 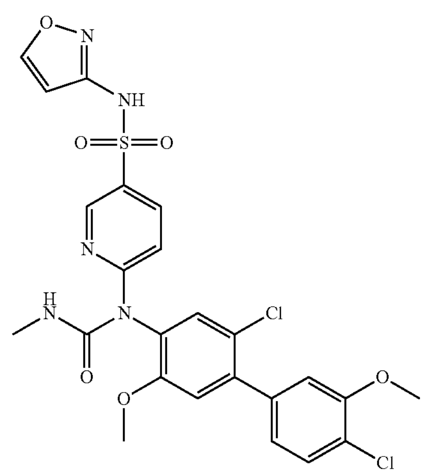 | 6-((2,4'-dichloro-3',5-dimethoxy-4-biphenylyl)(methyl-carbamoyl)amino)-N-3-isoxazolyl-3-pyridinesulfonamide | 1 | B | (4-chloro-3-methoxyphenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M stands for starting material, for example, S.M. A is Intermediate A.

| Ex. # | Chemical Structure | Name | Mtd | S.M | Reagent |
|---|---|---|---|---|---|
| 1-34 | 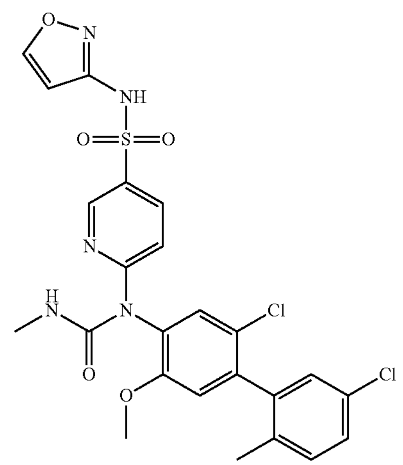 [SMILES: CNC(=O)N(c1ccc(S(=O)(=O)Nc2ccon2)cn1)c1cc(Cl)c(-c2cc(Cl)ccc2C)cc1OC] | 6-((2,5'-dichloro-5-methoxy-2'-methyl-4-biphenylyl)(methylcarbamoyl)amino)-N-3-isoxazolyl-3-pyridinesulfonamide | 1 | B | (5-chloro-2-methylphenyl)boronic acid |
| 1-35 | 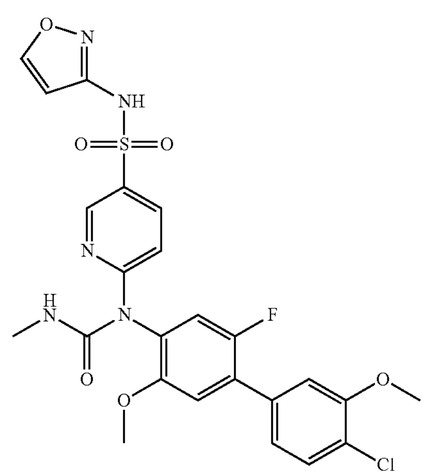 | 6-((4'-chloro-2-fluoro-3',5-dimethoxy-4-biphenylyl)(methylcarbamoyl)amino)-N-3-isoxazolyl-3-pyridinesulfonamide | 1 | B | (4-chloro-3-methoxyphenyl)boronic acid |
| 1-36 | 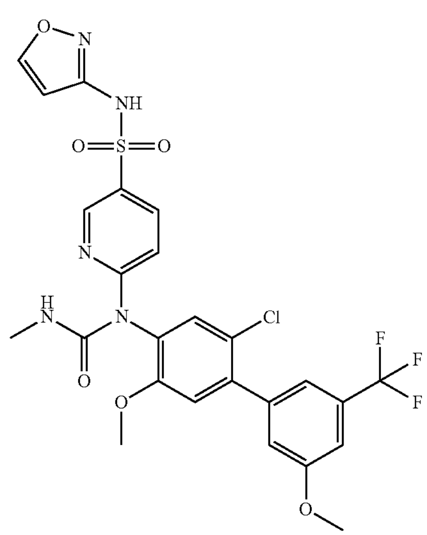 [SMILES: CNC(=O)N(c1ccc(S(=O)(=O)Nc2ccon2)cn1)c1cc(Cl)c(-c2cc(OC)cc(C(F)(F)F)c2)cc1OC] | 6-((2-chloro-3',5-dimethoxy-5'-(trifluoromethyl)-4-biphenylyl)(methylcarbamoyl)amino)-N-3-isoxazolyl-3-pyridinesulfonamide | 1 | B | (3-methoxy-5-(trifluoromethyl)phenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 1-37 | 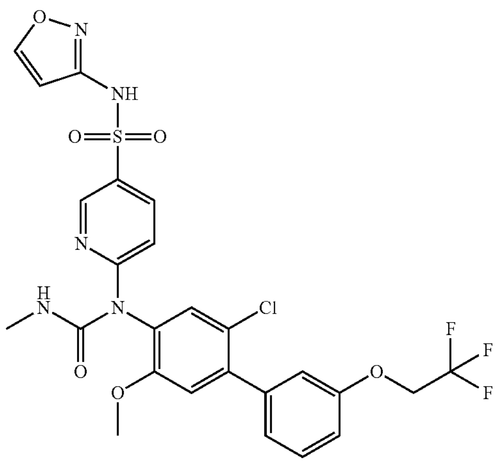 [SMILES: CNC(=O)N(c1ccc(S(=O)(=O)Nc2ccon2)cn1)c1cc(Cl)c(-c2cccc(OCC(F)(F)F)c2)cc1OC] | 6-((2-chloro-5-methoxy-3'-(2,2,2-trifluoroethoxy)-4-biphenylyl)(methyl-carbamoyl)amino)-N-3-isoxazolyl-3-pyridinesulfonamide | 1 | B | 3-(2,2,2-trifluoroethoxy)phenylboronic acid |
| 1-38 | 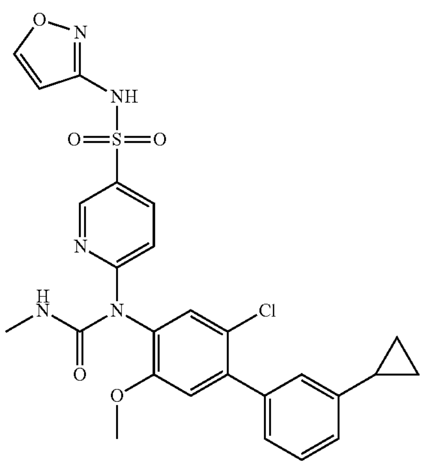 [SMILES: CNC(=O)N(c1ccc(S(=O)(=O)Nc2ccon2)cn1)c1cc(Cl)c(-c2cccc(C3CC3)c2)cc1OC] | 6-((2-chloro-3'-cyclopropyl-5-methoxy-4-biphenylyl)(methyl-carbamoyl)amino)-N-3-isoxazolyl-3-pyridinesulfonamide | 1 | B | 2-(3-cyclopropyl-phenyl)-4,4,5,5-tetramethyl-[1,3,2]dioxaborolane |
| 1-39 | 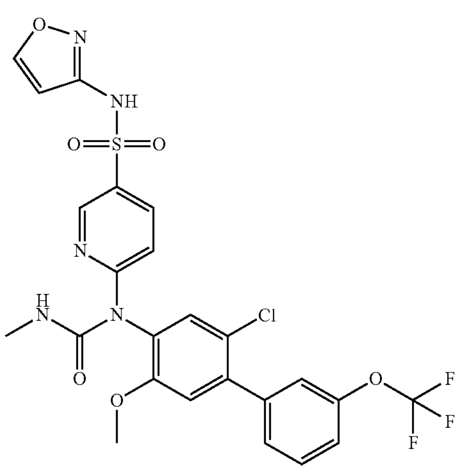 [SMILES: CNC(=O)N(c1ccc(S(=O)(=O)Nc2ccon2)cn1)c1cc(Cl)c(-c2cccc(OC(F)(F)F)c2)cc1OC] | 6-((2-chloro-5-methoxy-3'-(trifluoromethoxy)-4-biphenylyl)(methylcarbamoyl)amino)-N-3-isoxazolyl-3-pyridinesulfonamide | 1 | B | 3-(trifluoromethoxy)phenylboronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 1-40 | 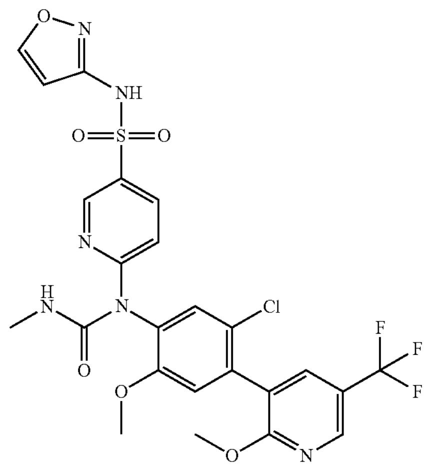 [SMILES: CNC(=O)N(c1ccc(S(=O)(=O)Nc2ccon2)cn1)c1cc(Cl)c(-c2cc(C(F)(F)F)cnc2OC)cc1OC] | 6-((5-chloro-2-methoxy-4-(2-methoxy-5-(trifluoromethyl)-3-pyridinyl)phenyl)(methylcarbamoyl)amino)-N-3-isoxazolyl-3-pyridinesulfonamide | 1 | B | (2-methoxy-5-(trifluoromethyl)pyridin-3-yl)boronic acid |
| 1-41 | 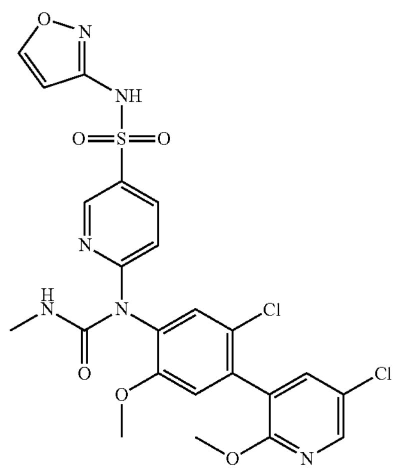 [SMILES: CNC(=O)N(c1ccc(S(=O)(=O)Nc2ccon2)cn1)c1cc(Cl)c(-c2cc(Cl)cnc2OC)cc1OC] | 6-((5-chloro-4-(5-chloro-2-methoxy-3-pyridinyl)-2-methoxyphenyl)(methylcarbamoyl)amino)-N-3-isoxazolyl-3-pyridinesulfonamide | 1 | B | (5-chloro-2-methoxypyridin-3-yl)boronic acid |
| 1-42 | 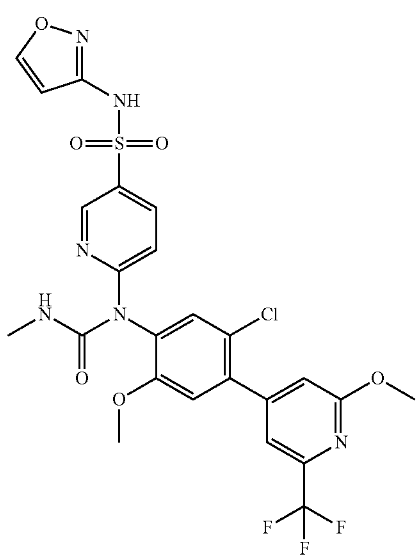 | 6-((5-chloro-2-methoxy-4-(2-methoxy-6-(trifluoromethyl)-4-pyridinyl)phenyl)(methylcarbamoyl)amino)-N-3-isoxazolyl-3-pyridinesulfonamide | 1 | B | (2-methoxy-6-(trifluoromethyl)pyridin-4-yl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 1-43 | 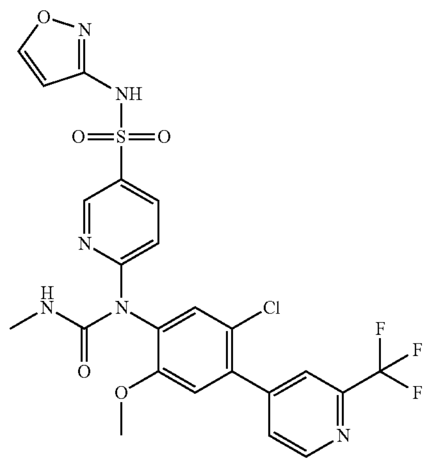 [SMILES: CNC(=O)N(c1ccc(S(=O)(=O)Nc2ccon2)cn1)c1cc(Cl)c(-c2ccnc(C(F)(F)F)c2)cc1OC] | 6-((5-chloro-2-methoxy-4-(2-(trifluoromethyl)-4-pyridinyl)phenyl)(methylcarbamoyl)amino)-N-3-isoxazolyl-3-pyridinesulfonamide | 1 | B | (2-(trifluoromethyl)pyridin-4-yl)boronic acid |
| 1-44 | 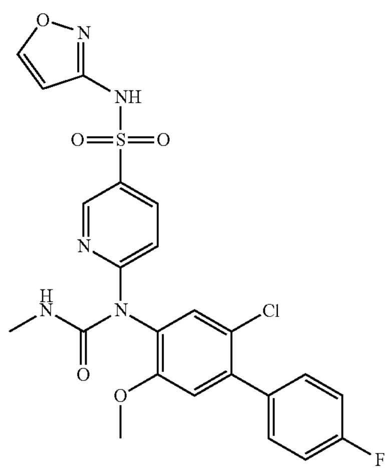 [SMILES: CNC(=O)N(c1ccc(S(=O)(=O)Nc2ccon2)cn1)c1cc(Cl)c(-c2ccc(F)cc2)cc1OC] | 6-((2-chloro-4'-fluoro-5-methoxy-4-biphenylyl)(methylcarbamoyl)amino)-N-3-isoxazolyl-3-pyridinesulfonamide | 1 | B | (4-fluorophenyl)boronic acid |
| 1-45 | 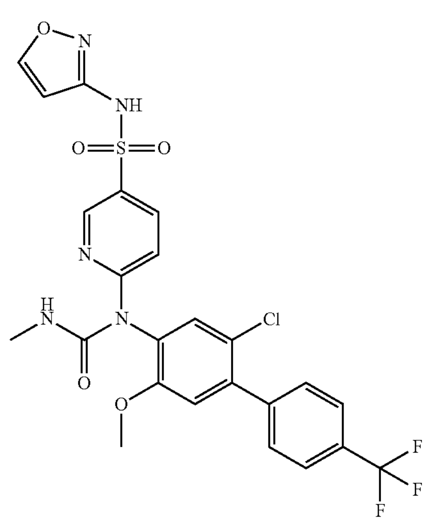 [SMILES: CNC(=O)N(c1ccc(S(=O)(=O)Nc2ccon2)cn1)c1cc(Cl)c(-c2ccc(C(F)(F)F)cc2)cc1OC] | 6-((2-chloro-5-methoxy-4'-(trifluoromethyl)-4-biphenylyl)(methylcarbamoyl)amino)-N-3-isoxazolyl-3-pyridinesulfonamide | 1 | B | (4-(trifluoromethyl)phenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 1-46 | 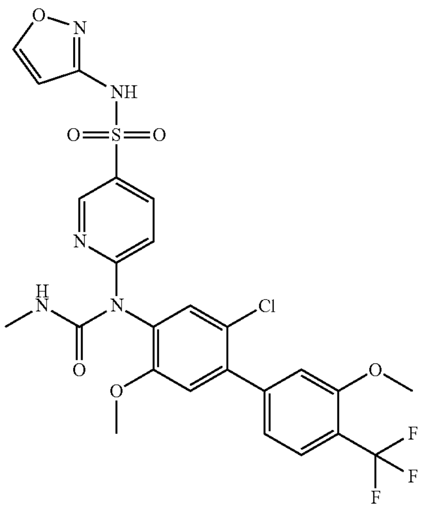 [SMILES: CNC(=O)N(c1ccc(S(=O)(=O)Nc2ccon2)cn1)c1cc(Cl)c(-c2ccc(C(F)(F)F)c(OC)c2)cc1OC] | 6-((2-chloro-3',5-dimethoxy-4'-(trifluoromethyl)-4-biphenylyl)(methyl-carbamoyl)amino)-N-3-isoxazolyl-3-pyridinesulfonamide | 1 | B | (3-methoxy-4-(trifluoromethyl)phenyl)boronic acid |
| 1-47 | 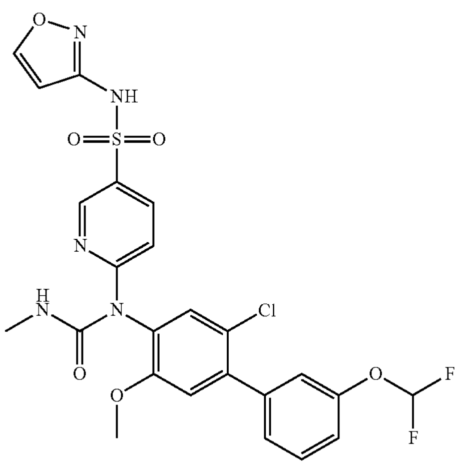 [SMILES: CNC(=O)N(c1ccc(S(=O)(=O)Nc2ccon2)cn1)c1cc(Cl)c(-c2cccc(OC(F)F)c2)cc1OC] | 6-((2-chloro-3'-(difluoromethoxy)-5-methoxy-4-biphenylyl)(methyl-carbamoyl)amino)-N-3-isoxazolyl-3-pyridinesulfonamide | 1 | B | (3-(difluoromethoxy)phenyl)boronic acid |
| 1-48 | 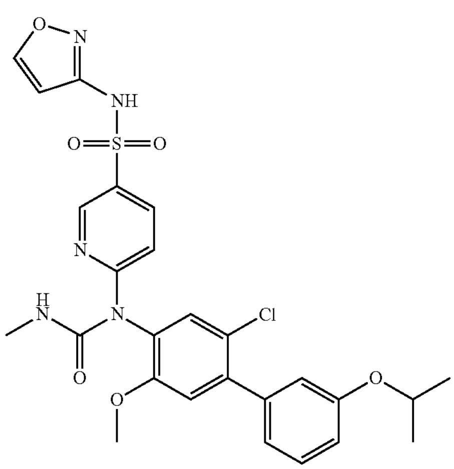 [SMILES: CNC(=O)N(c1ccc(S(=O)(=O)Nc2ccon2)cn1)c1cc(Cl)c(-c2cccc(OC(C)C)c2)cc1OC] | 6-((2-chloro-5-methoxy-3'-(1-methylethoxy)-4-biphenylyl)(methyl-carbamoyl)amino)-N-3-isoxazolyl-3-pyridinesulfonamide | 1 | B | (3-isopropoxy-phenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M stands for starting material, for example, S.M. A is Intermediate A.

| Ex. # | Chemical Structure | Name | Mtd | S.M | Reagent |
|---|---|---|---|---|---|
| 1-49 | 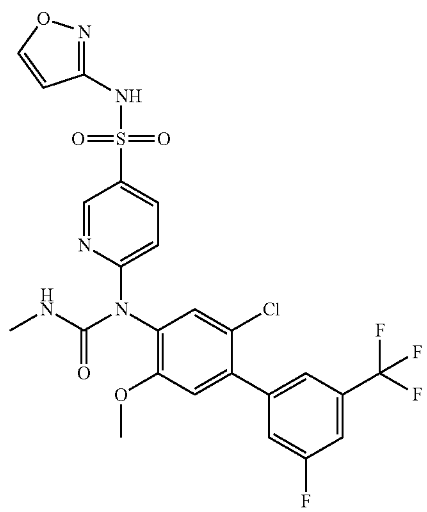 [SMILES: CNC(=O)N(c1ccc(S(=O)(=O)Nc2ccon2)cn1)c1cc(Cl)c(-c2cc(F)cc(C(F)(F)F)c2)cc1OC] | 6-((2-chloro-3'-fluoro-5-methoxy-5'-(trifluoromethyl)-4-biphenylyl)(methylcarbamoyl)amino)-N-3-isoxazolyl-3-pyridinesulfonamide | 1 | B | (3-fluoro-5-(trifluoromethyl)phenyl)boronic acid |
| 1-50 | 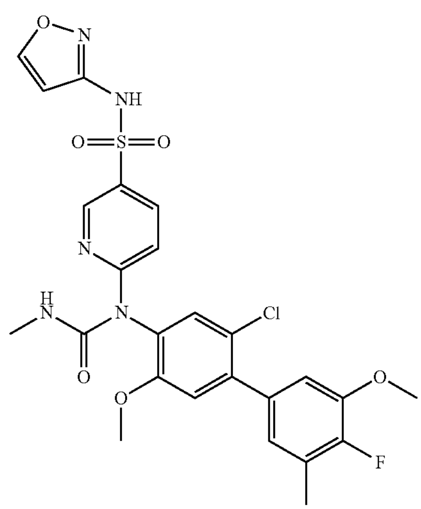 | 6-((2-chloro-4'-fluoro-3',5-dimethoxy-5'-methyl-4-biphenylyl)(methylcarbamoyl)amino)-N-3-isoxazolyl-3-pyridinesulfonamide | 1 | B | (4-fluoro-3-methoxy-5-methylphenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 1-51 | 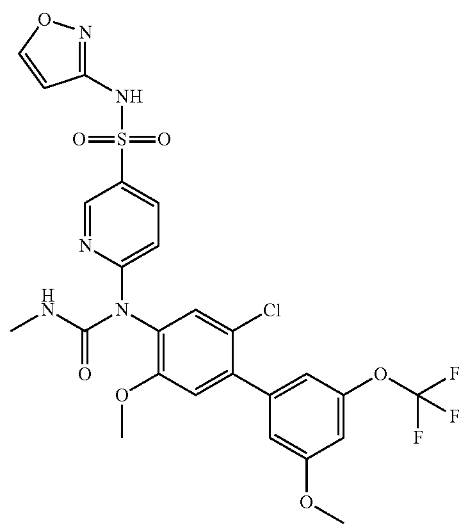 [SMILES: CNC(=O)N(c1ccc(S(=O)(=O)Nc2ccon2)cn1)c1cc(Cl)c(-c2cc(OC)cc(OC(F)(F)F)c2)cc1OC] | 6-((2-chloro-3',5-dimethoxy-5'-(trifluoromethoxy)-4-biphenylyl)(methylcarbamoyl)amino)-N-3-isoxazolyl-3-pyridinesulfonamide | 1 | B | (3-methoxy-5-(trifluoromethoxy)phenyl)boronic acid |
| 1-52 | 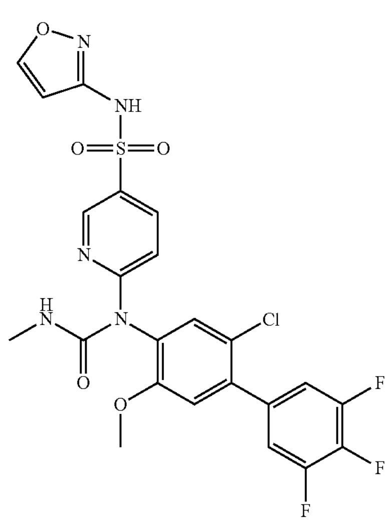 [SMILES: CNC(=O)N(c1ccc(S(=O)(=O)Nc2ccon2)cn1)c1cc(Cl)c(-c2cc(F)c(F)c(F)c2)cc1OC] | 6-((2-chloro-3',4',5'-trifluoro-5-methoxy-4-biphenylyl)(methylcarbamoyl)amino)-N-3-isoxazolyl-3-pyridinesulfonamide | 1 | B | (3,4,5-trifluorophenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 1-53 | 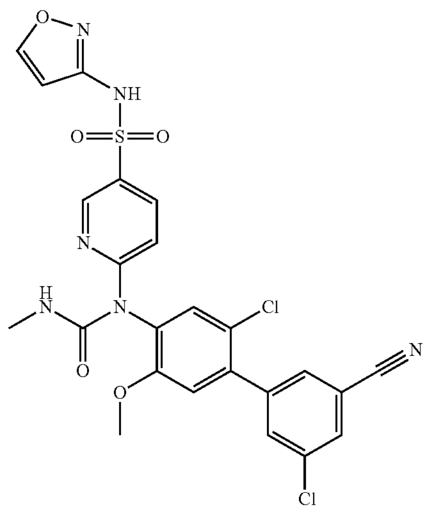 [SMILES: CNC(=O)N(c1ccc(S(=O)(=O)Nc2ccon2)cn1)c1cc(Cl)c(-c2cc(Cl)cc(C#N)c2)cc1OC] | 6-((2,3'-dichloro-5'-cyano-5-methoxy-4-biphenylyl)(methyl-carbamoyl)amino)-N-3-isoxazolyl-3-pyridinesulfonamide | 1 | B | (3-chloro-5-cyanophenyl)boronic acid |
| 1-54 | 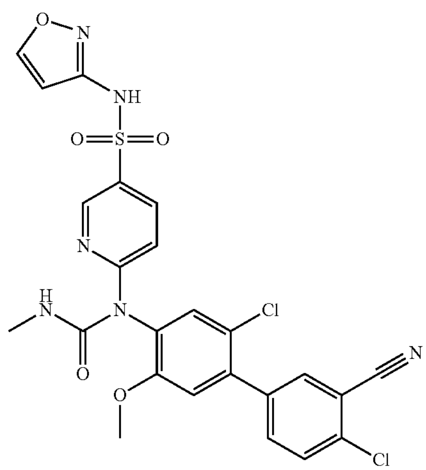 [SMILES: CNC(=O)N(c1ccc(S(=O)(=O)Nc2ccon2)cn1)c1cc(Cl)c(-c2ccc(Cl)c(C#N)c2)cc1OC] | 6-((2,4'-dichloro-3'-cyano-5-methoxy-4-biphenylyl)(methyl-carbamoyl)amino)-N-3-isoxazolyl-3-pyridinesulfonamide | 1 | B | (4-chloro-3-cyanophenyl)boronic acid |
| 1-55 | 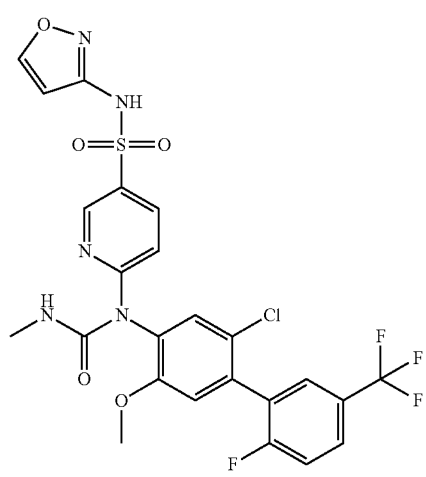 [SMILES: CNC(=O)N(c1ccc(S(=O)(=O)Nc2ccon2)cn1)c1cc(Cl)c(-c2cc(C(F)(F)F)ccc2F)cc1OC] | 6-((2-chloro-2'-fluoro-5-methoxy-5'-(trifluoromethyl)-4-biphenylyl)(methylcarbamoyl)amino)-N-3-isoxazolyl-3-pyridinesulfonamide | 1 | B | (2-fluoro-5-(trifluoromethyl)phenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 1-56 | 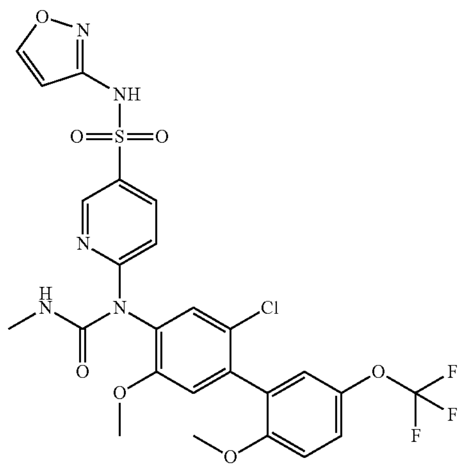 [SMILES: CNC(=O)N(c1ccc(S(=O)(=O)Nc2ccon2)cn1)c1cc(Cl)c(-c2cc(OC(F)(F)F)ccc2OC)cc1OC] | 6-((2-chloro-2',5-dimethoxy-5'-(trifluoromethoxy)-4-biphenylyl)(methylcarbamoyl)amino)-N-3-isoxazolyl-3-pyridinesulfonamide | 1 | B | (2-methoxy-5-(trifluoromethoxy)phenyl)boronic acid |
| 1-57 | 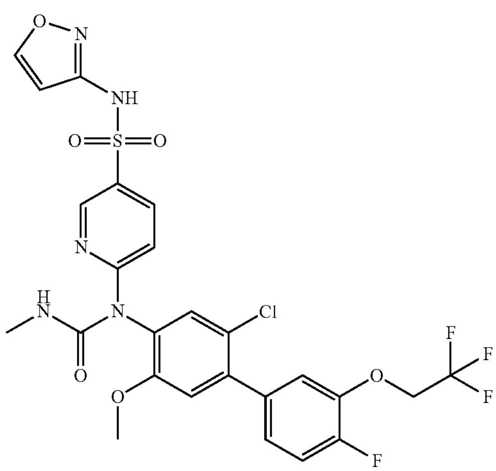 [SMILES: CNC(=O)N(c1ccc(S(=O)(=O)Nc2ccon2)cn1)c1cc(Cl)c(-c2ccc(F)c(OCC(F)(F)F)c2)cc1OC] | 6-((2-chloro-4'-fluoro-5-methoxy-3'-(2,2,2-trifluoroethoxy)-4-biphenylyl)(methylcarbamoyl)amino)-N-3-isoxazolyl-3-pyridinesulfonamide | 1 | B | (4-fluoro-3-(2,2,2-trifluoroethoxy)phenyl)boronic acid |
| 1-58 | 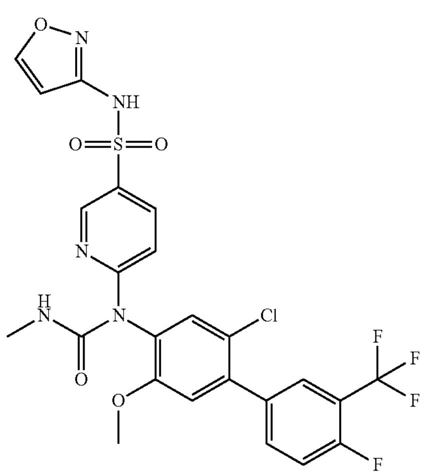 [SMILES: CNC(=O)N(c1ccc(S(=O)(=O)Nc2ccon2)cn1)c1cc(Cl)c(-c2ccc(F)c(C(F)(F)F)c2)cc1OC] | 6-((2-chloro-4'-fluoro-5-methoxy-3'-(trifluoromethyl)-4-biphenylyl)(methylcarbamoyl)amino)-N-3-isoxazolyl-3-pyridinesulfonamide | 1 | B | 2-(4-fluoro-3-(trifluoromethyl)phenyl)-4,4,5,5-tetramethyl-1,3,2-dioxaborolane |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
| --- | --- | --- | --- | --- | --- |
| 1-59 | 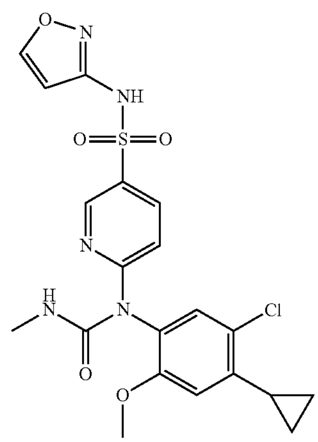 [SMILES: CNC(=O)N(c1ccc(S(=O)(=O)Nc2ccon2)cn1)c1cc(Cl)c(C2CC2)cc1OC] | 6-((5-chloro-4-cyclopropyl-2-methoxyphenyl)(methylcarbamoyl)amino)-N-3-isoxazolyl-3-pyridinesulfonamide | 1 | B | cyclopropylboronic acid |
| 1-60 | 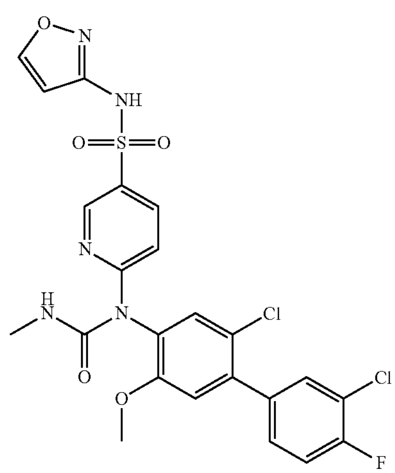 [SMILES: CNC(=O)N(c1ccc(S(=O)(=O)Nc2ccon2)cn1)c1cc(Cl)c(-c2ccc(F)c(Cl)c2)cc1OC] | 6-((2,3'-dichloro-4'-fluoro-5-methoxy-4-biphenylyl)(methylcarbamoyl)amino)-N-3-isoxazolyl-3-pyridinesulfonamide | 1 | B | (3-chloro-4-fluorophenyl)boronic acid |
| 1-61 | 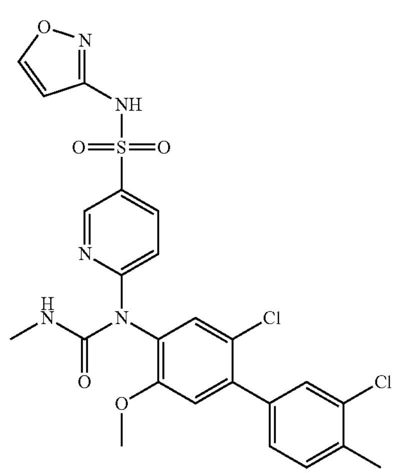 [SMILES: CNC(=O)N(c1ccc(S(=O)(=O)Nc2ccon2)cn1)c1cc(Cl)c(-c2ccc(C)c(Cl)c2)cc1OC] | 6-((2,3'-dichloro-5-methoxy-4'-methyl-4-biphenylyl)(methylcarbamoyl)amino)-N-3-isoxazolyl-3-pyridinesulfonamide | 1 | B | (3-chloro-4-methylphenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M stands for starting material, for example, S.M. A is Intermediate A.

| Ex. # | Chemical Structure | Name | Mtd | S.M | Reagent |
|---|---|---|---|---|---|
| 1-62 | 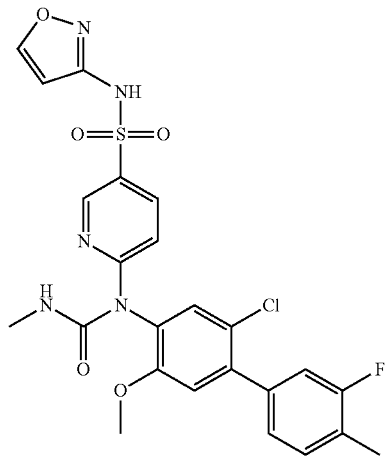 | 6-((2-chloro-3'-fluoro-5-methoxy-4'-methyl-4-biphenylyl)(methyl-carbamoyl)amino)-N-3-isoxazolyl-3-pyridinesulfonamide | 1 | B | (3-fluoro-4-methylphenyl) boronic acid |
| 1-63 | 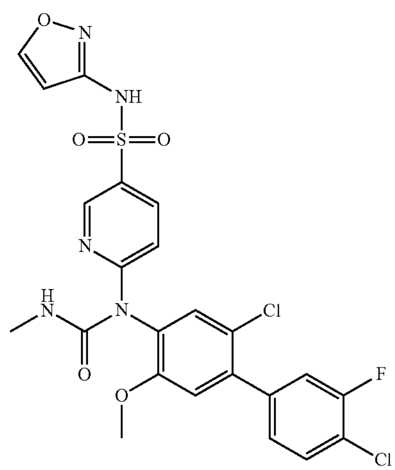 [SMILES: CNC(=O)N(c1ccc(S(=O)(=O)Nc2ccon2)cn1)c1cc(Cl)c(-c2ccc(Cl)c(F)c2)cc1OC] | 6-((2,4'-dichloro-3'-fluoro-5-methoxy-4-biphenylyl)(methyl-carbamoyl)amino)-N-3-isoxazolyl-3-pyridinesulfonamide | 1 | B | (4-chloro-3-fluorophenyl) boronic acid |
| 1-64 | 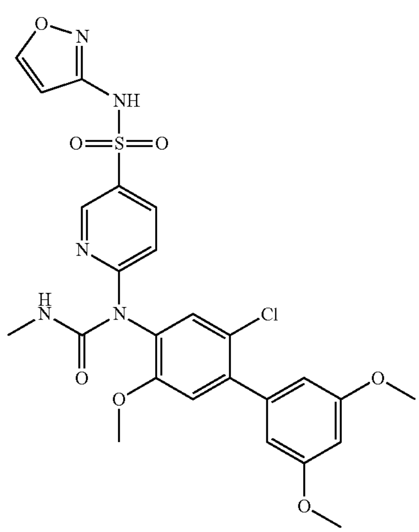 | 6-((2-chloro-3',5,5'-trimethoxy-4-biphenylyl)(methyl-carbamoyl)amino)-N-3-isoxazolyl-3-pyridinesulfonamide | 1 | B | (3,5-dimethoxyphenyl) boronic acid |

TABLE 5-continued

Examples 1-1 to 1-90, 2-1 to 2-14, 3-1 to 3-16, and 4-1 to 4-9 were prepared following
the procedures described in Methods 1-4 above. Ex. # stands for Example no.
Mtd. stands for Method, and S.M. stands for starting material, for example,
S.M. A is Intermediate A.

| Ex. # | Chemical Structure | Name | Mtd | S.M | Reagent |
|---|---|---|---|---|---|
| 1-65 | 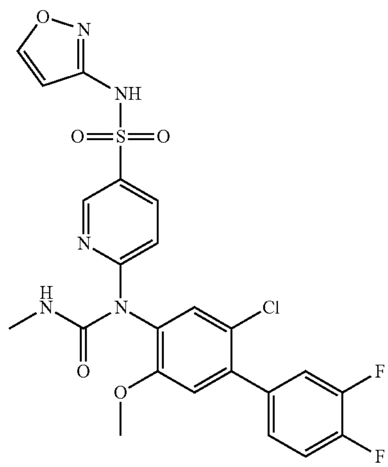 [SMILES: CNC(=O)N(c1ccc(S(=O)(=O)Nc2ccon2)cn1)c1cc(Cl)c(-c2ccc(F)c(F)c2)cc1OC] | 6-((2-chloro-3',4'-difluoro-5-methoxy-4-biphenylyl)(methyl-carbamoyl)amino)-N-3-isoxazolyl-3-pyridinesulfonamide | 1 | B | (3,4-difluorophenyl) boronic acid |
| 1-66 | 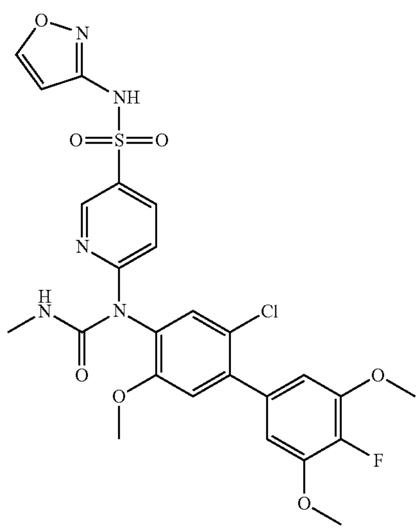 | 6-((2-chloro-4'-fluoro-3',5,5'-trimethoxy-4-biphenylyl)(methyl-carbamoyl)amino)-N-3-isoxazolyl-3-pyridinesulfonamide | 1 | B | (4-fluoro-3,5-dimethoxyphenyl) boronic acid |
| 1-67 | 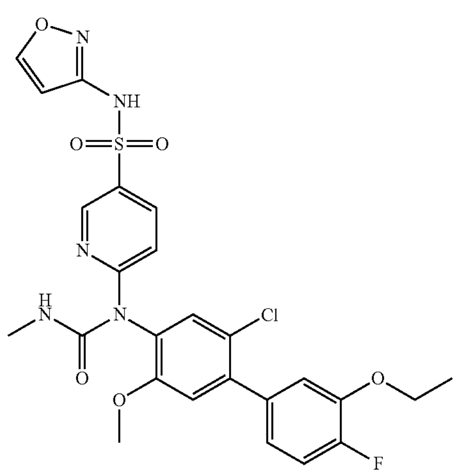 [SMILES: CCOc1cc(-c2cc(OC)c(N(C(=O)NC)c3ccc(S(=O)(=O)Nc4ccon4)cn3)cc2Cl)ccc1F] | 6-((2-chloro-3'-ethoxy-4'-fluoro-5-methoxy-4-biphenylyl)(methyl-carbamoyl)amino)-N-3-isoxazolyl-3-pyridinesulfonamide | 1 | B | (3-ethoxy-4-fluorophenyl) boronic acid |

TABLE 5-continued

Examples 1-1 to 1-90, 2-1 to 2-14, 3-1 to 3-16, and 4-1 to 4-9 were prepared following
the procedures described in Methods 1-4 above. Ex. # stands for Example no.
Mtd. stands for Method, and S.M. stands for starting material, for example,
S.M. A is Intermediate A.

| Ex. # | Chemical Structure | Name | Mtd | S.M | Reagent |
|---|---|---|---|---|---|
| 1-68 | 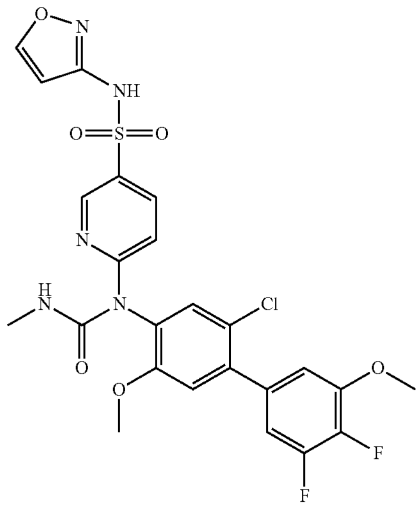 | 6-((2-chloro-3',4'-difluoro-5,5'-dimethoxy-4-biphenylyl)(methyl-carbamoyl)amino)-N-3-isoxazolyl-3-pyridinesulfonamide | 1 | B | (3,4-difluoro-5-methoxyphenyl)boronic acid |
| 1-69 | 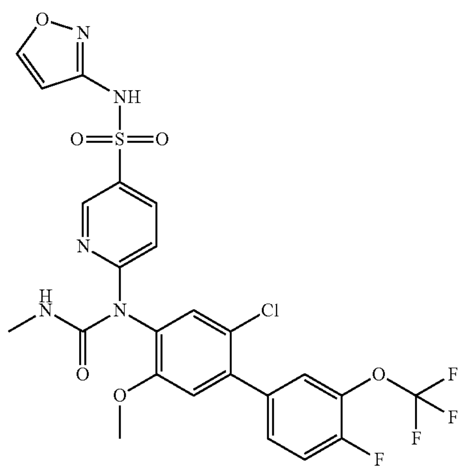 [SMILES: CNC(=O)N(c1ccc(S(=O)(=O)Nc2ccon2)cn1)c1cc(Cl)c(-c2ccc(F)c(OC(F)(F)F)c2)cc1OC] | 6-((2-chloro-4'-fluoro-5-methoxy-3'-(trifluoro-methoxy)-4-biphenylyl)(methylcarbamoyl)amino)-N-3-isoxazolyl-3-pyridinesulfonamide | 1 | B | (4-fluoro-3-(trifluoromethoxy)phenyl)boronic acid |
| 1-70 | 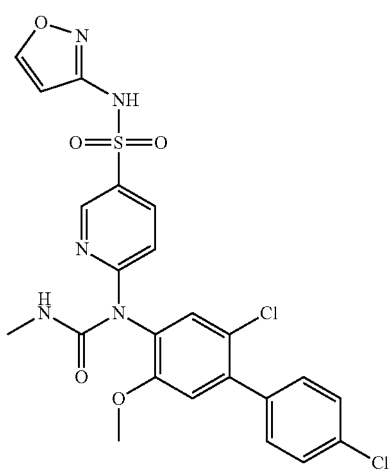 [SMILES: CNC(=O)N(c1ccc(S(=O)(=O)Nc2ccon2)cn1)c1cc(Cl)c(-c2ccc(Cl)cc2)cc1OC] | 6-((2,4'-dichloro-5-methoxy-4-biphenylyl)(methyl-carbamoyl)amino)-N-3-isoxazolyl-3-pyridinesulfonamide | 1 | B | (4-chlorophenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 1-71 | 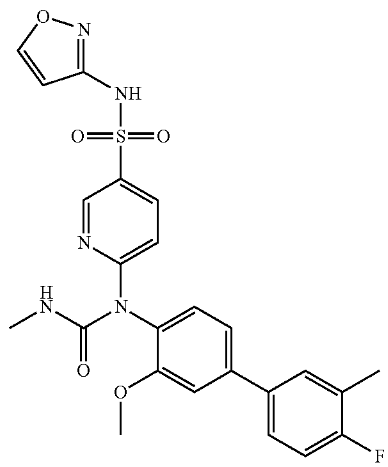 [SMILES: CNC(=O)N(c1ccc(S(=O)(=O)Nc2ccon2)cn1)c1ccc(-c2ccc(F)c(C)c2)cc1OC] | 6-((4'-fluoro-3-methoxy-3'-methyl-4-biphenylyl)(methyl-carbamoyl)amino)-N-3-isoxazolyl-3-pyridinesulfonamide | 1 | C | 4-fluoro-3-methylphenyl-boronic acid |
| 1-72 | 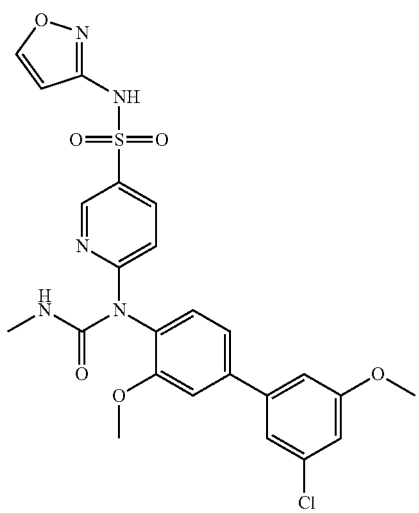 | 6-((3'-chloro-3,5'-dimethoxy-4-biphenylyl)(methyl-carbamoyl)amino)-N-3-isoxazolyl-3-pyridinesulfonamide | 1 | C | (3-chloro-5-methoxyphenyl) boronic acid |
| 1-73 | 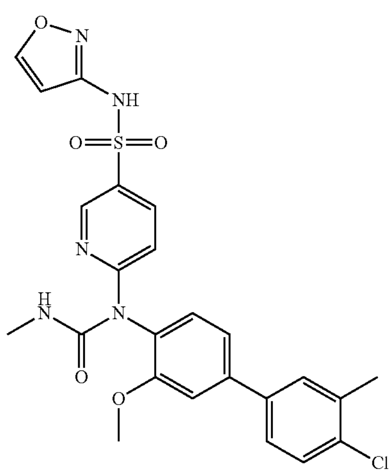 [SMILES: CNC(=O)N(c1ccc(S(=O)(=O)Nc2ccon2)cn1)c1ccc(-c2ccc(Cl)c(C)c2)cc1OC] | 6-((4'-chloro-3-methoxy-3'-methyl-4-biphenylyl)(methyl-carbamoyl)amino)-N-3-isoxazolyl-3-pyridinesulfonamide | 1 | C | (4-chloro-3-methylphenyl) boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 1-74 | 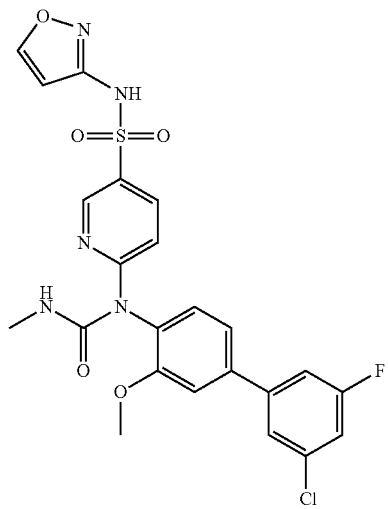 [SMILES: CNC(=O)N(c1ccc(S(=O)(=O)Nc2ccon2)cn1)c1ccc(-c2cc(F)cc(Cl)c2)cc1OC] | 6-((3'-chloro-5'-fluoro-3-methoxy-4-biphenylyl)(methylcarbamoyl)amino)-N-3-isoxazolyl-3-pyridinesulfonamide | 1 | C | (3-chloro-5-fluorophenyl)boronic acid |
| 1-75 | 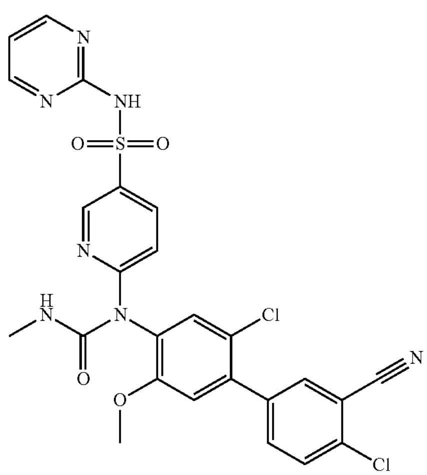 [SMILES: CNC(=O)N(c1ccc(S(=O)(=O)Nc2ncccn2)cn1)c1cc(Cl)c(-c2ccc(Cl)c(C#N)c2)cc1OC] | 6-((2,4'-dichloro-3'-cyano-5-methoxy-4-biphenylyl)(methylcarbamoyl)amino)-N-2-pyrimidinyl-3-pyridinesulfonamide | 1 | D | (4-chloro-3-cyanophenyl)boronic acid |
| 1-76 | 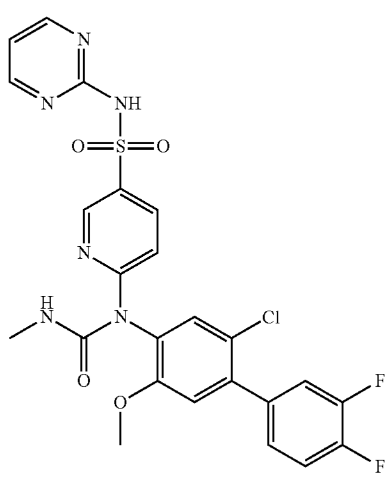 [SMILES: CNC(=O)N(c1ccc(S(=O)(=O)Nc2ncccn2)cn1)c1cc(Cl)c(-c2ccc(F)c(F)c2)cc1OC] | 6-((2-chloro-3',4'-difluoro-5-methoxy-4-biphenylyl)(methylcarbamoyl)amino)-N-2-pyrimidinyl-3-pyridinesulfonamide | 1 | D | (3,4-difluorophenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 1-77 | 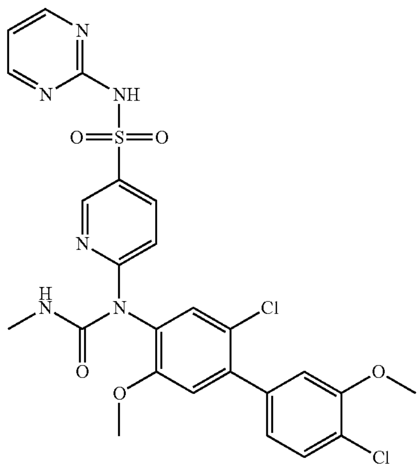 | 6-((2,4'-dichloro-3',5-dimethoxy-4-biphenylyl)(methyl-carbamoyl)amino)-N-2-pyrimidinyl-3-pyridinesulfonamide | 1 | D | (4-chloro-3-methoxyphenyl) boronic acid |
| 1-78 | 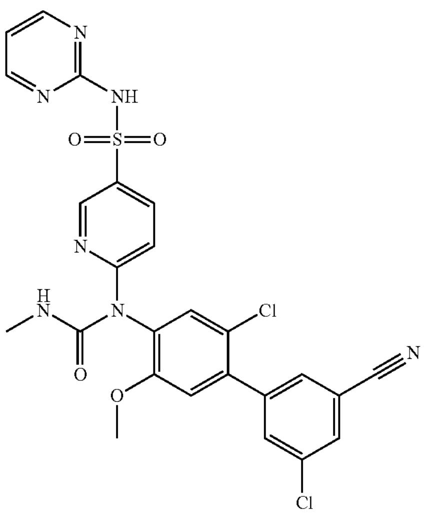 [SMILES: CNC(=O)N(c1ccc(S(=O)(=O)Nc2ncccn2)cn1)c1cc(Cl)c(-c2cc(Cl)cc(C#N)c2)cc1OC] | 6-((2,3'-dichloro-5'-cyano-5-methoxy-4-biphenylyl)(methyl-carbamoyl)amino)-N-2-pyrimidinyl-3-pyridinesulfonamide | 1 | D | (3-chloro-5-cyanophenyl) boronic acid |
| 1-79 | 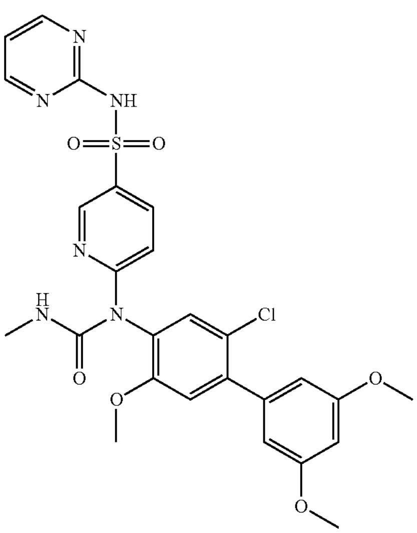 | 6-((2-chloro-3',5,5'-trimethoxy-4-biphenylyl)(methyl-carbamoyl)amino)-N-2-pyrimidinyl-3-pyridinesulfonamide | 1 | D | (3,5-dimethoxyphenyl) boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M stands for starting material, for example, S.M. A is Intermediate A.

| Ex. # | Chemical Structure | Name | Mtd | S.M | Reagent |
|---|---|---|---|---|---|
| 1-80 | 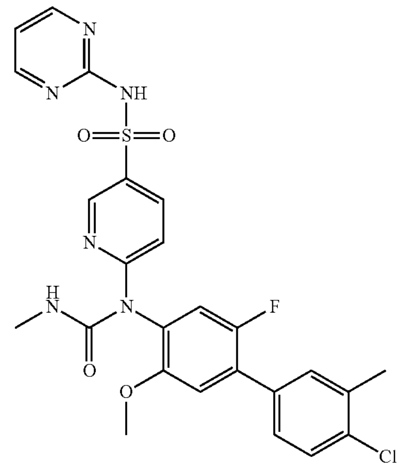 [SMILES: CNC(=O)N(c1ccc(S(=O)(=O)Nc2ncccn2)cn1)c1cc(F)c(-c2ccc(Cl)c(C)c2)cc1OC] | 6-((4'-chloro-2-fluoro-5-methoxy-3'-methyl-4-biphenylyl)(methyl-carbamoyl)amino)-N-2-pyrimidinyl-3-pyridinesulfonamide | 1 | E | (4-chloro-3-methylphenyl)boronic acid |
| 1-81 | 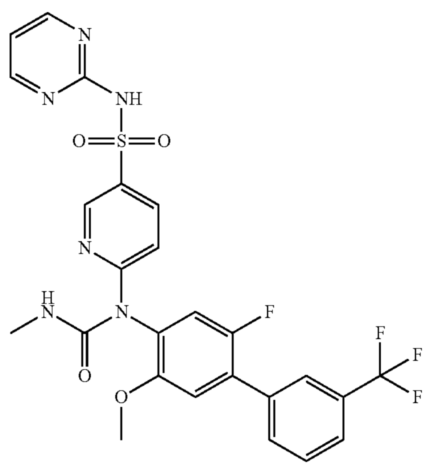 [SMILES: CNC(=O)N(c1ccc(S(=O)(=O)Nc2ncccn2)cn1)c1cc(F)c(-c2cccc(C(F)(F)F)c2)cc1OC] | 6-((2-fluoro-5-methoxy-3'-(trifluoromethyl)-4-biphenylyl)(methyl-carbamoyl)amino)-N-2-pyrimidinyl-3-pyridinesulfonamide | 1 | E | (3-(trifluoromethyl)phenyl)boronic acid |
| 1-82 | 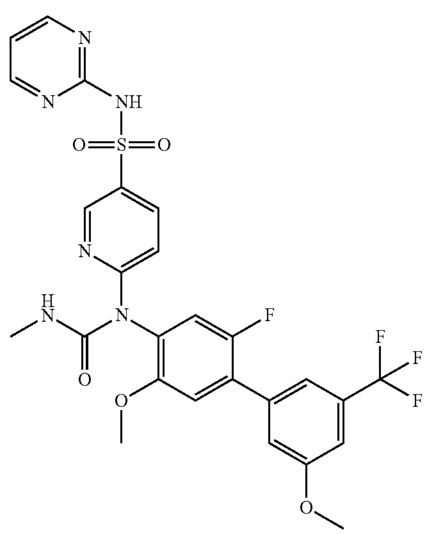 [SMILES: CNC(=O)N(c1ccc(S(=O)(=O)Nc2ncccn2)cn1)c1cc(F)c(-c2cc(OC)cc(C(F)(F)F)c2)cc1OC] | 6-((2-fluoro-3',5-dimethoxy-5'-(trifluoromethyl)-4-biphenylyl)(methyl-carbamoyl)amino)-N-2-pyrimidinyl-3-pyridinesulfonamide | 1 | E | (3-methoxy-5-(trifluoromethyl)phenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 1-83 | 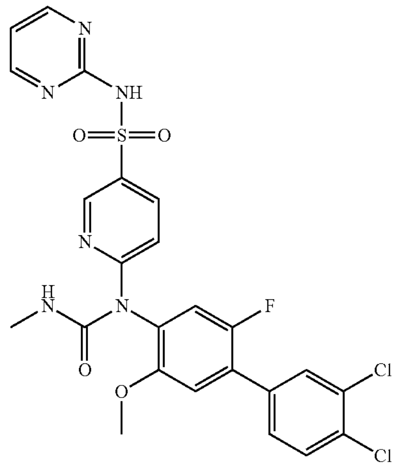 [SMILES: CNC(=O)N(c1ccc(S(=O)(=O)Nc2ncccn2)cn1)c1cc(F)c(-c2ccc(Cl)c(Cl)c2)cc1OC] | 6-((3',4'-dichloro-2-fluoro-5-methoxy-4-biphenylyl)(methylcarbamoyl)amino)-N-2-pyrimidinyl-3-pyridinesulfonamide | 1 | E | (3,4-dichlorophenyl)boronic acid |
| 1-84 | 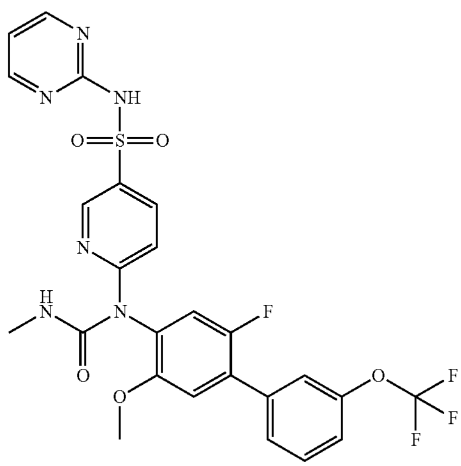 [SMILES: CNC(=O)N(c1ccc(S(=O)(=O)Nc2ncccn2)cn1)c1cc(F)c(-c2cccc(OC(F)(F)F)c2)cc1OC] | 6-((2-fluoro-5-methoxy-3'-(trifluoromethoxy)-4-biphenylyl)(methylcarbamoyl)amino)-N-2-pyrimidinyl-3-pyridinesulfonamide | 1 | E | (3-(trifluoromethoxy)phenyl)boronic acid |
| 1-85 | 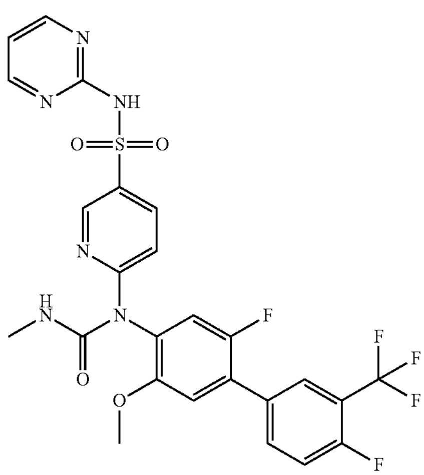 | 6-((2,4'-difluoro-5-methoxy-3'-(trifluoromethyl)-4-biphenylyl)(methylcarbamoyl)amino)-N-2-pyrimidinyl-3-pyridinesulfonamide | 1 | E | (4-fluoro-3-(trifluoromethyl)phenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 1-86 | 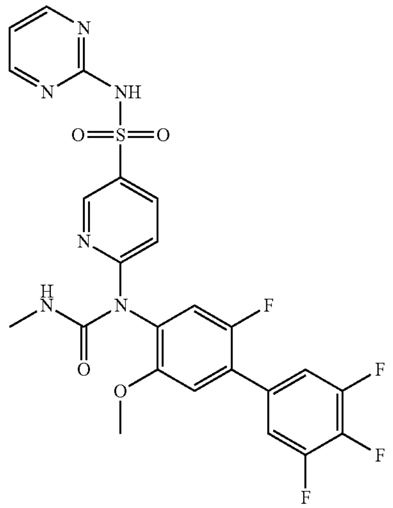 [SMILES: CNC(=O)N(c1ccc(S(=O)(=O)Nc2ncccn2)cn1)c1cc(F)c(-c2cc(F)c(F)c(F)c2)cc1OC] | 6-((methyl-carbamoyl)(2,3',4',5'-tetrafluoro-5-methoxy-4-biphenylyl)amino)-N-2-pyrimidinyl-3-pyridinesulfonamide | 1 | E | (3,4,5-trifluorophenyl)boronic acid |
| 1-87 | 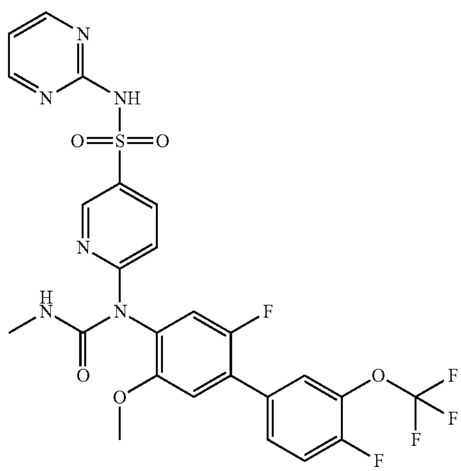 [SMILES: CNC(=O)N(c1ccc(S(=O)(=O)Nc2ncccn2)cn1)c1cc(F)c(-c2ccc(F)c(OC(F)(F)F)c2)cc1OC] | 6-((2,4'-difluoro-5-methoxy-3'-(trifluoromethoxy)-4-biphenylyl)(methylcarbamoyl)amino)-N-2-pyrimidinyl-3-pyridinesulfonamide | 1 | E | (4-fluoro-3-(trifluoromethoxy)phenyl)boronic acid |
| 1-88 | 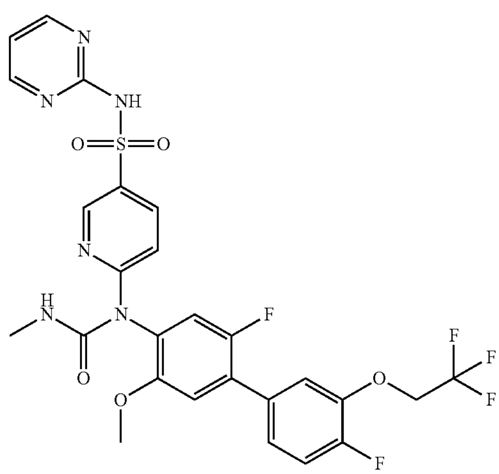 [SMILES: CNC(=O)N(c1ccc(S(=O)(=O)Nc2ncccn2)cn1)c1cc(F)c(-c2ccc(F)c(OCC(F)(F)F)c2)cc1OC] | 6-((2,4'-difluoro-5-methoxy-3'-(2,2,2-trifluoroethoxy)-4-biphenylyl)(methylcarbamoyl)amino)-N-2-pyrimidinyl-3-pyridinesulfonamide | 1 | E | (4-fluoro-3-(2,2,2-trifluoroethoxy)phenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 1-89 | 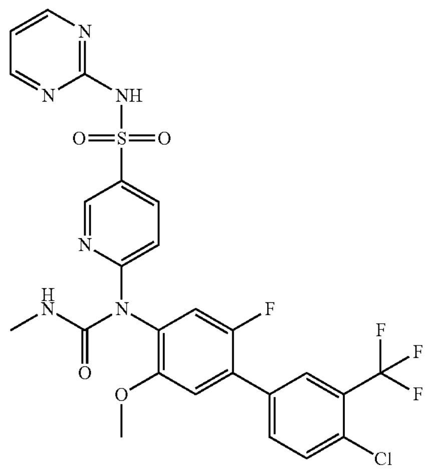 [SMILES: CNC(=O)N(c1ccc(S(=O)(=O)Nc2ncccn2)cn1)c1cc(F)c(-c2ccc(Cl)c(C(F)(F)F)c2)cc1OC] | 6-((4'-chloro-2-fluoro-5-methoxy-3'-(trifluoromethyl)-4-biphenylyl)(methylcarbamoyl)amino)-N-2-pyrimidinyl-3-pyridinesulfonamide | 1 | E | (4-chloro-3-(trifluoromethyl)phenyl)boronic acid |
| 1-90 | 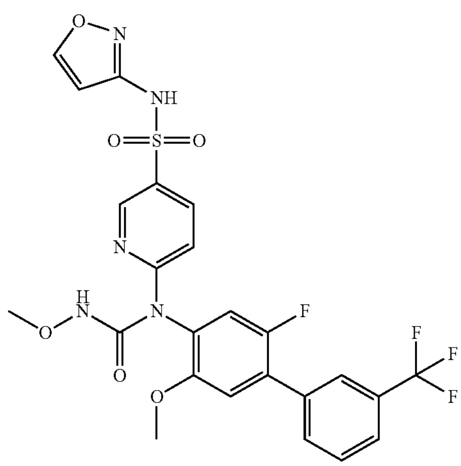 [SMILES: CONC(=O)N(c1ccc(S(=O)(=O)Nc2ccon2)cn1)c1cc(F)c(-c2cccc(C(F)(F)F)c2)cc1OC] | 6-((2-fluoro-5-methoxy-3'-(trifluoromethyl)-4-biphenylyl)(methoxycarbamoyl)amino)-N-3-isoxazolyl-3-pyridinesulfonamide | 1 | F | (3-(trifluoromethyl)phenyl)boronic acid |
| 2-1 | 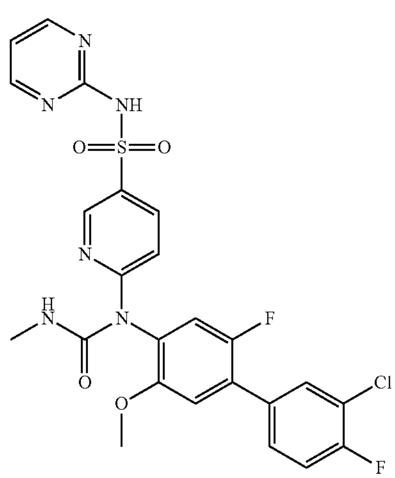 [SMILES: CNC(=O)N(c1ccc(S(=O)(=O)Nc2ncccn2)cn1)c1cc(F)c(-c2ccc(F)c(Cl)c2)cc1OC] | 6-((3'-chloro-2,4'-difluoro-5-methoxy-4-biphenylyl)(methylcarbamoyl)amino)-N-2-pyrimidinyl-3-pyridinesulfonamide | 2 | L | (3-chloro-4-fluorophenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 2-2 | 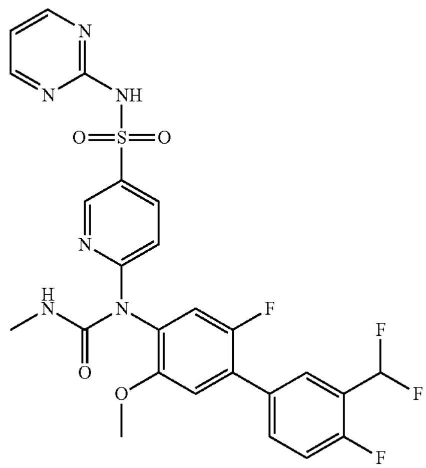 [SMILES: CNC(=O)N(c1ccc(S(=O)(=O)Nc2ncccn2)cn1)c1cc(F)c(-c2ccc(F)c(C(F)F)c2)cc1OC] | 6-((3'-(difluoromethyl)-2,4'-difluoro-5-methoxy-4-biphenylyl)(methyl-carbamoyl)amino)-N-2-pyrimidinyl-3-pyridinesulfonamide | 2 | L | 2-(3-(difluoromethyl)-4,5-difluorophenyl)-4,4,5,5-tetramethyl-1,3,2-dioxaborolane |
| 2-3 | 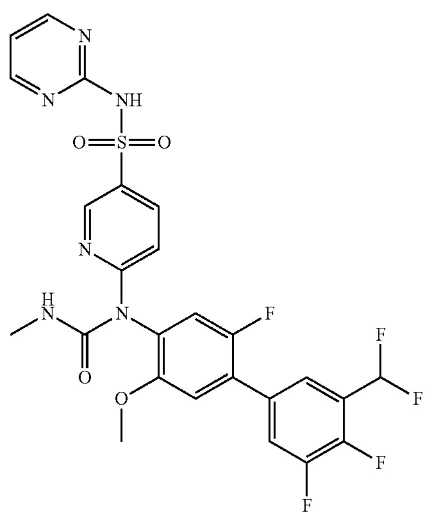 [SMILES: CNC(=O)N(c1ccc(S(=O)(=O)Nc2ncccn2)cn1)c1cc(F)c(-c2cc(F)c(F)c(C(F)F)c2)cc1OC] | 6-((3'-(difluoromethyl)-2,4',5'-trifluoro-5-methoxy-4-biphenylyl)(methyl-carbamoyl)amino)-N-2-pyrimidinyl-3-pyridinesulfonamide | 2 | L | 2-(3-(difluoromethyl)-4-fluorophenyl)-4,4,5,5-tetramethyl-1,3,2-dioxaborolane |
| 2-4 | 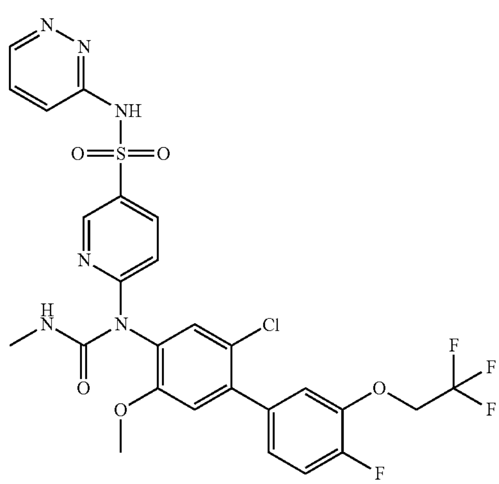 [SMILES: CNC(=O)N(c1ccc(S(=O)(=O)Nc2cccnn2)cn1)c1cc(Cl)c(-c2ccc(F)c(OCC(F)(F)F)c2)cc1OC] | 6-((2-chloro-4'-fluoro-5-methoxy-3'-(2,2,2-trifluoroethoxy)-4-biphenylyl)(methyl-carbamoyl)amino)-N-3-pyridazinyl-3-pyridinesulfonamide | 2 | M | (4-fluoro-3-(2,2,2-trifluoroethoxy)phenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 2-5 | 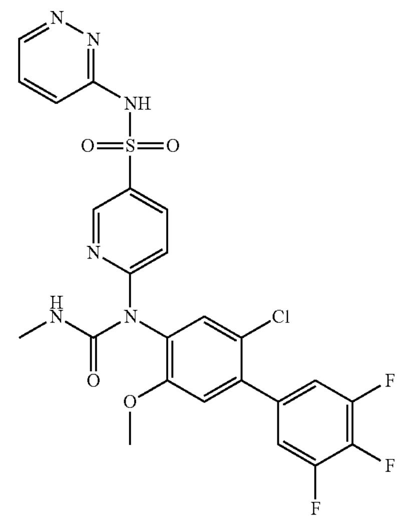 [SMILES: CNC(=O)N(c1ccc(S(=O)(=O)Nc2cccnn2)cn1)c1cc(Cl)c(-c2cc(F)c(F)c(F)c2)cc1OC] | 6-((2-chloro-3',4',5'-trifluoro-5-methoxy-4-biphenylyl)(methylcarbamoyl)amino)-N-3-pyridazinyl-3-pyridinesulfonamide | 2 | M | (3,4,5-trifluorophenyl)boronic acid |
| 2-6 | 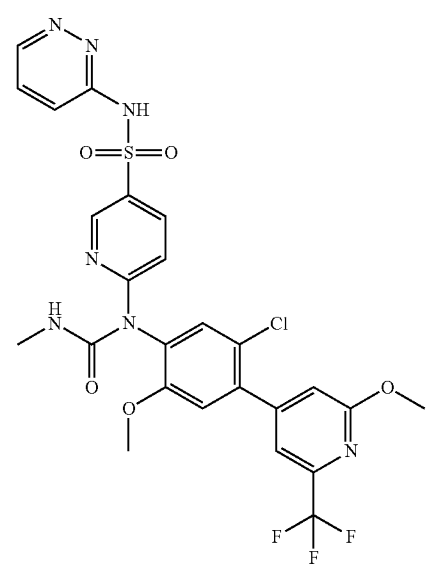 | 6-((5-chloro-2-methoxy-4-(2-methoxy-6-(trifluoromethyl)-4-pyridinyl)phenyl)(methylcarbamoyl)amino)-N-3-pyridazinyl-3-pyridinesulfonamide | 2 | M | 2-methoxy-4-(4,4,5,5-tetramethyl-1,3,2-dioxaborolan-2-yl)-6-(trifluoromethyl)pyridine |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 2-7 | 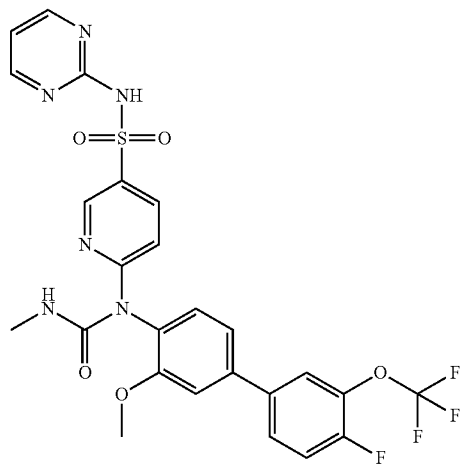 [SMILES: CNC(=O)N(c1ccc(S(=O)(=O)Nc2ncccn2)cn1)c1ccc(-c2ccc(F)c(OC(F)(F)F)c2)cc1OC] | 6-((4'-fluoro-3-methoxy-3'-(trifluoromethoxy)-4-biphenylyl)(methylcarbamoyl)amino)-N-2-pyrimidinyl-3-pyridinesulfonamide | 2 | N | (4-fluoro-3-(trifluoromethoxy)phenyl)boronic acid |
| 2-8 | 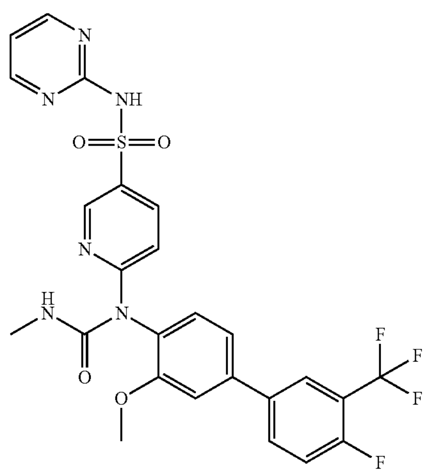 [SMILES: CNC(=O)N(c1ccc(S(=O)(=O)Nc2ncccn2)cn1)c1ccc(-c2ccc(F)c(C(F)(F)F)c2)cc1OC] | 6-((4'-fluoro-3-methoxy-3'-(trifluoromethyl)-4-biphenylyl)(methylcarbamoyl)amino)-N-2-pyrimidinyl-3-pyridinesulfonamide | 2 | N | (4-fluoro-3-(trifluoromethyl)phenyl)boronic acid |
| 2-9 | 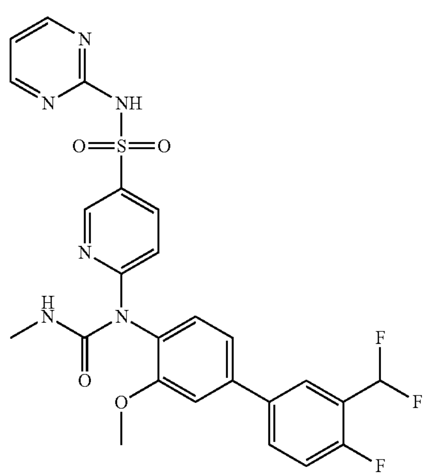 [SMILES: CNC(=O)N(c1ccc(S(=O)(=O)Nc2ncccn2)cn1)c1ccc(-c2ccc(F)c(C(F)F)c2)cc1OC] | 6-((3'-(difluoromethyl)-4'-fluoro-3-methoxy-4-biphenylyl)(methylcarbamoyl)amino)-N-2-pyrimidinyl-3-pyridinesulfonamide | 2 | N | 2-(3-(difluoromethyl)-4-fluorophenyl)-4,4,5,5-tetramethyl-1,3,2-dioxaborolane |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 2-10 | 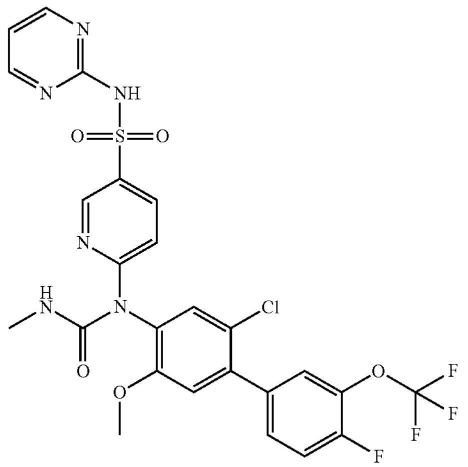 [SMILES: CNC(=O)N(c1ccc(S(=O)(=O)Nc2ncccn2)cn1)c1cc(Cl)c(-c2ccc(F)c(OC(F)(F)F)c2)cc1OC] | 6-((2-chloro-4'-fluoro-5-methoxy-3'-(trifluoromethoxy)-4-biphenylyl)(methylcarbamoyl)amino)-N-2-pyrimidinyl-3-pyridinesulfonamide | 2 | O | (4-fluoro-3-(trifluoromethoxy)phenyl)boronic acid |
| 2-11 | 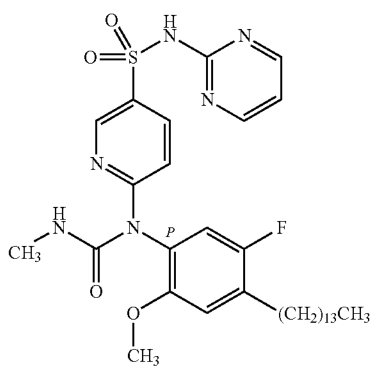 | 6-(1-(5-Fluoro-2-methoxy-4-tetradecylphenyl)-3-methylureido)-N-(pyrimidin-2-yl)pyridine-3-sulfonamide | 2 | L | tetradecylzinc bromide Pd(OAc)$_2$ CPhos |
| 2-12 | 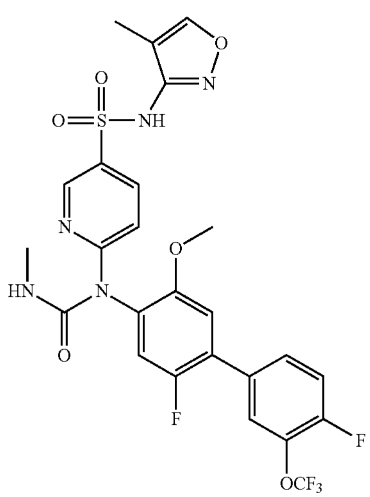 [SMILES: CNC(=O)N(c1ccc(S(=O)(=O)Nc2nocc2C)cn1)c1cc(F)c(-c2ccc(F)c(OC(F)(F)F)c2)cc1OC] | 6-(1-(2,4'-difluoro-5-methoxy-3'-(trifluoromethoxy)-[1,1'-biphenyl]-4-yl)-3-methylureido)-N-(4-methylisoxazol-3-yl)pyridine-3-sulfonamide | 2A | I | (4-fluoro-3-(trifluoromethoxy)phenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 2-13 | 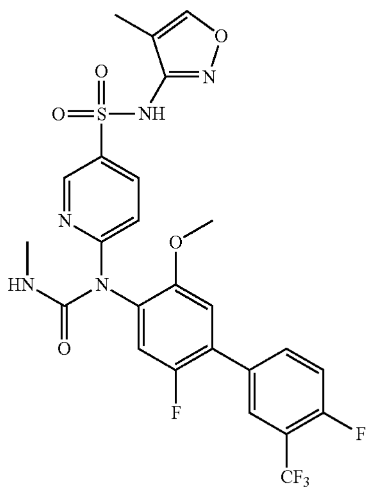 [SMILES: CNC(=O)N(c1ccc(S(=O)(=O)Nc2nocc2C)cn1)c1cc(F)c(-c2ccc(F)c(C(F)(F)F)c2)cc1OC] | 6-(1-(2,4'-difluoro-5-methoxy-3'-(trifluoromethyl)-[1,1'-biphenyl]-4-yl)-3-methyl-ureido)-N-(4-methylisoxazol-3-yl)pyridine-3-sulfonamide | 2A | O-1 | 4-fluoro-3-trifluoromethyl-phenylboronic acid |
| 2-14 | 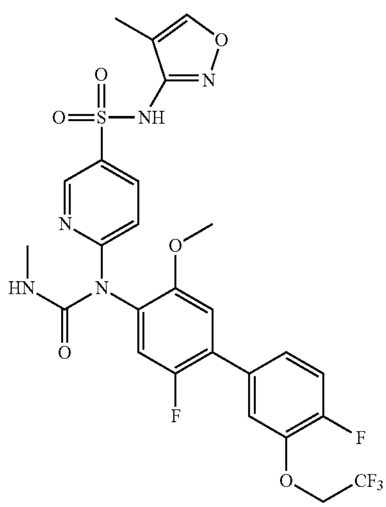 [SMILES: CNC(=O)N(c1ccc(S(=O)(=O)Nc2nocc2C)cn1)c1cc(F)c(-c2ccc(F)c(OCC(F)(F)F)c2)cc1OC] | 6-(1-(2,4'-difluoro-5-methoxy-3'-(2,2,2-trifluoroethoxy)-[1,1'-biphenyl]-4-yl)-3-methyl-ureido)-N-(4-methylisoxazol-3-yl)pyridine-3-sulfonamide | 2A | O-2 | 4-fluoro-3-(2,2,2-trifluoroethoxy)phenylboronic acid |
| 3-1 | 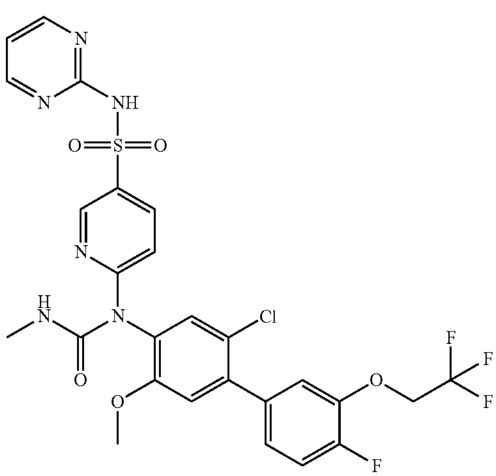 [SMILES: CNC(=O)N(c1ccc(S(=O)(=O)Nc2ncccn2)cn1)c1cc(Cl)c(-c2ccc(F)c(OCC(F)(F)F)c2)cc1OC] | 6-((2-chloro-4'-fluoro-5-methoxy-3'-(2,2,2-trifluoroethoxy)-4-biphenylyl)(methyl-carbamoyl)amino)-N-2-pyrimidinyl-3-pyridinesulfonamide | 3 | P | 2-amino-pyrimidine |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 3-2 | 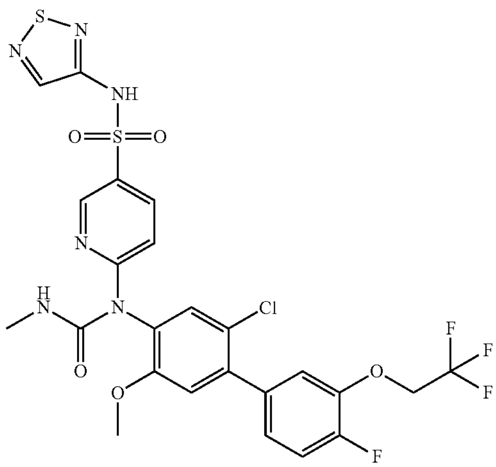 [SMILES: CNC(=O)N(c1ccc(S(=O)(=O)Nc2cnsn2)cn1)c1cc(Cl)c(-c2ccc(F)c(OCC(F)(F)F)c2)cc1OC] | 6-((2-chloro-4'-fluoro-5-methoxy-3'-(2,2,2-trifluoroethoxy)-4-biphenylyl)(methylcarbamoyl)amino)-N-1,2,5-thiadiazol-3-yl-3-pyridinesulfonamide | 3 | P | 1,2,5-thiadiazol-3-amine |
| 3-3 | 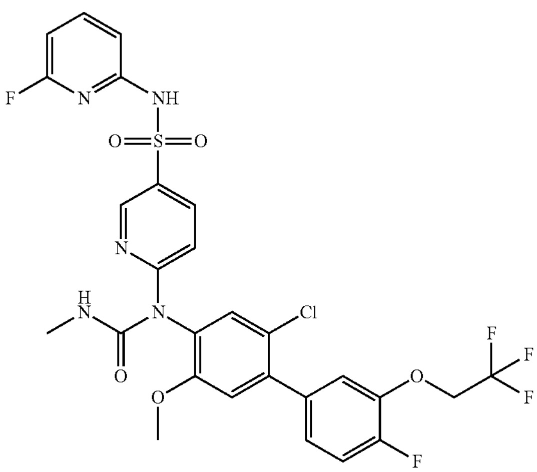 [SMILES: CNC(=O)N(c1ccc(S(=O)(=O)Nc2cccc(F)n2)cn1)c1cc(Cl)c(-c2ccc(F)c(OCC(F)(F)F)c2)cc1OC] | 6-((2-chloro-4'-fluoro-5-methoxy-3'-(2,2,2-trifluoroethoxy)-4-biphenylyl)(methylcarbamoyl)amino)-N-(6-fluoro-2-pyridinyl)-3-pyridinesulfonamide | 3 | P | 2-amino-6-fluoropyridine |
| 3-4 | 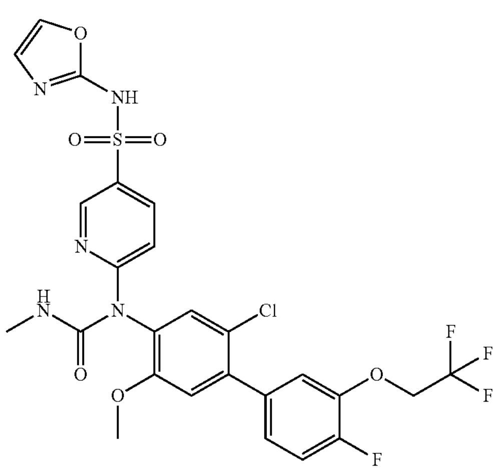 [SMILES: CNC(=O)N(c1ccc(S(=O)(=O)Nc2ncco2)cn1)c1cc(Cl)c(-c2ccc(F)c(OCC(F)(F)F)c2)cc1OC] | 6-((2-chloro-4'-fluoro-5-methoxy-3'-(2,2,2-trifluoroethoxy)-4-biphenylyl)(methylcarbamoyl)amino)-N-1,3-oxazol-2-yl-3-pyridinesulfonamide | 3 | P | 2-aminooxazole |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 3-5 | 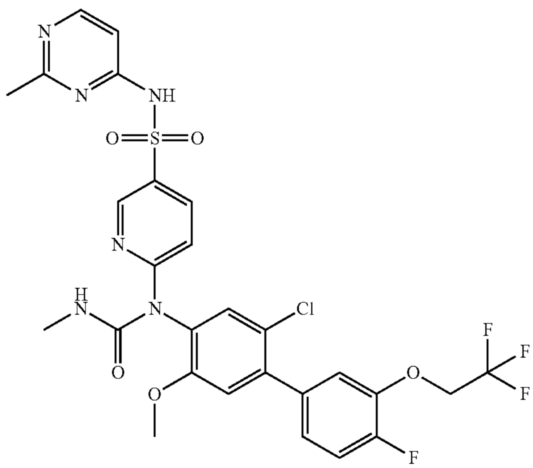 [SMILES: CNC(=O)N(c1ccc(S(=O)(=O)Nc2ccnc(C)n2)cn1)c1cc(Cl)c(-c2ccc(F)c(OCC(F)(F)F)c2)cc1OC] | 6-((2-chloro-4'-fluoro-5-methoxy-3'-(2,2,2-trifluoroethoxy)-4-biphenylyl)(methylcarbamoyl)amino)-N-(2-methyl-4-pyrimidinyl)-3-pyridinesulfonamide | 3 | P | 2-methyl-4-pyrimidinamine |
| 3-6 | 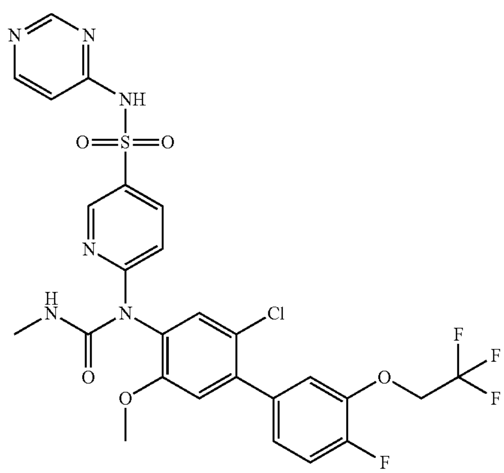 [SMILES: CNC(=O)N(c1ccc(S(=O)(=O)Nc2ccncn2)cn1)c1cc(Cl)c(-c2ccc(F)c(OCC(F)(F)F)c2)cc1OC] | 6-((2-chloro-4'-fluoro-5-methoxy-3'-(2,2,2-trifluoroethoxy)-4-biphenylyl)(methylcarbamoyl)amino)-N-4-pyrimidinyl-3-pyridinesulfonamide | 3 | P | 4-aminopyrimidine |
| 3-7 | 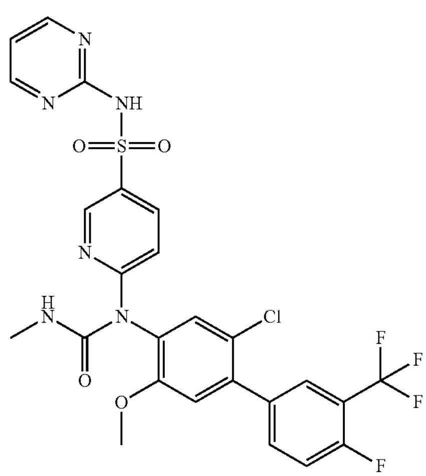 [SMILES: CNC(=O)N(c1ccc(S(=O)(=O)Nc2ncccn2)cn1)c1cc(Cl)c(-c2ccc(F)c(C(F)(F)F)c2)cc1OC] | 6-((2-chloro-4'-fluoro-5-methoxy-3'-(trifluoromethyl)-4-biphenylyl)(methylcarbamoyl)amino)-N-2-pyrimidinyl-3-pyridinesulfonamide | 3 | Q | 2-aminopyrimidine |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 3-8 | 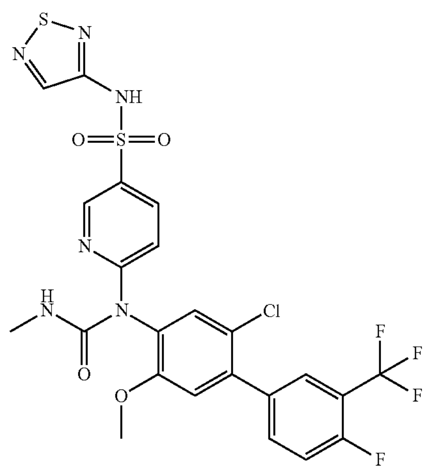 [SMILES: CNC(=O)N(c1ccc(S(=O)(=O)Nc2cnsn2)cn1)c1cc(Cl)c(-c2ccc(F)c(C(F)(F)F)c2)cc1OC] | 6-((2-chloro-4'-fluoro-5-methoxy-3'-(trifluoromethyl)-4-biphenylyl)(methylcarbamoyl)amino)-N-1,2,5-thiadiazol-3-yl-3-pyridinesulfonamide | 3 | Q | 1,2,5-thiadiazol-3-amine |
| 3-9 | 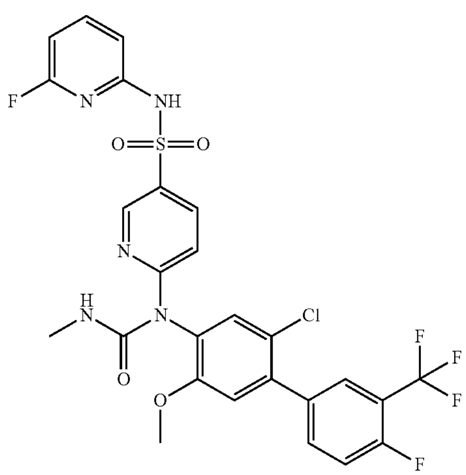 [SMILES: CNC(=O)N(c1ccc(S(=O)(=O)Nc2cccc(F)n2)cn1)c1cc(Cl)c(-c2ccc(F)c(C(F)(F)F)c2)cc1OC] | 6-((2-chloro-4'-fluoro-5-methoxy-3'-(trifluoromethyl)-4-biphenylyl)(methylcarbamoyl)amino)-N-(6-fluoro-2-pyridinyl)-3-pyridinesulfonamide | 3 | Q | 2-amino-6-fluoropyridine |
| 3-10 | 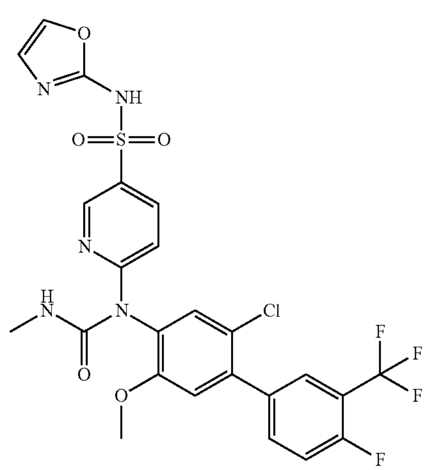 [SMILES: CNC(=O)N(c1ccc(S(=O)(=O)Nc2ncco2)cn1)c1cc(Cl)c(-c2ccc(F)c(C(F)(F)F)c2)cc1OC] | 6-((2-chloro-4'-fluoro-5-methoxy-3'-(trifluoromethyl)-4-biphenylyl)(methylcarbamoyl)amino)-N-1,3-oxazol-2-yl-3-pyridinesulfonamide | 3 | Q | 2-aminooxazole |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 3-11 | 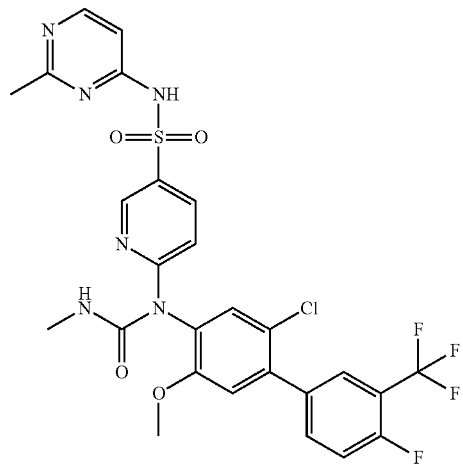 [SMILES: CNC(=O)N(c1ccc(S(=O)(=O)Nc2ccnc(C)n2)cn1)c1cc(Cl)c(-c2ccc(F)c(C(F)(F)F)c2)cc1OC] | 6-((2-chloro-4'-fluoro-5-methoxy-3'-(trifluoromethyl)-4-biphenylyl)(methylcarbamoyl)amino)-N-(2-methyl-4-pyrimidinyl)-3-pyridinesulfonamide | 3 | Q | 2-methyl-4-pyrimidinamine |
| 3-12 | 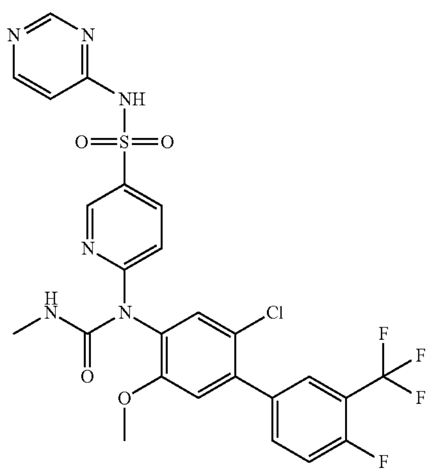 [SMILES: CNC(=O)N(c1ccc(S(=O)(=O)Nc2ccncn2)cn1)c1cc(Cl)c(-c2ccc(F)c(C(F)(F)F)c2)cc1OC] | 6-((2-chloro-4'-fluoro-5-methoxy-3'-(trifluoromethyl)-4-biphenylyl)(methylcarbamoyl)amino)-N-4-pyrimidinyl-3-pyridinesulfonamide | 3 | Q | 4-aminopyrimidine |
| 3-13 | 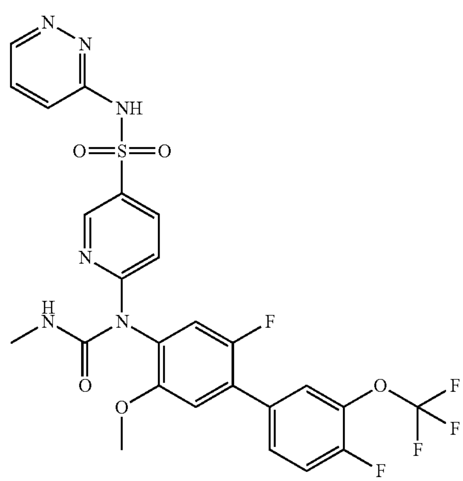 [SMILES: CNC(=O)N(c1ccc(S(=O)(=O)Nc2cccnn2)cn1)c1cc(F)c(-c2ccc(F)c(OC(F)(F)F)c2)cc1OC] | 6-((2,4'-difluoro-5-methoxy-3'-(trifluoromethoxy)-4-biphenylyl)(methylcarbamoyl)amino)-N-3-pyridazinyl-3-pyridinesulfonamide | 3 | R | 3-aminopyridazine |

TABLE 5-continued

Examples 1-1 to 1-90, 2-1 to 2-14, 3-1 to 3-16, and 4-1 to 4-9 were prepared following
the procedures described in Methods 1-4 above. Ex. # stands for Example no.
Mtd. stands for Method, and S.M. stands for starting material, for example,
S.M. A is Intermediate A.

| Ex. # | Chemical Structure | Name | Mtd | S.M | Reagent |
|---|---|---|---|---|---|
| 3-14 | 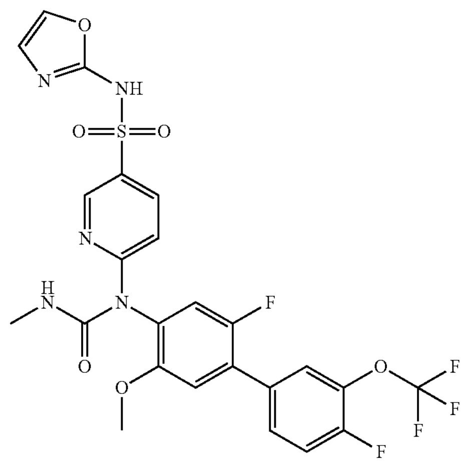 [SMILES: CNC(=O)N(c1ccc(S(=O)(=O)Nc2ncco2)cn1)c1cc(F)c(-c2ccc(F)c(OC(F)(F)F)c2)cc1OC] | 6-((2,4'-difluoro-5-methoxy-3'-(trifluoromethoxy)-4-biphenylyl)(methylcarbamoyl)amino)-N-1,3-oxazol-2-yl-3-pyridinesulfonamide | 3 | R | 2-aminooxazole |
| 3-15 | 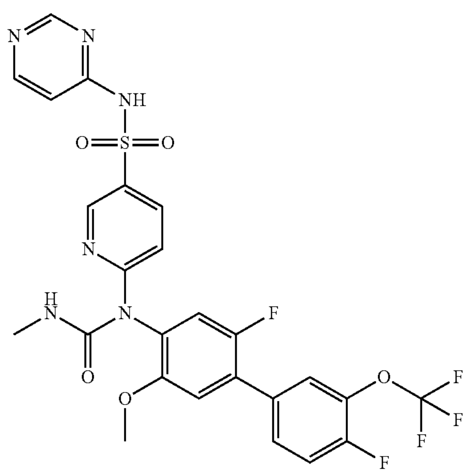 [SMILES: CNC(=O)N(c1ccc(S(=O)(=O)Nc2ccncn2)cn1)c1cc(F)c(-c2ccc(F)c(OC(F)(F)F)c2)cc1OC] | 6-((2,4'-difluoro-5-methoxy-3'-(trifluoromethoxy)-4-biphenylyl)(methylcarbamoyl)amino)-N-4-pyrimidinyl-3-pyridinesulfonamide | 3 | R | 4-aminopyrimidine |
| 3-16 | 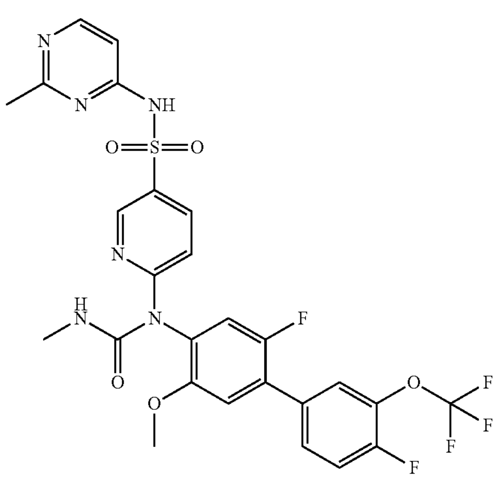 [SMILES: CNC(=O)N(c1ccc(S(=O)(=O)Nc2ccnc(C)n2)cn1)c1cc(F)c(-c2ccc(F)c(OC(F)(F)F)c2)cc1OC] | 6-((2,4'-difluoro-5-methoxy-3'-(trifluoromethoxy)-4-biphenylyl)(methylcarbamoyl)amino)-N-(2-methyl-4-pyrimidinyl)-3-pyridinesulfonamide | 3 | R | 2-methyl-4-pyrimidinamine |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 4.1 | 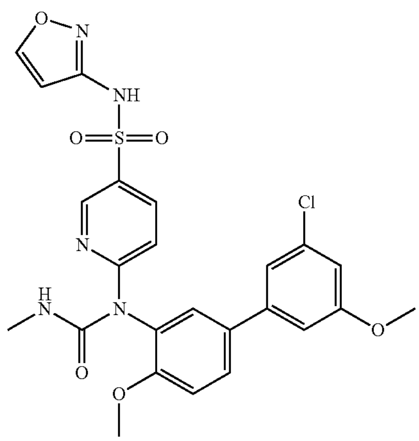 | 6-((3'-chloro-4,5'-dimethoxy-3-biphenylyl)(methylcarbamoyl)amino)-N-3-isoxazolyl-3-pyridinesulfonamide | 4 | G | (3-chloro-5-methoxyphenyl)boronic acid |
| 4.2 | 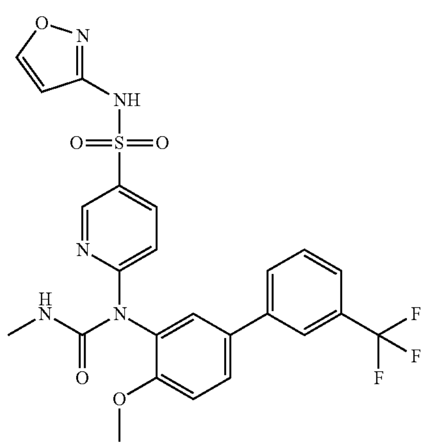 [SMILES: CNC(=O)N(c1ccc(S(=O)(=O)Nc2ccon2)cn1)c1cc(-c2cccc(C(F)(F)F)c2)ccc1OC] | N-3-isoxazolyl-6-((4-methoxy-3'-(trifluoromethyl)-3-biphenylyl)(methylcarbamoyl)amino)-3-pyridinesulfonamide | 4 | G | (3-(trifluoromethyl)phenyl)boronic acid |
| 4.3 | 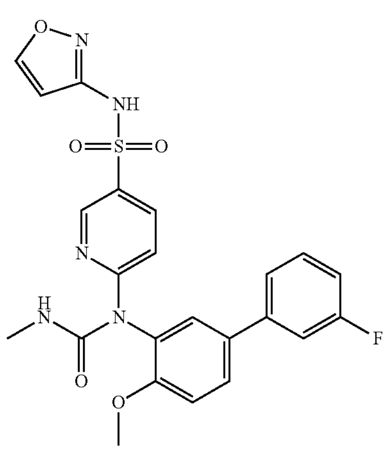 [SMILES: CNC(=O)N(c1ccc(S(=O)(=O)Nc2ccon2)cn1)c1cc(-c2cccc(F)c2)ccc1OC] | 6-((3'-fluoro-4-methoxy-3-biphenylyl)(methylcarbamoyl)amino)-N-3-isoxazolyl-3-pyridinesulfonamide | 4 | G | (3-fluorophenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 4.4 | 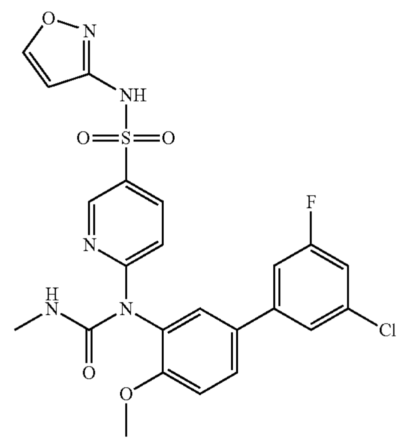 [SMILES: CNC(=O)N(c1ccc(S(=O)(=O)Nc2ccon2)cn1)c1cc(-c2cc(F)cc(Cl)c2)ccc1OC] | 6-((3'-chloro-5'-fluoro-4-methoxy-3-biphenylyl)(methylcarbamoyl)amino)-N-3-isoxazolyl-3-pyridinesulfonamide | 4 | G | (3-chloro-5-fluorophenyl)boronic acid |
| 4.5 | 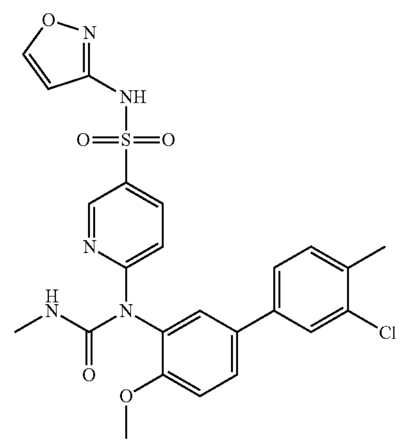 [SMILES: CNC(=O)N(c1ccc(S(=O)(=O)Nc2ccon2)cn1)c1cc(-c2ccc(C)c(Cl)c2)ccc1OC] | 6-((3'-chloro-4-methoxy-4'-methyl-3-biphenylyl)(methylcarbamoyl)amino)-N-3-isoxazolyl-3-pyridinesulfonamide | 4 | G | (3-chloro-4-methylphenyl)boronic acid |
| 4.6 | 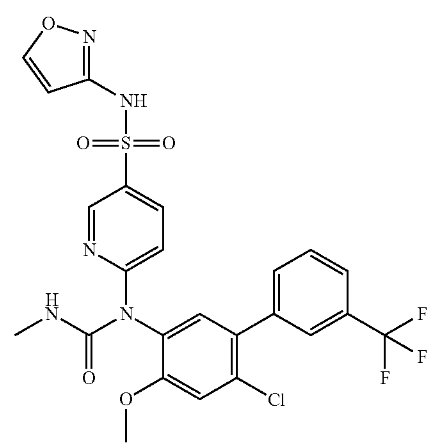 [SMILES: CNC(=O)N(c1ccc(S(=O)(=O)Nc2ccon2)cn1)c1cc(-c2cccc(C(F)(F)F)c2)c(Cl)cc1OC] | 6-((6-chloro-4-methoxy-3'-(trifluoromethyl)-3-biphenylyl)(methylcarbamoyl)amino)-N-3-isoxazolyl-3-pyridinesulfonamide | 4 | G | (3-(trifluoromethyl)phenyl)boronic acid |

TABLE 5-continued

Examples 1-1 to 1-90, 2-1 to 2-14, 3-1 to 3-16, and 4-1 to 4-9 were prepared following the procedures described in Methods 1-4 above. Ex. # stands for Example no. Mtd. stands for Method, and S.M. stands for starting material, for example, S.M. A is Intermediate A.

| Ex. # | Chemical Structure | Name | Mtd | S.M | Reagent |
|---|---|---|---|---|---|
| 4.7 | 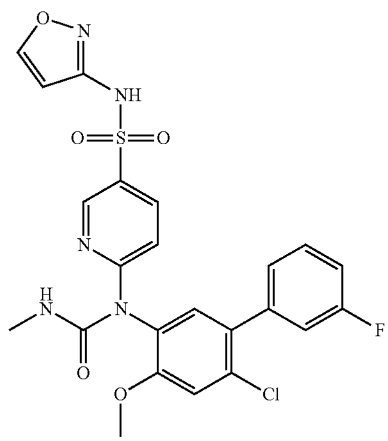 [SMILES: CNC(=O)N(c1ccc(S(=O)(=O)Nc2ccon2)cn1)c1cc(-c2cccc(F)c2)c(Cl)cc1OC] | 6-((6-chloro-3'-fluoro-4-methoxy-3-biphenylyl)(methylcarbamoyl)amino)-N-3-isoxazolyl-3-pyridinesulfonamide | 4 | G | (3-fluorophenyl)boronic acid |
| 4.8 | 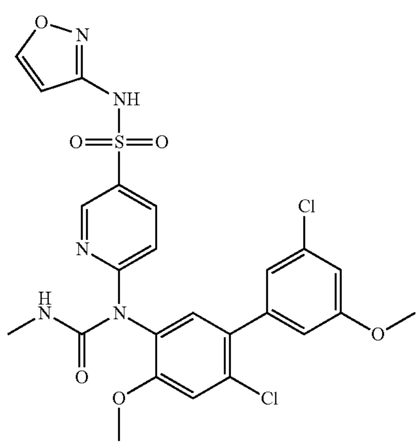 | 6-((3',6-dichloro-4,5'-dimethoxy-3-biphenylyl)(methyl-carbamoyl)amino)-N-3-isoxazolyl-3-pyridinesulfonamide | 4 | G | (3-chloro-5-methoxyphenyl)boronic acid |
| 4.9 | 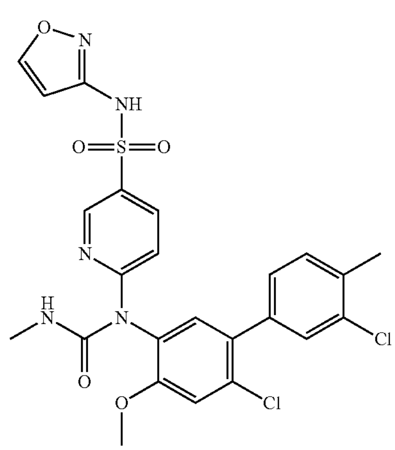 [SMILES: CNC(=O)N(c1ccc(S(=O)(=O)Nc2ccon2)cn1)c1cc(-c2ccc(C)c(Cl)c2)c(Cl)cc1OC] | 6-((3',6-dichloro-4-methoxy-4'-methyl-3-biphenylyl)(methyl-carbamoyl)amino)-N-3-isoxazolyl-3-pyridinesulfonamide | 4 | G | (3-chloro-4-methylphenyl)boronic acid |

147

Example 5-1

6-(1-(2-chloro-5-methoxy-3'-(trifluoromethyl)-[1,1'-biphenyl]-4-yl)ureido)-N-(isoxazol-3-yl)pyridine-3-sulfonamide Method 5

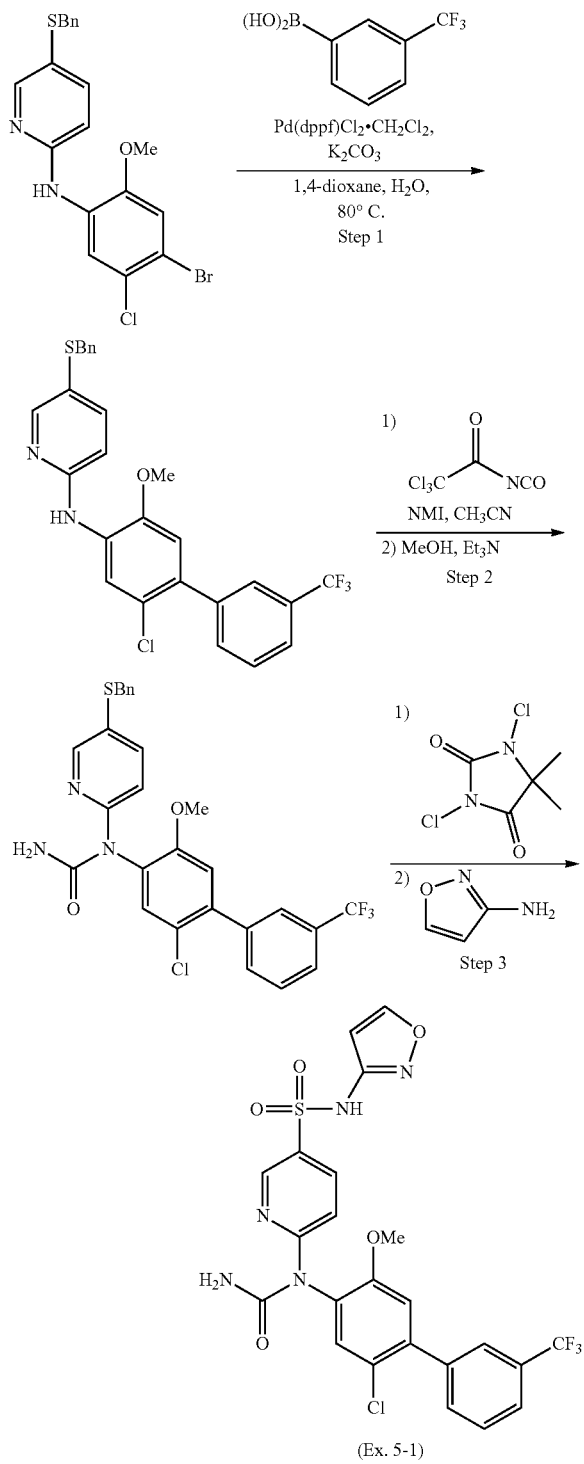

(Ex. 5-1)

148

Step 1: 5-(benzylthio)-N-(2-chloro-5-methoxy-3'-(trifluoromethyl)-[1,1'-biphenyl]-4-yl) pyridine-2-amine To a 20 ml vial containing [1,1'-Bis(diphenylphosphino)ferrocene]dichloropalladium(II), complex with dichloromethane (86 mg, 0.10 mmol), potassium carbonate (731 mg, 5.3 mmol), (3-(trifluoromethyl)phenyl)boronic acid (402 mg, 2.116 mmol) and 5-(benzylthio)-N-(4-bromo-5-chloro-2-methoxyphenyl)pyridine-2-amine (Intermediate J-1, 461 mg, 1.058 mmol, prepared according to Method 1, by using 4-bromo-5-chloro-2-methoxyaniline in in Step 2, LC/MS m/z=435.0, 437.0 M+H) were added 1,4-dioxane (4 mL) and water (1.3 mL). The vial was evacuated and backfilled three times with nitrogen. The reaction mixture was then heated to 80° C. and stirred for 4 h. After cooling, the organic layer was partitioned between water and ethyl acetate. The aqueous phase was separated and further extracted with ethyl acetate (2x). The combined organic phases were washed with brine, dried over $Mg_2SO_4$, filtered over CELITE® and concentrated. The crude material was adsorbed onto a plug of silica gel and purified by chromatography through a biotage pre-packed silica gel column, eluting with a gradient of 0% to 35% ethyl acetate in heptane, to provide 5-(benzylthio)-N-(2-chloro-5-methoxy-3'-(trifluoromethyl)-[1,1'-biphenyl]-4-yl)pyridine-2-amine (341 mg, 0.681 mmol, 64.3% yield) as yellow oil, LRMS (ESI, +ve ion) m/z 501, 503 (M+H)+; $^1$H NMR (400 MHz, CHLOROFORM-d) δ ppm 8.45 (1H, s), 8.25 (1H, d, J=2.07 Hz), 7.72 (1H, br s), 7.63-7.70 (1H, m), 7.52-7.61 (1H, m), 7.42 (1H, dd, J=8.55, 2.38 Hz), 7.27-7.32 (2H, m), 7.23-7.26 (1H, m), 7.14-7.23 (3H, m), 6.82 (1H, s), 6.71 (1H, d, J=8.97 Hz), 3.97 (2H, s), 3.93 (3H, s).

Step 2: 1-(5-(benzylthio)yridine-2-yl)-1-(2-chloro-5-methoxy-3'-(trifluoromethyl)-[1,1'-biphenyl]-4-yl) urea To a solution of 5-(benzylthio)-N-(2-chloro-5-methoxy-3'-(trifluoromethyl)-[1,1'-biphenyl]-4-yl)yridine-2-amine (68.6 mg g, 0.137 mmol) in acetonitrile (0.46 mL) was added 1-methylimidazole (10.92 μL, 0.137 mmol) followed by dropwise addition of trichloroacetyl isocyanate (33 μL, 0.274 mmol). The reaction mixture was stirred at room temperature for 1 h, when the reaction was complete by LCMS. MeOH (0.48 mL, 11.85 mmol) followed by Et$_3$N (24 μL, 0.172 mmol) were added to the reaction mixture, which was then stirred at RT for 5 h. The reaction mixture was partitioned between EtOAc and water. The organic phase was separated and the aqueous phase was further extracted with EtOAc (2x). The combined organic phases were washed successively with saturated aqueous NH$_4$Cl and brine, dried over MgSO$_4$, filtered and concentrated. The resulting crude 1-(5-(benzylthio)yridine-2-yl)-1-(2-chloro-5-methoxy-3'-(trifluoromethyl)-[1,1'-biphenyl]-4-yl)urea was used as such in the next step assuming 100% yield. LRMS: (ESI, +ve ion) m/z 544, 546 (M+H)$^+$.

Step 3: 6-(1-(2-chloro-5-methoxy-3'-(trifluoromethyl)-[1,1'-biphenyl]-4-yl)ureido)-N-(isoxazol-3-yl)pyridine-3-sulfonamide Step 3-1: To a solution of 1-(5-(benzylthio)yridine-2-yl)-1-(2-chloro-5-methoxy-3'-(trifluoromethyl)-[1,1'-biphenyl]-4-yl)urea (74 mg, 0.136 mmol) in acetonitrile (1.28 mL), acetic acid (49 μL) and water (32 μL) at 0° C. was slowly added 1,3-dichloro-5,5-dimethylimidazolidine-2,4-dione (38 mg, 0.190 mmol). The reaction mixture was stirred at 0° C. for 2 hr. Solid NaHSO$_3$ was added at 0° C. and the reaction mixture was diluted with EtOAc. Na$_2$SO$_4$ was then added and the reaction mixture was filtered and concentrated under vacuo. The resulting residue was taken up with toluene and a small amount of EtOAc and filtered over a 2" pad of silica gel, washing with 50% EtOAc in heptane, The filtrate was concentrated under vacuo to give 6-(1-(2-chloro-5-methoxy-3'-(trifluoromethyl)-[1,1'-biphenyl]-4-yl)ureido)pyridine-3 sulfonyl chloride, which was used as such in the next step assuming 100% yield. LRMS: (ESI, +ve ion) m/z 520, 522 (M+H)$^+$.

Step 3-2: 6-(1-(2-chloro-5-methoxy-3'-(trifluoromethyl)-[1,1'-biphenyl]-4-yl)ureido)pyridine-3-sulfonyl chloride obtained in the previous step was azeotroped with toluene and diluted with DCM (1.3 mL). Isoxazol-3-amine (14 μL, 0.190 mmol) and pyridine (0.11 ml, 1.360 mmol) were added and the reaction mixture was stirred at RT overnight. Half of the solvent was concentrated under reduced pressure and the resulting crude solution was adsorbed onto a plug of silica gel and purified by chromatography through a pre-packed RediSep® Rf Gold® silica gel column (5 g), eluting with a gradient of 20% to 100% ethyl acetate in heptane, to provide 6-(1-(2-chloro-5-methoxy-3'-(trifluoromethyl)-[1,1'-biphenyl]-4-yl)ureido)-N-(isoxazol-3-yl)pyridine-3-sulfonamide (17.7 mg, 0.031 mmol, 22.91% yield) as a white powder, (see table 7 for analytical data)

TABLE 6

Examples 5-2 to 5-5 below were prepared following the procedure reported in Method 5 with the modifications described below.

| Ex. # | Chemical Structure | Name | Preparation |
|---|---|---|---|
| 5-2 | 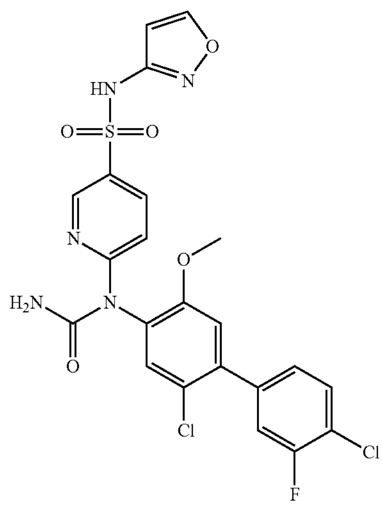 [SMILES: COc1cc(-c2ccc(Cl)c(F)c2)c(Cl)cc1N(C(N)=O)c1ccc(S(=O)(=O)Nc2ccon2)cn1] | 6-(carbamoyl(2,4'-dichloro-3'-fluoro-5-methoxy-4-biphenylyl)amino)-N-3-isoxazolyl-3-pyridinesulfonamide | (4-chloro-3-fluorophenyl)boronic acid was used in place of (3-(trifluoromethyl)phenyl) boronic acid in step 1. |
| 5-3 | 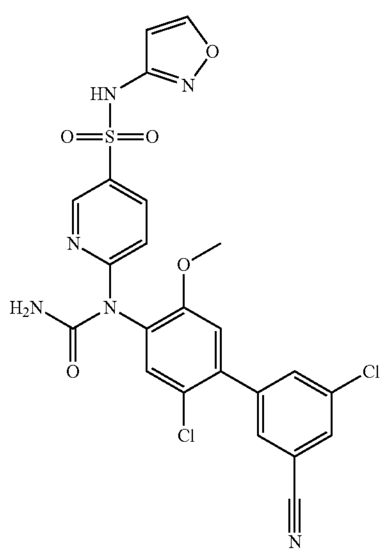 [SMILES: COc1cc(-c2cc(Cl)cc(C#N)c2)c(Cl)cc1N(C(N)=O)c1ccc(S(=O)(=O)Nc2ccon2)cn1] | 6-(carbamoyl(2,3'-dichloro-5'-cyano-5-methoxy-4-biphenylyl)amino)-N-3-isoxazolyl-3-pyridinesulfonamide | (3-chloro-5-cyanophenyl)boronic acid was used in place of (3-(trifluoromethyl)phenyl) boronic acid in step 1. |

TABLE 6-continued

Examples 5-2 to 5-5 below were prepared following the procedure reported in Method 5 with the modifications described below.

| Ex. # | Chemical Structure | Name | Preparation |
|---|---|---|---|
| 5-4 | 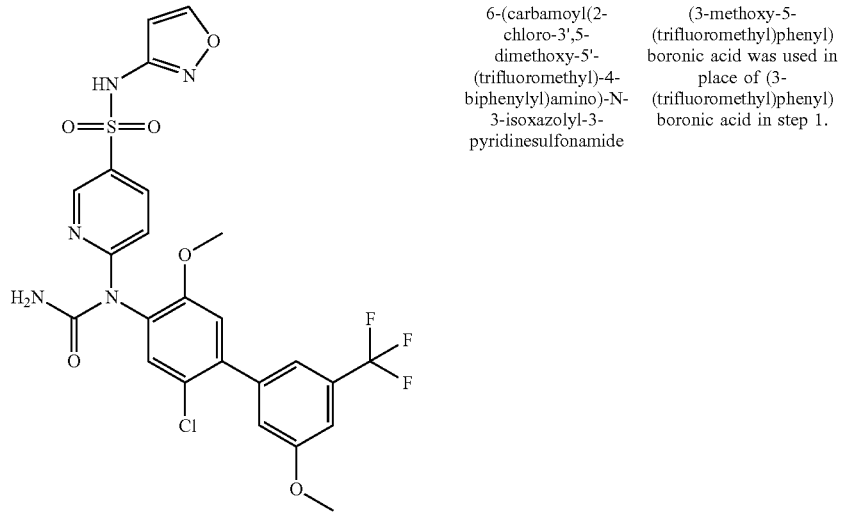 | 6-(carbamoyl(2-chloro-3',5-dimethoxy-5'-(trifluoromethyl)-4-biphenylyl)amino)-N-3-isoxazolyl-3-pyridinesulfonamide | (3-methoxy-5-(trifluoromethyl)phenyl)boronic acid was used in place of (3-(trifluoromethyl)phenyl)boronic acid in step 1. |
| 5-5 | 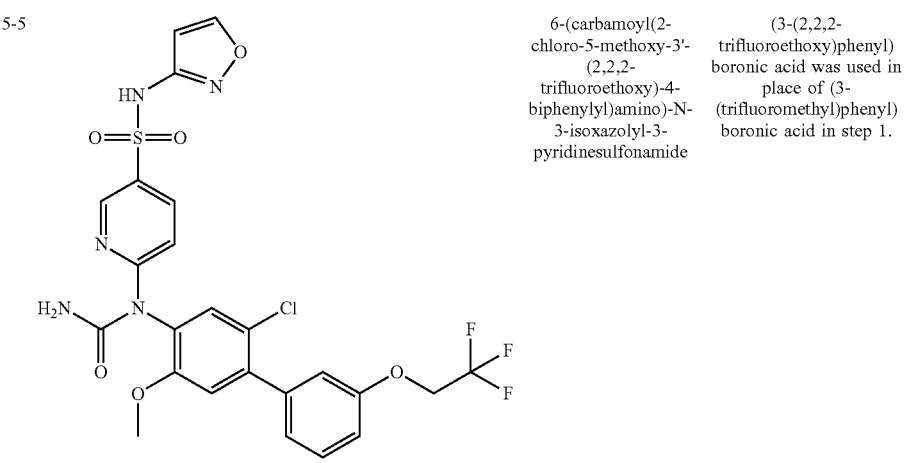 | 6-(carbamoyl(2-chloro-5-methoxy-3'-(2,2,2-trifluoroethoxy)-4-biphenylyl)amino)-N-3-isoxazolyl-3-pyridinesulfonamide | (3-(2,2,2-trifluoroethoxy)phenyl)boronic acid was used in place of (3-(trifluoromethyl)phenyl)boronic acid in step 1. |

153

Example 6

Methyl (2-chloro-5-methoxy-3'-(trifluoromethyl)-[1,1'-biphenyl]-4-yl)(5-(N-(isoxazol-3-yl)sulfamoyl)pyridine-2-yl)carbamate

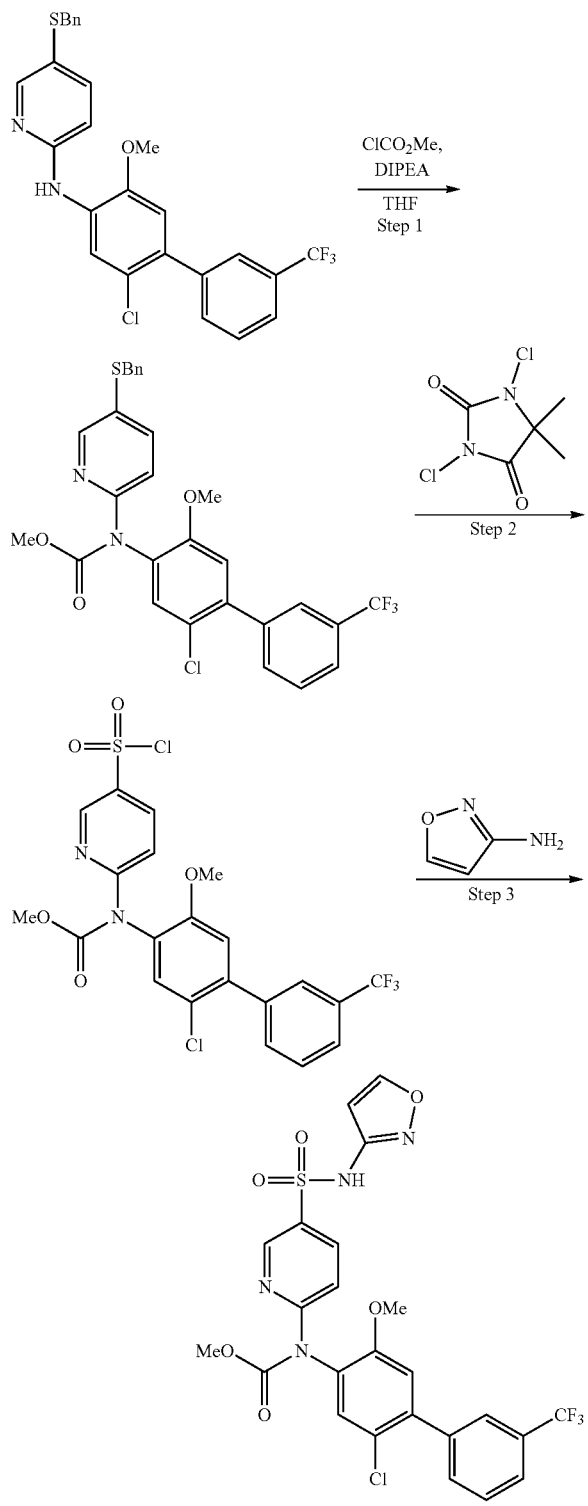

154

Step 1: Methyl (5-(benzylthio)pyridine-2-yl)(2-chloro-5-methoxy-3'-(trifluoromethyl)-[1,1'-biphenyl]-4-yl)carbamate To a solution of 5-(benzylthio)-N-(2-chloro-5-methoxy-3'-(trifluoromethyl)-[1,1'-biphenyl]-4-yl)yridine-2-amine (67.9 mg, 0.139 mmol) in tetrahydrofuran (0.4 mL) was added N,N-diisopropylethylamine (73 µL, 0.417 mmol) followed by methyl chloroformate (26 µL, 0.334 mmol). The reaction mixture was stirred at 70° C. for 1.5 h. After cooling, the reaction mixture was quenched with saturated aqueous NaHCO$_3$ and diluted with ethyl acetate. The organic layer was separated and the aqueous phase was further extracted with ethyl acetate (2×). The combined organic layers were washed with brine, dried over MgSO$_4$, filtered and concentrated under vacuo. The resulting crude methyl (5-(benzylthio)-pyridine-2-yl)(2-chloro-5-methoxy-3'-(trifluoromethyl)-[1,1'-biphenyl]-4-yl)carbamate was used as such in the next step assuming 100% yield. LRMS (ESI, +ve ion) m/z 559, 561 (M+H)$^+$.

Step 2: methyl (2-chloro-5-methoxy-3'-(trifluoromethyl)-[1,1'-biphenyl]-4-yl)(5-(chlorosulfonyl)-pyridine-2-yl)carbamate To a solution of methyl (5-(benzylthio)pyridine-2-yl)(2-chloro-5-methoxy-3'-(trifluoromethyl)-[1,1'-biphenyl]-4-yl)carbamate (78 mg, 0.139 mmol) in acetonitrile (1.31 mL), acetic acid (50 µL) and water (33 µL) at 0° C. was slowly added 1,3-dichloro-5,5-dimethylimidazolidine-2,4-dione (38 mg, 0.195 mmol). The reaction mixture was stirred at 0° C. for 2 hrs. NaHSO$_3$ solid was added at 0° C. and the reaction mixture was diluted with EtOAc. Na$_2$SO$_4$ was then added and the reaction mixture was filtered and concentrated in vacuo. The resulting residue was taken up with toluene and a small amount of DCM and filtered over a 2 inch pad of silica gel, washing with 20% EtOAc in heptane. The filtrate was concentrated under vacuo to give methyl (2-chloro-5-methoxy-3'-(trifluoromethyl)-[1,1'-biphenyl]-4-yl)(5-(chlorosulfonyl)yridine-2-yl)carbamate (67.8 mg, 0.127 mmol, 91% yield). LRMS: (ESI, +ve ion) m/z 535, 537 (M+H)+.

Step 3: Methyl (2-chloro-5-methoxy-3'-(trifluoromethyl)-[1,1'-biphenyl]-4-yl)(5-(N-(isoxazol-3-yl)sulfamoyl)pyridine-2-yl)carbamate Methyl (2-chloro-5-methoxy-3'-(trifluoromethyl)-[1,1'-biphenyl]-4-yl)(5-(chlorosulfonyl)pyridine-2-yl) carbamate (67.8 mg, 0.127 mmol) obtained in the previous step was azeotroped with toluene and diluted with DCM (1.4 mL). Isoxazol-3-amine (13 µL, 0.18 mmol) and pyridine (104 µL, 1.27 mmol) were added and the reaction mixture was stirred at RT overnight. Half of the solvent was concentrated under reduced pressure and the resulting crude solution was absorbed onto a plug of silica gel and purified by chromatography through a pre-packed RediSep® Rf Gold® silica gel column (5 g), eluting with a gradient of 0% to 50% ethyl acetate in heptane, to provide methyl (2-chloro-5-methoxy-3'-(trifluoromethyl)-[1,1'-biphenyl]-4-yl)(5-(N-(isoxazol-3-yl)sulfamoyl)yridine-2-yl)carbamate (19.5 mg, 0.033 mmol, 24% yield) as a white powder, (see Table 7 for analytical data).

Example 7

6-((5-chloro-4-(cyclopentylethynyl)-2-methoxyphenyl)(methylcarbamoyl)amino)-N-3-isoxazolyl-3-pyridinesulfonamide

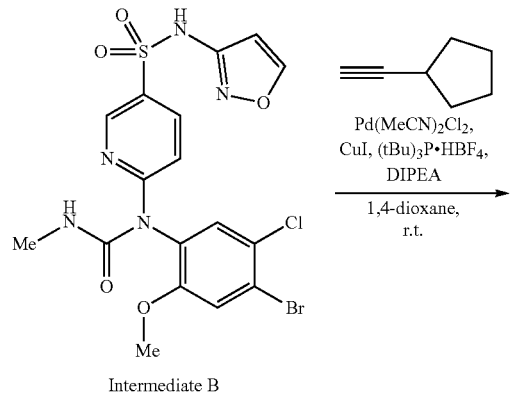

Intermediate B

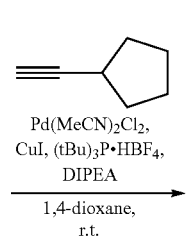

6-(1-(4-bromo-5-chloro-2-methoxyphenyl)-3-methylureido)-N-(isoxazol-3-yl)pyridine-3-sulfonamide (Intermediate B, 0.2 g, 0.387 mmol), bis(acetonitrile)dicholoropalladium(ii) (6.02 mg, 0.023 mmol), tri-tert-butylphosphonium tetrafluoroborate (0.013 g, 0.046 mmol), and copper(i) iodide (2.95 mg, 0.015 mmol) were added to a 1 dram vial and evacuated and backfilled with $N_2$ 3 times. 1,4-dioxane (0.774 ml), and cyclopentylacetylene (0.135 ml, 1.161 mmol) were added and the solution was sparged for 3 min. diisopropylamine (0.193 ml, 1.355 mmol) was added while sparging and the vial was sealed with a new cap and stirred at r.t. o/n. Full conversion was observed in the morning by LC/MS. After filtering through a 0.45 μm filter, RP-HPLC (30-80% MeCN/H₂O w0.1% TFA) provided the product in ~70% purity. MPLC (24 g Grace, 15-80% [3:1, EtOAc:EtOH]/hep w/5% DCM additive) provided 6-(1-(5-chloro-4-(cyclopentylethynyl)-2-methoxyphenyl)-3-methylureido)-N-(isoxazol-3-yl)pyridine-3-sulfonamide (see table 7 for analytical data).

Example 8

6-((5-fluoro-2-methoxy-4-(3,3,3-trifluoropropyl)phenyl)(methylcarbamoyl)amino)-N-3-isoxazolyl-3-pyridinesulfonamide

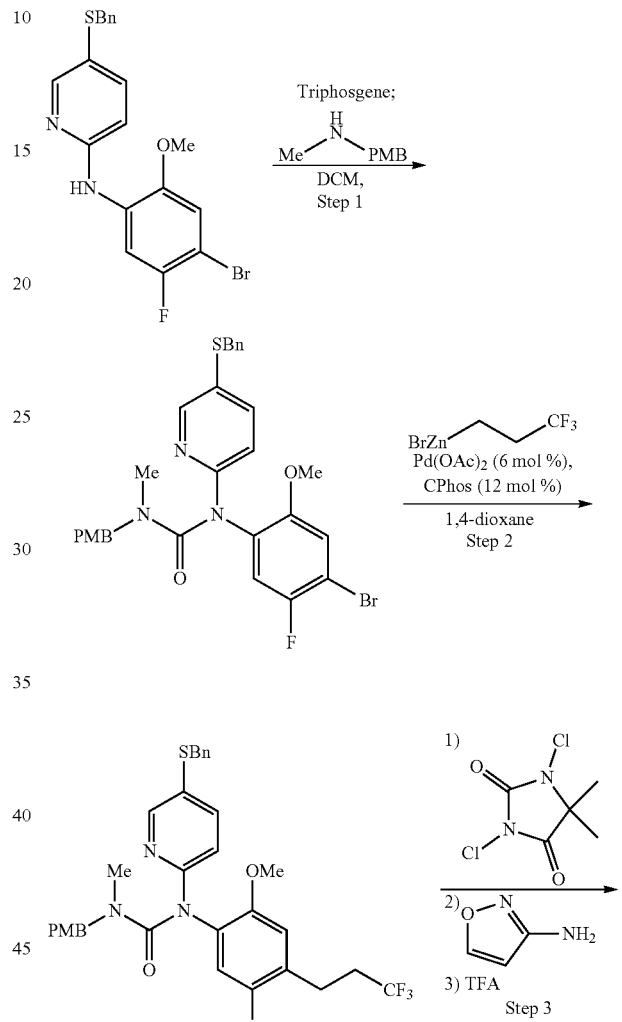

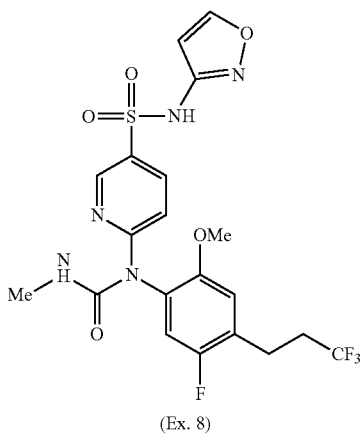

(Ex. 8)

Step 1: 1-(5-(benzylthio)pyridin-2-yl)-1-(4-bromo-5-fluoro-2-methoxyphenyl)-3-(4-methoxybenzyl)-3-methylurea DCM was added to bis(trichloromethyl) carbonate (0.330 g, 1.112 mmol) and 5-(benzylthio)-N-(4-bromo-5-fluoro-2-methoxyphenyl)pyridin-2-amine (1 g, 2.385 mmol) in a 20 mL vial. Hunig's base (1.250 ml, 7.15 mmol) was added dropwise to the sealed vial while the reaction was stirred at r.t. After 2 h, starting material remained and an additional 80 mg of triphosgene was added. After 1.5 h. 4-methoxy-n-methylbenzylamine (0.721 ml, 4.77 mmol) was added along with an additional 0.5 ml of DCM to maintain stirring. After 1 hour no chloro-formamide was observed and the reaction was quenched with saturated NH$_4$Cl, extracted 2× with EtOAc and the combined organics were washed with brine, dried over Na2SO4 and concentrated to a white foam which was used crude. LRMS: (ESI, +ve ion) m/z 481.0, 483.0 (M+H)$^+$, 503.0, 505.0 (M+Na).

Step 2: 1-(5-(benzylthio)pyridin-2-yl)-1-(5-fluoro-2-methoxy-4-(3,3,3-trifluoropropyl)phenyl)-3-(4-methoxybenzyl)-3-methylurea A 20 ml vial was charged with activated zinc solution (Rieke zinc) (2.63 ml, 2.012 mmol) and cooled to 0° C. 3-bromo-1,1,1-trifluoropropane (0.143 ml, 1.341 mmol) was added slowly dropwise. The reaction was warmed to room temperature and stirred for one hour. A solution of palladium (ii) acetate (4.52 mg, 0.020 mmol), 2'-(dicyclohexylphosphino)-N2,N2,N6,N6-tetramethyl-[1,1'-biphenyl]-2,6-diamine (CPhos) (0.018 g, 0.040 mmol), and 1-(5-(benzylthio)pyridin-2-yl)-1-(4-bromo-5-fluoro-2-methoxyphenyl)-3-(4-methoxybenzyl)-3-methylurea (0.2 g, 0.335 mmol) in 1 ml of 1,4-dioxane were added and the reaction was sealed and stirred overnight at 50° C. The reaction was quenched with a 1:1 solution of saturated NH$_4$Cl and 1M HCl and the reaction was extracted with EtOAc 2×. The combined organics were washed with brine, dried over Na2SO4, concentrated and purified by MPLC (4 g RediSep® Rf Gold®, 10-100% E:H) to provide 1-(5-(benzylthio)pyridin-2-yl)-1-(5-fluoro-2-methoxy-4-(3,3,3-trifluoropropyl)phenyl)-3-(4-methoxybenzyl)-3-methylurea (0.126 g, 0.178 mmol) 61% yield. LRMS: (ESI, +ve ion) m/z 614.2 (M+H)$^+$.

Step 3: 6-(1-(5-fluoro-2-methoxy-4-(3,3,3-trifluoropropyl)phenyl)-3-methylureido)-N-(isoxazol-3-yl)pyridine-3-sulfonamide 1-(5-(benzylthio)pyridin-2-yl)-1-(5-fluoro-2-methoxy-4-(3,3,3-trifluoropropyl)phenyl)-3-(4-methoxybenzyl)-3-methylurea (0.109 g, 0.178 mmol) was dissolved in acetonitrile (1.671 ml), acetic acid (0.063 ml) and water (0.042 ml) in a 4 mL vial and cooled to 0° C. 1,3-dichloro-5,5-dimethylimidazolidine-2,4-dione (0.052 g, 0.266 mmol) was added slowly. After 2 h, the sulfonyl chloride is observed by LC/MS. NaHSO$_3$ was added at 0° C. and the reaction was diluted with EtOAc. The reaction was washed with brine, dried over Na$_2$SO$_4$, filtered over a 1" plug of silica and concentrated. The crude oil was brought up in DCM (0.5 ml) and 3-aminoisoxazole (0.028 ml, 0.355 mmol) and pyridine (0.058 ml, 0.710 mmol) were added at RT. After concentrating, RP-HPLC purification (30-70% MeCN/H$_2$O w/0.1% TFA) and lyophilization of fractions containing the product gave 6-(1-(5-fluoro-2-methoxy-4-(3,3,3-trifluoropropyl)phenyl)-3-methylureido)-N-(isoxazol-3-yl)pyridine-3-sulfonamide (0.037 g, 0.072 mmol, 40.3% yield) as the TFA salt as a tan powder. (See Table 7 for analytical data of the TFA salt compound). Purification via MPLC can be used to obtain the title compound.

Example 9

4-(1-(4'-chloro-3-methoxy-3'-methyl-[1,1'-biphenyl]-4-yl)-3methylureido)-N-(isoxazol-3-yl)benzenesulfonamide

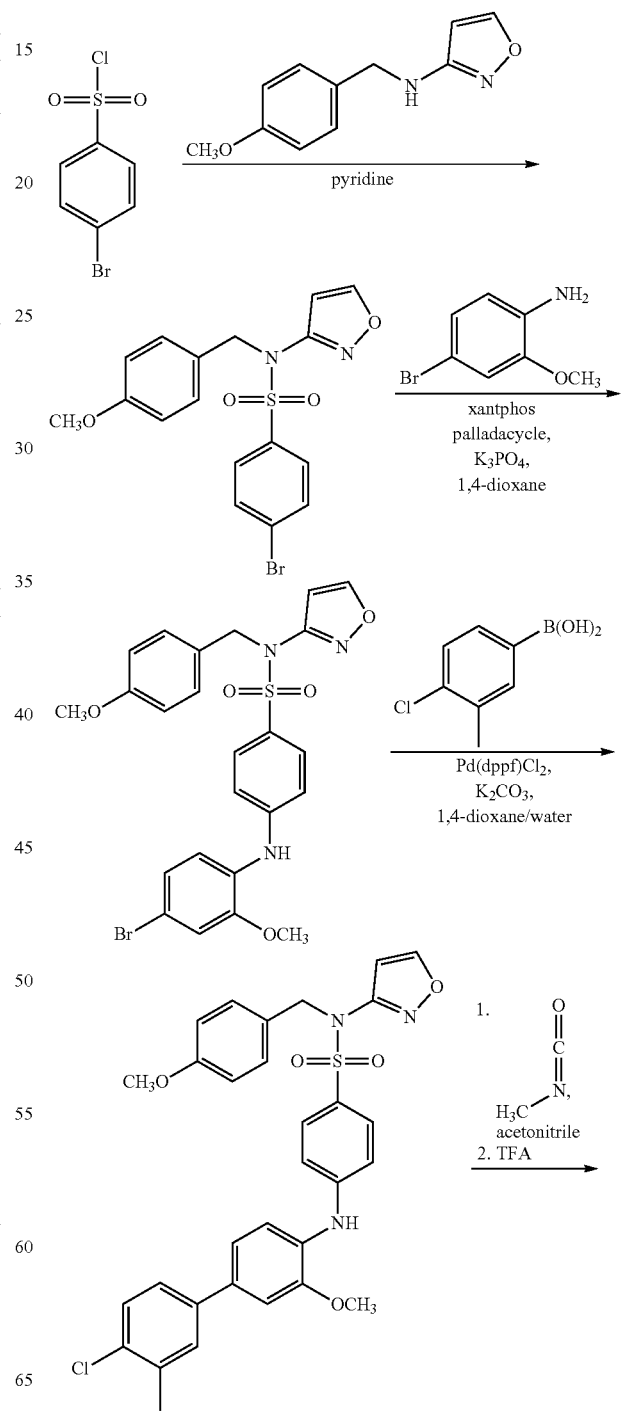

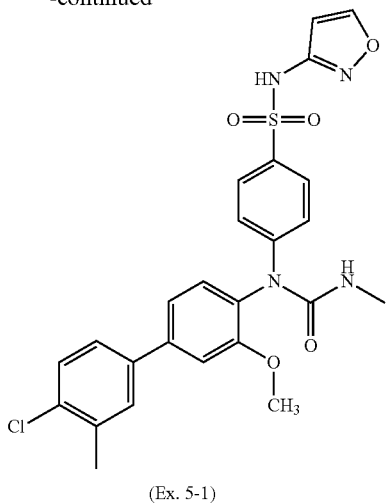

(Ex. 5-1)

Step 1: 4-bromo-N-(isoxazol-3-yl)-N-(4-methoxybenzyl) benzenesulfonamide

N-(4-methoxybenzyl)isoxazol-3-amine (1.001 g, 4.9 mmol) was dissolved in pyridine (3.96 ml, 49.0 mmol) and treated with 4-bromobenzene-1-sulfonyl chloride (1.878 ml, 7.35 mmol) at room temperature. After 2 hours, the reaction was diluted with saturated $NH_4Cl$ and extracted three times with EtOAc. The combined organics were washed with brine, dried over $Na_2SO_4$, filtered and concentrated to provide 4-bromo-N-(isoxazol-3-yl)-N-(4-methoxybenzyl)benzenesulfonamide (1.68 g, 3.97 mmol, 81% yield) which was used without further purification in the next step. LC/MS m+Na=444.8/446.8

Step 2: N-(isoxazol-3-yl)-4-(isoxazol-3-yl(4-methoxybenzyl)amino)-N-(4-methoxybenzyl)benzenesulfonamide 4-bromo-N-(isoxazol-3-yl)-N-(4-methoxybenzyl)benzenesulfonamide (1 g, 2.362 mmol), 4-bromo-2-methoxyaniline (0.477 g, 2.362 mmol), xantphos palladacycle precatalyst: [Chloro[9,9-dimethyl-4,5-bis(diphenylphosphino)xanthene][2'-amino-1,1'-biphenyl]palladium(II) dichloromethane adduct] (0.112 g, 0.118 mmol), and finely ground potassium phosphate (1.504 g, 7.09 mmol) were dissolved in 1,4-dioxane (9.45 ml) in a 40 ml vial and the vial was evacuated and backfilled three times with $N_2$ before being fitted with a fresh cap and heated to 100° C. on an aluminum block. After 4 hours, complete conversion was observed. THF was added and the reaction was filtered over CELITE® and concentrated. MPLC purification (100 g snap ultra, 2-75% EtOAc:Heptane) provided N-(isoxazol-3-yl)-4-(isoxazol-3-yl(4-methoxybenzyl)amino)-N-(4-methoxybenzyl)benzenesulfonamide LC/MS m+H=544.0, 545.0

Step 3: 4-((4'-chloro-3-methoxy-3'-methyl-[1,1'-biphenyl]-4-yl)amino)-N-(isoxazol-3-yl)-N-(4-methoxybenzyl)benzenesulfonamide 4-((4-bromo-2-methoxyphenyl)amino)-N-(isoxazol-3-yl)-N-(4-methoxybenzyl)benzenesulfonamide (0.5 g, 0.918 mmol), 4-chloro-3-methylphenylboronic acid (0.313 g, 1.837 mmol), were combined in a 20 ml vial. Dioxane and water were added and the vial was evacuated and backfilled three times with $N_2$. After switching the cap under $N_2$, the reaction was heated to 80° C. After 5 hours, full conversion was observed by LC/MS. The reaction was cooled and the organic layer was separated. Water was added and the reaction was extracted twice with EtOAc and the combined organics were concentrated and purified by MPLC (25 g snap ultra, 2-50% EtOAc:Heptane) to provide 4-((4'-chloro-3-methoxy-3'-methyl-[1,1'-biphenyl]-4-yl)amino)-N-(isoxazol-3-yl)-N-(4-methoxybenzyl)benzenesulfonamide (0.434 g, 0.735 mmol, 80% yield) LC/MS m+H=590.2, 592.2.

Step 4: 4-(1-(4'-chloro-3-methoxy-3'-methyl-[1,1'-biphenyl]-4-yl)-3-methylureido)-N-(isoxazol-3-yl) benzenesulfonamide 4-(1-(4'-chloro-3-methoxy-3'-methyl-[1,1'-biphenyl]-4-yl)-3-methylureido)-N-(isoxazol-3-yl)-N-(4-methoxybenzyl)benzenesulfonamide was dissolved in acetonitrile (0.508 ml) and treated with (methylimino)(oxo)methane (0.047 ml, 0.763 mmol), which was heated in a sealed vial to 80° C. for 12 hours and to 120° C. for 6 hours to provide 50% conversion to the urea product. The reaction was concentrated and purified by MPLC purification (10 g snap ultra, 5-50% E:H) to provide 4-(1-(4'-chloro-3-methoxy-3'-methyl-[1,1'-biphenyl]-4-yl)-3-methylureido)-N-(isoxazol-3-yl)-N-(4-methoxybenzyl)benzenesulfonamide, which was dissolved in 1 ml of DCM and treated with 1 ml of TFA. After 12 hours, the reaction was concentrated and purified by MPLC (10 g snap ultra, 60% E:H) to provide 4-(1-(4'-chloro-3-methoxy-3'-methyl-[1,1'-biphenyl]-4-yl)-3-methylureido)-N-(isoxazol-3-yl)benzenesulfonamide (0.049 g, 0.093 mmol, 36.6% yield) as a white solid. LC/MS m+H=527.0, 529.0 $^1$H NMR (400 MHz, DMSO-$d_6$) δ ppm 11.45 (s, 1H), 8.71 (d, J=1.76 Hz, 1H), 7.77 (d, J=1.97 Hz, 1H), 7.70 (d, J=8.06 Hz, 2H), 7.61 (dd, J=8.34, 2.23 Hz, 1H), 7.51 (d, J=8.29 Hz, 1H), 7.43 (d, J=1.76 Hz, 1H), 7.30-7.35 (m, 1H), 7.26-7.30 (m, 1H), 7.20-7.26 (m, 2H), 6.41 (d, J=1.76 Hz, 1H), 6.19-6.25 (m, 1H), 3.80 (s, 3H), 2.58 (d, J=4.35 Hz, 3H), 2.42 (s, 3H).

Example 10

4-(1-(2,4'-difluoro-5-methoxy-3'-(trifluoromethoxy)-[1,1'-biphenyl]-4-yl)-3-methylureido)-N-(isoxazol-3-yl)benzenesulfonamide

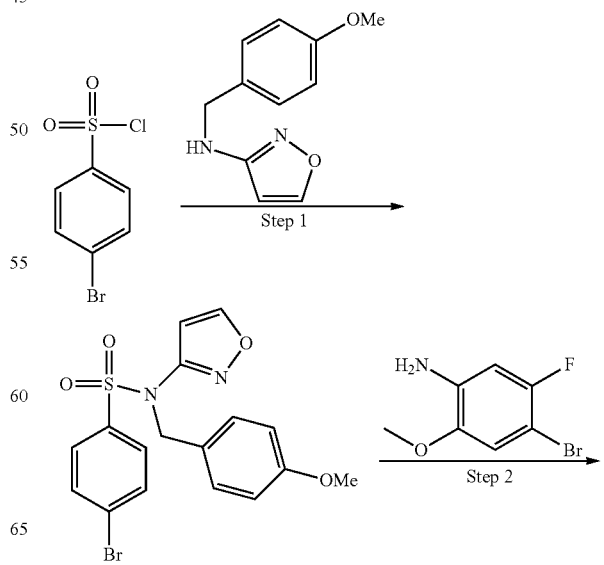

-continued

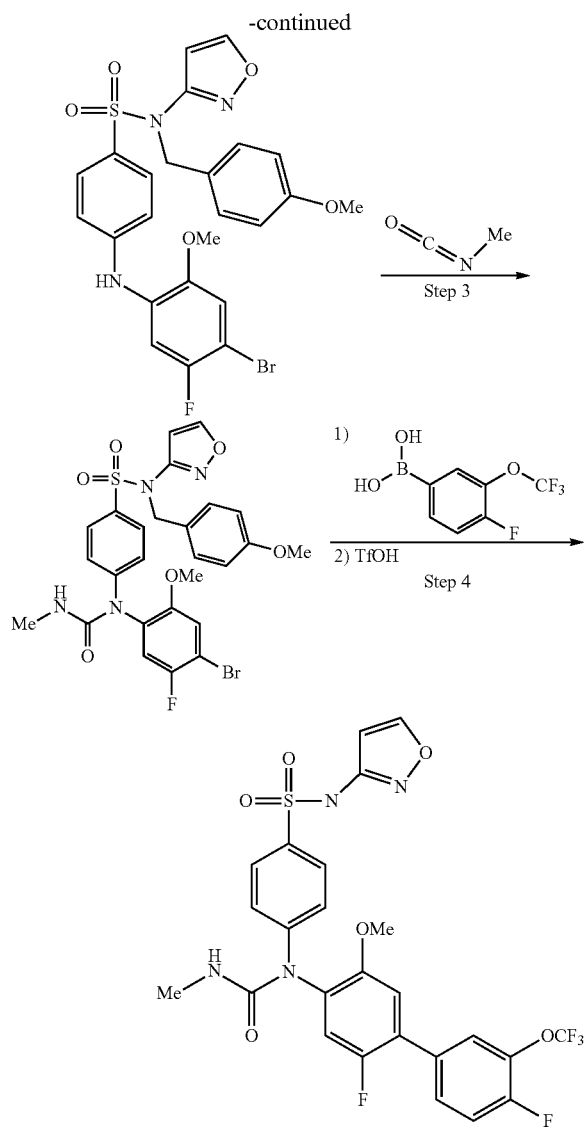

Step 1: 4-bromo-N-(isoxazol-3-yl)-N-(4-methoxybenzyl)benzenesulfonamide

A 250 mL round-bottom flask was charged with N-(4-methoxybenzyl)isoxazol-3-amine (4.00 g, 19.6 mmol), 4-bromobenzene-1-sulfonyl chloride (5.00 g, 19.6 mmol) and THF (100 ml) then cooled to −78° C. before a solution of LHMDS in THF (29.4 mL, 29.4 mmol, 1.0 M) was added dropwise via addition funnel. After 2 hours, a saturated aqueous solution of ammonium chloride was introduced and the resultant mixture was allowed to warm to ambient temperature. EtOAc (50 mL) was introduced and the layers were separated. The aqueous layer was further extracted with EtOAc (2×50 mL). The combined organic layers were dried over magnesium sulfate, filtered, and concentrated under reduced pressure. The product was purified via column chromatography RediSep® Rf Gold®100 g, gradient elution 0 to 50% EtOAc in heptane to afford 4-bromo-N-(isoxazol-3-yl)-N-(4-methoxybenzyl)benzenesulfonamide (4.60 g, 10.9 mmol, 55.5% yield) as an off-white solid. LRMS (ESI, +ve ion) m/z 423.0 (M+H)+; $^1$H NMR (500 MHz, DMSO-d6) δ ppm 3.72 (s, 3H) 4.89 (s, 2H) 6.70 (d, J=1.82 Hz, 1H) 6.87 (m, J=8.69 Hz, 2H) 7.24 (m, J=8.56 Hz, 2H) 7.76 (m, J=8.69 Hz, 2H) 7.84 (m, J=8.56 Hz, 2H) 8.82 (d, J=1.69 Hz, 1H).

Step 2: 4-((4-bromo-5-fluoro-2-methoxyphenyl)amino)-N-(isoxazol-3-yl)-N-(4-methoxybenzyl)benzenesulfonamide A 100 mL round-bottom flask was charged with 4-bromo-N-(isoxazol-3-yl)-N-(4-methoxybenzyl)benzenesulfonamide (1.96 g, 4.63 mmol), Methanesulfonato[9,9-dimethyl-4,5-bis(diphenylphosphino)xanthene] (2'-methylamino-1,1'-biphenyl-2-yl)palladium(II) (0.223 g, 0.232 mmol), cesium carbonate (3.02 g, 9.26 mmol), 4-bromo-5-fluoro-2-methoxyaniline (1.12 g, 5.09 mmol) and 1,4-dioxane (23.2 ml). The reaction mixture was sparged with nitrogen gas for 10 mins. The reaction mixture was then warmed to 80° C. After 20 hours, the reaction mixture was cooled to ambient temperature and poured into a 1:1 mixture of water (50 mL) and EtOAc (50 mL). The layers were separated and the aqueous layer was extracted with EtOAc (3×25 mL). The combined organic layers were dried over magnesium sulfate, filtered, concentrated under reduced pressure. The product was purified via column chromatography RediSep® Rf Gold® 100 g, gradient elution 0 to 50% EtOAc in heptane to afford 4-((4-bromo-5-fluoro-2-methoxyphenyl)amino)-N-(isoxazol-3-yl)-N-(4-methoxybenzyl)benzenesulfonamide (2.13 g, 3.79 mmol, 82.0% yield) s pink foam. LRMS (ESI, +ve ion) m/z 564.0 (M+H)+; $^1$H NMR (400 MHz, DMSO-d$_6$) δ ppm 3.71 (s, 3H) 3.82 (s, 3H) 4.84 (s, 2H) 6.69 (d, J=1.76 Hz, 1H) 6.87 (d, J=8.71 Hz, 2H) 7.06 (d, J=8.91 Hz, 2H) 7.21-7.38 (m, 4H) 7.61 (d, J=8.91 Hz, 2H) 8.55 (s, 1H) 8.76 (d, J=1.76 Hz, 1H).

Step 3: 4-(1-(4-bromo-5-fluoro-2-methoxyphenyl)-3-methylureido)-N-(isoxazol-3-yl)-N-(4-methoxybenzyl)benzenesulfonamide A 40 mL vial was charged with 4-((4-bromo-5-fluoro-2-methoxyphenyl)amino)-N-(isoxazol-3-yl)-N-(4-methoxybenzyl)benzenesulfonamide (1.00 g, 1.78 mmol), acetonitrile (8.89 ml), N,N-diisopropylethylamine (0.93 ml, 5.33 mmol), and (methylimino)(oxo)methane (0.21 ml, 3.56 mmol) then sparged with nitrogen gas for 5 mins before being sealed. The reaction mixture was warmed to 80° C. After 16 hours, the reaction mixture was poured into a mixture of EtOAc (10 mL) and an aqueous solution of HCl (1.0 M). The layers were separated and the aqueous layer was extracted with EtOAc (2×10 mL). The combined organic layers were dried over magnesium sulfate, filtered and concentrated under reduced pressure to afford a tan solid. The product was purified via column chromatography RediSep® Rf Gold® 50 g, gradient elution 0% to 50% EtOAc in heptane to afford 4-(1-(4-bromo-5-fluoro-2-methoxyphenyl)-3-methylureido)-N-(isoxazol-3-yl)-N-(4-methoxybenzyl)benzenesulfonamide (900 mg, 1.45 mmol, 82.0% yield) as an off-white solid. LRMS (ESI, +ve ion) m/z 619.0 (M+H)+; $^1$H NMR (500 MHz, DMSO-d6) δ ppm 8.78 (d, J=1.82 Hz, 1H) 7.66-7.71 (m, 2H) 7.54 (d, J=6.36 Hz, 1H) 7.45 (d, J=8.82 Hz, 1H) 7.24 (dd, J=8.89, 3.05 Hz, 4H) 6.86 (m, J=8.82 Hz, 2H) 6.68 (d, J=1.82 Hz, 1H) 6.43 (q, J=4.24 Hz, 1H) 4.85 (s, 2H) 3.71 (d, J=2.72 Hz, 6H) 2.56 (d, J=4.41 Hz, 3H).

Step 4: 4-(1-(2,4'-difluoro-5-methoxy-3'-(trifluoromethoxy)-[1,1'-biphenyl]-4-yl)-3-methylureido)-N-(isoxazol-3-yl)benzenesulfonamide A 20 mL vial was charged with 4-(1-(4-bromo-5-fluoro-2-methoxyphenyl)-3-methylureido)-N-(isoxazol-3-yl)-N-

(4-methoxybenzyl)benzenesulfonamide (200 mg, 0.32 mmol), potassium carbonate (178 mg, 1.29 mmol), 2-(dicyclohexylphosphino)-3,6-dimethoxy-2'-4'-6'-tri-1-propyl-1,1'biphenyl (3.47 mg, 6.46 µmol), crotyl(2-dicyclohexylphosphino-2',4',6'-triisopropyl-3,6-dimethoxy-1,1'-biphenyl)palladium(II) triflate (6.02 mg, 7.10 µmol), 1,4-dioxane (1.21 mL) and water (404 µl). The reaction mixture was then sparged with nitrogen gas for 10 mins. The vial was sealed and the reaction mixture was warmed to 80° C. After 2 hours, the reaction was cooled to ambient temperature and diluted with an aqueous solution of HCl (10 mL, 1.0 M) and EtOAc (10 mL). The layers were separated and the aqueous layer was extracted with EtOAc (2×10 mL). The combined organic layers were dried over magnesium sulfate, filtered, and concentrated under reduced pressure to afford a tan solid. A solution of the product in dichloromethane (1.0 mL) was prepared in a 4 mL vial. Trifluoromethanesulfonic acid (0.1 mL) was introduced via syringe to afford a purple solution. After 1 hour, the reaction mixture was diluted with dichloromethane (10 mL) and carefully poured into saturated aqueous solution of sodium bicarbonate (10 mL). The layers were separated and the aqueous layer was extracted with dichloromethane (2×10 mL). The combined organic layers were dried over magnesium sulfate, filtered, and concentrated under reduced pressure. The product was purified via column chromatography RediSep® Rf Gold® 25 g, gradient elution 0 to 50% EtOAc/EtOH (3:1) in heptane to afford 4-(1-(2,4'-difluoro-5-methoxy-3'-(trifluoromethoxy)-[1,1'-biphenyl]-4-yl)-3-methylureido)-N-(isoxazol-3-yl)benzenesulfonamide (90 mg, 0.15 mmol, 46.6% yield) as an off-white solid. LRMS (ESI, +ve ion) m/z 599.0 (M+H)$^+$; $^1$H NMR (500 MHz, DMSO-d6) δ ppm 11.48 (s, 1H) 8.71 (d, J=1.43 Hz, 1H) 7.81 (br d, J=7.14 Hz, 1H) 7.65-7.76 (m, 4H) 7.25-7.37 (m, 4H) 6.41 (s, 1H) 6.39 (d, J=6.44 Hz, 1H) 3.75 (s, 3H) 2.59 (d, J=4.28 Hz, 3H).

Biological Examples and Analytical Data

The following assays may be used in testing the exemplary compounds of the invention. Data for those examples tested in accordance with the procedures described in the Nav 1.7 In Vitro PX Assay below are presented in Table 7 below.

Nav 1.7 or Nav 1.5 In Vitro Assay

HEK 293 cells stably transfected with either Nav 1.7 or with Nav 1.5 were recorded in population patch-clamp mode with the IonWorks® Quattro automated electrophysiology system in accordance with the manufacturer's specifications (Molecular Devices, LLC, Sunnyvale, Calif.). Sodium channel currents were measured in response to a train of depolarizations that induced successively greater inactivation.

Cells were held at −110 mV for three seconds (Nav 1.7) or half a second (Nav 1.5) from a holding voltage of −15 mV, then put through a series of 26 pulses of 150 msec duration to −20 mV at a frequency of 5 Hz. Cells were then left unclamped for a period of 3 to 8 minutes while a single concentration of test compound was added. Cells were then reclamped and put through the same voltage protocol. Current at the end of the 26$^{th}$ pulse to −20 mV was subtracted from the peak current evoked by the 26$^{th}$ pulse to −20 mV to correct for leak current. Percent block was calculated for each concentration in duplicate, and IC$_{50}$ curves were fitted to percent block as a function of concentration. Data for compounds of the present invention are shown in the table below. It is noted that more than one experiment may have been conducted and the number presented may be the average of the results of more than one experiment.

Nav 1.7 In Vitro PX Assay

HEK 293 cells stably transfected with human Nav1.7 were recorded in whole cell voltage clamp mode with the PatchXpress automated electrophysiology system (Molecular Devices, LLC, Sunnyvale, Calif.). Compound effects were measured on a partially inactivated state of the sodium channel. Cells were clamped to a holding potential yielding 20 to 50% inactivation. To elicit sodium current, channels were activated by pulsing to −10 mV for 20 msec. This voltage protocol was repeated at a rate of 0.1 Hz throughout the experiment. A single concentration of test compound was applied to cells for a duration of 3 minutes. Peak sodium current was measured at the end of the compound addition period to determine percent inhibition. Three to five cells were tested per concentration, and IC$_{50}$ curves were fitted to percent inhibition as a function of concentration.

Nav 1.5 In Vitro PX Assay

HEK 293 cells stably transfected with Nav 1.5 were recorded in whole cell voltage clamp mode with the PatchXpress automated electrophysiology system according the manufacturer's specifications (Molecular Devices, LLC, Sunnyvale, Calif.). Cells were held at a holding potential of −50 mV to inactivate sodium channels. To elicit sodium currents the voltage was changed to −120 mV to recover a portion of the channels, followed by delivery of test pulses of 20 msec duration to 0 mV, at 0.1 Hz. A single concentration of test compound was applied to cells for a duration of 5 minutes. Peak sodium current was measured at the end of the compound addition period to determine percent inhibition. A minimum of two cells were tested per concentration. IC$_{50}$ curves were fitted to percent inhibition as a function of concentration.

The compounds of the present invention may also be tested in the following in vivo assays.

Rat Formalin Model of Persistent Pain

On the test day, animals (Naïve, male Sprague Dawley rats) weighing between 260-300 g at the start of testing can be obtained from Harlan (Indianapolis, Ind.). All animals may be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. Animals are pretreated with the appropriate test compound either by oral gavage or intraperitoneal injection at the desired pretreatment time (typically two hours before test onset) and then returned to their home cages. After dosing and at least 30 minutes prior to test onset, animals can be acclimated to the individual testing chambers. At test time, each animal can be gently wrapped in a towel with the left hindpaw exposed. A dilute solution of formalin (2.5%) in phosphate buffered saline can be injected subcutaneously into the dorsal surface of the left hindpaw in a volume to 50 µL with a 30 g needle. Immediately following injection, a small metal band can be affixed to the plantar side of the left hindpaw with a drop of LOCTITE (adhesive). Animals may be then placed into the testing chambers and the number of flinches can be recorded between 10 to 40 minutes after formalin injection. A flinch is defined as a quick and spontaneous movement of the injected hindpaw not associated with ambulation. Flinches can be quantified with the aid of the Automated Nociception Analyzer built by the University of California, San Diego Department of Anesthesiology. Individual data can be expressed as a % maximal potential effect (% MPE) calculated with the following formula:(-(Individual score-Vehicle average score)/Vehicle average score))*100=% MPE.

Statistical analysis can be performed by analysis of variance (ANOVA), with post-hoc analysis using Bonferroni compared to the vehicle group for a significant main effect. Data can be represented as mean % MPE+/-standard error for each group.

Rat Open Field Assay

On the test day, animals (Naïve, male Sprague Dawley rats) weighing between 260-300 g at the start of testing may be obtained from Harlan (Indianapolis, Ind.). All animals can be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. In a room separate from the testing room, animals can be pretreated with the appropriate test compound either by oral gavage or intraperitoneal injection at the desired pretreatment time (typically two hours before test onset) and then can be returned to their home cages until the pretreatment has elapsed. At test time, animal can be transferred to the open field testing room in their home cages. Each animal may be placed in a separate testing chamber and the motion tracking system is started. The house lights in the testing room should be turned off and the animals can be allowed to explore the novel open field for 30 minutes. An automated motion tracker, made by San Diego Instruments, San Diego, Calif., can be used to capture animal exploration with the aid of infrared photo beams to detect animal movement. These behaviors include basic movement and vertical rearing, which can be used as the primary endpoints for this assay. At the end of the test, house lights can be turned on and the animals should be removed from the testing apparatus. Data can be expressed as a percent change from the vehicle control using the following equation:

(1-(Test mean/Vehicle mean))*100=% Change.

Statistical analysis can be performed by analysis of variance (ANOVA), with post-hoc analysis using Dunnett to follow up significant main effects.

Mouse Formalin Model of Persistent Pain

Mice (Naïve, male C57Bl/6) weighing between 22-30 g at the start of testing were obtained from Harlan (Indianapolis, Ind.). All animals were housed under a 12/12 h light/dark cycle with lights on at 0630. Rodents were singly housed on solid bottom cages with corn cob bedding and had access to food and water ad libitum. Animals were allowed to habituate to the vivarium for at least five days before testing was begun and were brought into the testing room at least 30 minutes prior to dosing. Animals were pretreated with the appropriate test compound either by oral gavage or intraperitoneal injection at the desired pretreatment time (typically two hours before test onset) and then returned to their home cages. After dosing and at least 5 minutes prior to test onset, animals were acclimated to the individual testing chambers. At test time, each animal was gently wrapped in a cloth glove with the left hind paw exposed. A dilute solution of formalin (2%) in phosphate buffered saline was injected subcutaneously into the dorsal surface of the left hind paw in a volume to 20 µL with a 30 g needle. Animals were then placed into the observation chambers and the behaviors were recorded for 60 minutes following the formalin injection. A pain-like behavior was defined as licking and/or non-weight bearing of the injected hind paw not associated with ambulation.

Statistical analysis was performed by analysis of variance (ANOVA), with post-hoc analysis using the Dunnett post-hoc test compared to the vehicle group for any significant main effect. Data were represented as mean+/-standard error for each group.

Mouse Open Field Assay

Mice (Naïve, male C57Bl/6) weighing between 22-30 g at the start of testing were obtained from Harlan (Indianapolis, Ind.). All animals were housed under a 12/12 h light/dark cycle with lights on at 0630. Rodents were singly housed on solid bottom cages with corn cob bedding and had access to food and water ad libitum. Animals were allowed to habituate to the vivarium for at least five days before testing was begun and were brought into the testing room at least 30 minutes prior to dosing. In a room separate from the testing room, animals were pretreated with the appropriate test compound either by oral gavage or intraperitoneal injection at the desired pretreatment time (typically two hours before test onset) and then returned to their home cages until the pretreatment has elapsed. At test time, animal were transferred to the open field testing room in their home cages. Each animal was placed in a separate testing chamber and the motion tracking system was started. The house lights in the testing room were turned off and the animals were allowed to explore the novel open field for 30 minutes. An automated motion tracker, made by Kinder Scientific, Poway, Calif., was used to capture animal exploration with the aid of infrared photo beams to detect animal movement. These behaviors include basic movement and vertical rearing, which were used as the primary endpoints for this assay. At the end of the test, house lights were turned on and the animals were removed from the testing apparatus.

Statistical analysis was performed by analysis of variance (ANOVA), with post-hoc analysis using the Dunnett post-hoc test compared to the vehicle group for any significant main effect. Data were represented as mean+/-standard error for each group. Data was also expressed as a percent change from the vehicle control using the following equation:

(1-(Test mean/Vehicle mean))*100=% Change

CFA-Thermal Assay

Animals (Naïve, male Sprague Dawley rats) weighing between 260-300 g at the start of testing) can be obtained from Harlan (Indianapolis, Ind.). All animals can be housed under a 12/12 h light/dark cycle with lights on at 0600. Rodents may be housed two to a cage on solid bottom cages with corn cob bedding with access to food and water ad libitum. Animals can be allowed to habituate to the vivarium for at least five days before testing was begun and may be brought into the testing room at least 30 minutes prior to dosing. The Complete Freund's Adjuvant (CFA)-thermal assay may use a three continuous day testing schedule consisting of a habituation day, a baseline day, and a test day. On day 1, animals can be brought into the testing room, labeled, and placed in their individual testing boxes on the testing apparatus. Animals may be allowed to explore this environment for at least an hour without actually being tested. After habituating, animals can be placed back in their home cages and returned to the vivarium. On day 2, animals can be brought back into the testing room and placed on the testing apparatus and allowed to calm down (typically 30-45 minutes). A basal thermal threshold should be then taken with the following procedure: once calm, a Ugo Basile plantar device is placed under the animals left hindpaw; the start button is depressed turning on a steadily increasing thermal source and a timer; when the animal reaches its thermal threshold it will flinch its hindpaw, stopping the timer and the thermal stimulus. This latency to flinch can be recorded three times for each animal, with at least 5 minutes between trials, and the mean score can be used as the animal's baseline threshold. After testing, animals can be injected intraplantarly with a 25 μg/50 μl of complete Freund's adjuvant into the left hindpaw. Animals are then returned to their home cages and returned to the vivarium. On test day, animals can be again placed on the thermal testing apparatus and their post-CFA baselines obtained with the procedure outlined above. Animals can be pretreated with the appropriate test compound either by oral gavage or intraperitoneal injection at the desired pretreatment time (typically two hours before test onset) and then can be returned to their home cages. Thirty minutes prior to testing, animals can be placed on the apparatus again. Once the pretreatment time has elapsed, animals can be again tested with the procedure above. Data may be expressed as a percent maximal potential effect with the following formula:

((Post-Drug Mean−Pre-Drug Mean)/(Baseline Mean−Pre-Drug Mean))*100=% MPE

Statistical analysis can be performed by analysis of variance (ANOVA), with post-hoc analysis using Bonferroni compared to the vehicle group for a significant main effect. Data can be represented as mean % MPE+/−standard error for each group.

Spinal Nerve Ligation (Chung)

Animals (Naïve, male Sprague Dawley rats) weighing between 150-200 g at the start of first time testing can be obtained from Harlan (Indianapolis, Ind.). All animals may be housed under a 12/12 h light/dark cycle with lights on at 0600. Rodents can be housed two to a cage on solid bottom cages with corn cob bedding with access to food and water ad libitum. Animals may be allowed to habituate to the vivarium for at least five days before testing is begun. Surgery may be then performed based on the method described by Kim and Chung (1992). Briefly, animals can be placed under isoflurane anesthesia and placed in a sterile surgical field. The area of the lumbar spine is excised and the spinal nerves at L4-L5 are exposed. The L5 spinal nerve is identified and tightly ligated with 5-0 silk suture. The muscle may be closed with absorbable suture and the skin with wound clip. Animals may be returned to the vivarium for 7-14 days and monitored daily. On test day, animals can be brought into the testing room and placed on a wire mesh floor in individual testing chambers. They may be allowed to acclimate to the chambers until they are calm. A series of Semmes-Weinstein monofilaments (von Frey hairs) with calibrated bending forces are then applied to determine a hyperalgesic baseline following the method set forth by Chaplan et al. (1994). Briefly, filaments are applied with an increasing force (if there was not reaction to the previous stimulus) or decreasing force (if there was a reaction to the previous stimulus) until a baseline value is reached. Animals are then pretreated with the appropriate test compound either by oral gavage or intraperitoneal injection at the desired pretreatment time (typically two hours before test onset) and then returned to their home cages. Thirty minutes prior to testing, animals are placed on the apparatus again. After the pretreatment time had elapsed, the procedure above is repeated to determine drug efficacy. Data can be expressed as the mean gram force to elicit a nociceptive behavior. Statistical analysis can be performed by analysis of variance (ANOVA), with post-hoc analysis using Bonferroni compared to the vehicle group for a significant main effect.

Table 7 provides data for compounds exemplified in the present application and priority document thereof, as representative compounds of the present invention, as follows: LRMS data, $^1$H NMR data, and biological data including in-vitro Nav 1.7 PX data ($IC_{50}$ in uM), where available. Ex. # refers to Example No.

TABLE 7

BIOLOGICAL AND ANALYTICAL DATA

| Ex. # | LRMS: (ESI, +ve ion) m/z | NMR | Nav1.7 PX $IC_{50}$ (μM) |
|---|---|---|---|
| 1-1 | 546.0, 548.0 | 1H NMR (400 MHz, DMSO-d6) δ ppm 2.43 (s, 3 H) 2.71 (d, J = 4.56 Hz, 3 H) 3.71 (s, 3 H) 6.46 (d, J = 1.76 Hz, 1 H) 7.21-7.38 (m, 3 H) 7.47-7.59 (m, 2 H) 7.65 (s, 1 H) 8.07 (dd, J = 9.07, 2.64 Hz, 1 H) 8.13 (d, J = 4.15 Hz, 1 H) 8.64 (d, J = 2.59 Hz, 1 H) 8.77 (d, J = 1.76 Hz, 1 H) 11.70 (br. s., 1 H) | 0.057 |
| 1-2 | 557.00 | 1H NMR (400 MHz, DMSO-d6) δ ppm 2.42 (s, 3 H) 2.71 (d, J = 4.46 Hz, 3 H) 3.71 (s, 3 H) 7.13 (d, J = 8.91 Hz, 1 H) 7.24 (d, J = 7.15 Hz, 1 H) 7.29 (d, J = 10.78 Hz, 1 H) 7.46-7.51 (m, 1 H) 7.53-7.57 (m, 1 H) 7.64 (s, 1 H) 7.71 (dd, J = 9.54, 4.15 Hz, 1 H) 7.90 (br. s., 1 H) 8.05 (dd, J = 8.91, 2.59 Hz, 1 H) 8.25 (d, J = 4.66 Hz, 1 H) 8.31-8.41 (m, 1 H) 8.65 (d, J = 2.07 Hz, 1 H) 14.33-14.80 (m, 1 H) | 0.106 |
| 1-3 | 577.00 | 1H NMR (400 MHz, DMSO-d6) δ ppm 2.72 (d, J = 4.46 Hz, 3 H) 3.73 (s, 3 H) 7.16 (d, J = 9.54 Hz, 1 H) 7.33 (s, 1 H) 7.35 (d, J = 3.42 Hz, 1 H) 7.71 (dd, J = 9.54, 4.15 Hz, 1 H) 7.74-7.85 (m, 2 H) 7.86-8.00 (m, 3 H) 8.05 (dd, J = 8.97, 2.54 Hz, 1 H) 8.22 (q, J = 4.08 Hz, 1 H) 8.31-8.41 (m, 1 H) 8.63-8.68 (m, 1 H) 14.28-14.80 (m, 1 H) | 0.040 |
| 1-4 | 566.00 | 1H NMR (400 MHz, DMSO-d6) δ ppm 2.72 (d, J = 4.46 Hz, 3 H) 3.73 (s, 3 H) 6.46 (d, J = 1.87 Hz, 1 H) 7.31 (dd, J = 9.07, 0.67 Hz, 1 H) 7.35 (d, J = 7.15 Hz, 1 H) 7.38 (d, J = 10.68 Hz, 1 H) 7.75-7.87 (m, 2 H) 7.96 (br. s., 2 H) 8.04-8.09 (m, 1 H) 8.09-8.15 (m, 1 H) 8.64 (dd, J = 2.64, 0.78 Hz, 1 H) 8.77 (d, J = 1.87 Hz, 1 H) 11.71 (s, 1 H) | 0.033 |
| 1-5 | 550.00 | 1H NMR (400 MHz, DMSO-d6) δ ppm 2.71 (d, J = 4.46 Hz, 3 H) 3.73 (s, 3 H) 6.46 (d, J = 1.87 Hz, 1 H) 7.25-7.31 (m, 1 H) 7.35 (d, J = 7.15 Hz, 1 H) 7.38 (d, J = 10.88 Hz, 1 H) 7.52-7.64 (m, 3 H) 8.07 (dd, J = 9.12, 2.59 Hz, 1 H) 8.09-8.16 (m, 1 H) 8.63 (dd, J = 2.54, 0.67 Hz, 1 H) 8.77 (d, J = 1.76 Hz, 1 H) 11.70 (s, 1 H) | 0.092 |
| 1-6 | 562.0, 563.0 | 1H NMR (400 MHz, DMSO-d6) δ ppm 2.71 (d, J = 4.46 Hz, 3 H) 3.72 (s, 3 H) 3.86 (s, 3 H) 6.46 (d, J = 1.76 Hz, 1 H) 7.14 (d, J = 1.87 Hz, 1 H) 7.16 (d, J = 1.45 Hz, 1 H) 7.27-7.30 (m, 3 H) 7.31-7.36 (m, 1 H) 8.07 (dd, J = 9.07, 2.64 Hz, 1 H) 8.09-8.16 (m, 1 H) 8.63 (dd, J = 2.59, 0.73 Hz, 1 H) 8.77 (d, J = 1.87 Hz, 1 H) 11.70 (s, 1 H) | 0.051 |
| 1-7 | 612.20 | 1H NMR (400 MHz, DMSO-d6) δ ppm 2.70 (d, J = 4.56 Hz, 3 H) 3.71 (s, 3 H) 3.88 (s, 3 H) 6.45 (d, J = 1.87 Hz, 1 H) 7.04 (d, J = 0.83 Hz, 1 H) 7.19 (s, 1 H) 7.24 (dt, J = 2.31, 1.18 Hz, 1 H) 7.27-7.38 (m, 3 H) 8.02-8.11 (m, 2 H) 8.62 (dd, J = 2.59, 0.73 Hz, 1 H) 8.76 (d, J = 1.76 Hz, 1 H) 11.69 (br. s., 1 H) | 0.018 |

TABLE 7-continued

BIOLOGICAL AND ANALYTICAL DATA

| Ex. # | LRMS: (ESI, +ve ion) m/z | NMR | Nav1.7 PX IC$_{50}$ (μM) |
|---|---|---|---|
| 1-8 | 528.00 | 1H NMR (400 MHz, DMSO-d6) δ ppm 2.71 (d, J = 4.46 Hz, 3 H) 3.70 (s, 3 H) 3.82 (s, 3 H) 6.44 (d, J = 1.87 Hz, 1 H) 7.02 (ddd, J = 8.29, 2.54, 0.88 Hz, 1 H) 7.14-7.19 (m, 1 H) 7.18-7.33 (m, 4 H) 7.40-7.46 (m, 1 H) 8.06 (dd, J = 9.12, 2.59 Hz, 1 H) 8.12 (q, J = 4.28 Hz, 1 H) 8.63 (dd, J = 2.59, 0.62 Hz, 1 H) 8.76 (d, J = 1.76 Hz, 1 H) 11.69 (br. s., 1 H) | 0.206 |
| 1-9 | 596.00 | 1H NMR (400 MHz, DMSO-d6) δ ppm 2.71 (d, J = 4.46 Hz, 3 H) 3.72 (s, 3 H) 3.92 (s, 3 H) 6.45 (d, J = 1.76 Hz, 1 H) 7.28-7.39 (m, 4 H) 7.48 (s, 1 H) 7.51 (s, 1 H) 8.03-8.13 (m, 2 H) 8.62 (d, J = 2.59, 0.73 Hz, 1 H) 8.76 (d, J = 1.76 Hz, 1 H) 11.69 (s, 1 H) | 0.018 |
| 1-10 | 566.00 | 1H NMR (400 MHz, DMSO-d6) δ ppm 2.70 (d, J = 4.46 Hz, 3 H) 3.71 (s, 3 H) 6.44 (d, J = 1.76 Hz, 1 H) 7.28 (dd, J = 9.12, 0.62 Hz, 1 H) 7.32 (d, J = 7.15 Hz, 1 H) 7.35 (d, J = 10.78 Hz, 1 H) 7.66 (dt, J = 8.40, 1.92 Hz, 1 H) 7.79 (d, J = 8.40 Hz, 1 H) 7.93 (dd, J = 1.97, 0.93 Hz, 1 H) 8.06 (dd, J = 9.02, 2.59 Hz, 1 H) 8.10 (q, J = 4.35 Hz, 1 H) 8.62 (dd, J = 2.59, 0.73 Hz, 1 H) 8.76 (d, J = 1.76 Hz, 1 H) 11.69 (br. s., 1 H) | 0.009 |
| 1-11 | 600.00 | 1H NMR (400 MHz, DMSO-d6) δ ppm 2.71 (d, J = 4.46 Hz, 3 H) 3.72 (s, 3 H) 6.44 (d, J = 1.76 Hz, 1 H) 7.30 (dd, J = 9.07, 0.67 Hz, 1 H) 7.35-7.42 (m, 2 H) 7.87-7.93 (m, 1 H) 7.95-8.01 (m, 1 H) 8.03-8.11 (m, 3 H) 8.62 (dd, J = 2.64, 0.67 Hz, 1 H) 8.76 (d, J = 1.87 Hz, 1 H) 11.69 (br. s., 1 H) | 0.014 |
| 1-12 | 596.00 | 1H NMR (400 MHz, DMSO-d6) δ ppm 2.71 (d, J = 4.56 Hz, 3 H) 3.71 (s, 3 H) 4.86 (q, J = 8.91 Hz, 2 H) 6.44 (d, J = 1.87 Hz, 1 H) 7.14 (dd, J = 8.19, 1.76 Hz, 1 H) 7.26 (d, J = 8.29 Hz, 2 H) 7.29-7.36 (m, 3 H) 7.44-7.52 (m, 1 H) 8.06 (dd, J = 9.12, 2.59 Hz, 1 H) 8.14 (d, J = 4.46 Hz, 1 H) 8.60-8.66 (m, 1 H) 8.76 (d, J = 1.87 Hz, 1 H) 11.69 (br. s., 1 H) | 0.085 |
| 1-13 | 538.20 | 1H NMR (400 MHz, DMSO-d6) δ ppm 0.71-0.79 (m, 2 H) 0.95-1.04 (m, 2 H) 1.96-2.06 (m, 1 H) 2.71 (d, J = 4.46 Hz, 3 H) 3.70 (s, 3 H) 6.44 (d, J = 1.76 Hz, 1 H) 7.09-7.16 (m, 1 H) 7.21 (d, J = 7.15 Hz, 1 H) 7.24-7.34 (m, 3 H) 7.38 (d, J = 4.77 Hz, 2 H) 8.06 (dd, J = 9.02, 2.59 Hz, 1 H) 8.14 (q, J = 4.22 Hz, 1 H) 8.63 (dd, J = 2.59, 0.62 Hz, 1 H) 8.76 (d, J = 1.76 Hz, 1 H) 11.69 (br. s., 1 H) | 0.046 |
| 1-14 | 582.20 | 1H NMR (400 MHz, DMSO-d6) δ ppm 2.71 (d, J = 4.46 Hz, 3 H) 3.72 (s, 3 H) 6.45 (d, J = 1.76 Hz, 1 H) 7.28-7.33 (m, 2 H) 7.35 (d, J = 10.68 Hz, 1 H) 7.46 (dt, J = 7.90, 1.18 Hz, 1 H) 7.60-7.75 (m, 3 H) 8.06 (dd, J = 9.12, 2.59 Hz, 2 H) 8.63 (dd, J = 2.59, 0.73 Hz, 1 H) 8.76 (d, J = 1.76 Hz, 1 H) 11.69 (br. s., 1 H) | 0.017 |
| 1-15 | 530, 531 | 1H NMR (500 MHz, DMSO-d6) δ ppm 8.47-8.62 (2 H, m), 8.40 (1 H, s), 8.09 (1 H, s), 7192-7195 (1 H, m), 7.39-7.48 (3 H, m), 7.24-7.28 (2 H, m), 6.94 (1 H, br d, J = 9.0 Hz), 6.20 (1 H, s), 3.72 (3 H, s), 2.73 (3 H, br d, J = 4.2 Hz), 2.30 (3 H, s) | 0.124 |
| 1-16 | 530, 531 | 1H NMR (500 MHz, DMSO-d6) δ ppm 8.58-8.63 (1 H, m), 8.54 (1 H, br s), 8.40 (1 H, s)1 7199 (1 H, s), 7.90-7.97 (1 H, m), 7.53-7.73 (2 H, m), 7.16-7.34 (3 H, m), 6.91 (1 H, br d, J = 8.8 Hz), 6.20 (1 H, s), 3.71 (3 H, s), 2.73 (3 H, br d, J = 4.2 Hz), 2.32 (3 H, s) | 0.061 |
| 1-17 | 546, 548 | 1H NMR (500 MHz, DMSO-d6) δ ppm 8.56 (1 H, s), 8.47 (2 H, br s), 7.95 (1 H, br d, J = 8.9 Hz), 7.70 (1 H, s), 7.46-7.57 (2 H, m), 7.13-7.33 (3 H, m), 7.00 (1 H, br d, J = 8.8 Hz), 6.25 (1 H, s), 3.72 (3 H, s), 2.73 (3 H, br d, J = 4.2 Hz), 2.40 (3 H, s) | 0.031 |
| 1-18 | 530, 531 | 1H NMR (500 MHz, DMSO-d6) δ ppm 8.57 (2H, m), 8.39 (1 H, br s), 7.99 (1 H, br d, J = 9.0 Hz), 7.23-7.34 (4 H, m), 7.04-7.15 (2 H, m), 6.31 (1 H, s), 3.71 (3 H, s), 2.72 (3 H, br d, J = 4.2 Hz), 2.41 (3 H, s) | 0.146 |
| 1-19 | 546, 548 | 1H NMR (500 MHz, DMSO-d6) δ ppm 8.52-8.62 (2 H, m), 8.40 (1 H, br s), 7.98 (1 H, br d, J = 8.9 Hz), 7.49 (1 H, s), 7.44 (1 H, s), 7.35 (1 H, s), 7.22-7.33 (2 H, m), 7.06 (1 H, br d,J = 9.0 Hz), 6.30 (1 H, s), 3.71 (3 H, s), 2.72 (3 H, br d, J = 4.2 Hz), 2.40 (3 H, s) | 0.047 |
| 1-20 | 550, 552 | 1H NMR (500 MHz, DMSO-d6) δ ppm 8.59 (2 H, s), 8.30 (1 H, br s), 8.00 (1 H, br d, J = 8.9 Hz), 7.70-7.78 (2 H, m), 7.55 (1 H, br d, J = 8.2 Hz), 7.27-7.36 (2 H, m), 7.12 (1 H, br d, J = 8.6 Hz), 6.33 (1 H, s), 3.72 (3 H, s), 2.72 (3 H, br d, J = 4.2 Hz) | 0.050 |
| 1-21 | 550, 552 | 1H NMR (500 MHz, DMSO-d6) δ ppm 8.57 (1 H, s), 8.51 (1 H, br s), 8.43 (1 H, br s), 7.94-8.03 (1 H, m), 7.89 (1 H, br d, J = 6.7 Hz), 7.66-7.71 (1 H, m), 7.51-7.63 (1 H, m), 7.25-7.35 (2 H, m), 7.03 (1 H, br d, J = 9.1 Hz), 6.28 (1 H, s), 3.72 (3 H, s), 2.72 (3 H, br d, J = 4.2 Hz) | 0.037 |
| 1-22 | 534, 535 | 1H NMR (500 MHz, DMSO-d6) δ ppm 8.58 (2 H, s), 8.33 (1 H, br s), 8.00 (1 H, br d, J = 9.0 Hz), 7.72-7.81 (1 H, m), 7.48-7.63 (2 H, m), 7.24-7.39 (2 H, m), 7.10 (2 H, br d, J = 8.8 Hz), 6.33 (1 H, s), 3.72 (3 H, s), 2.72 (3 H, br d, J = 4.2 Hz) | 0.199 |
| 1-23 | 576, 577 | 1H NMR (500 MHz, DMSO-d6) δ ppm 8.66 (1 H, s), 8.60 (1 H, s), 8.23 (1 H, br s), 8.03 (1 H, br d, J = 9.0 Hz), 7.22-7.34 (2 H, m), 7.18 (1 H, br d, J = 9.0 Hz), 6.98 (2 H, br d, J = 6.6 Hz), 6.38 (1 H, s), 3.90 (6 H, s), 3.72 (3 H, s), 2.72 (3 H, br d, J = 4.0 Hz) | 0.151 |
| 1-24 | 551, 553 | 1H NMR (500 MHz, DMSO-d6) δ ppm 8.63 (1 H, br s), 8.59 (1 H, d, J = 2.01 Hz), 8.31-8.35 (1 H, m), 7.97-8.12 (3 H, m), 7.65-7.72 (1 H, m), 7.35 (2 H, br d, J = 8.2 Hz), 7.11 (1 H, br d, J = 8.2 Hz), 6.32 (1 H, s), 3.72 (3 H, s), 2.72 (3 H, d, J = 4.3 Hz) | 0.086 |
| 1-25 | 580, 582 | 1H NMR (500 MHz, DMSO-d6) δ ppm 8.66 (1 H, s), 8.60 (1 H, d, J = 2.1 Hz), 8.22-8.26 (1 H, m), 8.03 (1 H, dd, J = 9.1, 2.3 Hz), 7.28-7.40 (4 H, m), 7.17 (1 H, br d, J = 9.1 Hz), 6.38 (1 H, s), 3.96 (3 H, s), 3.72 (3 H, s), 2.72 (3 H, d, J = 4.3 Hz) | 0.016 |
| 1-26 | 584, 585 | 1H NMR (500 MHz, DMSO-d6) δ ppm 8.55-8.64 (2 H, m), 8.31-8.36 (1 H, m), 7.97-8.12 (3 H, m), 7.65-7.72 (1 H, m), 7.35 (2 H, br d, J = 8.2 Hz), 7.11 (1 H, br d, J = 8.2 Hz), 6.32 (1 H, s), 3.72 (3 H, s), 2.72 (3 H, d, J = 4.3 Hz) | 0.012 |
| 1-27 | 600, 601 | 1H NMR (500 MHz, DMSO-d6) δ ppm 8.61 (1 H, br s), 8.59 (1 H, br d, J = 1.9 Hz), 8.23-8.28 (1 H, m), 8.01 (1 H, dd, J = 9.1, 2.3 Hz), 7.84 (1 H, br d, J = 6.6 Hz), 7.75-7.78 (1 H, m), 7.65 7.71 (1 H, m), | 0.020 |

TABLE 7-continued

BIOLOGICAL AND ANALYTICAL DATA

| Ex. # | LRMS: (ESI, +ve ion) m/z | NMR | Nav1.7 PX IC$_{50}$ (μM) |
|---|---|---|---|
| 1-28 | 546.00 | 7.24-7.36 (2 H, m), 7.16 (1 H, br d, J = 9.3 Hz), 6.35 (1 H, s), 3.72 (3 H, s), 2.72 (3 H, d, J = 4.3 Hz)<br>1H NMR (400 MHz, DMSO-d6) δ ppm 2.32 (d, J = 1.55 Hz, 3 H) 2.71 (d, J = 4.56 Hz, 3 H) 3.69 (s, 3 H) 6.45 (d, J = 1.76 Hz, 1 H) 7.15 (s, 1 H) 7.22-7.31 (m, 2 H) 7.45 (s, 3 H) 8.06 (dd, J = 9.07, 2.64 Hz, 1 H) 8.14-8.26 (m, 1 H) 8.64 (dd, J = 2.59, 0.73 Hz, 1 H) 8.76 (d, J = 1.87 Hz, 1 H) 11.69 (s, 1 H) | 0.058 |
| 1-29 | 562.00 | 1H NMR (400 MHz, DMSO-d6) δ ppm 2.42 (s, 3 H) 2.71 (d, J = 4.46 Hz, 3 H) 3.69 (s, 3 H) 6.45 (d, J = 1.76 Hz, 1 H) 7.17 (s, 1 H) 7.25 (dd, J = 9.07, 0.67 Hz, 1 H) 7.35-7.40 (m, 1 H) 7.47 (s, 1 H) 7.51 (d, J = 1.87 Hz, 1 H) 7.54 (d, J = 8.19 Hz, 1 H) 8.06 (dd, J = 9.02, 2.59 Hz, 1 H) 8.17 (q, J = 4.35 Hz, 1 H) 8.64 (dd, J = 2.59, 0.73 Hz, 1 H) 8.76 (d, J = 1.76 Hz, 1 H) 11.69 (s, 1 H) | 0.020 |
| 1-30 | 566.8, 567.8 | 1H NMR (400 MHz, DMSO-d6) δ ppm 2.71 (d, J = 4.56 Hz, 3 H) 3.71 (s, 3 H) 6.45 (d, J = 1.87 Hz, 1 H) 7.22-7.28 (m, 2 H) 7.41 (ddd, J = 9.46, 2.36, 1.45 Hz, 1 H) 7.46 (t, J = 1.50 Hz, 1 H) 7.51 (s, 1 H) 7.56 (dt, J = 8.81, 2.13 Hz, 1 H) 8.06 (dd, J = 9.02, 2.59 Hz, 1 H) 8.17 (q, J = 4.32 Hz, 1 H) 8.64 (dd, J = 2.64, 0.78 Hz, 1 H) 8.76 (d, J = 1.76 Hz, 1 H) 11.69 (br. s, 1 H) | 0.028 |
| 1-31 | 582.00 | 1H NMR (400 MHz, DMSO-d6) δ ppm 2.72 (d, J = 4.46 Hz, 3 H) 3.71 (s, 3 H) 6.45 (d, J = 1.76 Hz, 1 H) 7.26 (s, 1 H) 7.29 (dd, J = 9.02, 0.73 Hz, 1 H) 7.52 (s, 1 H) 7.73-7.89 (m, 4 H) 8.06 (dd, J = 9.02, 2.59 Hz, 1 H) 8.14 (q, J = 4.60 Hz, 1 H) 8.64 (dd, J = 2.59, 0.73 Hz, 1 H) 8.76 (d, J = 1.76 Hz, 1 H) 11.69 (s, 1 H) | 0.016 |
| 1-32 | 578.00 | 1H NMR (400 MHz, DMSO-d6) δ ppm 2.71 (d, J = 4.46 Hz, 3 H) 3.70 (s, 3 H) 3.85 (s, 3 H) 6.45 (d, J = 1.87 Hz, 1 H) 7.01-7.05 (m, 1 H) 7.10-7.15 (m, 2 H) 7.21 (s, 1 H) 7.26 (dd, J = 9.07, 0.67 Hz, 1 H) 7.48 (s, 1 H) 8.06 (dd, J = 9.12, 2.59 Hz, 1 H) 8.16 (q, J = 4.39 Hz, 1 H) 8.63 (dd, J = 2.59, 0.73 Hz, 1 H) 8.76 (d, J = 1.76 Hz, 1 H) 11.69 (s, 1 H) | 0.014 |
| 1-33 | 578.2, 580.0 | 1H NMR (400 MHz, DMSO-d6) δ ppm 2.71 (d, J = 4.56 Hz, 3 H) 3.70 (s, 3 H) 3.93 (s, 3 H) 6.45 (d, J = 1.76 Hz, 1 H) 7.11 (dd, J = 8.14, 1.92 Hz, 1 H) 7.22 (s, 1 H) 7.24 (d, J = 1.87 Hz, 1 H) 7.27 (dd, J = 9.07, 0.67 Hz, 1 H) 7.48 (s, 1 H) 7.55 (d, J = 8.19 Hz, 1 H) 8.07 (dd, J = 9.12, 2.59 Hz, 1 H) 8.15 (q, J = 4.22 Hz, 1 H) 8.63 (dd, J = 2.59, 0.73 Hz, 1 H) 8.76 (d, J = 1.87 Hz, 1 H) 11.69 (s, 1 H) | 0.043 |
| 1-34 | 562.0, 564.0 | 1H NMR (400 MHz, DMSO-d6) δ ppm 2.15 (s, 3 H) 2.74 (d, J = 4.56 Hz, 3 H) 3.66 (s, 3 H) 6.45 (d, J = 1.76 Hz, 1 H) 7.11 (s, 1 H) 7.15 (dd, J = 9.07, 0.67 Hz, 1 H) 7.25 (d, J = 2.07 Hz, 1 H) 7.36-7.45 (m, 2 H) 7.48 (s, 1 H) 8.06 (dd, J = 9.07, 2.64 Hz, 1 H) 8.37 (d, J = 4.46 Hz, 1 H) 8.66 (dd, J = 2.64, 0.67 Hz, 1 H) 8.76 (d, J = 1.76 Hz, 1 H) 11.69 (s, 1 H) | 0.027 |
| 1-35 | 562.00 | 1H NMR (400 MHz, DMSO-d6) δ ppm 2.71 (d, J = 4.46 Hz, 3 H) 3.71 (s, 3 H) 3.95 (s, 3 H) 6.44 (d, J = 1.76 Hz, 1 H) 7.22 (dt, J = 8.19, 1.87 Hz, 1 H) 7.26-7.36 (m, 4 H) 7.56 (d, J = 8.19 Hz, 1 H) 8.06 (dd, J = 9.12, 2.59 Hz, 1 H) 8.07-8.13 (m, 1 H) 8.62 (dd, J = 2.59, 0.73 Hz, 1 H) 8.76 (d, J = 1.76 Hz, 1 H) 11.68 (s, 1 H) | 0.185 |
| 1-36 | 612.00 | 1H NMR (400 MHz, DMSO-d6) δ ppm 2.72 (d, J = 4.46 Hz, 3 H) 3.71 (s, 3 H) 3.91 (s, 3 H) 6.45 (d, J = 1.87 Hz, 1 H) 7.24-7.31 (m, 2 H) 7.32-7.42 (m, 3 H) 7.50 (s, 1 H) 8.06 (dd, J = 9.12, 2.59 Hz, 1 H) 8.14 (q, J = 4.39 Hz, 1 H) 8.63 (dd, J = 2.64, 0.67 Hz, 1 H) 8.76 (d, J = 1.76 Hz, 1 H) 11.70 (br. s., 1 H) | 0.011 |
| 1-37 | 612.00 | 1H NMR (400 MHz, DMSO-d6) δ ppm 2.72 (d, J = 4.46 Hz, 3 H) 3.70 (s, 3 H) 4.84 (q, J = 8.91 Hz, 2 H) 6.45 (d, J = 1.76 Hz, 1 H) 7.14 (ddd, J = 8.32, 2.67, 0.83 Hz, 1 H) 7.17-7.28 (m, 4 H) 7.43-7.52 (m, 2 H) 8.07 (dd, J = 9.02, 2.59 Hz, 1 H) 8.21 (q, J = 4.39 Hz, 1 H) 8.64 (dd, J = 2.59, 0.73 Hz, 1 H) 8.76 (d, J = 1.76 Hz, 1 H) 11.70 (br. s., 1 H) | 0.011 |
| 1-38 | 554.00 | 1H NMR (400 MHz, DMSO-d6) δ ppm 0.70-0.77 (m, 2 H) 0.96-1.03 (m, 2 H) 1.95-2.05 (m, 1 H) 2.71 (d, J = 4.46 Hz, 3 H) 3.69 (s, 3 H) 6.45 (d, J = 1.87 Hz, 1 H) 7.11-7.16 (m, 2 H) 7.19 (t, J = 1.66 Hz, 1 H) 7.23-7.30 (m, 2 H) 7.33-7.40 (m, 1 H) 7.44 (s, 1 H) 8.06 (dd, J = 9.12, 2.59 Hz, 1 H) 8.18 (q, J = 4.39 Hz, 1 H) 8.64 (dd, J = 2.64, 0.67 Hz, 1 H) 8.76 (d, J = 1.76 Hz, 1 H) 11.69 (br. s., 1 H) | 0.021 |
| 1-39 | 598.00 | 1H NMR (400 MHz, DMSO-d6) δ ppm 2.71 (d, J = 4.46 Hz, 3 H) 3.71 (s, 3 H) 6.45 (d, J = 1.87 Hz, 1 H) 7.24 (s, 1 H) 7.29 (dd, J = 9.12, 0.73 Hz, 1 H) 7.44-7.49 (m, 1 H) 7.50 (s, 2 H) 7.59 (dt, J = 7.88, 1.24 Hz, 1 H) 7.63-7.70 (m, 1 H) 8.07 (dd, J = 9.12, 2.59 Hz, 1 H) 8.14 (q, J = 4.32 Hz, 1 H) 8.64 (dd, J = 2.59, 0.73 Hz, 1 H) 8.76 (d, J = 1.76 Hz, 1 H) 11.70 (br. s., 1 H) | 0.011 |
| 1-40 | 613.00 | 1H NMR (500 MHz, DMSO-d6) δ ppm 2.75 (br d, J = 4.15 Hz, 3 H) 3.68 (s, 3 H) 3.99 (s, 3 H) 6.25 (s, 1 H) 6.85-6.97 (m, 1 H) 7.28 (s, 1 H) 7.44 (s, 1 H) 7.94-8.01 (m, 1 H) 8.04 (br s, 1 H) 8.47 (br s, 1 H) 8.59 (s, 1 H) 8.71 (br s, 1H) | 0.032 |
| 1-41 | 579.00 | 1H NMR (500 MHz, DMSO-d6) δ ppm 2.73 (br d, J = 4.28 Hz, 3 H) 3.71 (s, 3 H) 3.92 (s, 1 H) 4.02 (s, 3 H) 6.22 (s, 1 H) 6.94 (br d, J = 8.89 Hz, 1 H) 7.27 (s, 1 H) 7.47 (s, 1 H) 7.95 (d, J = 8.49 Hz, 1 H) 8.10 (s, 1 H) 8.32 (s, 1 H) 8.42 (s, 1 H) 8.55 (br s, 2 H) | 0.166 |
| 1-42 | 613.00 | 1H NMR (500 MHz, DMSO-d6) δ ppm 2.74 (br d, J = 4.22 Hz, 3 H) 3.72 (s, 3 H) 3.98 (s, 3 H) 6.10 (s, 1 H) 6.80 (br d, J = 8.76 Hz, 1 H) 7.32 (br d, J = 5.19 Hz, 2 H) 7.50 (s, 1 H) 7.63 (s, 1 H) 7.88 (br d, J = 8.82 Hz, 1 H) 8.24 (s, 1 H) 8.51 (s, 1 H) 8.73 (br d, J = 3.57 Hz, 1 H) | 0.029 |
| 1-43 | 583.00 | 1H NMR (500 MHz, DMSO-d6) δ ppm 2.75 (br d, J = 4.28 Hz, 3 H) 3.73 (s, 3 H) 6.07 (s, 1 H) 6.78 (d, J = 8.76 Hz, 1 H) 7.35 (s, 1 H) 7.52 (s, 1 H) 7.88 (dd, J = 8.73, 2.04 Hz, 1 H) 7.93 (br d, J = 4.48 Hz, 1 H) 8.06 (s, 1 H) 8.20 (s, 1 H) 8.51 (d, J = 1.82 Hz, 1 H) 8.75-8.82 (m, 1 H) 8.92 (br d, J = 4.80 Hz, 1 H) | 0.131 |
| 1-44 | 532.00 | 1H NMR (500 MHz, DMSO-d6) δ ppm 2.74 (br d, J = 4.22 Hz, 3 H) 3.70 (s, 3 H) 6.20 (s, 1 H) 6.92 (br d, J = 8.89 Hz, 1 H) 7.16 (s, 1 H) 7.34 (br t, J = 8.66 Hz, 2 H) | 0.125 |

TABLE 7-continued

BIOLOGICAL AND ANALYTICAL DATA

| Ex. # | LRMS: (ESI, +ve ion) m/z | NMR | Nav1.7 PX IC$_{50}$ (μM) |
|---|---|---|---|
| | | 7.43 (s, 1 H) 7.55-7.62 (m, 2 H) 7.94 (dd, J = 8.86, 2.17 Hz, 1 H) 8.39 (s, 1 H) 8.55 (d, J = 1.95 Hz, 1 H) 8.63 (br s, 1H) | |
| 1-45 | 582.00 | 1H NMR (500 MHz, DMSO-d6) δ ppm 2.73 (br d, J = 4.15 Hz, 3 H) 3.71 (s, 3 H) 6.24 (s, 1 H) 7.00 (br d, J = 8.56 Hz, 1 H) 7.23 (s, 1 H) 7.49 (s, 1 H) 7.77 (br d, J = 7.91 Hz, 2 H) 7.88 (br d, J = 8.04 Hz, 2 H) 7.94-8.02 (m, 1 H) 8.45 (br s, 1 H) 8.50-8.55 (m, 1 H) 8.57 (br s, 1 H) | 0.065 |
| 1-46 | 612.00 | 1H NMR (500 MHz, DMSO-d6) δ ppm 2.74 (br d, J = 4.22 Hz, 3 H) 3.72 (s, 3 H) 3.97 (s, 3 H) 6.22 (s, 1 H) 6.96 (br d, J = 9.02 Hz, 1 H) 7.21-7.29 (m, 2 H) 7.37 (s, 1 H) 7.47 (s, 1 H) 7.74 (br d, J = 7.78 Hz, 1 H) 7.92-8.00 (m, 1 H) 8.42 (br s, 1 H) 8.56 (br s, 2 H) | 0.046 |
| 1-47 | 580.00 | 1H NMR (500 MHz, DMSO-d6) δ ppm 2.74 (br d, J = 4.28 Hz, 3 H) 3.71 (s, 3 H) 6.17 (s, 1 H) 6.89 (br d, J = 8.82 Hz, 1 H) 7.19 (s, 3 H) 7.24-7.69 (m, 9 H) 7.88-7.98 (m, 1 H) 8.19 (s, 1 H) 8.35 (s, 1 H) 8.54 (br d, J = 1.95 Hz, 1 H) 8.62-8.72 (m, 1 H) | 0.072 |
| 1-48 | 572.00 | 1H NMR (500 MHz, DMSO-d6) δ ppm 1.30 (br d, J = 5.90 Hz, 6 H) 2.74 (br d, J = 4.15 Hz, 3 H) 3.70 (s, 3 H) 4.68 (dt, J = 11.58, 5.76 Hz, 1 H) 6.22 (s, 1 H) 6.87-7.09 (m, 6 H) 7.15 (s, 1 H) 7.29-7.34 (m, 1 H) 7.35-7.43 (m, 2 H) 7.91-8.02 (m, 2 H) 8.42 (br s, 1 H) 8.56 (s, 1 H) 8.60 (br s, 1 H) | 0.071 |
| 1-49 | 600.00 | 1H NMR (500 MHz, DMSO-d6) δ ppm 2.74 (br d, J = 4.09 Hz, 3 H) 3.72 (s, 3 H) 6.18 (s, 1 H) 6.90 (br d, J = 9.08 Hz, 1 H) 7.29 (s, 1 H) 7.49 (s, 1 H) 7.72-7.83 (m, 3 H) 7.92 (br d, J = 8.69 Hz, 1 H) 8.36 (br s, 1 H) 8.54 (br s, 1 H) 8.63 (br s, 1 H) | 0.028 |
| 1-50 | 576.20 | 1H NMR (500 MHz, DMSO-d6) δ ppm 2.30 (s, 3 H) 2.74 (br d, J = 4.22 Hz, 3 H) 3.70 (s, 4 H) 3.81 (s, 3 H) 6.22 (s, 1 H) 6.92 (br d, J = 8.89 Hz, 1 H) 6.98 (br d, J = 4.93 Hz, 1 H) 7.10 (br d, J = 7.59 Hz, 2 H) 7.16 (s, 1 H) 7.25 (br d, J = 6.36 Hz, 1 H) 7.37 (br d, J = 8.69 Hz, 1 H) 7.41 (s, 1 H) 7.95 (br dd, J = 8.79, 1.91 Hz, 1 H) 8.01 (s, 2 H) 8.42 (s, 1 H) 8.55 (s, 1 H) 8.61 (br s, 1 H) | 0.049 |
| 1-51 | 628.00 | 1H NMR (500 MHz, DMSO-d6) δ ppm 2.73 (br d, J = 4.22 Hz, 3 H) 3.71 (s, 3 H) 3.87 (s, 3 H) 6.22 (s, 1 H) 6.98 (br d, J = 8.56 Hz, 1 H) 7.03 (br s, 1 H) 7.07 (br s, 1 H) 7.13 (s, 1 H) 7.22 (s, 1 H) 7.45 (s, 1 H) 7.91-8.00 (m, 1 H) 8.42 (br s, 1 H) 8.49-8.58 (m, 2 H) | 0.009 |
| 1-52 | 568.00 | 1H NMR (500 MHz, DMSO-d6) δ ppm 2.74 (br d, J = 4.28 Hz, 3 H) 3.71 (s, 3 H) 6.14 (s, 1 H) 6.81 (br d, J = 8.89 Hz, 1 H) 7.22 (s, 1 H) 7.46 (s, 1 H) 7.51-7.61 (m, 2 H) 7.91 (br d, J = 9.02 Hz, 1 H) 8.31 (s, 1 H) 8.53 (s, 1 H) 8.71 (br s, 1 H) | 0.031 |
| 1-53 | 573.00 | 1H NMR (500 MHz, DMSO-d6) δ ppm 2.74 (br d, J = 4.15 Hz, 3 H) 3.72 (s, 3 H) 6.15 (s, 1 H) 6.82 (br d, J = 8.50 Hz, 1 H) 7.30 (s, 1 H) 7.49 (s, 1 H) 7.91 (br d, J = 8.76 Hz, 1 H) 7.96-8.05 (m, 2 H) 8.14 (s, 1 H) 8.32 (br s, 1 H) 8.53 (s, 1 H) 8.73 (br s, 1 H) | 0.048 |
| 1-54 | 573.00 | 1H NMR (500 MHz, DMSO-d6) δ ppm 2.74 (br d, J = 4.22 Hz, 3 H) 3.72 (s, 3 H) 6.16 (s, 1 H) 6.84 (br d, J = 8.82 Hz, 1 H) 7.28 (s, 1 H) 7.48 (s, 1 H) 7.84-7.98 (m, 4 H) 8.17 (s, 1 H) 8.33 (br s, 1 H) 8.53 (s, 1 H) 8.70 (br s, 1 H) | 0.052 |
| 1-55 | 600.00 | 1H NMR (500 MHz, DMSO-d6) δ ppm 2.75 (br d, J = 4.22 Hz, 3 H) 3.70 (s, 3 H) 6.08 (s, 1 H) 6.72 (br d, J = 8.43 Hz, 1 H) 7.30 (s, 1 H) 7.48 (s, 1 H) 7.63 (br t, J = 8.79 Hz, 1 H) 7.84-7.92 (m, 3 H) 7.93 (br d, J = 3.63 Hz, 1 H) 8.22 (s, 1 H) 8.52 (s, 1 H) 8.90 (br d, J = 1.95 Hz, 1 H) | 0.017 |
| 1-56 | 628.00 | 1H NMR (500 MHz, DMSO-d6) δ ppm 2.75 (br d, J = 4.22 Hz, 3 H) 3.66 (s, 3 H) 3.83 (s, 3 H) 6.17 (s, 1 H) 6.80 (br s, 1 H) 7.13 (s, 1 H) 7.19-7.30 (m, 2 H) 7.38 (s, 1 H) 7.41-7.48 (m, 1 H) 7.93 (dd, J = 8.89, 2.01 Hz, 1 H) 8.34 (s, 1 H) 8.49-8.63 (m, 1 H) 8.71-8.90 (m, 1 H) | 0.019 |
| 1-57 | 630.00 | 1H NMR (500 MHz, DMSO-d6) δ ppm 2.73 (br d, J = 4.22 Hz, 3 H) 3.72 (s, 3 H) 4.94 (q, J = 8.74 Hz, 3 H) 6.26 (s, 1 H) 6.98 (br d, J = 8.95 Hz, 1 H) 7.19 (s, 1 H) 7.21-7.30 (m, 2 H) 7.36-7.52 (m, 4 H) 7.98 (dd, J = 8.92, 2.24 Hz, 1 H) 8.01-8.19 (m, 1 H) 8.48 (s, 1 H) 8.51-8.55 (m, 1 H) 8.55-8.61 (m, 1 H) | 0.024 |
| 1-58 | 600.00 | 1H NMR (400 MHz, DMSO-d6) δ ppm 2.72 (d, J = 4.46 Hz, 3 H) 3.71 (s, 3 H) 6.45 (d, J = 1.76 Hz, 1 H) 7.26 (d, J = 0.73 Hz, 1 H) 7.27-7.32 (m, 2 H) 7.52 (s, 1 H) 7.68 (dd, J = 10.62, 8.86 Hz, 1 H) 7.87 (dd, J = 6.95, 2.18 Hz, 1 H) 7.90-7.96 (m, 1 H) 8.06 (dd, J = 9.12, 2.59 Hz, 1 H) 8.15 (q, J = 4.39 Hz, 1 H) 8.64 (dd, J = 2.59, 0.73 Hz, 1 H) 8.76 (d, J = 1.76 Hz, 1 H) 11.69 (br. s., 1 H) | 0.009 |
| 1-59 | 478.00 | 1H NMR (500 MHz, DMSO-d6) δ ppm 0.85 (br d, J = 4.54 Hz, 3 H) 1.05 (br d, J = 8.30 Hz, 2 H) 2.72 (br d, J = 4.02 Hz, 3 H) 3.65 (s, 3 H) 3.99 (s, 1 H) 6.04 (s, 1 H) 6.59 (d, J = 8.82 Hz, 1 H) 6.63-6.75 (m, 2 H) 6.89 (s, 1 H) 7.22 (s, 1 H) 7.77-7.86 (m, 1 H) 8.17 (s, 1 H) 8.46 (s, 1 H) 8.92 (br d, J = 3.37 Hz, 1 H) | 3.020 |
| 1-60 | 566.00 | 1H NMR (500 MHz, DMSO-d6) δ ppm 2.73 (br d, J = 4.15 Hz, 3 H) 3.71 (s, 3 H) 6.20 (br s, 1 H) 6.87-6.91 (m, 1 H) 7.22 (s, 1 H) 7.33-7.42 (m, 1 H) 7.45 (s, 1 H) 7.56 (br d, J = 7.66 Hz, 2 H) 7.76 (br d, J = 6.62 Hz, 2 H) 7.88-7.97 (m, 2 H) 8.27 (s, 1 H) 8.39 (s, 1 H) 8.52-8.60 (m, 1 H) 8.62 (br s, 1 H) | 0.019 |
| 1-61 | 562.0, 564.0 | 1H NMR (500 MHz, DMSO-d6) δ ppm 2.40 (s, 3 H) 2.73 (br d, J = 4.15 Hz, 3 H) 3.70 (s, 3 H) 6.20 (s, 1 H) 6.89 (s, 1 H) 6.92 (br d, J = 8.56 Hz, 1 H) 7.17 (s, 1 H) 7.43 (s, 2 H) 7.45-7.52 (m, 1 H) 7.56 (s, 1 H) 7.93 (br d, J = 8.69 Hz, 1 H) 8.40 (br s, 1 H) 8.55 (s, 1 H) 8.58-8.74 (m, 1 H) | 0.020 |
| 1-62 | 546.0, 547.0 | 1H NMR (500 MHz, DMSO-d6) δ ppm 2.31 (s, 4 H) 2.73 (br d, J = 4.15 Hz, 3 H) 3.70 (s, 3 H) 6.24 (s, 1 H) 6.97 (br d, J = 8.82 Hz, 1 H) 7.17 (s, 1 H) 7.26-7.35 (m, 2 H) 7.39-7.45 (m, 2 H) 7.96 (br d, J = 8.82 Hz, 1 H) 8.45 (br s, 1 H) 8.56 (br s, 2 H) | 0.064 |
| 1-63 | 566.0, 568.0 | 1H NMR (500 MHz, DMSO-d6) δ ppm 2.72 (br d, J = 3.89 Hz, 3 H) 3.70 (s, 3 H) 6.24 (s, 1 H) 6.98 (br d, J = 8.95 Hz, 1 H) 7.20 (s, 1 H) 7.42 (br d, J = 8.43 Hz, 1 H) 7.45 (s, 1 H) 7.60 (br d, J = 10.12 Hz, 1 H) 7.72 (br t, J = 8.17 Hz ,1 H) 7.96 (br d, J = 8.82 Hz, 1 H) 8.46 (br s, 1 H) 8.49-8.55 (m, 1 H) 8.57 (s, 1 H) | 0.028 |
| 1-64 | 574.0, 576.20 | 1H NMR (500 MHz, DMSO-d6) δ ppm 2.73 (br d, J = 4.15 Hz, 3 H) 3.70 (s, 3 H) 3.80 (s, 6 H) 6.23 (s, 1 H) 6.57 (br s, 1 H) | 0.078 |

TABLE 7-continued

BIOLOGICAL AND ANALYTICAL DATA

| Ex. # | LRMS: (ESI, +ve ion) m/z | NMR | Nav1.7 PX IC50 (μM) |
|---|---|---|---|
| | | 6.64 (s, 2 H) 6.89 (s, 1 H) 6.96 (br d, J = 8.56 Hz, 1 H) 7.15 (s, 1 H) 7.40 (s, 1 H) 7.95 (br d, J = 8.95 Hz, 1 H) 8.44 (br s, 1 H) 8.50-8.60 (m, 2 H) | |
| 1-65 | 550.00 | 1H NMR (500 MHz, DMSO-d6) δ ppm 2.73 (br d, J = 4.02 Hz, 3 H) 3.70 (s, 3 H) 6.24 (s, 1 H) 6.97 (br d, J = 9.34 Hz, 1 H) 7.19 (s, 1 H) 7.41 (br s, 1 H) 7.45 (s, 1 H) 7.52-7.61 (m, 1 H) 7.61-7.69 (m, 1 H) 7.96 (br d, J = 9.21 Hz, 1 H) 8.46 (br s, 1 H) 8.52-8.56 (m, 1 H) 8.56 (br s, 1 H) | 0.054 |
| 1-66 | 592.0, 594.0 | 1H NMR (500 MHz, DMSO-d6) δ ppm 2.73 (br d, J = 4.02 Hz, 3 H) 3.70 (s, 3 H) 3.87 (s, 6 H) 6.24 (s, 1 H) 6.88 (br d, J = 6.62 Hz, 2 H) 6.97 (br d, J = 9.08 Hz, 1 H) 7.19 (s, 1 H) 7.41 (s, 1 H) 7.96 (br d, J = 8.82 Hz, 1 H) 8.46 (br s, 1 H) 8.53 (br s, 1 H) 8.56 (br s, 1 H) | 0.059 |
| 1-67 | 576.0, 578.0 | 1H NMR (500 MHz, DMSO-d6) δ ppm 1.37-1.40 (m, 3 H) 2.74 (br d, J = 4.15 Hz, 3 H) 3.71 (s, 3 H) 4.18 (q, J = 6.88 Hz, 3 H) 6.14 (s, 1 H) 6.83 (br d, J = 8.95 Hz, 1 H) 6.89 (s, 1 H) 7.09 (br d, J = 2.72 Hz, 1 H) 7.17 (s, 1 H) 7.27 (br d, J = 8.17 Hz, 1 H) 7.32 (br dd, J = 11.35, 8.63 Hz, 2 H) 7.41 (s, 1 H) 7.91 (br d, J = 8.82 Hz, 1 H) 8.06 (s, 1 H) 8.30 (s, 1 H) 8.52 (s, 1 H) 8.73 (br s, 1 H) | 0.034 |
| 1-68 | 580.0, 582.0 | 1H NMR (500 MHz, DMSO-d6) δ ppm 2.73 (br d, J = 4.15 Hz, 3 H) 3.71 (s, 3 H) 3.95 (s, 3 H) 6.28 (s, 1 H) 6.89 (s, 1 H) 7.01 (br d, J = 8.30 Hz, 1 H) 7.16 (br d, J = 5.06 Hz, 2 H) 7.22 (s, 1 H) 7.46 (s, 1 H) 7.98 (br d, J = 9.08 Hz, 1 H) 8.47 (br s, 1 H) 8.51 (br s, 1 H) 8.57 (s, 1 H) | 0.023 |
| 1-69 | 616.1, 617.0 | 1H NMR (400 MHz, DMSO-d6) δ ppm 2.71 (d, J = 4.56 Hz, 3 H) 3.71 (s, 3 H) 6.44 (d, J = 1.87 Hz, 1 H) 7.20-7.27 (m, 2 H) 7.47-7.59 (m, 3 H) 8.06 (dd, J = 9.12, 2.59 Hz, 1 H) 8.18 (d, J = 4.25 Hz, 1 H) 8.63 (dd, J = 2.59, 0.73 Hz, 1 H) 8.76 (d, J = 1.76 Hz, 1 H) 11.69 (s, 1 H) | 0.006 |
| 1-70 | 548, 550.0 | 1H NMR (500 MHz, DMSO-d6) δ ppm 2.73 (br d, J = 4.28 Hz, 3 H) 3.70 (s, 3 H) 6.26 (br s, 1 H) 6.89 (s, 1 H) 7.00 (br d, J = 9.08 Hz, 1 H) 7.17 (s, 1 H) 7.45 (s, 1 H) 7.57 (s, 4 H) 7.97 (br d, J = 8.82 Hz, 1 H) 8.48 (br s, 2 H) 8.57 (br s, 1 H) | 0.052 |
| 1-71 | 512.00 | 1H NMR (400 MHz, DMSO-d6) δ ppm 2.28 (d, J = 1.50 Hz, 3 H) 2.67 (d, J = 4.51 Hz, 3 H) 3.70 (s, 3 H) 6.39 (d, J = 1.76 Hz, 1 H) 7.02-7.10 (m, 1 H) 7.17-7.28 (m, 3 H) 7.32 (d, J = 1.76 Hz, 1 H) 7.52-7.60 (m, 1 H) 7.65 (dd, J = 7.41, 1.92 Hz, 1 H) 7.98 (dd, J = 9.10, 2.62 Hz, 1 H) 8.22 (q, J = 4.18 Hz, 1 H) 8.58 (dd, J = 2.59, 0.62 Hz, 1 H) 8.71 (d, J = 1.81 Hz, 1 H) 11.62 (s, 1 H) | 0.398 |
| 1-72 | 544.0, 546.0 | 1H NMR (500 MHz, DMSO-d6) δ ppm 2.72 (d, J = 4.35 Hz, 3 H) 3.76 (s, 3 H) 3.87 (s, 3 H) 6.44 (d, J = 1.62 Hz, 1 H) 7.07 (s, 1 H) 7.13 (d, J = 9.08 Hz, 1 H) 7.23-7.31 (m, 2 H) 7.32-7.38 (m, 1 H) 7.41 (d, J = 7.27 Hz, 2 H) 8.04 (dd, J = 9.08, 2.47 Hz, 1 H) 8.23 (d, J = 4.28 Hz, 1 H) 8.62 (d, J = 2.21 Hz, 1 H) 8.75 (d, J = 1.62 Hz, 1 H) 11.65 (br. s., 1 H) | 0.101 |
| 1-73 | 528.0, 530.0 | 1H NMR (500 MHz, DMSO-d6) δ ppm 2.43 (s, 3 H) 2.72 (d, J = 4.35 Hz, 3 H) 3.75 (s, 3 H) 6.44 (d, J = 1.62 Hz, 1 H) 7.12 (d, J = 9.02 Hz, 1 H) 7.24-7.29 (m, 1 H) 7.33 (d, J = 7.98 Hz, 1 H) 7.40 (s, 1 H) 7.52 (d, J = 8.24 Hz, 1 H) 7.62 (d, J = 8.30 Hz, 1 H) 7.77 (s, 1 H) 8.03 (dd, J = 9.12, 2.50 Hz, 1 H) 8.24 (d, J = 4.41 Hz, 1 H) 8.62 (d, J = 2.21 Hz, 1 H) 8.75 (d, J = 1.69 Hz, 1 H) 11.57-11.71 (m, 1 H) | 0.065 |
| 1-74 | 532.0, 534.0 | 1H NMR (500 MHz, DMSO-d6) δ ppm 2.71 (d, J = 4.41 Hz, 3 H) 3.77 (s, 3 H) 6.44 (d, J = 1.69 Hz, 1 H) 7.13 (d, J = 9.02 Hz, 1 H) 7.28 (d, J = 8.04 Hz, 1 H) 7.38-7.52 (m, 3 H) 7.69 (d, J = 9.80 Hz, 1 H) 7.75 (s, 1 H) 8.04 (dd, J = 9.08, 2.47 Hz, 1 H) 8.22 (d, J = 4.22 Hz, 1 H) 8.62 (d, J = 2.21 Hz, 1 H) 8.75 (d, J = 1.69 Hz, 1 H) 11.65 (br. s., 1 H) | 0.084 |
| 1-75 | 584, 586 | 1H NMR (400 MHz, CHLOROFORM-d) δ ppm 9.87 (1 H, br s) 9.06 (1 H, br s) 8.65 (2 H, br s) 8.22 (1 H, br s) 7.61-7.88 (3 H, m) 7.30-7.43 (1 H, m) 7.07 (1 H, br s) 6.95 (1 H, br s) 6.54 (1 H, br s) 3.78 (3 H, br s) 3.02 (3 H, br s) | 0.106 |
| 1-76 | 561, 563 | 1H NMR (400 MHz, CHLOROFORM-d) δ ppm 9.83 (1 H, br s) 9.06 (1 H, br s) 8.66 (2 H, br s) 8.21 (1 H, br s) 7.29-7.40 (3 H, m) 7.19-7.25 (1 H, m) 7.07 (1 H, br s) 6.92-7.04 (1 H, m) 6.56 (1 H, br s) 3.77 (3 H, br s) 3.02 (3 H, br s) | 0.116 |
| 1-77 | 589, 591 | 1H NMR (400 MHz, CHLOROFORM-d) δ ppm 9.92-10.10 (1 H, m), 9.06 (1 H, d, J = 2.2 Hz), 8.84 (1 H, br s), 8.65 (2 H, d, J = 4.9 Hz), 8.22 (1 H, dd, J = 9.1, 2.4 Hz), 7.46 (1 H, d, J = 8.1 Hz), 7.32 (1 H, s), 7.04-7.12 (2 H, m), 6.98-7.02 (2 H, m), 6.58 (1 H, d, J = 9.1 Hz), 3.96 (3 H, s), 3.76 (3 H, s), 3.03 (3 H, d, J = 3.3 Hz) | 0.070 |
| 1-78 | 584, 586 | 1H NMR (400 MHz, CHLOROFORM-d) δ ppm 9.99 (1 H, m) 9.08 (1 H, br s) 8.64 (2 H, br s) 8.24 (1 H, br s) 7.66-7.81 (3 H, m) 7.29-7.43 (3 H, m) 7.10 (1 H, br s) 6.93-7.00 (1 H, m) 6.54 (1 H, br s) 3.79 (3 H, br s) 3.03 (3 H, br s) | 0.123 |
| 1-79 | 585, 587 | 1H NMR (400 MHz, CHLOROFORM-d) δ ppm 9.78-9.80 (1 H, m), 9.03 (1 H, d, J = 2.2 Hz), 8.65 (2 H, d, J = 4.9 Hz), 8.19 (1 H, dd, J = 9.1, 2.4 Hz), 7.30 (1 H, s), 7.04-7.07 (1 H, m), 7.01 (1 H, s), 6.63 (2 H, d, J = 2.2 Hz), 6.58 (1 H, d, J = 9.1 Hz), 6.52-6.55 (1 H, m), 3.85 (6 H, s), 3.74 (3 H, s), 3.01 (3 H, d, J = 4.5 Hz) | 0.166 |
| 1-80 | 557.00 | 1H NMR (400 MHz, DMSO-d6) δ ppm 2.42 (s, 3 H) 2.72 (d, J = 4.56 Hz, 3 H) 3.69 (s, 3 H) 7.16 (d, J = 9.12 Hz, 1 H) 7.24 (d, J = 7.26 Hz, 1 H) 7.30 (d, J = 10.68 Hz, 1 H) 7.50 (d, J = 1.76 Hz, 1 H) 7.53-7.58 (m, 1 H) 7.64 (s, 1 H) 8.17 (dd, J = 9.07, 2.54 Hz, 1 H) 8.28 (br d, J = 4.35 Hz, 1 H) 8.53 (d, J = 4.87 Hz, 2 H) 8.73-8.78 (m, 1 H) | 0.039 |
| 1-81 | 577.20 | 1H NMR (400 MHz, DMSO-d6) δ ppm 1.23 (br s, 2 H) 1.75 (s, 1 H) 2.72 (d, J = 4.46 Hz, 11 H) 3.70-3.78 (m, 2H) 7.08 (t, J = 4.90 Hz, 1 H) 7.19 (d, J = 9.02 Hz, 1 H) 7.32-7.38 (m, 7 H) 7.75-7.85 (m, 7H) 7.94-7.99 (m, 7 H) 8.17 (dd, J = 9.02, 2.54 Hz, 4 H) 8.25 (br d, J = 4.46 Hz, 4 H) 8.53 (d, J = 4.87 Hz, 7 H) 8.75 (d, J = 2.23 Hz, 4 H) | 0.143 |
| 1-82 | 607.00 | 1H NMR (400 MHz, DMSO-d6) δ ppm 2.72 (d, J = 4.46 Hz, 3 H) 3.71 (s, 3 H) 3.92 (s, 3 H) 7.08 (t, J = 4.82 Hz, 1 H) 7.19 (d, J = 9.12 Hz, 1 H) 7.30-7.39 (m, 3 H) 7.49 (d, J = 10.26 Hz, 2 H) 8.17 (dd, J = 9.02, 2.49 Hz, 1 H) 8.23 (d, J = 4.66 Hz, 1 H) 8.53 (d, J = 4.87 Hz, 2 H) 8.75 (dd, J = 2.54, 0.67 Hz, 1 H) | 0.018 |

TABLE 7-continued

BIOLOGICAL AND ANALYTICAL DATA

| Ex. # | LRMS: (ESI, +ve ion) m/z | NMR | Nav1.7 PX IC$_{50}$ (μM) |
|---|---|---|---|
| 1-83 | 577.00 | 1H NMR (400 MHz, DMSO-d6) δ ppm 2.71 (d, J = 4.56 Hz, 3 H) 3.70 (s, 3 H) 7.08 (t, J = 4.87 Hz, 1 H) 7.17 (d, J = 9.12 Hz, 1 H) 7.29-7.38 (m, 2 H) 7.66 (dt, J = 8.40, 1.92 Hz, 1 H) 7.79 (d, J = 8.40 Hz, 1 H) 7.93 (dd, J = 2.02, 0.88 Hz, 1 H) 8.17 (dd, J = 9.02, 2.59 Hz, 1 H) 8.25 (d, J = 4.77 Hz, 1 H) 8.53 (d, J = 4.87 Hz, 2 H) 8.75 (dd, J = 2.54, 0.67 Hz, 1 H) | 0.032 |
| 1-84 | 593.20 | 1H NMR (400 MHz, DMSO-d6) δ ppm 2.72 (d, J = 4.46 Hz, 3 H) 3.70 (s, 3 H) 7.08 (t, J = 4.72 Hz, 1 H) 7.20 (d, J = 9.02 Hz, 1 H) 7.30 (d, J = 7.15 Hz, 1 H) 7.34 (d, J = 10.78 Hz, 1 H) 7.47 (dt, J = 7.98, 1.19 Hz, 1 H) 7.62-7.76 (m, 3 H) 8.17 (dd, J = 9.02, 2.59 Hz, 1 H) 8.23 (d, J = 4.25 Hz, 1 H) 8.53 (d, J = 4.87 Hz, 2 H) 8.75 (dd, J = 2.59, 0.62 Hz, 1 H) | 0.062 |
| 1-85 | 595.00 | 1H NMR (500 MHz, DMSO-d6) δ ppm 2.75 (d, J = 4.35 Hz, 3 H) 3.72 (s, 3 H) 6.48 (br s, 1 H) 6.75 (br d, J = 8.76 Hz, 1 H) 7.28-7.36 (m, 2 H) 7.68 (br t, J = 9.63 Hz, 1 H) 7.96-8.07 (m, 3 H) 8.16 (br d, J = 4.48 Hz, 2 H) 8.62 (d, J = 1.88 Hz, 1 H) 8.84 (br s, 1 H) | 0.032 |
| 1-86 | 563.20 | 1H NMR (500 MHz, DMSO-d6) δ ppm 2.74 (d, J = 4.35 Hz, 3 H) 3.72 (s, 3 H) 6.44 (t, J = 4.61 Hz, 1 H) 6.70 (d, J = 8.76 Hz, 1 H) 7.27-7.34 (m, 2 H) 7.65-7.73 (m, 2 H) 7.98 (dd, J = 8.82, 2.21 Hz, 1 H) 8.13 (d, J = 4.67 Hz, 2 H) 8.61 (d, J = 2.01 Hz, 1 H) 8.88 (br d, J = 4.09 Hz, 1 H) | 0.220 |
| 1-87 | 611.20 | 1H NMR (500 MHz, DMSO-d6) äppm 2.74 (d, J = 4.41 Hz, 3 H) 3.72 (s, 4 H) 6.55 (br t, J = 4.35 Hz, 1H) 6.81 (br d, J = 8.82 Hz, 1 H) 7.25-71 34 (m, 2H) 7.64-7.71 (m, 1 H) 7.77 (br s, 1 H) 7.85 (br d, J = 6.81 Hz, 1 H) 8.01 (dd, J = 8.86, 1.65 Hz, 1 H) 8.20 (d, J = 4.61 Hz, 2 H) 8.59-8.69 (m, 1 H) 8.74 (br d, J = 4.15 Hz, 1 H) | 0.014 |
| 1-88 | 625.20 | 1H NMR (500 MHz, DMSO-d6) δ ppm 2.74 (d, J = 4.41 Hz, 3 H) 3.71 (s, 3 H) 4.96 (q, J = 8.78 Hz, 2 H) 6.73 (br s, 1 H) 6.89 (br d, J = 8.76 Hz, 1 H) 7.18-7.32 (m, 2 H) 7.34 (br s, 1 H) 7.43 (dd, J = 11.00, 8.60 Hz, 1 H) 7.55 (br d, J = 7.27 Hz, 1 H) 8.07 (dd, J = 8.89, 2.21 Hz, 1 H) 8.31 (br d, J = 4.41 Hz, 2 H) 8.60-8.69 (m, 2 H) | 0.040 |
| 1-89 | 611.2, 613.0 | 1H NMR (400 MHz, DMSO-d6) δ ppm 2.72 (d, J = 4.46 Hz, 3 H) 3.71 (s, 3 H) 7.08 (t, J = 4.87 Hz, 1 H) 7.19 (d, J = 8.91 Hz, 1 H) 7.36 (d, J = 3.11 Hz, 1 H) 7.38 (s, 1 H) 7.87-7.93 (m, 1 H) 7.95-8.01 (m, 1 H) 8.05 (s, 1 H) 8.17 (dd, J = 9.07, 2.54 Hz, 1 H) 8.20-8.27 (m, 1 H) 8.53 (d, J = 4.98 Hz, 2 H) 8.75 (dd, J = 2.54, 0.67 Hz, 1 H) | 0.045 |
| 1-90 | 582.00 | 1H NMR (400 MHz, DMSO-d6) δ ppm 11.74 (br. s., 1 H), 10.98 (br. s., 1 H), 8.77 (br. s., 1 H), 8.65 (br. s., 1 H), 8.13 (d, J = 7.46 Hz, 1 H), 7.96 (br. s., 2 H), 7.65-7.89 (m, 2 H), 7.28-7.52 (m, 3 H), 6.46 (br. s., 1 H), 3.76 (br. s., 3 H), 3.63 (br. s., 3 H) | 0.069 |
| 2-1 | 561.2, 563.0 | 1H NMR (400 MHz, DMSO-d6) δ ppm 2.72 (d, J = 4.46 Hz, 3 H) 3.70 (s, 3 H) 7.08 (s, 1 H) 7.16 (d, J = 9.02 Hz, 1 H) 7.28-7.31 (m, 1 H) 7.31-7.36 (m, 1 H) 7.54-7.61 (m, 1 H) 7.65-7.71 (m, 1 H) 7.86-7.91 (m, 1 H) 8.14-8.19 (m, 1 H) 8.17 (dd, J = 9.07, 2.54 Hz, 1 H) 8.27 (d, J = 4.41 Hz, 1 H) 8.53 (d, J = 4.92 Hz, 2 H) 8.75 (d, J = 2.02 Hz, 1 H) 11.27-12.53 (m, 1 H) | 0.018 |
| 2-2 | 577.20 | 1H NMR (500 MHz, DMSO-d6) δ ppm 2.72 (d, J = 4.41 Hz, 3 H) 3.70 (s, 3 H) 7.08 (br. s., 1 H) 7.15-7.22 (m, 1 H) 7.26-7.40 (m, 3 H) 7.52-7.59 (m, 1 H) 7.88 (d, J = 6.23 Hz, 2 H) 8.17 (dd, J = 9.08, 2.21 Hz, 1 H) 8.25 (d, J = 3.89 Hz, 1 H) 8.53 (d, J = 4.54 Hz, 2 H) 8.75 (d, J = 2.21 Hz, 1 H) 11.64-12.12 (m, 1 H) | 0.007 |
| 2-3 | 595.40 | 1H NMR (500 MHz, DMSO-d6) δ ppm 2.72 (d, J = 4.54 Hz, 3 H) 3.71 (s, 3 H) 7.08 (br. s., 1 H) 7.17 (d, J = 9.21 Hz, 1 H) 7.22-7.48 (m, 3 H) 7.73 (d, J = 4.54 Hz, 1 H) 7.97-8.06 (m, 1 H) 8.17 (dd, J = 9.15, 2.40 Hz, 1 H) 8.25 (d, J = 4.54 Hz, 1 H) 8.53 (d, J = 4.93 Hz, 2 H) 8.75 (d, J = 2.34 Hz, 1 H) 11.65-12.12 (m, 1 H) | — |
| 2-4 | 641.0, 643.0 | 1H NMR (400 MHz, DMSO-d6) δ ppm 2.72 (d, J = 4.56 Hz, 3 H) 2.75 (s, 1 H) 3.72 (s, 3 H) 4.94 (q, J = 8.91 Hz, 3 H) 7.09 (d, J = 9.02 Hz, 1 H) 7.19 (s, 1 H) 7.22 (s, 2 H) 7.38-7.50 (m, 4 H) 7.71 (dd, J = 9.54, 4.15 Hz, 1 H) 7.90 (br. s., 1 H) 8.06 (dd, J = 8.91, 2.59 Hz, 1 H) 8.33 (d, J = 4.46 Hz, 1 H) 8.66 (d, J = 2.80 Hz, 1 H) 14.45-14.66 (m, 1 H) | 0.054 |
| 2-5 | 579.20, 580.0 | 1H NMR (400 MHz, DMSO-d6) δ ppm 2.72 (d, J = 4.56 Hz, 3 H) 3.71 (s, 3 H) 7.09 (d, J = 9.12 Hz, 1 H) 7.24 (s, 1 H) 7.48 (s, 1 H) 7.55 (dd, J = 8.86, 6.79 Hz, 3 H) 7.71 (dd, J = 9.64, 4.15 Hz, 1 H) 8.06 (dd, J = 8.97, 2.54 Hz, 1 H) 8.30 (d, J = 4.35 Hz, 1 H) 8.65 (d, J = 2.28 Hz, 1 H) 14.60 (s, 1 H) | 0.075 |
| 2-6 | 624.0, 625.8 | 1H NMR (400 MHz, DMSO-d6) δ ppm 2.71 (d, J = 4.46 Hz, 4 H) 3.72 (s, 3 H) 3.98 (s, 3 H) 7.15 (d, J = 8.81 Hz, 1 H) 7.30-7.34 (m, 2 H) 7.53 (s, 1 H) 7.61 (d, J = 1.14 Hz, 1 H) 7.71 (dd, J = 9.48, 3.99 Hz, 1 H) 8.05 (d, J = 9.07, 2.44 Hz, 1 H) 8.22 (d, J = 4.66 Hz, 1 H) 8.65 (d, J = 2.07 Hz, 1 H) 14.58 (s, 1 H) | 0.026 |
| 2-7 | 593.20 | 1H NMR (400 MHz, DMSO-d6) δ ppm 2.72 (d, J = 4.46 Hz, 3 H) 3.75 (s, 3 H) 7.04 (d, J = 9.33 Hz, 1 H) 7.08 (t, J = 4.92 Hz, 1 H) 7.28 (d, J = 7.98 Hz, 1 H) 7.33-7.39 (m, 1 H) 7.44 (d, J = 1.97 Hz, 1 H) 7.64 (dd, J = 10.21, 8.76 Hz, 1 H) 7.89 (ddd, J = 8.68, 4.54, 2.33 Hz, 1 H) 7.99 (dd, J = 7.31, 1.09 Hz, 1 H) 8.14 (dd, J = 9.12, 2.59 Hz, 1 H) 8.38 (d, J = 4.15 Hz, 1 H) 8.53 (d, J = 4.87 Hz, 2 H) 8.75 (dd, J = 2.54, 0.67 Hz, 1 H) | 0.004 |
| 2-8 | 577.20 | 1H NMR (400 MHz, DMSO-d6) δ ppm 2.72 (d, J = 4.46 Hz, 3 H) 3.76 (s, 3 H) 7.03 (d, J = 9.02 Hz, 1 H) 7.08 (t, J = 4.92 Hz, 1 H) 7.29 (d, J = 8.09 Hz, 1 H) 7.39 (dd, J = 8.09, 1.97 Hz, 1 H) 7.48 (d, J = 1.97 Hz, 1 H) 7.61-7.70 (m, 1 H) 8.08 (dd, J = 6.89, 2.02 Hz, 1 H) 8.12-8.19 (m, 2 H) 8.41 (d, J = 4.35 Hz, 1 H) 8.53 (d, J = 4.87 Hz, 2 H) 8.75 (d, J = 2.54, 0.67 Hz, 1 H) 11.37-12.38 (m, 1 H) | 0.017 |
| 2-9 | 559.20 | 1H NMR (400 MHz, DMSO-d6) δ ppm 2.72 (d, J = 4.46 Hz, 3 H) 3.75 (s, 3 H) 7.03 (d, J = 9.12 Hz, 1 H) 7.08 (t, J = 4.92 Hz, 1 H) 7.13 (s, 1 H) 7.29 (t, J = 54.15 Hz, 1 H) 7.32-7.36 (m, 1 H) 7.40 (s, 1 H) 7.43 (d, J = 1.76 Hz, 1 H) 7.48-7.55 (m, 1 H) 7.97-8.05 (m, 2 H) 8.15 (dd, J = 9.02, 2.49 Hz, 1 H) 8.41 (d, J = 4.56 Hz, 1 H) 8.53 (d, J = 4.87 Hz, 2 H) 8.75 (d, J = 1.97 Hz, 1 H) | Not available |

TABLE 7-continued

BIOLOGICAL AND ANALYTICAL DATA

| Ex. # | LRMS: (ESI, +ve ion) m/z | NMR | Nav1.7 PX IC$_{50}$ (μM) |
|---|---|---|---|
| 2-10 | 627.3, 629.3 | 1H NMR (400 MHz, DMSO-d6) δ ppm 2.72 (d, J = 4.46 Hz, 3 H) 3.70 (s, 3 H) 7.08 (t, J = 4.92 Hz, 1 H) 7.18 (d, J = 8.91 Hz, 1 H) 7.25 (s, 1 H) 7.50 (s, 1 H) 7.61-7.77 (m, 3 H) 8.17 (dd, J = 9.02, 2.59 Hz, 1 H) 8.28 (d, J = 4.46 Hz, 1 H) 8.54 (d, J = 4.87 Hz, 2 H) 8.76 (d, J = 2.38 Hz, 1 H) 11.57-12.25 (m, 1 H) | 0.008 |
| 2-11 3365201 | Not available | 1H NMR (400 MHz, DMSO-d6) δ ppm 8.74 (1 H, d, J = 2.38 Hz), 8.53 (2 H, d, J = 4.87 Hz), 8.42(1 H, br s), 8.13 (1 H, dd, J = 8.97, 2.54 Hz), 7.06 (3 H, m), 6.97(1 H, d, J = 8.91 Hz), 3.61 (3 H, s), 2.71 (3 H, d, J = 4.56 Hz), 1.61 (2 H, m), 1.24 (24 H, bs), 0.85 (3 H, m) | 0.014 |
| 2-12 3365825 | 614.2 | 1H NMR (600 MHz, DMSO-d6) δ ppm 11.01 (br s, 1 H), 8.63 (s, 1 H), 8.53 (d, J = 1.09 Hz), 8.23 (d, J = 6.98 Hz, 1 H), 8.07 (dd, J = 9.11, 2.57 Hz, 1 H), 7.86 (br d, J = 7.01 Hz, 1 H), 7.75-7.81 (m, 1 H), 7.69 (dd, J = 10.16, 8.76 Hz, 1 H), 7.37 (d, J = 10.67 Hz, 1 H), 7.32 (d, J = 7.16 Hz, 1 H), 7.24 (d, J = 8.95 Hz, 1 H), 3.74 (s, 3 H), 2.73 (d, J = 4.52 Hz, 3 H), 1.88 (d, J = 1.09 Hz, 3 H). | 0.06353 |
| 2-13 3365826 | 598.2 | 1H NMR (600 MHz, DMSO-d6) δ ppm 11.02 (br s, 1 H), 8.63 (d, J = 2.57 Hz, 1 H), 8.53 (d, J = 1.09 Hz, 1 H), 8.21-8.28 (m, 1 H), 8.02-8.09 (m, 2 H), 8.00 (br d, J = 6.46 Hz, 1 H), 7.69 (t, J = 9.61 Hz, 1 H), 7.34-7.40 (m, 2 H), 7.23 (d, J = 9.34 Hz, 1 H), 3.74 (s, 3 H), 2.73 (d, J = 4.52 Hz, 3 H), 1.88 (d, J = 1.01 Hz, 3 H). | 0.1156 |
| 2-14 3365827 | 628.2 | 1H NMR (600 MHz, DMSO-d6) δ ppm 11.01 (br s, 1 H), 8.64 (d, J = 2.57 Hz, 1 H), 8.54 (d, J = 1.09 Hz, 1 H), 8.28 (q, J = 4.13 Hz, 1 H), 8.08 (dd, J = 9.11, 2.57 Hz, 1 H), 7.55 (d, J = 8.04 Hz, 1 H), 7.44 (dd, J = 11.13, 8.49 Hz, 1 H), 7.34 (d, J = 8.75 Hz, 2 H), 7.27 (d, J = 7.16 Hz, 1 H), 7.22 (d, J = 9.03 Hz, 1 H), 4.97 (q, J = 8.77 Hz, 2 H), 3.74 (s, 3 H), 2.73 (d, J = 4.52 Hz, 3 H), 1.88, (d, J = 0.93 Hz, 3 H). | 0.621 |
| 3-1 | 641.0, 643.2 | 1H NMR (400 MHz, DMSO-d6) δ ppm 2.73 (d, J = 4.46 Hz, 3 H) 3.70 (s, 3 H) 4.94 (q, J = 8.81 Hz, 2 H) 7.08 (t, J = 4.92 Hz, 1 H) 7.12 (d, J = 9.02 Hz, 1 H) 7.20 (s, 1 H) 7.23 (ddd, J = 8.40, 4.35, 2.07 Hz, 1 H) 7.37-7.50 (m, 3 H) 8.18 (dd, J = 9.02, 2.49 Hz, 1 H) 8.37 (d, J = 4.46 Hz, 1 H) 8.54 (d, J = 4.98 Hz, 2 H) 8.76 (d, J = 2.28 Hz, 1 H) | 0.033 |
| 3-2 | 647.2, 648.8 | 1H NMR (400 MHz, DMSO-d6) δ ppm 2.71 (d, J = 4.46 Hz, 3 H) 3.70 (s, 3 H) 4.94 (q, J = 8.81 Hz, 2 H) 7.18-7.26 (m, 3 H) 7.38-7.46 (m, 2 H) 7.47 (s, 1 H) 8.14 (dd, J = 9.02, 2.59 Hz, 1 H) 8.20 (q, J = 4.39 Hz, 1 H) 8.43 (s, 1 H) 8.72 (dd, J = 2.64, 0.67 Hz, 1 H) 12.19-12.46 (m, 1 H) | 0.031 |
| 3-3 | 658.0, 658.8 | 1H NMR (400 MHz, DMSO-d6) δ ppm 2.72 (d, J = 4.46 Hz, 3 H) 3.69 (s, 3 H) 4.94 (q, J = 8.81 Hz, 2 H) 6.76 (dd, J = 7.98, 2.28 Hz, 1 H) 6.93 (dd, J = 7.98, 1.87 Hz, 1 H) 7.17-7.26 (m, 3 H) 7.39-7.46 (m, 2 H) 7.47 (s, 1 H) 7.87 (q, J = 8.05 Hz, 1 H) 8.14 (dd, J = 9.02, 2.59 Hz, 1 H) 8.23 (q, J = 4.18 Hz, 1 H) 8.72 (dd, J = 2.54, 0.67 Hz, 1 H) 11.51 (s, 1 H) | 0.073 |
| 3-4 | 630.0, 632.2 | 1H NMR (400 MHz, DMSO-d6) δ ppm 2.73 (d, J = 4.46 Hz, 3 H) 3.73 (s, 3 H) 4.94 (q, J = 8.81 Hz, 3 H [3H due to TFA, the neutral compound should be 2 H]) 7.08 (dd, J = 9.02, 0.62 Hz, 1 H) 7.18-7.27 (m, 2 H) 7.32 (d, J = 1.76 Hz, 1 H) 7.38-7.49 (m, 3 H) 7.65 (d, J = 1.76 Hz, 1 H) 8.06 (dd, J = 8.97, 2.54 Hz, 1 H) 8.37 (q, J = 4.35 Hz, 1 H) 8.64 (dd, J = 2.54, 0.67 Hz, 1 H) 12.25 (br. s., 1 H) | 0.053 |
| 3-5 | 655.2, 657.0 | 1H NMR (400 MHz, DMSO-d6) δ ppm 2.38 (s, 3 H) 2.72 (d, J = 4.46 Hz, 3 H) 3.72 (s, 3 H) 4.94 (q, J = 8.74 Hz, 2 H) 6.85 (br. s., 1 H) 7.08 (d1 J = 9.12 Hz, 1 H) 7.17-7.27 (m, 2 H) 7.38-7.47 (m, 3 H) 8.05-8.16 (m, 2 H) 8.37 (d, J = 4.56 Hz, 1 H) 8.66 (dd, J = 2.54, 0.67 Hz, 1 H) | 0.076 |
| 3-6 | 641.0, 643.2 | 1H NMR (400 MHz, DMSO-d6) δ ppm 2.72 (d, J = 4.46 Hz, 3 H) 3.71 (s, 3 H) 4.94 (q, J = 8.81 Hz, 3 H) 6.97 (d, J = 5.91 Hz, 1 H) 7.11 (d, J = 8.91 Hz, 1 H) 7.17-7.26 (m, 2 H) 7.38-7.49 (m, 3 H) 8.12 (dd, J = 9.02, 2.49 Hz, 1 H) 8.30 (d, J = 6.63 Hz, 1 H) 8.35 (d, J = 4.04 Hz, 1 H) 8.64 (s, 1 H) 8.71 (d, J = 1.97 Hz, 1 H) | 0.051 |
| 3-7 | 611.0, 613.0 | 1H NMR (400 MHz, DMSO-d6) δ ppm 2.72 (d, J = 4.46 Hz, 3 H) 3.70 (s, 3 H) 7.08 (t, J = 4.92 Hz, 1 H) 7.14-7.20 (m, 1 H) 7.29 (s, 1 H) 7.51 (s, 1 H) 7.63-7.72 (m, 1 H) 7.68 (dd, J = 10.57, 8.71 Hz, 1 H) 7.88 (dd, J = 6.95, 2.18 Hz, 1 H) 7.90-7.96 (m, 1 H) 8.17 (dd, J = 9.02, 2.59 Hz, 1 H) 8.27-8.34 (m, 1 H) 8.54 (d, J = 4.98 Hz, 2 H) 8.76 (dd, J = 2.59, 0.73 Hz, 1 H) | 0.028 |
| 3-8 | 617.0, 619.0 | 1H NMR (400 MHz, DMSO-d6) δ ppm 2.71 (d, J = 4.46 Hz, 3 H) 3.70 (s, 3 H) 7.27 (d, J = 9.12 Hz, 1 H) 7.29 (s, 1 H) 7.51 (s, 1 H) 7.64-7.73 (m, 1 H) 7.87 (dd, J = 6.95, 1.87 Hz, 1 H) 7.92 (td, J = 5.52, 2.64 Hz, 1 H) 8.10-8.17 (m, 2 H) 8.43 (s, 1 H) 8.72 (d, J = 2.49 Hz, 1 H) 12.32 (br. s., 1 H) | 0.014 |
| 3-9 | 628.2, 630.0 | 1H NMR (400 MHz, DMSO-d6) δ ppm 2.72 (d, J = 4.46 Hz, 3 H) 3.69 (s, 3 H) 6.76 (dd, J = 7.98, 2.18 Hz, 1 H) 6.93 (dd, J = 7.88, 1.87 Hz, 1 H) 7.25 (dd, J = 9.07, 0.67 Hz, 1 H) 7.29 (s, 1 H) 7.51 (s, 1 H) 7.68 (dd, J = 10.57, 8.71 Hz, 1 H) 7.83-7.90 (m, 2 H) 7.90-7.96 (m, 1 H) 8.13 (dd, J = 9.12, 2.59 Hz, 1 H) 8.18 (q, J = 4.25 Hz, 1 H) 8.71 (dd, J = 2.59, 0.73 Hz, 1 H) 11.51 (s, 1 H) | 0.053 |
| 3-10 | 600.0, 602.0 | 1H NMR (400 MHz, DMSO-d6) δ ppm 2.73 (d, J = 4.46 Hz, 3 H) 3.73 (s, 3 H) 7.13 (dd, J = 9.02, 0.73 Hz, 1 H) 7.29 (s, 1 H) 7.32 (d, J = 1.76 Hz, 1 H) 7.50 (s, 1 H) 7.65 (d, J = 1.76 Hz, 1 H) 7.68 (dd, J = 10.68, 8.81 Hz, 1 H) 7.88 (dd, J = 6.84, 2.18 Hz, 1 H) 7.91-7.97 (m, 1 H) 8.05 (dd, J = 8.97, 2.54 Hz, 1 H) 8.30 (q, J = 4.49 Hz, 1 H) 8.64 (dd, J = 2.59, 0.73 Hz, 1 H) 12.25 (br. s., 1 H) | 0.020 |
| 3-11 | 625.2, 626.0 | 1H NMR (400 MHz, DMSO-d6) δ ppm 2.38 (s, 3 H) 2.72 (d, J = 4.46 Hz, 3 H) 3.72 (s, 3 H) 6.85 (d, J = 5.70 Hz, 1 H) 7.13 (d, J = 9.43 Hz, 1 H) 7.29 (s, 1 H) 7.49 (s, 1 H) 7.68 (dd, J = 10.57, 8.81 Hz, 1 H) 7.88 (dd, J = 6.84, 2.18 Hz, 1 H) 7.90-7.97 (m, 1 H) 8.09 (dd, J = 8.91, 2.49 Hz, 1 H) 8.13 (d, J = 6.63 Hz, 1 H) 8.29 (d, J = 4.46 Hz, 1 H) 8.66 (dd, J = 2.59, 0.73 Hz, 1 H) | 0.026 |
| 3-12 | 611.0, 613.0 | 1H NMR (400 MHz, DMSO-d6) δ ppm 2.72 (d, J = 4.46 Hz, 3 H) 3.71 (s, 3 H) 6.97 (d, J = 6.12 Hz, 1 H) 7.16 (d, J = 9.23 Hz, 1 H) 7.29 (s, 1 H) 7.50 (s, 1 H) 7.62-7.74 (m, 1 H) 7.88 (dd, J = 6.74, 2.07 Hz, 1 H) 7.90-7.98 (m, 1 H) 8.11 (dd, J = | 0.024 |

TABLE 7-continued

BIOLOGICAL AND ANALYTICAL DATA

| Ex. # | LRMS: (ESI, +ve ion) m/z | NMR | Nav1.7 PX IC$_{50}$ (μM) |
|---|---|---|---|
| | | 9.02, 2.59 Hz, 1 H) 8.24-8.33 (m, 2 H) 8.64 (s, 1 H) 8.70 (dd, J = 2.54, 0.67 Hz, 1 H) | |
| 3-13 | 611.20 | 1H NMR (400 MHz, DMSO-d6) δ ppm 2.71 (d, J = 4.56 Hz, 3 H) 3.73 (s, 3 H) 7.13-7.19 (m, 1 H) 7.28-7.35 (m, 2 H) 7.74-7.80 (m, 1 H) 7.85 (d, J = 7.15 Hz, 1 H) 7.87-7.95 (m, 1 H) 8.05 (dd, J = 8.97, 2.54 Hz, 1 H) 8.08 (s, 1 H) 8.17-8.23 (m, 1 H) 8.35 (br. s., 1 H) 8.64 (dd, J = 2.54, 0.67 Hz, 1 H) | 0.007 |
| 3-14 | 600.20 | 1H NMR (400 MHz, DMSO-d6) δ ppm 2.72 (d, J = 4.46 Hz, 3 H) 3.74 (s, 3 H) 3.77-3.77 (m, 1 H) 3.77-3.77 (m, 1 H) 7.14 (dd, J = 9.02, 0.73 Hz, 1 H) 7.28-7.38 (m, 4 H) 7.64 (d, J = 1.66 Hz, 1 H) 7.65-7.72 (m, 1 H) 7.74-7.81 (m, 1 H) 7.85 (d, J = 6.43 Hz, 1 H) 8.05 (dd, J = 8.97, 2.54 Hz, 1 H) 8.08-8.13 (m, 1 H) 8.24 (d, J = 4.46 Hz, 1 H) 8.63 (dd, J = 2.59, 0.73 Hz, 1 H) | 0.017 |
| 3-15 | 611.20 | 1H NMR (400 MHz, DMSO-d6) δ ppm 2.72 (d, J = 4.56 Hz, 3 H) 3.72 (s, 3 H) 6.90-7.01 (m, 1 H) 7.14-7.21 (m, 1 H) 7.17 (d, J = 9.23 Hz, 1 H) 7.28-7.38 (m, 2 H) 7.68 (dd, J = 10.21, 8.76 Hz, 1 H) 7.77 (br. s., 1 H) 7.85 (d, J = 7.77 Hz, 1 H) 8.11 (dd, J = 8.91, 2.38 Hz, 1 H) 8.17-8.25 (m, 1 H) 8.25-8.35 (m, 1 H) 8.63 (s, 1 H) 8.67-8.71 (m, 1 H) 8.69 (d, J = 2.49 Hz, 1 H) | — |
| 3-16 | 625.20 | 1H NMR (400 MHz, DMSO-d6) δ ppm 2.37 (s, 3 H) 2.72 (d, J = 4.46 Hz, 3 H) 3.72 (s, 3 H) 6.79-6.88 (m, 1 H) 7.14 (d, J = 8.91 Hz, 1 H) 7.28-7.31 (m, 2 H) 7.68 (dd, J = 10.26, 8.71 Hz, 1 H) 7.74-7.82 (m, 1 H) 7.85 (d, J = 7.57 Hz, 1 H) 8.04-8.15 (m, 2 H) 8.25 (br. s., 1 H) 8.65 (d, J = 1.76 Hz, 1 H) | Not available |
| 4.1 | 544, 546 | 1H NMR (400 MHz, CHLOROFORM-d) δ ppm 9.38 (1 H, br s), 8.72 (1 H, d, J = 2.1 Hz), 8.26 (1 H, d, J = 1.7 Hz), 7.93 (1 H, s), 7.82 (1 H, dd, J = 9.1, 2.6 Hz), 7.63 (1 H, d, J = 8.6, 2.3 Hz), 7.40 (1 H, d, J = 2.3 Hz), 7.07-7.14 (2 H, m), 6.94-6.97 (1 H, m), 6.85 (1 H, app t, J = 2.02 Hz), 6.55 (2 H, d, J = 7.6 Hz), 3.83 (3 H, s), 3.79 (3 H, s), 2.98 (3 H, s) | 0.461 |
| 4.2 | 548, 549 | 1H NMR (400 MHz, CHLOROFORM-d) δ ppm 9.42 (1 H, br s), 8.74 (1 H, d, J = 2.1 Hz), 8.28 (1 H, d, J = 1.7 Hz), 7.83 (1 H, dd, J = 9.2, 2.6 Hz), 7.79 (1 H, br s), 7.73 (1 H, m), 7.69 (1 H, dd, J = 8.6, 2.4 Hz), 7.47-7.59 (3 H, m), 7.46 (1 H, d, J = 2.3 Hz), 7.15 (1 H, d, J = 8.7 Hz), 6.56-6.60 (2 H, m), 3.81 (3 H, s), 2.99 (3 H, s) | 0.187 |
| 4.3 | 498, 499 | 1H NMR (400 MHz, CHLOROFORM-d) δ ppm 9.39 (1 H, br s), 8.73 (1 H, d, J = 2.1 Hz), 8.25 (1 H, d, J = 1.8 Hz), 8.23 (1 H, br s), 7.82 (1 H, dd, J = 9.2, 2.5 Hz), 7.64 (1 H, dd, J = 8.6, 2.4 Hz), 7.43 (1 H, d, J = 2.3 Hz), 7.29-7.39 (2 H, m), 7.23-7.28 (1 H, m), 7.11 (1 H, d, J = 8.7 Hz), 6.97-7.03 (1 H, m), 6.53-6.58 (2 H, m), 3.79 (3 H, s), 2.98 (3 H, s) | 2.373 |
| 4.4 | 532, 534 | 1H NMR (400 MHz, CHLOROFORM-d + drops of acetone-d) δ ppm 9.73 (1 H, s), 9.43 (1 H, br s), 8.63 (1 H, d, J = 2.0 Hz), 8.16 (1 H, d, J = 1.6 Hz), 7.78 (1 H, dd, J = 9.1, 2.4 Hz), 7.52 (1 H, dd, J = 8.6, 2.2 Hz), 7.30 (1 H, d, J = 2.2 Hz), 7.21 (1 H, br s), 6.99-7.07 (2 H, m), 6.87-6.90 (1 H, m), 6.36-6.43 (2 H, m), 3.67 (3 H, s), 2.83 (3 H, s) | 0.173 |
| 4.5 | 528, 530 | 1H NMR (400 MHz, CHLOROFORM-d) δ ppm 9.34 (1 H, br s), 8.73 (1 H, d, J = 2.1 Hz), 8.27 (1 H, d, J = 1.7 Hz), 7.82 (1 H, dd, J = 9.2, 2.6 Hz), 7.75 (1 H, br s), 7.63 (1 H, dd, J = 8.6, 2.3 Hz), 7.53 (1 H, d, J = 1.8 Hz), 7.40 (1 H, d, J = 2.3 Hz), 7.29-7.36 (1 H, m), 7.23-7.26 (1 H, m), 7.10 (1 H, d, J = 8.7 Hz), 6.56-6.60 (2 H, m), 3.79 (3 H, s), 2.98 (3 H, s), 2.39 (3 H, s) | 0.442 |
| 4.6 | 582, 584 | 1H NMR (400 MHz, CHLOROFORM-d) δ ppm 9.71-9.77 (1 H, m), 8.74 (1 H, d, J = 2.3 Hz), 8.30 (1 H, d, J = 1.8 Hz), 7.87 (1 H, dd, J = 9.1, 2.5 Hz), 7.78 (1 H, br s), 7.69 (1 H, br s), 7.61-7.65 (2 H, m), 7.50-7.57 (1 H, m), 7.21 (1 H, s), 7.18 (1 H, s), 6.61 (1 H, d, J = 1.7 Hz), 6.56 (1 H, d, J = 9.0 Hz), 3.81 (3 H, s), 3.00 (5 H, d, J = 4.6 Hz) | 0.090 |
| 4.7 | 532, 534 | 1H NMR (400 MHz, CHLOROFORM-d) δ ppm 9.74-9.78 (1 H, m), 8.74 (1 H, d, J = 2.1 Hz), 8.29 (1 H, d, J = 1.8 Hz), 7.93 (1 H, br s), 7.87 (1 H, dd, J = 9.1, 2.6 Hz), 7.33-7.40 (1 H, m), 7.14-7.22 (4 H, m), 7.03-7.08 (1 H, m), 6.61 (1 H, d, J = 1.8 Hz), 6.57 (1 H, d, J = 9.1 Hz), 3.80 (3 H, s), 3.00 (3 H, d, J = 4.6 Hz) | 0.891 |
| 4.8 | 578, 580 | 1H NMR (400 MHz, CHLOROFORM-d) δ ppm 9.74-9.78 (1 H, m), 8.74 (1 H, d, J = 2.3 Hz), 8.30 (1 H, d, J = 1.8 Hz), 7.87 (2 H, dd, J = 9.1, 2.5 Hz), 7.17 (1 H, s), 7.15 (1 H, s), 6.99 (1 H, app t, J = 1.58 Hz), 6.86-6.91 (2 H, m), 6.61 (1 H, d, J = 1.7 Hz), 6.55 (1 H, d, J = 9.1 Hz), 3.82 (3 H, s), 3.80 (3 H, s), 3.00 (3 H, d, J = 4.4 Hz) | 0.081 |
| 4.9 | 562, 564 | 1H NMR (400 MHz, CHLOROFORM-d) δ ppm 9.63-9.70 (1 H, m), 8.74 (1 H, d, J = 2.0 Hz), 8.30 (1 H, d, J = 1.5 Hz), 7.87 (1 H, dd, J = 9.1, 2.2 Hz), 7.61 (1 H, br s), 7.42 (1 H, br s), 7.24-7.26 (2 H, m), 7.19 (1 H, s), 7.17 (1 H, s), 6.61 (1 H, d, J = 1.5 Hz), 6.57 (1 H, d, J = 9.1 Hz), 3.80 (3 H, s), 2.99 (3 H, d, J = 3.9 Hz), 2.41 (3 H, s) | 0.076 |
| 5.1 | 568, 570 | 1H NMR (400 MHz, CHLOROFORM-d) δ ppm 8.79 (1 H, d, J = 2.2 Hz), 8.74 (1 H, br s), 8.30 (1 H, d, J = 1.8 Hz), 7.85 (1 H, dd, J = 9.1, 2.5 Hz), 7.76 (1 H, br s), 7.70-7.72 (2 H, m), 7.59-7.65 (1 H, m), 7.37 (1 H, s), 7.02 (1 H, s), 6.60-6.63 (2 H, m), 3.82 (3 H, s) | 0.007 |
| 5.2 | 554, 553 | 1H NMR (400 MHz, CHLOROFORM-d) δ ppm 8.79-8.81 (1 H, m), 8.31-8.33 (1 H, m), 8.02 (1 H, br s), 7.92-7.97 (1 H, m), 7.50-755 (1 H, m), 7.35 (1 H, d, J = 1.8 Hz), 7.30-7.34 (1 H, m), 7.22-7.26 (1 H, m), 6.98 (1 H, d, J = 1.6 Hz), 6.61-6.67 (2 H, m), 3.79 (3 H, d, J = 1.61 Hz) | 0.010 |
| 5.3 | 561, 562 | 1H NMR (400 MHz, CHLOROFORM-d) δ ppm 8.80 (1 H, d, J = 2.1 Hz), 8.32 (1 H, d, J = 1.8 Hz), 8.03 (1 H, br s), 7.93 (1 H, dd, J = 9.1, 2.5 Hz), 7.70-7.76 (3 H, m), 7.39 (1 H, s), 6.97 (1 H, s), 6.57-6.66 (2 H, m), 3.81 (3 H, s) | 0.031 |
| 5.4 | 600, 599 | 1H NMR (400 MHz, CHLOROFORM-d) δ ppm 8.79 (1 H, d, J = 2.1 Hz), 8.31 (1 H, d, J = 1.8 Hz), 8.09 (1 H, br s), 7.91 (1 H, dd, J = 9.1, 2.5 Hz), 7.36 (1 H, s), 7.33 (1 H, br s), 7.19-7.23 (2 H, m), 7.01 (1 H, | 0.007 |

TABLE 7-continued

BIOLOGICAL AND ANALYTICAL DATA

| Ex. # | LRMS: (ESI, +ve ion) m/z | NMR | Nav1.7 PX IC$_{50}$ (μM) |
|---|---|---|---|
| 5.5 | 598, 600 | s), 6.64 (1 H, d, J = 9.1 Hz), 6.62 (1 H, d, J = 1.8 Hz), 3.92 (3 H, s), 3.80 (3 H, s) 1H NMR (400 MHz, CHLOROFORM-d) δ ppm 8.80(1 H, d, J = 2.1 Hz), 8.31 (1 H, d, J = 1.8 Hz), 8.22 (1 H, br s), 7.90 (1 H, dd, J = 9.1, 2.6 Hz), 7.45 (1 H, t, J = 8.0 Hz), 7.35 (1 H, s), 7.18-7.20 (1 H, m), 7.09-7.10 (1 H, m), 7.00-7.06 (2 H, m), 6.65 (1 H, d, J = 9.1 Hz), 6.61 (1 H, d, J = 1.8 Hz), 4.43 (2 H, q, J = 8.1 Hz), 3.79 (3 H, s) | 0.016 |
| 6 | 583, 585 | 1H NMR (400 MHz, CHLOROFORM-d) δ ppm 8.65-8.66 (1 H, m), 8.29 (1 H, d, J = 1.7 Hz), 8.17-8.19 (1 H, m), 8.10-8.13 (1 H, m), 7.78 (1 H, br s), 7.68-7.73 (2 H, m), 7.58-7.62 (1 H, m), 7.34 (1H, br s), 7.29 (1H, s), 6.92(1 H, s), 6.60(1 H, d, J = 1.8 Hz), 3.82 (3 H, s), 3.74 (3 H, s) | 0.167 |
| 7 | 530.00 | 1H NMR (400 MHz, DMSO-d6) δ ppm 1.57-1.79 (m, 6 H) 1.92-2.06 (m, 2 H) 2.67 (d, J = 4.46 Hz, 3 H) 2.96 (t, J = 7.00 Hz, 1 H) 3.65 (s, 3 H) 6.43 (d, J = 1.76 Hz, 1 H) 7.23 (s, 1 H) 7.27 (d, J = 9.23 Hz, 1 H) 7.41 (s, 1 H) 8.03 (dd, J = 9.12, 2.59 Hz, 2 H) 8.59 (dd, J = 2.59, 0.73 Hz, 1 H) 8.74 (d, J = 1.66 Hz, 1 H) 11.67 (s, 1 H) | 0.068 |
| 8 | 518.20 | 1H NMR (400 MHz, DMSO-d6) δ ppm 2.69 (d, J = 4.46 Hz, 5 H) 2.85-2.95 (m, 2 H) 3.63 (s, 3 H) 6.44 (d, J = 1.87 Hz, 1 H) 7.10 (dd, J = 9.02, 0.73 Hz, 1 H) 7.16 (d, J = 9.95 Hz, 1 H) 7.21 (d, J = 6.95 Hz, 1 H) 8.03 (dd, J = 9.12, 2.59 Hz, 1 H) 8.21 (q, J = 4.32 Hz, 1 H) 8.61 (dd, J = 2.64, 0.78 Hz, 1 H) 8.75 (d, J = 1.87 Hz, 1 H) 11.67 (s, 1 H) | 0.849 |
| 9 | 528.1 | 1H NMR (400 MHz, DMSO-d6) δ ppm 11.45 (s, 1 H), 8.71 (d, J = 1.76 Hz, 1 H), 7.77(d, J = 1.97 Hz, 1 H), 7.70 (d, J = 8.06 Hz, 2 H), 7.61 (dd, J = 8.34, 2.23 Hz, 1 H), 7.51 (d, J = 8.29 Hz, 1 H), 7.43 (d, J = 1.76 Hz, 1 H), 7.30-7.35 (m, 1 H), 7.26-7.30 (m, 1 H), 7.20-7.26 (m, 2 H), 6.41 (d, J = 1.76 Hz, 1 H), 6.19-6.25 (m, 1 H), 3.80 (s, 3 H), 2.58 (d, J = 4.35 Hz, 3 H), 2.42 (s, 3 H). | 0.40 |
| 10 | 599.0 | 1H NMR (500 MHz, DMSO-d6) δ ppm 11.48 (s, 1 H) 8.71 (d, J = 1.43 Hz, 1 H) 7.81 (br d, J = 7.14 Hz, 1 H) 7.65-7.76 (m, 4 H) 7.25-7.37 (m, 4 H) 6.41 (s, 1 H) 6.39 (d, J = 6.44 Hz, 1 H) 3.75 (s, 3 H) 2.59 (d, J = 4.28 Hz, 3 H). | 0.21 |

Indications

Voltage gated sodium channels are present in all excitable cells including myocytes of muscles and neurons of the central and peripheral nervous system. In neuronal cell, sodium channels are primarily responsible for generating the rapid upstroke of the action potential and nerve firing of the cells. As such, sodium channels are critical to the initiation and propagation of electrical signals in the nervous system. Proper and ordinary function of sodium channels is necessary for the neurons to function normally. Thus, aberrant sodium channel activity is believed to be the underlying cause of a variety of medical disorders Hubne C A, Jentsch T J, *Hum. Mol. Genet.*, 11(20):2435-2445 (2002) for a review of inherited ion channel disorders), including epilepsy (Yogeeswari et al, *Curr. Drug Targets,* 5(7):589-502 (2004)), arrhythmia (Noble D., *Proc. Natl. Acad Sci. USA,* 99(9): 5755-5756 (200)), mytonia (Cannon, S C, *Kidney Int.* 57(3): 772-779 (2000)) and pain (Wood, J N et al., *J. Neurobiol.,* 61(1): 55-71 (2004).

Evidence suggests that Nav1.7 may pay a key role in various pain states, including acute pain, inflammatory pain, and/or neuropathic pain. Gain of function lutations of Nav1.7 both familial an sporadic, have been linked to primary erythermalgia, a disease characterized by burning pain and inflammation of the extremities (Yan et al, *J. Med Genet.,* 41(3):171-174 (2004), and paroxysmal extreme pain disorder (Waxman, S G, *Neurology* 769(6):505-507 (2007).

Congruent with this observation is the report that non-selective sodium channel blockers lidocaine and mexiletine can provide symptomatic relief in cases of familial erythermalgia (Legroux-Crepe et al., *Ann. Dermatol Venereol.,* 130: 429-433) and carbamazepine is effective in reducing the number and severity of attack in PEPD (Fertlemen et al., *Neuron.* 52(5): 767-774 (2006).

Nav 1.7 inhibitors are, therefore, potentially useful in the treatment of a wide variety of disorders, particularly pain including acute pain, chronic pain, neuropathic pain, inflammatory pain, visceral pain, nociceptive pain including post-surgical pain and mixed pain types involving the viscera, gastrointestinal tract, cranial structures, musculoskeletal system, spine, urogenital system, cardiovascular system and CNS including cancer pain, back and orofacial pain.

The compounds of the invention are selective Nav 1.7 channel inhibitors. More specifically, the preferred compounds of the invention show an affinity or potency for the Nav 1.7 channel over some other Nav channels, and in particular, over Nav 1.5 channel. Selectivity for Nav 1.7 over Nav 1.5 is believed to lead to one or more improved side effect profile for the compounds of the invention. Such selectivity is believed to reduce any cardiovascular liabilities which are believed to be associated with the inhibition of Nav 1.5 channel. Hence, it is preferred that compounds of the invention possess at least a 10-fold selectivity profile over Nav 1.5, more preferably 30-fold selective and most preferable at least 100-fold more selective for Nav 1.7 over Nav 1.5.

The compounds of the invention have been shown to modulate, and specifically inhibit the activity of Nav 1.7 sodium gated voltage channels. To this end, compounds of the invention are useful for, but not limited to, the prevention or treatment of pain. In one embodiment of the invention, there is provided a method of treating a disorder related to the activity of Nav 1.7 in a subject, the method comprising administering to the subject an effective dosage amount of a compound of Formulas I or II, or a sub-formula thereof. In another embodiment, there is provided a method of reducing pain in a subject by administering to the subject an effective dosage amount of a compound of Formula I or II and sub-formulas thereof including formulas I-A, I—B and II-A. In yet another embodiment, the invention provides a method of treating a pain selected from acute pain, chronic pain, neuropathic pain, inflammatory pain, visceral pain and nociceptive pain or a combination thereof in a subject, the method comprising administering by administering to the subject an effective dosage amount of a compound of Formula I or II, or sub-formulas thereof. In yet another embodiment, the invention provides a method of treating post-surgical pain and mixed pain types involving the viscera, gastrointestinal tract, cranial structures, musculoskeletal system, spine, urogenital system, cardiovascular system and CNS including cancer pain, back and orofacial pain, the method comprising administering by administering to the subject an effective dosage amount of a compound of Formula I, II and sub-formulas thereof.

In one embodiment, the compounds of the invention are provided for the manufacture of a medicament, or a pharmaceutical composition, for the therapeutic and/or prophylactic treatment of pain. In another embodiment, the invention provides compounds, in effective dosage amounts, for the therapeutic and/or prophylactic treatment of a pain selected from acute pain, chronic pain, neuropathic pain, inflammatory pain, visceral pain and nociceptive pain or a combination thereof in a subject.

Besides being useful for human treatment, the compounds of the invention may be useful for veterinary treatment of companion animals, exotic animals and farm animals, including mammals, rodents, and the like. For example, animals including horses, dogs, and cats may be treated with compounds provided herein.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of Formula (I):

(I)

or a pharmaceutically acceptable salt thereof, wherein:
$X^1$ is N or $CR^3$;
$X^2$ is N or $CR^4$;
$X^3$ is N or $CR^5$;
$X^4$ is N or $CR^6$;
$X^5$ is N or $CR^7$;
$X^6$ is N or $CR^8$;
$X^7$ is $CL^1$;
$X^8$ is $CR^{10}$;
$X^9$ is N or $CR^{11}$;
wherein 0, 1, 2, 3, or 4 of $X^1$, $X^2$, $X^3$, $X^4$, $X^5$, $X^6$ and $X^9$ are N;
$R^1$ is —NH-$L^2$;
$R^2$ is $NH_2$, $NHC_{1-8}$alk, $NHC_{1-4}$haloalk, NH—$OR^a$, NH—$OR^c$, —$OR^a$, or —$OR^c$;
$R^3$ is H, halo, CN, $C_{1-8}$alk, or $C_{1-4}$haloalk;
$R^4$ is H, halo, CN, $C_{1-8}$alk, or $C_{1-4}$haloalk;
$R^5$ is H, halo, CN, $C_{1-8}$alk, or $C_{1-4}$haloalk;
$R^6$ is H, halo, CN, $C_{1-8}$alk, or $C_{1-4}$haloalk;
$R^7$ is CN, halo, $C_{1-8}$alk, or $C_{1-8}$haloalk, —$OR^a$, or —$OR^c$;
$R^8$ is H, halo, $C_{1-8}$alk, or $C_{1-4}$haloalk;
$R^9$ is H, halo, $C_{1-20}$alk, or $C_{1-20}$haloalk;
$R^{10}$ is H, halo, $C_{1-8}$alk, or $C_{1-8}$haloalk;
$R^{11}$ is H, halo, $C_{1-8}$alk, or $C_{1-8}$haloalk;
$L^1$ is $C_{0-6}$alk-linked saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atoms selected from O and S, which is substituted by 0, 1, 2 or 3 $R^d$ groups selected from F, Cl, Br, $C_{1-6}$alk —$OR^a$, —$OR^c$, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{1-6}$alkNR$^a$R$^a$, —$OC_{1-6}$alk OR$^a$, —SR$^a$, —S(=O)$R^b$, —S(=O)$_2R^b$, —S(=O)$_2NR^aR^a$, —NR$^a$R$^a$, —N(R$^a$)C(=O)$R^b$, —N(R$^a$)C(=O) OR$^b$, —N(R$^a$)C(=O)NR$^a$R$^a$, —N(R$^a$)C(=NR$^a$)NR$^a$R$^a$, —N(R$^a$)S(=O)$_2R^b$, —N(R$^a$)S(=O)2NR$^a$R$^a$, —NR$^a$C$_{1-6}$alkNR$^a$R$^a$, —NR$^a$C$_{1-6}$alkOR$^a$, and oxo;
wherein each of said $C_{1-6}$alk is substituted by 0, 1, 2 or 3 substituents selected from halo, $C_{1-3}$haloalk, —$OR^a$, —NR$^a$R$^a$, —N(R$^a$)C(=O)$R^b$, —OC(=O)$R^b$, C(=O)NR$^a$R$^a$, or C(=O)$OR^a$;

$L^2$ is $C_{0-6}$alk-linked saturated, partially-saturated or unsaturated 5- or 6-membered monocyclic ring containing 0, 1, 2 or 3 N atoms and 0 or 1 atoms selected from O and S, which is substituted by 0, 1, 2 or 3 $R^e$ groups selected from F, Cl, Br, $C_{1-6}$alk, or $C_{1-4}$haloalk;
$R^a$ is independently, at each instance, H or $R^b$;
$R^b$ is independently, at each instance, phenyl, benzyl or $C_{1-6}$alk, wherein the phenyl, benzyl and $C_{1-6}$alk is substituted by 0, 1, 2 or 3 substituents selected from halo, $C_{1-4}$alk, $C_{1-3}$haloalk, —$OC_{1-4}$alk, —$NH_2$, —$NHC_{1-4}$alk, and —N($C_{1-4}$alk)$C_{1-4}$alk; and
$R^c$ is a $C_{0-1}$alk-linked saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atoms selected from O and S, which is substituted by 0, 1, 2 or 3 $R^{13}$ groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)NR$^a$R$^a$, —C(=NR$^a$)NR$^a$R$^a$, —OC(=O)$R^b$, —OC(=O)NR$^a$R$^a$, —$OC_{2-6}$alkNR$^a$R$^a$, —$OC_{2-6}$alkOR$^a$, —SR$^a$, —S(=O)$R^b$, —S(=O)$_2R^b$, —S(=O)$_2$NR$^a$R$^a$, —NR$^a$R$^a$, —N(R$^a$)C(=O)$R^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2R^b$, —N(R$^a$)S(=O)2NR$^a$R$^a$, —NR$^a$C$_{2-6}$alkNR$^a$R$^a$, —NR$^a$C$_{2-6}$alkOR$^a$, —$C_{1-6}$alkNR$^a$R$^a$, —$C_{1-6}$alkOR$^a$, —$C_{1-6}$alkN(R$^a$)C(=O)$R^b$, —$C_{1-6}$alkOC(=O)$R^b$, —$C_{1-6}$alkC(=O)NR$^a$R$^a$, —$C_{1-6}$alkC(=O)$OR^a$ and oxo.

2. The compound in accordance with claim 1, or a pharmaceutically acceptable salt thereof, wherein $X^3$ is N.

3. The compound in accordance with claim 1, or a pharmaceutically acceptable salt thereof, wherein $X^7$ is $CL^1$ and $X^8$ is $CR^{10}$.

4. The compound in accordance with claim 1, or a pharmaceutically acceptable salt thereof, wherein each of $X^1$, $X^2$ and $X^4$ are CH and $X^3$ is N.

5. The compound in accordance with claim 1, or a pharmaceutically acceptable salt thereof, wherein $X^5$ is $CR^7$; $X^6$ is $CR^8$; and $X^9$ are $CR^{11}$.

6. The compound in accordance with claim 1, or a pharmaceutically acceptable salt thereof, wherein $R^2$ is $NH_2$, $NH(CH_3)$, $NH(OCH_3)$, or —$OCH_3$.

7. The compound in accordance with claim 1, or a pharmaceutically acceptable salt thereof, wherein $R^7$ is —$OR^a$.

8. The compound in accordance with claim 1, or a pharmaceutically acceptable salt thereof, wherein $R^7$ is —$OCH_3$.

9. The compound in accordance with claim 1, or a pharmaceutically acceptable salt thereof, wherein $R^{10}$ is halo.

10. The compound in accordance with claim 1, or a pharmaceutically acceptable salt thereof, wherein $R^1$ is-N-$L^2$, wherein $L^2$ is unsaturated 5- or 6-membered monocyclic ring containing 0, 1, 2 or 3 N atoms.

11. The compound in accordance with claim 1, or a pharmaceutically acceptable salt thereof, wherein $L^2$ is oxazolyl, imidazolyl, thiadiazolyl, pyrazinyl, pyridinyl, pyrimidinyl, or pyridazinyl, each of which is substituted by 0, 1, 2 or 3 $R^e$ groups selected from F, Cl, Br, $C_{1-6}$alk, $C_{1-4}$haloalk, or —$OR^a$.

12. The compound in accordance with claim 1, or a pharmaceutically acceptable salt thereof, wherein $L^2$ is selected from:

[structures]

each of which is substituted by 0, 1, 2 or 3 $R^e$ groups selected from F, Cl, Br, $C_{1-6}$alk $C_{1-4}$haloalk, or —O—$C_{1-6}$alk.

13. The compound in accordance with claim 1, or a pharmaceutically acceptable salt thereof, wherein $L^1$ is saturated 3-, 4-, 5-, or 6-membered monocyclic ring containing 0, 1, 2 or 3 N atoms, or unsaturated 5- or 6-membered monocyclic ring containing 0, 1, 2 or 3 N atoms.

14. The compound in accordance with claim 1, or a pharmaceutically acceptable salt thereof, wherein $L^1$ is cyclopropyl, —C≡C-cyclopentyl, phenyl, or pyridinyl ring.

15. The compound in accordance with claim 1, or a pharmaceutically acceptable salt thereof, wherein $L^1$ is phenyl ring having the formula:

[structure with $R^{14}$, $R^{15}$, $R^{16}$, $R^{17}$, $R^{18}$]

wherein:
$R^{14}$ is H, halo, $C_{1-8}$alk, $C_{1-4}$haloalk, —$OR^a$ or —$OR^c$;
$R^{15}$ is H, halo, $C_{1-8}$alk, $C_{1-4}$haloalk, —$OR^a$ or —$OR^c$;
$R^{16}$ is H, halo, $C_{1-8}$alk, $C_{1-4}$haloalk, —$OR^a$ or —$OR^c$;
$R^{17}$ is H, halo, $C_{1-8}$alk, $C_{1-4}$haloalk, —$OR^a$ or —$OR^c$; and
$R^{18}$ is H, halo, $C_{1-8}$alk, $C_{1-4}$haloalk, —$OR^a$ or —$OR^c$.

16. The compound in accordance with claim 1, or a pharmaceutically acceptable salt thereof, wherein:
each of $X^1$, $X^2$, $X^4$, $X^6$, and $X^9$ are CH;
$X^3$ is N;
$X^5$ is —C(OCH$_3$);
$X^7$ is $CL^1$, wherein $L^1$ is cyclopropyl, —C≡C-cyclopentyl, phenyl or pyridinyl ring, each of which is substituted by 0, 1, 2 or 3 $R^d$ groups selected from F, Cl, Br, $C_{1-6}$alk, $C_{1-4}$haloalk, or —$OR^a$;
$X^8$ is CH, CF, CCl, or C-methyl;
$R^1$ is —N-$L^2$, wherein $L^2$ is unsaturated 5- or 6-membered monocyclic ring containing 0, 1, 2 or 3 N atoms, each of which is substituted by 0, 1, 2 or 3 R groups selected from F, Cl, Br, $C_{1-6}$alk, $C_{1-4}$haloalk, or —$OR^a$; and
$R^2$ is NH$_2$, NH(CH$_3$), NH(OCH$_3$), or —OCH$_3$.

17. The compound in accordance with claim 1, or a pharmaceutically acceptable salt thereof, selected from the group consisting of:
6-((4'-chloro-2-fluoro-5-methoxy-3'-methyl-4-biphenylyl)(methylcarbamoyl)amino)-N-3-isoxazolyl-3-pyridinesulfonamide;
6-((4'-chloro-2-fluoro-5-methoxy-3'-methyl-4-biphenylyl)(methylcarbamoyl)amino)-N-3-pyridazinyl-3-pyridinesulfonamide;
6-((2-fluoro-5-methoxy-3'-(trifluoromethyl)-4-biphenylyl)(methylcarbamoyl)amino)-N-3-pyridazinyl-3-pyridinesulfonamide;
6-((2-fluoro-5-methoxy-3'-(trifluoromethyl)-4-biphenylyl)(methylcarbamoyl)amino)-N-3-isoxazolyl-3-pyridinesulfonamide;
6-((3'-chloro-2,5'-difluoro-5-methoxy-4-biphenylyl)(methylcarbamoyl)amino)-N-3-isoxazolyl-3-pyridinesulfonamide;
6-((3'-chloro-2-fluoro-5,5'-dimethoxy-4-biphenylyl)(methylcarbamoyl)amino)-N-3-isoxazolyl-3-pyridinesulfonamide;
6-((2-fluoro-3',5-dimethoxy-5'-(trifluoromethoxy)-4-biphenylyl)(methylcarbamoyl)amino)-N-3-isoxazolyl-3-pyridinesulfonamide;
6-((2-fluoro-3',5-dimethoxy-4-biphenylyl)(methylcarbamoyl)amino)-N-3-isoxazolyl-3-pyridinesulfonamide;
6-((2-fluoro-3',5-di methoxy-5'-(trifluoromethyl)-4-biphenylyl)(methylcarbamoyl)amino)-N-3-isoxazolyl-3-pyridinesulfonamide;
6-((3',4'-dichloro-2-fluoro-5-methoxy-4-biphenylyl)(methylcarbamoyl)amino)-N-3-isoxazolyl-3-pyridinesulfonamide;
6-((4'-chloro-2-fluoro-5-methoxy-3'-(trifluoromethyl)-4-biphenylyl)(methylcarbamoyl)amino)-N-3-isoxazolyl-3-pyridinesulfonamide;
6-((2-fluoro-5-methoxy-3'-(2,2,2-trifluoroethoxy)-4-biphenylyl)(methylcarbamoyl)amino)-N-3-isoxazolyl-3-pyridinesulfonamide;
6-((3'-cyclopropyl-2-fluoro-5-methoxy-4-biphenylyl)(methylcarbamoyl)amino)-N-3-isoxazolyl-3-pyridinesulfonamide;
6-((2-fluoro-5-methoxy-3'-(trifluoromethoxy)-4-biphenylyl)(methylcarbamoyl)amino)-N-3-isoxazolyl-3-pyridinesulfonamide;
6-((2,3'-difluoro-5-methoxy-4'-methyl-4-biphenylyl)(methylcarbamoyl)amino)-N-3-isoxazolyl-3-pyridinesulfonamide;
6-((2,4'-difluoro-5-methoxy-3'-methyl-4-biphenylyl)(methylcarbamoyl)amino)-N-3-isoxazolyl-3-pyridinesulfonamide;

6-((3'-chloro-2-fluoro-5-methoxy-4'-methyl-4-biphenylyl)(methylcarbamoyl)amino)-N-3-isoxazolyl-3-pyridinesulfonamide;
6-((2,3'-difluoro-5-methoxy-5'-methyl-4-biphenylyl)(methylcarbamoyl)amino)-N-3-isoxazolyl-3-pyridinesulfonamide;
6-((3'-chloro-2-fluoro-5-methoxy-5'-methyl-4-biphenylyl)(methylcarbamoyl)amino)-N-3-isoxazolyl-3-pyridinesulfonamide;
6-((4'-chloro-2,3'-difluoro-5-methoxy-4-biphenylyl)(methylcarbamoyl)amino)-N-3-isoxazolyl-3-pyridinesulfonamide;
6-((3'-chloro-2,4'-difluoro-5-methoxy-4-biphenylyl)(methylcarbamoyl)amino)-N-3-isoxazolyl-3-pyridinesulfonamide;
N-3-isoxazolyl-6-((methylcarbamoyl)(2,3',4'-trifluoro-5-methoxy-4-biphenylyl)amino)-3-pyridinesulfonamide;
6-((2,4'-difluoro-3',5,5'-trimethoxy-4-biphenylyl)(methylcarbamoyl)amino)-N-3-isoxazolyl-3-pyridinesulfonamide;
N-3-isoxazolyl-6-((methylcarbamoyl)(2,3',4',5'-tetrafluoro-5-methoxy-4-biphenylyl)amino)-3-pyridinesulfonamide;
6-((3'-chloro-2,4'-difluoro-5,5'-dimethoxy-4-biphenylyl)(methylcarbamoyl)amino)-N-3-isoxazolyl-3-pyridinesulfonamide;
6-((2,4'-difluoro-5-methoxy-3'-(trifluoromethyl)-4-biphenylyl)(methylcarbamoyl)amino)-N-3-isoxazolyl-3-pyridinesulfonamide;
6-((2,4'-difluoro-5-methoxy-3'-(trifluoromethoxy)-4-biphenylyl)(methylcarbamoyl)amino)-N-3-isoxazolyl-3-pyridinesulfonamide;
6-((2-chloro-4'-fluoro-5-methoxy-3'-methyl-4-biphenylyl)(methylcarbamoyl)amino)-N-3-isoxazolyl-3-pyridinesulfonamide;
6-((2,4'-dichloro-5-methoxy-3'-methyl-4-biphenylyl)(methylcarbamoyl)amino)-N-3-isoxazolyl-3-pyridinesulfonamide;
6-((2,3'-dichloro-5'-fluoro-5-methoxy-4-biphenylyl)(methylcarbamoyl)amino)-N-3-isoxazolyl-3-pyridinesulfonamide;
6-((2-chloro-5-methoxy-3'-(trifluoromethyl)-4-biphenylyl)(methylcarbamoyl)amino)-N-3-isoxazolyl-3-pyridinesulfonamide;
6-((2,3'-dichloro-5,5'-dimethoxy-4-biphenylyl)(methylcarbamoyl)amino)-N-3-isoxazolyl-3-pyridinesulfonamide;
6-((2,4'-dichloro-3',5-dimethoxy-4-biphenylyl)(methylcarbamoyl)amino)-N-3-isoxazolyl-3-pyridinesulfonamide;
6-((2,5'-dichloro-5-methoxy-2'-methyl-4-biphenylyl)(methylcarbamoyl)amino)-N-3-isoxazolyl-3-pyridinesulfonamide;
6-((4'-chloro-2-fluoro-3',5-dimethoxy-4-biphenylyl)(methylcarbamoyl)amino)-N-3-isoxazolyl-3-pyridinesulfonamide;
6-((2-chloro-3',5-dimethoxy-5'-(trifluoromethyl)-4-biphenylyl)(methylcarbamoyl)amino)-N-3-isoxazolyl-3-pyridinesulfonamide;
6-((2-chloro-5-methoxy-3'-(2,2,2-trifluoroethoxy)-4-biphenylyl)(methylcarbamoyl)amino)-N-3-isoxazolyl-3-pyridinesulfonamide;
6-((2-chloro-3'-cyclopropyl-5-methoxy-4-biphenylyl)(methylcarbamoyl)amino)-N-3-isoxazolyl-3-pyridinesulfonamide;
6-((2-chloro-5-methoxy-3'-(trifluoromethoxy)-4-biphenylyl)(methylcarbamoyl)amino)-N-3-isoxazolyl-3-pyridinesulfonamide;
6-((5-chloro-2-methoxy-4-(2-methoxy-5-(trifluoromethyl)-3-pyridinyl)phenyl)(methylcarbamoyl)amino)-N-3-isoxazolyl-3-pyridinesulfonamide;
6-((5-chloro-4-(5-chloro-2-methoxy-3-pyridinyl)-2-methoxyphenyl)(methylcarbamoyl)amino)-N-3-isoxazolyl-3-pyridinesulfonamide;
6-((5-chloro-2-methoxy-4-(2-methoxy-6-(trifluoromethyl)4-pyridinyl)phenyl)(methylcarbamoyl)amino)-N-3-isoxazolyl-3-pyridinesulfonamide;
6-((5-chloro-2-methoxy-4-(2-(trifluoromethyl)-4-pyridinyl)phenyl)(methylcarbamoyl)amino)-N-3-isoxazolyl-3-pyridinesulfonamide;
6-((2-chloro-4'-fluoro-5-methoxy-4-biphenylyl)(methylcarbamoyl)amino)-N-3-isoxazolyl-3-pyridinesulfonamide;
6-((2-chloro-5-methoxy-4'-(trifluoromethyl)-4-biphenylyl)(methylcarbamoyl)amino)-N-3-isoxazolyl-3-pyridinesulfonamide;
6-((2-chloro-3',5-dimethoxy-4'-(trifluoromethyl)-4-biphenylyl)(methylcarbamoyl)amino)-N-3-isoxazolyl-3-pyridinesulfonamide;
6-((2-chloro-3'-(difluoromethoxy)-5-methoxy-4-biphenylyl)(methylcarbamoyl)amino)-N-3-isoxazolyl-3-pyridinesulfonamide;
6-((2-chloro-5-methoxy-3'-(1-methylethoxy)-4-biphenylyl)(methylcarbamoyl)amino)-N-3-isoxazolyl-3-pyridinesulfonamide;
6-((2-chloro-3'-fluoro-5-methoxy-5'-(trifluoromethyl)-4-biphenylyl)(methylcarbamoyl)amino)-N-3-isoxazolyl-3-pyridinesulfonamide;
6-((2-chloro-4'-fluoro-3',5-dimethoxy-5'-methyl-4-biphenylyl)(methylcarbamoyl)amino)-N-3-isoxazolyl-3-pyridinesulfonamide;
6-((2-chloro-3',5-dimethoxy-5'-(trifluoromethoxy)-4-biphenylyl)(methylcarbamoyl)amino)-N-3-isoxazolyl-3-pyridinesulfonamide;
6-((2-chloro-3',4',5'-trifluoro-5-methoxy-4-biphenylyl)(methylcarbamoyl)amino)-N-3-isoxazolyl-3-pyridinesulfonamide;
6-((2,3'-dichloro-5'-cyano-5-methoxy-4-biphenylyl)(methylcarbamoyl)amino)-N-3-isoxazolyl-3-pyridinesulfonamide;
6-((2,4'-dichloro-3'-cyano-5-methoxy-4-biphenylyl)(methylcarbamoyl)amino)-N-3-isoxazolyl-3-pyridinesulfonamide;
6-((2-chloro-2'-fluoro-5-methoxy-5'-(trifluoromethyl)-4-biphenylyl)(methylcarbamoyl)amino)-N-3-isoxazolyl-3-pyridinesulfonamide;
6-((2-chloro-2',5-dimethoxy-5'-(trifluoromethoxy)-4-biphenylyl)(methylcarbamoyl)amino)-N-3-isoxazolyl-3-pyridinesulfonamide;
6-((2-chloro-4'-fluoro-5-methoxy-3'-(2,2,2-trifluoroethoxy)-4-biphenylyl)(methylcarbamoyl)amino)-N-3-isoxazolyl-3-pyridinesulfonamide;
6-((2-chloro-4'-fluoro-5-methoxy-3'-(trifluoromethyl)-4-biphenylyl)(methylcarbamoyl)amino)-N-3-isoxazolyl-3-pyridinesulfonamide;
6-((5-chloro-4-cyclopropyl-2-methoxyphenyl)(methylcarbamoyl)amino)-N-3-isoxazolyl-3-pyridinesulfonamide;
6-((2,3'-dichloro-4'-fluoro-5-methoxy-4-biphenylyl)(methylcarbamoyl)amino)-N-3-isoxazolyl-3-pyridinesulfonamide;

6-((2,3'-dichloro-5-methoxy-4'-methyl-4-biphenylyl)(methylcarbamoyl)amino)-N-3-isoxazolyl-3-pyridinesulfonamide;
6-((2-chloro-3'-fluoro-5-methoxy-4'-methyl-4-biphenylyl)(methylcarbamoyl)amino)-N-3-isoxazolyl-3-pyridinesulfonamide;
6-((2,4'-dichloro-3'-fluoro-5-methoxy-4-biphenylyl)(methylcarbamoyl)amino)-N-3-isoxazolyl-3-pyridinesulfonamide;
6-((2-chloro-3',5,5'-trimethoxy-4-biphenylyl)(methylcarbamoyl)amino)-N-3-isoxazolyl-3-pyridinesulfonamide;
6-((2-chloro-3',4'-difluoro-5-methoxy-4-biphenylyl)(methylcarbamoyl)amino)-N-3-isoxazolyl-3-pyridinesulfonamide;
6-((2-chloro-4'-fluoro-3',5,5'-trimethoxy-4-biphenylyl)(methylcarbamoyl)amino)-N-3-isoxazolyl-3-pyridinesulfonamide;
6-((2-chloro-3'-ethoxy-4'-fluoro-5-methoxy-4-biphenylyl)(methylcarbamoyl)amino)-N-3-isoxazolyl-3-pyridinesulfonamide;
6-((2-chloro-3',4'-difluoro-5,5'-dimethoxy-4-biphenylyl)(methylcarbamoyl)amino)-N-3-isoxazolyl-3-pyridinesulfonamide;
6-((2-chloro-4'-fluoro-5-methoxy-3'-(trifluoromethoxy)-4-biphenylyl)(methylcarbamoyl)amino)-N-3-isoxazolyl-3-pyridinesulfonamide;
6-((2,4'-dichloro-5-methoxy-4-biphenylyl)(methylcarbamoyl)amino)-N-3-isoxazolyl-3-pyridinesulfonamide;
6-((4'-fluoro-3-methoxy-3'-methyl-4-biphenylyl)(methylcarbamoyl)amino)-N-3-isoxazolyl-3-pyridinesulfonamide;
6-((3'-chloro-3,5'-dimethoxy-4-biphenylyl)(methylcarbamoyl)amino)-N-3-isoxazolyl-3-pyridinesulfonamide;
6-((4'-chloro-3-methoxy-3'-methyl-4-biphenylyl)(methylcarbamoyl)amino)-N-3-isoxazolyl-3-pyridinesulfonamide;
6-((3'-chloro-5'-fluoro-3-methoxy-4-biphenylyl)(methylcarbamoyl)amino)-N-3-isoxazolyl-3-pyridinesulfonamide;
6-((2,4'-dichloro-3'-cyano-5-methoxy-4-biphenylyl)(methylcarbamoyl)amino)-N-2-pyrimidinyl-3-pyridinesulfonamide;
6-((2-chloro-3',4'-difluoro-5-methoxy-4-biphenylyl)(methylcarbamoyl)amino)-N-2-pyrimidinyl-3-pyridinesulfonamide;
6-((2,4'-dichloro-3',5-dimethoxy-4-biphenylyl)(methylcarbamoyl)amino)-N-2-pyrimidinyl-3-pyridinesulfonamide;
6-((2,3-dichloro-5'-cyano-5-methoxy-4-biphenylyl)(methylcarbamoyl)amino)-N-2-pyrimidinyl-3-pyridinesulfonamide;
6-((2-chloro-3',5,5'-trimethoxy-4-biphenylyl)(methylcarbamoyl)amino)-N-2-pyrimidinyl-3-pyridinesulfonamide;
6-((4'-chloro-2-fluoro-5-methoxy-3'-methyl-4-biphenylyl)(methylcarbamoyl)amino)-N-2-pyrimidinyl-3-pyridinesulfonamide;
6-((2-fluoro-5-methoxy-3'-(trifluoromethyl)-4-biphenylyl)(methylcarbamoyl)amino)-N-2-pyrimidinyl-3-pyridinesulfonamide;
6-((2-fluoro-3',5-di methoxy-5'-(trifluoromethyl)-4-biphenylyl)(methylcarbamoyl)amino)-N-2-pyrimidinyl-3-pyridinesulfonamide;
6-((3',4'-dichloro-2-fluoro-5-methoxy-4-biphenylyl)(methylcarbamoyl)amino)-N-2-pyrimidinyl-3-pyridinesulfonamide;
6-((2-fluoro-5-methoxy-3'-(trifluoromethoxy)-4-biphenylyl)(methylcarbamoyl)amino)-N-2-pyrimidinyl-3-pyridinesulfonamide;
6-((2,4'-difluoro-5-methoxy-3'-(trifluoromethyl)-4-biphenylyl)(methylcarbamoyl)amino)-N-2-pyrimidinyl-3-pyridinesulfonamide;
6-((methylcarbamoyl)(2,3',4',5'-tetrafluoro-5-methoxy-4-biphenylyl)amino)-N-2-pyrimidinyl-3-pyridinesulfonamide;
6-((2,4'-difluoro-5-methoxy-3'-(trifluoromethoxy)-4-biphenylyl)(methylcarbamoyl)amino)-N-2-pyrimidinyl-3-pyridinesulfonamide;
6-((2,4'-difluoro-5-methoxy-3'-(2,2,2-trifluoroethoxy)-4-biphenylyl)(methylcarbamoyl)amino)-N-2-pyrimidinyl-3-pyridinesulfonamide;
6-((4'-chloro-2-fluoro-5-methoxy-3'-(trifluoromethyl)-4-biphenylyl)(methylcarbamoyl)amino)-N-2-pyrimidinyl-3-pyridinesulfonamide;
6-((2-fluoro-5-methoxy-3'-(trifluoromethyl)-4-biphenylyl)(methoxycarbamoyl)amino)-N-3-isoxazolyl-3-pyridinesulfonamide;
6-((3'-(difluoromethyl)-2,4'-difluoro-5-methoxy-4-biphenylyl)(methylcarbamoyl)amino)-N-2-pyrimidinyl-3-pyridinesulfonamide;
6-((3'-chloro-2,4'-difluoro-5-methoxy-4-biphenylyl)(methylcarbamoyl)amino)-N-2-pyrimidinyl-3-pyridinesulfonamide;
6-((3'-(difluoromethyl)-2,4',5'-trifluoro-5-methoxy-4-biphenylyl)(methylcarbamoyl)amino)-N-2-pyrimidinyl-3-pyridinesulfonamide;
6-((2-chloro-4'-fluoro-5-methoxy-3'-(2,2,2-trifluoroethoxy)-4-biphenylyl)(methylcarbamoyl)amino)-N-3-pyridazinyl-3-pyridinesulfonamide;
6-((2-chloro-3',4',5'-trifluoro-5-methoxy-4-biphenylyl)(methylcarbamoyl)amino)-N-3-pyridazinyl-3-pyridinesulfonamide;
6-((5-chloro-2-methoxy-4-(2-methoxy-6-(trifluoromethyl)-4-pyridinyl)phenyl)(methylcarbamoyl)amino)-N-3-pyridazinyl-3-pyridinesulfonamide;
6-((4'-fluoro-3-methoxy-3'-(trifluoromethoxy)-4-biphenylyl)(methylcarbamoyl)amino)-N-2-pyrimidinyl-3-pyridinesulfonamide;
6-((4'-fluoro-3-methoxy-3'-(trifluoromethyl)-4-biphenylyl)(methylcarbamoyl)amino)-N-2-pyrimidinyl-3-pyridinesulfonamide;
6-((3'-(difluoromethyl)-4'-fluoro-3-methoxy-4-biphenylyl)(methylcarbamoyl)amino)-N-2-pyrimidinyl-3-pyridinesulfonamide;
6-((2-chloro-4'-fluoro-5-methoxy-3'-(trifluoromethoxy)-4-biphenylyl)(methylcarbamoyl)amino)-N-2-pyrimidinyl-3-pyridinesulfonamide;
6-(1-(5-Fluoro-2-methoxy-4-tetradecylphenyl)-3-methylureido)-N-(pyrimidin-2-yl)pyridine-3-sulfonamide;
6-(1-(2,4'-difluoro-5-methoxy-3'-(trifluoromethoxy)-[1,1'-biphenyl]-4-yl)-3-methylureido)-N-(4-methylisoxazol-3-yl)pyridine-3-sulfonamide;
6-(1-(2,4'-difluoro-5-methoxy-3'-(trifluoromethyl)-[1,1'-biphenyl]-4-yl)-3-methylureido)-N-(4-methylisoxazol-3-yl)pyridine-3-sulfonamide;
6-(2,4'-difluoro-5-methoxy-3'-(2,2,2-trifluoroethoxy)-[1,1'-biphenyl]-4-yl)-3-methylureido)-N-(4-methylisoxazol-3-yl)pyridine-3-sulfonamide;

6-((2-chloro-4'-fluoro-5-methoxy-3'-(2,2,2-trifluoroethoxy)-4-biphenylyl)(methylcarbamoyl)amino)-N-2-pyrimidinyl-3-pyridinesulfonamide;

6-((2-chloro-4'-fluoro-5-methoxy-3'-(2,2,2-trifluoroethoxy)-4-biphenylyl)(methylcarbamoyl)amino)-N-1,2,5-thiadiazol-3-yl-3-pyridinesulfonamide;

6-((2-chloro-4'-fluoro-5-methoxy-3'-(2,2,2-trifluoroethoxy)-4-biphenylyl)(methylcarbamoyl)amino)-N-(6-fluoro-2-pyridinyl)-3-pyridinesulfonamide;

6-((2-chloro-4'-fluoro-5-methoxy-3'-(2,2,2-trifluoroethoxy)-4-biphenylyl)(methylcarbamoyl)amino)-N-1,3-oxazol-2-yl-3-pyridinesulfonamide;

6-((2-chloro-4'-fluoro-5-methoxy-3'-(2,2,2-trifluoroethoxy)-4-biphenylyl)(methylcarbamoyl)amino)-N-(2-methyl-4-pyrimidinyl)-3-pyridinesulfonamide;

6-((2-chloro-4'-fluoro-5-methoxy-3'-(2,2,2-trifluoroethoxy)-4-biphenylyl)(methylcarbamoyl)amino)-N-4-pyrimidinyl-3-pyridinesulfonamide;

6-((2-chloro-4'-fluoro-5-methoxy-3'-(trifluoromethyl)-4-biphenylyl)(methylcarbamoyl)amino)-N-2-pyrimidinyl-3-pyridinesulfonamide;

6-((2-chloro-4'-fluoro-5-methoxy-3'-(trifluoromethyl)-4-biphenylyl)(methylcarbamoyl)amino)-N-1,2,5-thiadiazol-3-yl-3-pyridinesulfonamide;

6-((2-chloro-4'-fluoro-5-methoxy-3'-(trifluoromethyl)-4-biphenylyl)(methylcarbamoyl)amino)-N-(6-fluoro-2-pyridinyl)-3-pyridinesulfonamide;

6-((2-chloro-4'-fluoro-5-methoxy-3'-(trifluoromethyl)-4-biphenylyl)(methylcarbamoyl)amino)-N-1,3-oxazol-2-yl-3-pyridinesulfonamide;

6-((2-chloro-4'-fluoro-5-methoxy-3'-(trifluoromethyl)-4-biphenylyl)(methylcarbamoyl)amino)-N-(2-methyl-4-pyrimidinyl)-3-pyridinesulfonamide;

6-((2-chloro-4'-fluoro-5-methoxy-3'-(trifluoromethyl)-4-biphenylyl)(methylcarbamoyl)amino)-N-4-pyrimidinyl-3-pyridinesulfonamide;

6-((2,4'-difluoro-5-methoxy-3'-(trifluoromethoxy)-4-biphenylyl)(methylcarbamoyl)amino)-N-3-pyridazinyl-3-pyridinesulfonamide;

6-((2,4'-difluoro-5-methoxy-3'-(trifluoromethoxy)-4-biphenylyl)(methylcarbamoyl)amino)-N-1,3-oxazol-2-yl-3-pyridinesulfonamide;

6-((2,4'-difluoro-5-methoxy-3'-(trifluoromethoxy)-4-biphenylyl)(methylcarbamoyl)amino)-N-4-pyrimidinyl-3-pyridinesulfonamide;

6-(1-(2-chloro-5-methoxy-3'-(trifluoromethyl)-[1,1'-biphenyl]-4-yl)ureido)-N-(isoxazol-3-yl)pyridine-3-sulfonamide;

6-(carbamoyl(2,4'-dichloro-3'-fluoro-5-methoxy-4-biphenylyl)amino)-N-3-isoxazolyl-3-pyridinesulfonamide;

6-(carbamoyl(2,3'-dichloro-5'-cyano-5-methoxy-4-biphenylyl)amino)-N-3-isoxazolyl-3-pyridinesulfonamide;

6-(carbamoyl(2-chloro-3',5-dimethoxy-5'-(trifluoromethyl)-4-biphenylyl)amino)-N-3-isoxazolyl-3-pyridinesulfonamide;

6-(carbamoyl(2-chloro-5-methoxy-3'-(2,2,2-trifluoroethoxy)-4-biphenylyl)amino)-N-3-isoxazolyl-3-pyridinesulfonamide;

Methyl (2-chloro-5-methoxy-3'-(trifluoromethyl)-[1,1'-biphenyl]-4-yl)(5-(N-(isoxazol-3-yl)sulfamoyl)pyridine-2-yl)carbamate, 6-((5-chloro-4-(cyclopentylethynyl)-2-methoxyphenyl)(methylcarbamoyl)amino)-N-3-isoxazolyl-3-pyridinesulfonamide;

6-((5-fluoro-2-methoxy-4-(3,3,3-trifluoropropyl)phenyl)(methylcarbamoyl)amino)-N-3-isoxazolyl-3-pyridinesulfonamide;

4-(1-(4'-chloro-3-methoxy-3'-methyl-[1,1'-biphenyl]-4-yl)-3methylureido)-N-(isoxazol-3-yl)benzenesulfonamide; and 4-(1-(2,4'-difluoro-5-methoxy-3'-(trifluoromethoxy)-[1,1'-biphenyl]-4-yl)-3-methylureido)-N-(isoxazol-3-yl)benzenesulfonamide.

18. A pharmaceutical composition comprising the compound in accordance with claim 1, or a pharmaceutically acceptable salt thereof, and a pharmaceutically acceptable excipient.

\* \* \* \* \*